United States Patent
Fabbro et al.

(10) Patent No.: US 11,918,586 B2
(45) Date of Patent: Mar. 5, 2024

(54) TREATMENT OF SKIN LESIONS

(71) Applicants: TORQUR AG, Basel (CH); THE TRUSTEES OF THE UNIVERSITY OF PENNSYLVANIA, Philadelphia, PA (US)

(72) Inventors: Doriano Fabbro, Arlesheim (CH); Paul Hebeisen, Basel (CH); Petra Hillmann-Wuellner, Oberengstringen (CH); Anton Stuetz, Altmuenster (CH); John T. Seykora, Broomall, PA (US); Florent Beaufils, Bartenheim (FR)

(73) Assignees: TORQUR AG, Basel (CH); THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 150 days.

(21) Appl. No.: 17/214,309

(22) Filed: Mar. 26, 2021

(65) Prior Publication Data
US 2021/0361665 A1 Nov. 25, 2021

Related U.S. Application Data

(63) Continuation of application No. 16/301,728, filed as application No. PCT/EP2017/025137 on May 17, 2017, now Pat. No. 10,993,947.

(30) Foreign Application Priority Data

Jan. 17, 2017 (EP) ..................................... 17151843

(51) Int. Cl.
*A61K 31/5377* (2006.01)
*A61K 31/5386* (2006.01)
(Continued)

(52) U.S. Cl.
CPC ...... *A61K 31/5377* (2013.01); *A61K 31/5386* (2013.01); *A61K 31/541* (2013.01); *A61P 17/02* (2018.01)

(58) Field of Classification Search
None
See application file for complete search history.

(56) References Cited

U.S. PATENT DOCUMENTS

2013/0178440 A1* 7/2013 Seykora ............. A61K 31/4709
514/47
2015/0065431 A1 3/2015 Xu et al.

FOREIGN PATENT DOCUMENTS

CN 103483345 * 1/2014
CN 103483345 A 1/2014
(Continued)

OTHER PUBLICATIONS

Manara et al. "NVP-BEZ235 as a New Therapeutic Option for Sarcomas," Clin Cancer Res; 16(2) Jan. 15, 2010, 530-540 (Year: 2010).*

(Continued)

*Primary Examiner* — Jeffrey S Lundgren
*Assistant Examiner* — Michael J Schmitt
(74) *Attorney, Agent, or Firm* — MEDLER FERRO WOODHOUSE & MILLS PLLC

(57) ABSTRACT

The present invention is relates to a compound of formula (I), wherein $X^1$, $X^2$ and $X^3$ are, independently of each other, N or CH; with the proviso that at least two of $X^1$ $X^2$ and $X^3$ are N; Y is N or CH; W is H or F; with the proviso that when W is F, then $X^1$, $X^2$ and $X^3$ are N; $R^1$ and $R^2$ are independently of each other (i) a morpholinyl of formula (II) wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, C1alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures wherein the arrows denote the bonds in formula (II); or (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxy$C_1$-$C_3$alkyl, $C_3$-$C_6$cycloalkyl; or two $R^7$ substituents form together a bivalent residue-$R^8R^9$— selected from Ci-C3alkylene optionally substituted with 1 to 4 F, —$CH_2$—O—$CH_2$— or —O—$CH_2CH_2$—O—; with the proviso that at least one of $R^1$ and $^{R2}$ is a morpholinyl of formula II; and prodrugs, metabolites, tautomers, solvates and pharmaceutically acceptable salts thereof, for use in the prevention or treatment of a skin lesion in a subject.

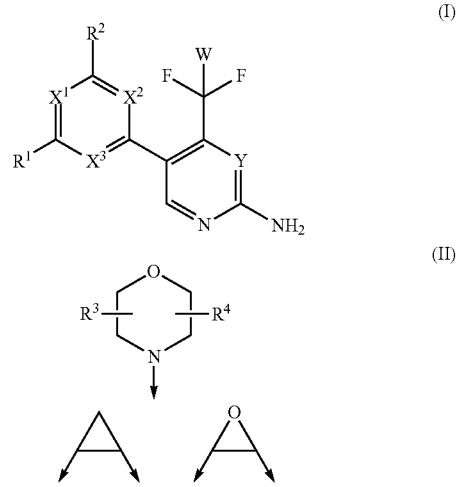

14 Claims, 10 Drawing Sheets

Related U.S. Application Data

(60) Provisional application No. 62/338,111, filed on May 18, 2016.

(51) Int. Cl.
*A61K 31/541* (2006.01)
*A61P 17/02* (2006.01)

(56) References Cited

FOREIGN PATENT DOCUMENTS

| CN | 104557871 | * | 4/2015 |
|---|---|---|---|
| CN | 104557871 A | | 4/2015 |
| WO | 2007/084786 A1 | | 7/2007 |
| WO | 2008/098058 A1 | | 8/2008 |
| WO | 2010/052569 A2 | | 5/2010 |
| WO | WO 2010052569 | * | 5/2010 |
| WO | 2012/101654 A2 | | 8/2012 |
| WO | 2012/109423 A1 | | 8/2012 |
| WO | 2014/072956 A1 | | 5/2014 |
| WO | 2014/090147 A1 | | 6/2014 |
| WO | 2015/162084 A1 | | 10/2015 |
| WO | 2015/181055 A1 | | 12/2015 |
| WO | 2016/075130 A1 | | 5/2016 |
| WO | 2017/198346 A1 | | 11/2017 |

OTHER PUBLICATIONS

International Search Report issued in PCT/EP2017/025137, dated Jul. 4, 2017.
Manara et al., "NVP-BEZ235 as a New Therapeutic Option for Sarcomas," Clin Cancer Res 16(2):530-540 (2010).
Zhang et al., "Design, Synthesis, and Biological Evaluation of Substituted Pyrimidines as Potential Phosphatidylinositol 3-Kinase (PI3K) Inhibitors," Journal of Medicinal Chemistry 59:7268-7274 (2016).

* cited by examiner

TREATMENT OF SKIN LESIONS

The present invention relates to compositions for use in the prevention or treatment of a skin lesion in a subject.

RELATED ART

Non-melanoma skin cancer (NMSC) is the most frequent malignancy worldwide, with more than 1 million cases diagnosed each year in the US alone (Bowden G T. Nat Rev Cancer. 2004; 4:23-35). NMSC refers to a group of diseases including actinic keratosis (AK), cutaneous squamous cell carcinoma (cSCC), cSCC in situ (cSCCis or Bowen's Disease (BD)) and basal cell carcinoma (BCC, also known as basalioma or basal cell cancer) (Di Magliano P. et al., Nature Rev. Cancer 2003, 3, 903-911). cSCC and BCC are the most common forms of NMSC and account for greater than 40% of newly diagnosed cancers (Bowden G T. Nat Rev Cancer. 2004, 4, 23-35). Although BCC has a very low metastatic risk, this tumor can cause significant disfigurement by invading surrounding tissues. BCC is a distinctive manifestation in nevoid basal cell carcinoma syndrome (NBCCS) patients. Both inherited and acquired mutations of patched 1 (PTCH1), a tumor-suppressor gene controlling the activity of Smoothened (SMO), are the primary cause of the constitutive activation of the Hedgehog (HH) pathway, leading to the emergence of BCCs in NBCCS (Di Magliano P. et al., Nature Rev. Cancer 2003; 3, 903-911; Merchant A A et al., Clin. Cancer Res. 2010, 16, 3130-3140). Smo inhibitors and PI3K pathway inhibitors have been shown to delay or prevent the development of resistance which is observed upon treatment with SMO antagonists alone (Buonamici S. et al., Science transl. Med. 2010, 2, 51ra70).

Several studies indicate that PI3K/mTOR signaling may play a critical role in NMSC, in particular in the AK and cSCC development (Ayli E E et al., J. Cutaneous Pathology 2008, 35, 273-277). Immunohistochemical (IHC) analysis of human epidermal tumors showed that mTOR itself, as well as its downstream effectors 4EBP1, S6K, and AKTSer473 are phosphorylated at much higher levels in SCC and precancerous actinic keratosis (AK) than normal skin (Chen S J, et al. Br J Dermatol. 2009; 160, 442-5). More recently, reverse phase protein microarray analysis of cSCC and AK revealed aberrantly activated mTOR pathways in the precancerous and transformed tissues compared to normal skin (Einspahr J G, et al. Cancer Prev Res (Phila). 5, 403-13). Thus, significant up-regulation of the PI3K/AKT/mTOR pathway was not only found in cSCC and in cSCCis (BD), but also in AK when compared to normal, healthy skin. Increased PI3K/mTOR pathway activity may already be seen in sun-damaged skin lesions (Ratushny V et al., J. Clin. Investigation 2012, 122, 464-472).

Low-risk cSCC on the trunk and extremities can be treated with electrodessication and curettage (ED&C). For invasive cSCC, surgical excision and Mohs micrographic surgery are the primary treatment options; with appropriate patient selection, these techniques have comparable cure rates. Radiation therapy is typically used as an adjuvant to surgery, to provide improved locoregional control, but it may be used as primary therapy in patients who are unable to undergo surgical excision. Chemotherapy may be considered as adjuvant therapy in select highest-risk cases of cSCC. In particular, emerging evidence suggests that epidermal growth factor receptor (EGFR) inhibitors may be useful adjuncts to surgical treatment. Systemic chemotherapy may be considered for metastatic cSCC.

Radiation therapy as primary treatment for cSCC is typically reserved for patients who are unable to undergo surgical excision. More frequently, radiation therapy is used as an adjuvant to surgery for improved locoregional control. Postoperative radiotherapy is considered for tumors that exhibit perineural invasion or other high-risk features and for those that involve regional metastasis.

A variety of different chemotherapeutic agents have been used to treat metastatic cSCC. Although many of these agents have an established role in chemotherapy for mucosal head and neck squamous cell carcinoma, high-quality data is frequently lacking for their use in cSCC. Among the most common nontargeted agents used in cSCC are cisplatin and carboplatin, 5-FU, and taxanes (Martinez J C et al., Dermatologic Surgery 2004, 30, 679-686).

Adjuvant medication may be considered in selected highest-risk cases of cSCC. Options include oral 5-fluorouracil (5-FU) and epidermal growth factor receptor (EGFR) inhibitors. Treatment should be administered through oncology treatment centers.

A variety of different chemotherapeutic agents have been used to treat metastatic cSCC. Although many of these agents have an established role in chemotherapy for mucosal head and neck squamous cell carcinoma, high-quality data is frequently lacking for their use in cSCC. Among the most common nontargeted agents used in cSCC are cisplatin and carboplatin, 5-FU, and taxanes.

Several treatment modalities exist for precancerous skin lesions, including cSCCis (BD) and actinic keratosis. Topical application of 5-FU or imiquimod and diclofenac used for the treatment of precancerous skin lesions have negative side effects including skin irritation and severe inflammation or show moderate/low efficacy (Kose O. et al., J. Dermatol. Treatment 2008, 19, 159-163). Similarly, liquid nitrogen cryotherapy or electrocautery and curettage may be used. The risks associated with cryotherapy include transient pain, edema, and blistering. Hypopigmentation and alopecia are also common and may be permanent, so treatment of hair-bearing areas and in darkly pigmented individuals is generally not recommended.

Cutaneous lymphomas are indolent but treatable (not curable) and usually not life-threatening.

Cutaneous T-cell lymphoma (CTCL) has variable limited skin involvement and may be accompanied by tumor formation, ulceration, and exfoliation, complicated by itching and infections. Cutaneous B-cell lymphomas (CBCL) are a less common version of cutaneous lymphomas, making up about 20-25% of all cutaneous lymphomas.

There are multiple treatments for cutaneous lymphoma (topical or systemic): Topical: Corticosteroids, Bexarotene (Targretin), Mechlorethamine (Mustargen and Valchlor), Carmustine (BCNU), Phototherapy, Local and total skin electron beam conventional radiotherapy. Systemic: Various targeted biological immuno-therapies, HDAC inhibitors and chemotherapies In conclusion, there is an ongoing need for improved therapies for skin lesions.

SUMMARY OF THE INVENTION

It has now surprisingly been found that the compounds of formula (I) are selective and specific inhibitors of mTOR and/or dual inhibitors of PI3K/mTOR and are highly effective in regressing skin lesions, in particular cutaneous squamous cell carcinoma (cSCC) and actinic keratosis (AK).

Thus, in a first aspect of the invention, there is provided a compound of formula (I),

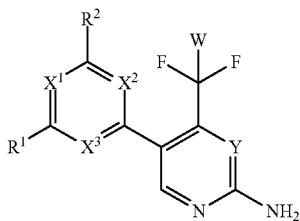

(I)

wherein
$X^1$, $X^2$ and $X^3$ are, independently of each other, N or CH; with the proviso that at least two of $X^1$, $X^2$ and $X^3$ are N;
Y is N or CH;
W is H or F; with the proviso that when W is F, then $X^1$, $X^2$ and $X^3$ are N;
$R^1$ and $R^2$ are independently of each other
  (i) a morpholinyl of formula (II)

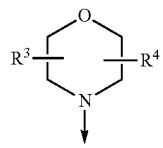

(II)

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

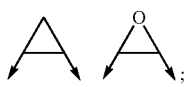

wherein the arrows denote the bonds in formula (II); or
  (ii) a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl optionally substituted with one or two OH, $C_1$-$C_2$fluoroalkyl, $C_1$-$C_2$alkoxy$C_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —CH$_2$—O—CH$_2$— or —O—CH$_2$CH$_2$—O—;
with the proviso that at least one of $R^1$ and $R^2$ is a morpholinyl of formula II; and prodrugs, metabolites, tautomers, solvates and pharmaceutically acceptable salts thereof,
for use in the prevention or treatment of a skin lesion in a subject.

DESCRIPTION OF FIGURES

K14-Fyn-Y528F mice were treated with a topical application of a gel containing Compound 1* (10 mg of Compound 1*) or nothing (control) were dissolved in 75 ul of DMSO and then propyleneglycol was added to 1000 mg (final concentration is 1% (w/w) (FIGS. 1A, B and C). The Compound 1* treated cohort contained 6 mice with 20 cSCC lesions (FIG. 1B) while the control cohort contained 6 mice with 15 cSCC lesions (FIG. 1A). The size of each SCC was measured using calipers before treatment and weekly thereafter. Gels were applied to lesions daily once Mo-Fr.

12 of 6-week-old K14-Fyn-Y528F mice were grouped in two cohorts (6 mice each) carrying either 15 cSCC lesion (control group) or 20 cSCC lesions (treatment group). Using Calipers, the size of the lesions was measured before start of treatment (and weekly thereafter) and varied from 4-68 mm2 (the size range of the lesions in each cohort was similar at the beginning). The lesions were treated topically by daily application (5× per week for 4 weeks) either with vehicle (1A) or compound 1* (1B); vehicle: 75 ul DMSO mixed with propyleneglycol to a total of 1000 mg, compound 1*: 10 mg of compound 1* dissolved in 75 ul of DMSO mixed with propyleneglycol to a total of 1000 mg. The various abbreviations denote the site of the individual lesions. The areas of each lesion for each time point were normalized to the area at the start (relative tumor area at WK0=100). In the vehicle group (1A), one of the individual lesion disappeared spontaneously (L back T2). In the compound-treated group (1B), all 20 individual lesion disappeared upon treatment. The mean values±SEM for the cSCC lesion-areas in both groups are compared in 1C and 1D. Significant reduction (50% mean-area, p<0.001) of the lesions in the treatment group occurred already after 5 days.

Figure 1A:
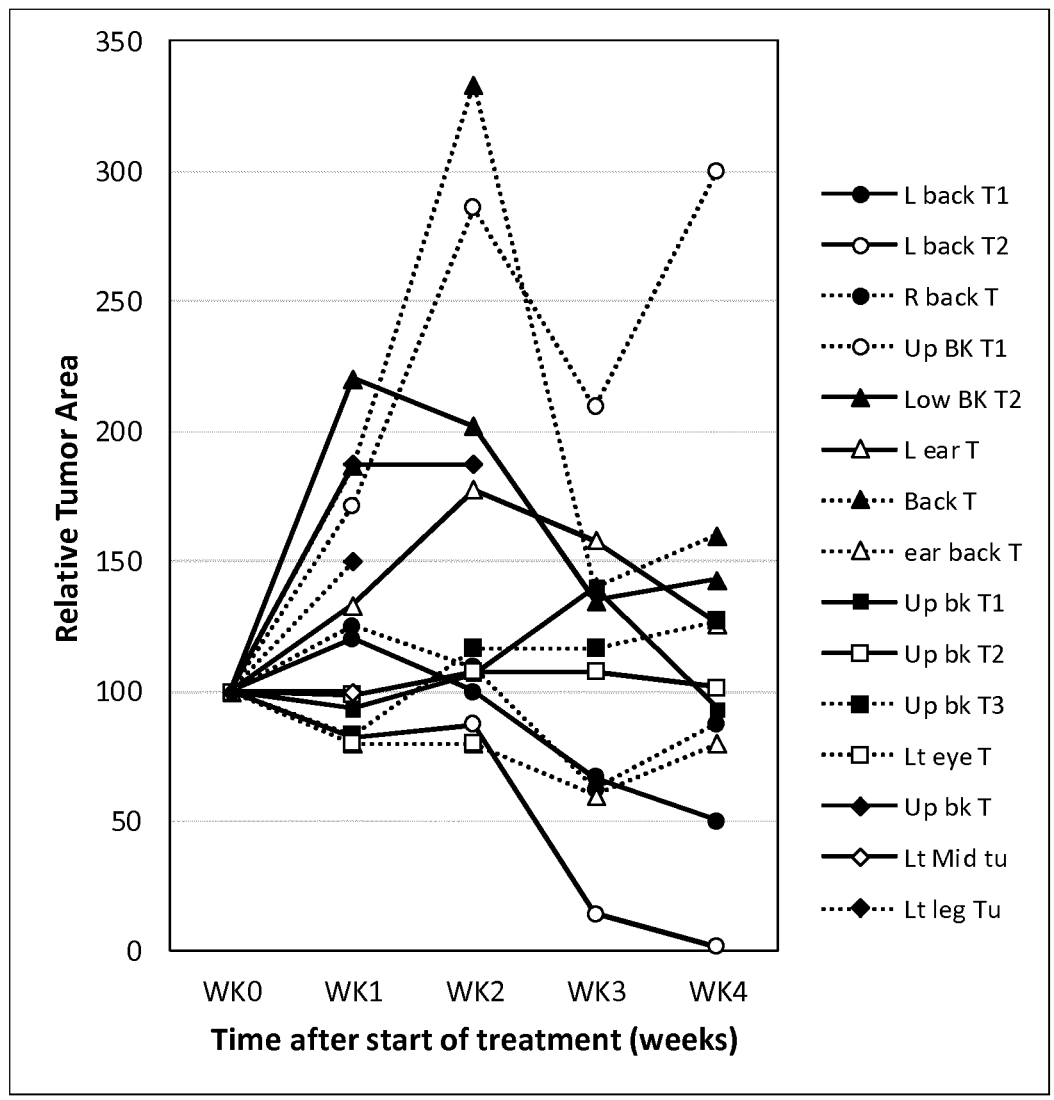
As shown in FIGS. 1B and 1C and the once daily topical application of Compound 1* gel induced almost complete regression of all cSCC lesions in the K14-Fyn Y528F model without prominent inflammation or ulceration within 4 weeks.
FIG. 1: Effect of topical application of compound 1* or vehicle on cSCC lesions in K14-Fyn-Y528F mice.

FIG. 1A: Vehicle (control) treatment of six-week-old K14-Fyn-Y528F mice carrying 15 individual cSCC lesions.

Figure 1B:
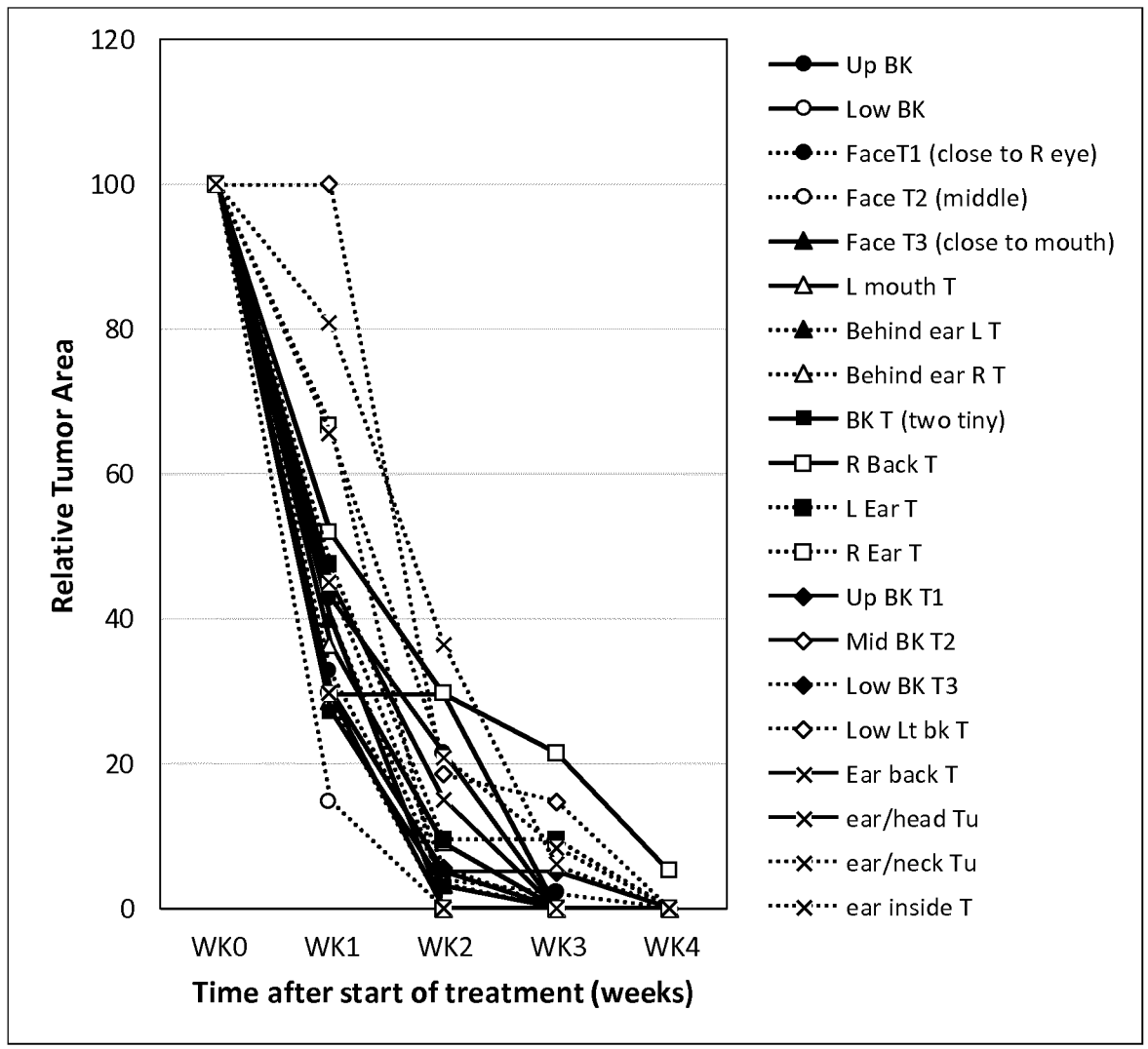

FIG. 1B: Effect of topical application of compound 1* on 20 cSCC lesions in six-week-old K14-Fyn-Y528F mice.

Figure 1C:
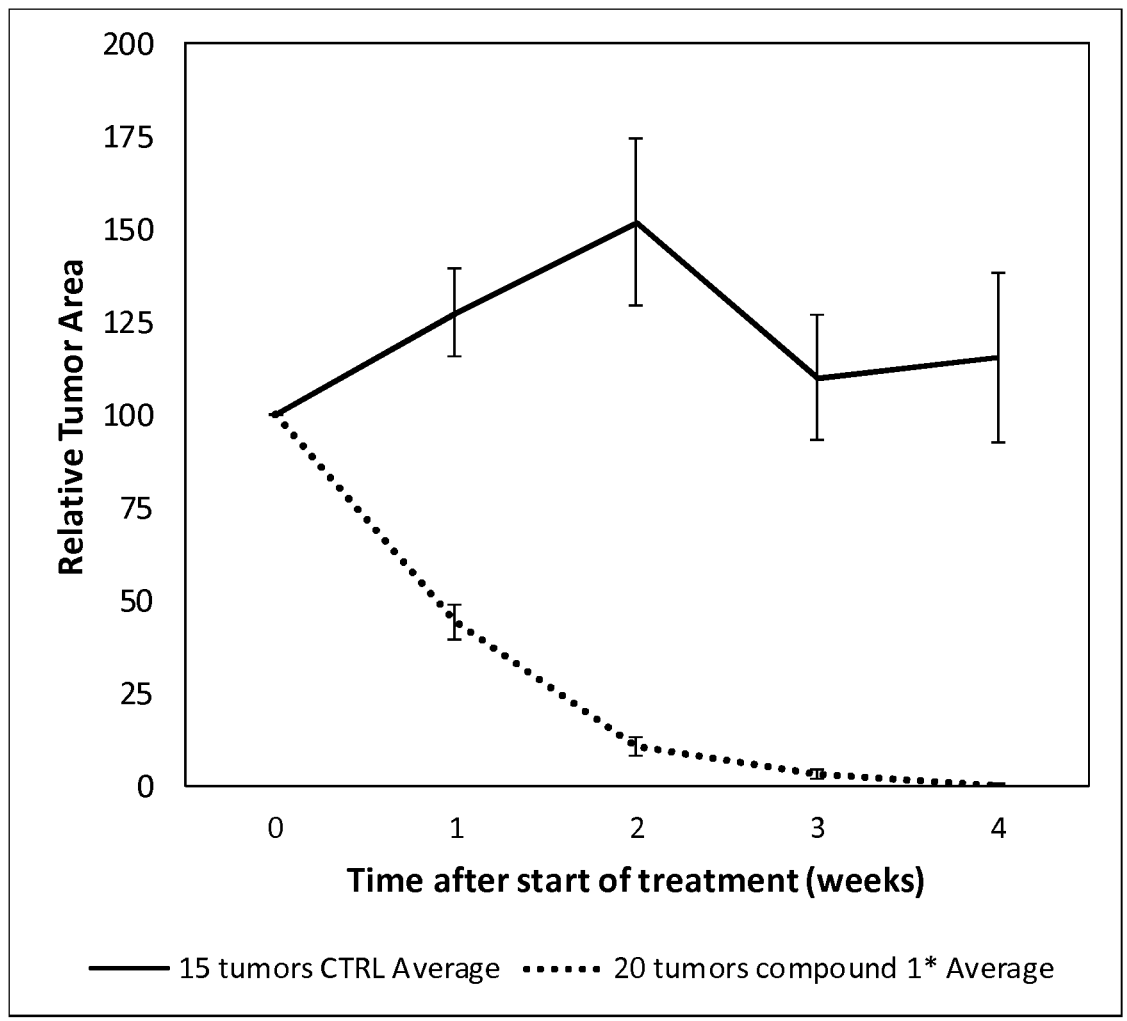

FIG. 1C: Treatment of cSCC lesions in K14-Fyn-Y528F mice: Comparison of compound 1* versus vehicle treatment (Curve). Vehicle: n=15; treated: n=20.

Figure 1D:
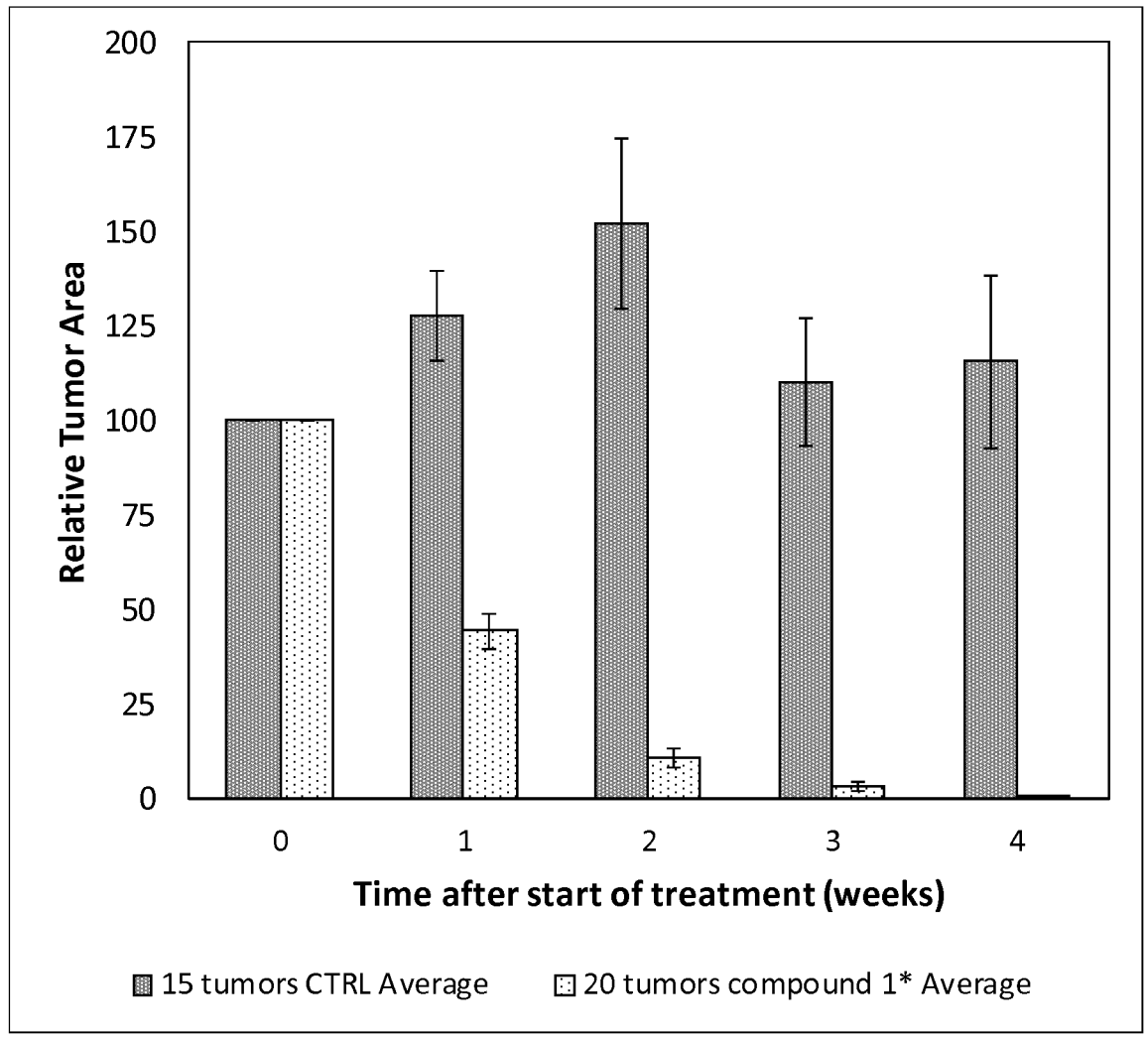

FIG. 1D: Treatment of cSCC lesions in K14-Fyn-Y528F mice: Comparison of compound 1* versus vehicle treatment (Bar graph). Vehicle: n=15; treated: n=20.

Figure 2:
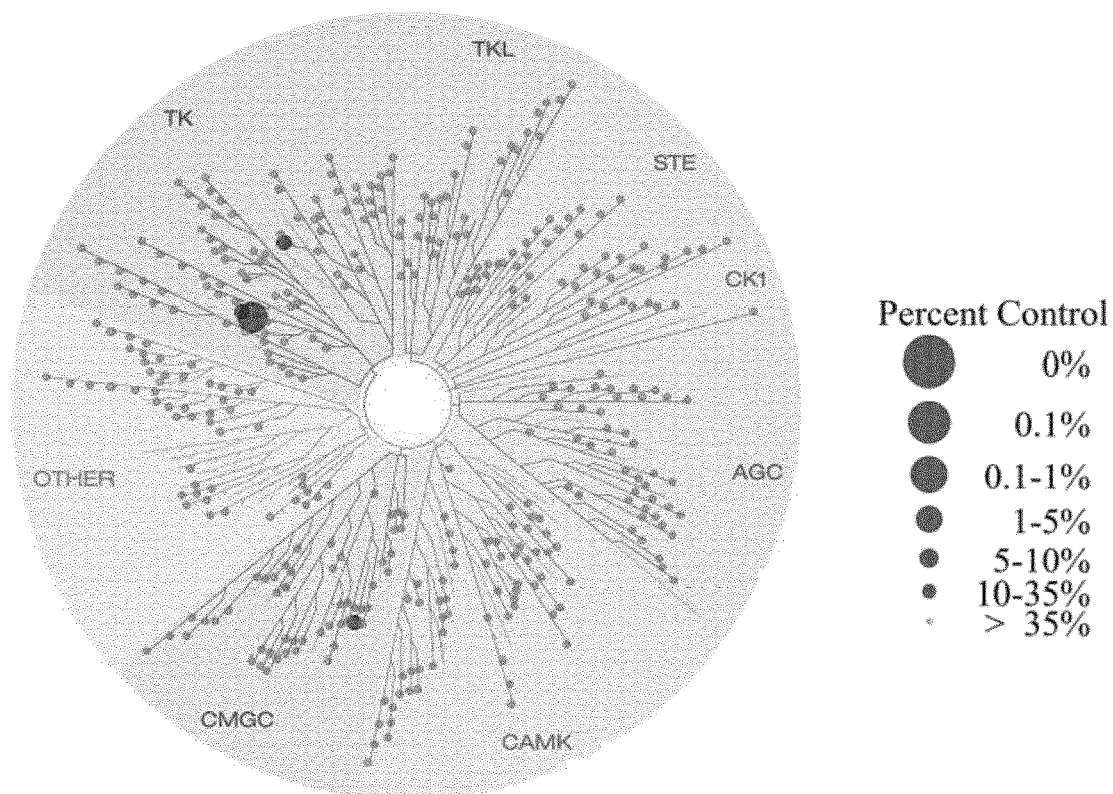
Figure 2:
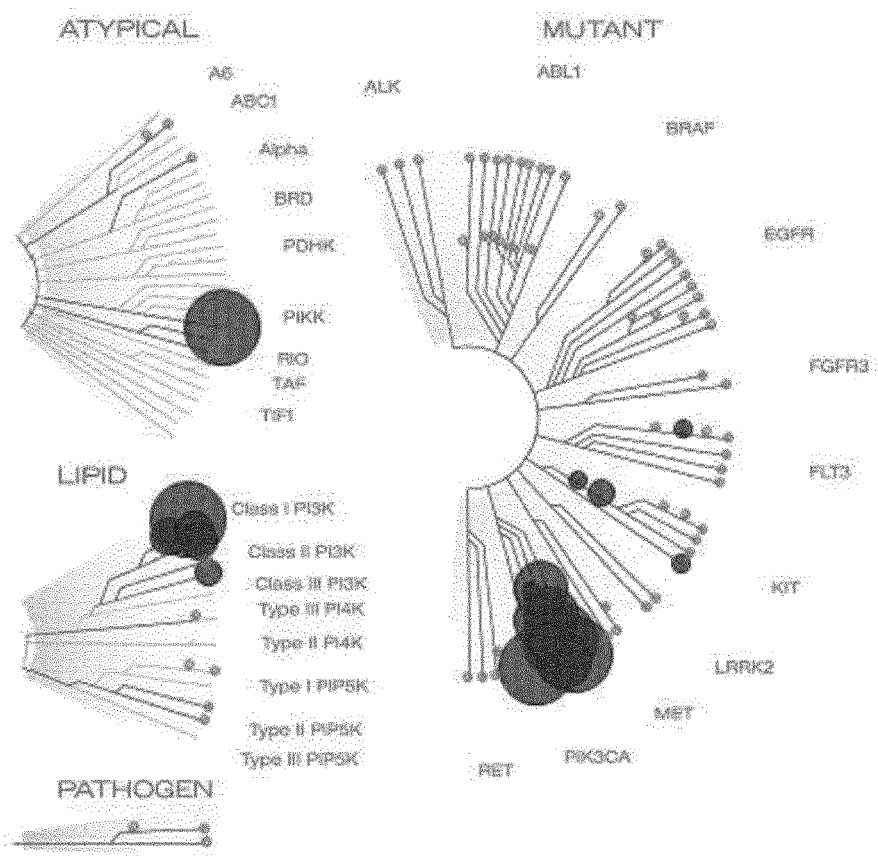

FIG. 2: Treespot of Compound 1*. The human kinome is represented as circular phylogenetic tree with the 8 main groups of typical protein kinases and 9 groups of atypical protein kinases. The mutant variants of some protein kinases are also shown, as well as the lipid kinase panel, which is not integral part of the human kinome. The results are reported as a map (Treespot), which allows visualizing compound interactions across the human kinome and lipid kinase panel. Kinases found to bind to Compound 1* are marked with circles, where larger circles indicate higher-affinity.

Figure 3:
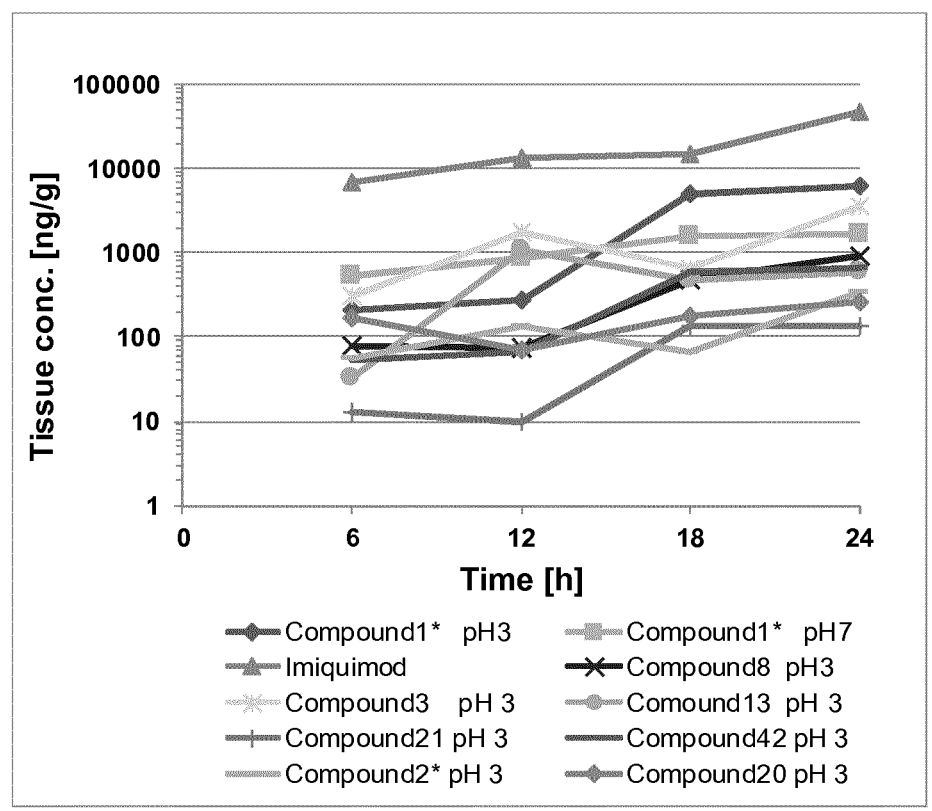

FIG. 3: PK profiles of nine formulations comprising the inventive compounds and control have been assessed. The control formulation Aldara (5% imiquimod) was applied to detect variations in skin permeability (local variability in the same animal and inter-subject variability). The stratum corneum was removed by tape stripping to avoid contamination during the biopsy extraction. From the application sites dosed with the 9 test formulations, 3 replicate biopsies were taken at 6 hours, 12 hours, 18 hours and 24 hours post dose. One biopsy was taken from each control site. Additionally, 5 blank samples were taken.

Figure 4:
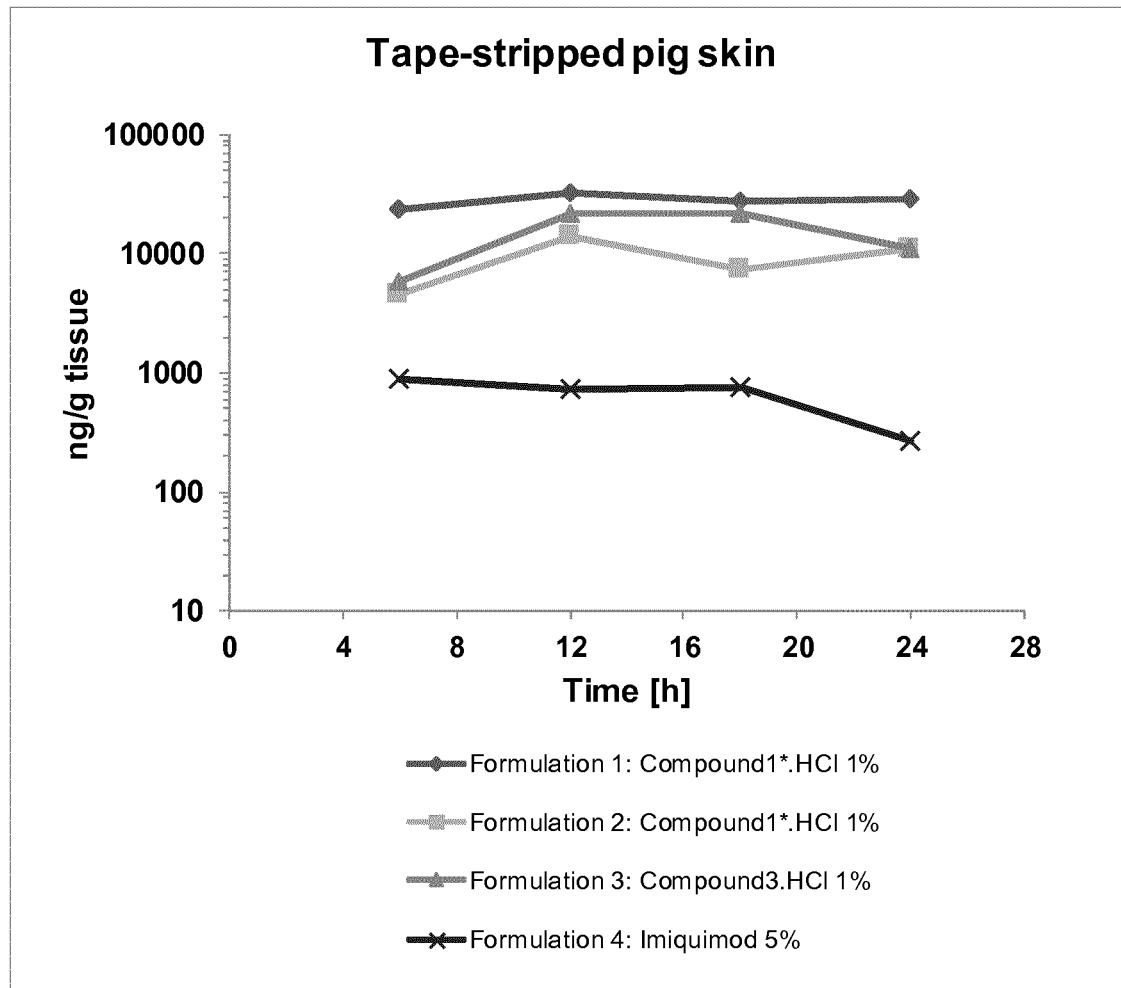

FIG. 4: PK profiles of three formulations comprising the inventive compounds. Excised pig skin was placed in a climate chamber to control temperature and humidity. From every application site (20×40 mm) three replicate biopsies were taken at 6 hours, 12 hours, 18 hours and 24 hours post dose. Before biopsies were taken the stratum corneum was removed by tape stripping and biopsies consisted of the remaining epidermis and entire dermis.

Figure 5:
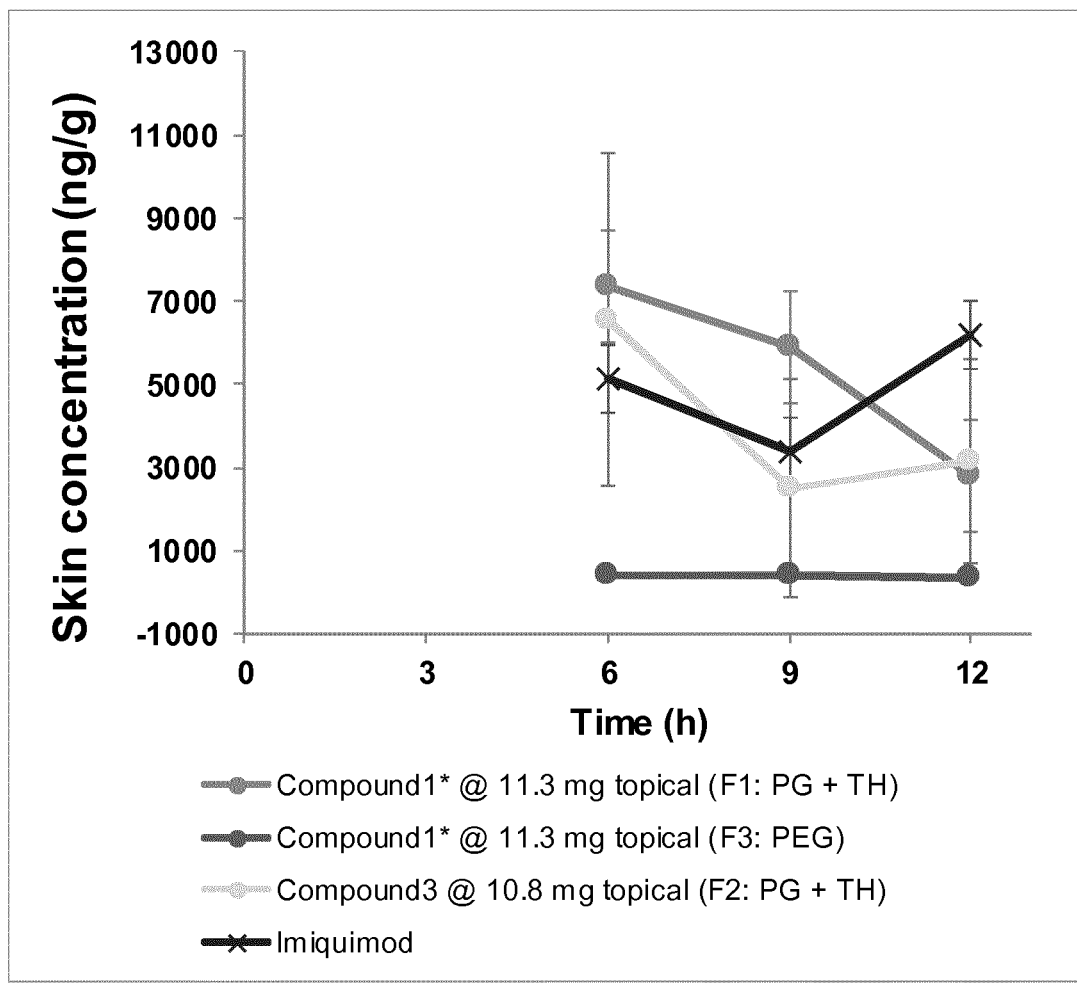

FIG. 5: PK of 1% Cpd1* in either propylene glycol or PEG. A 30-45 kg domestic pig was anaesthetized for a duration of 12 hours. Each of the four formulations were applied 6 times (2 replicates for each of the three time points—6, 9 and 12 hours) on 24 different application sites At the end of the study the pig was sacrificed and stratum corneum removed by tape stripping.

Figure 6A:
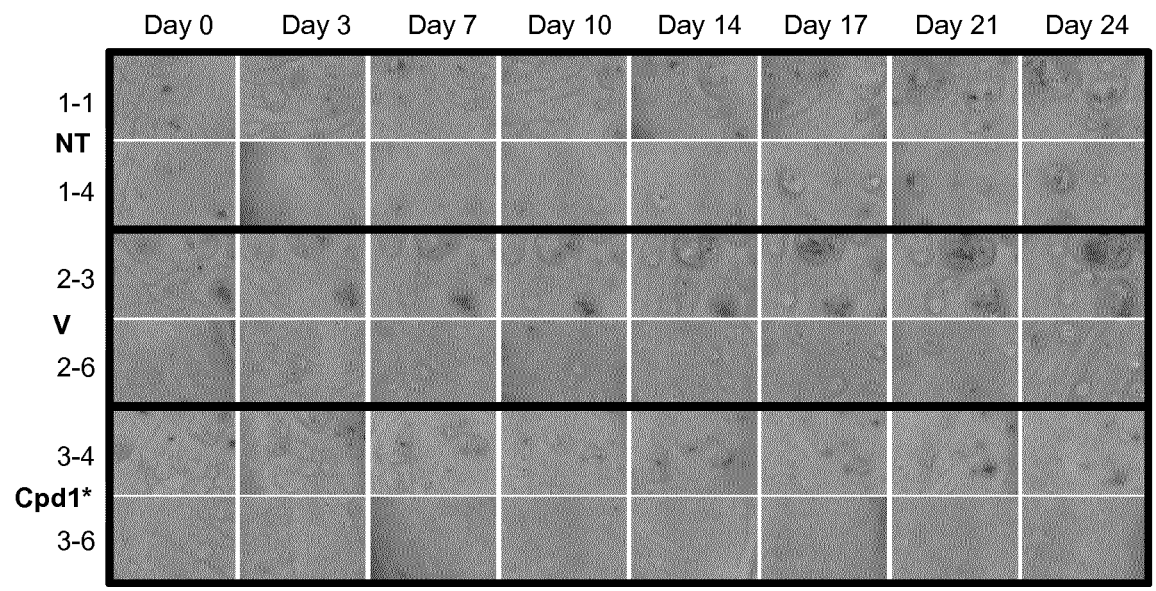
Figure 6B:
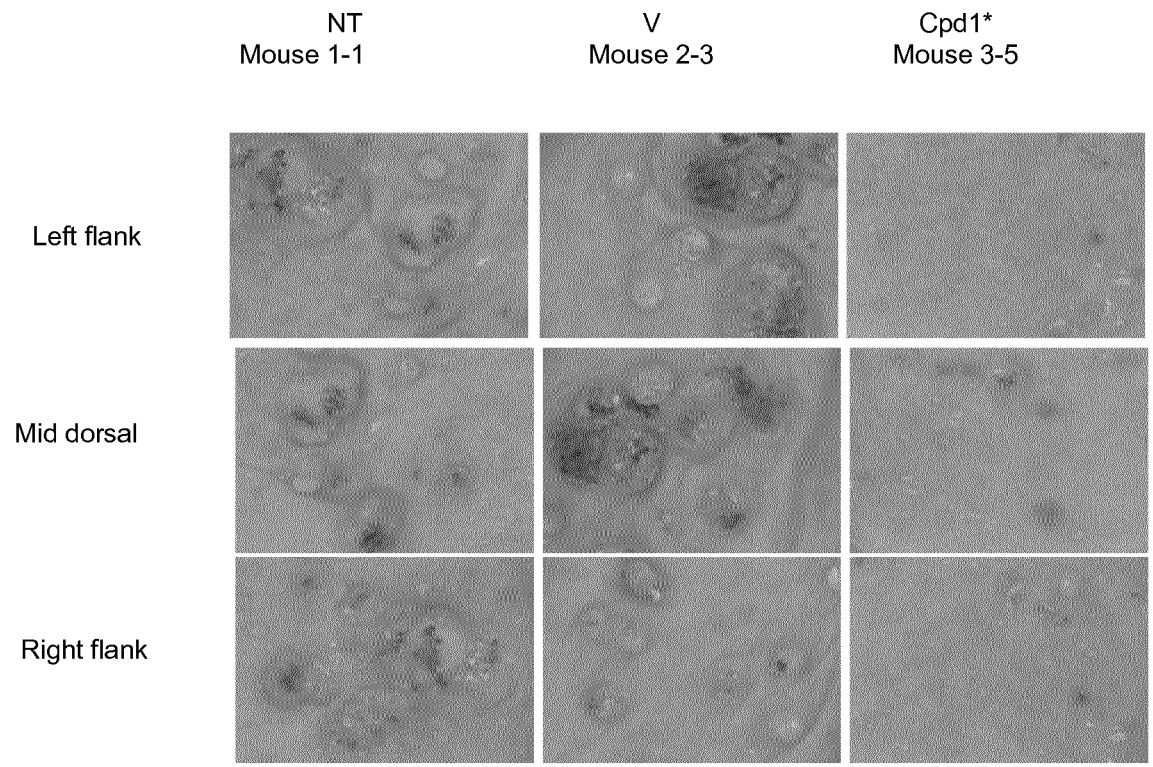

FIG. 6: Effect of Cpd1* on SKH1 UV-B irradiated mice during the 24 day treatment (FIG. 6A) and at the end of 24 day treatment (FIG. 6B).

Hairless SKH1 mice were irradiated as described below for 102 days prior to treatment with Cpd1*. NT=Not treated, V=Vehicle. In vivo topical treatment of Actinic Keratosis on SKH1-UVB induced mice model was performed with either NT or V or Cpd1* 3 mg/mouse/day using a non-optimized formulation as described for the cSCC mouse model.

Mid dorsal photo on two selected mice by group is shown (NT: mouse 1-1 and mouse 1-4; V: mouse 2-3 and mouse 2-6; Cpd1*: mouse 3-4 and mouse 3-6).

Hairless SKH-1 mice (Charles River Laboratories) were used for all in vivo experiments and they were fed with standard chow. SKH-1 mice (6-8 weeks old, weighting 18-20 g) in individual housing (one mouse/cage) were UV-B-exposed every single day for about 14-15 weeks in dedicated cabinet. Medium wave UV-B lamps T-40.M were from Vilber Lourmat (Eberhardzell, Germany), and run from 280 to 320 nm with an energy peak at 312 nm. The MED (minimal erythemal dose) of this device was defined at 0.06 $J/cm^2/day$, which represents about 20 minutes UV-B exposure per day for SKH-1 mice. UV-B irradiation dose was internally calibrated before each experiment to adjust irradiation period. To generate AK lesions and to prevent the risk of skin burn, gradual exposure was performed as follow: 10 days at 0.05 $J/cm^2/day$, 10 days at 0.055 $J/cm^2/day$ and then the MED was applied for the up to 102 days.

Figure 7:
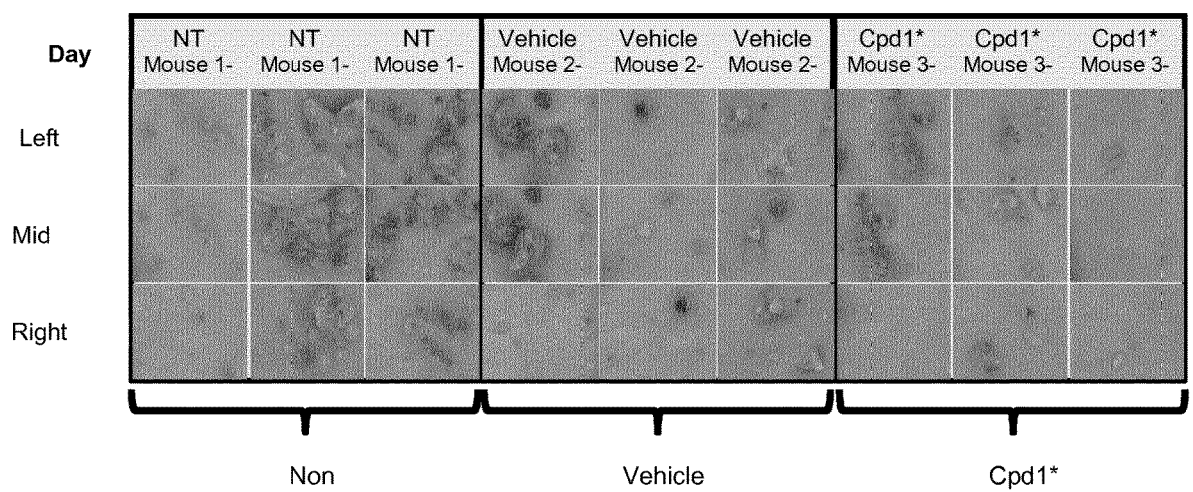

FIG. 7: Effect of Cpd1* on SKH1 UV-B irradiated mice after discontinuation of treatment for 17 days.

Hairless SKH1 mice were irradiated as described in FIG. 6. After treatment for 24 days with Cpd1* at 3 mg/mouse/day using a non-optimized formulation as described for the cSCC mouse model the treatment was discontinued. After 17 days of discontinuation of treatment photos of the Left flank, Mid dorsal and Right flank were taken for 3 selected mice per group (NT: mouse 1-4 and mouse 1-5 and 1-6; Vehicle: mouse 2-4 and mouse 2-5 and mouse 2-6; Cpd1*: mouse 3-4 and mouse 3-5 and mouse 3-6).

DETAILED DESCRIPTION OF THE INVENTION

Reference will now be made in detail to the presented and further aspects and the presented and further embodiments of the invention, examples of which are illustrated in the accompanying structures and formulas. While the invention will be described in conjunction with the enumerated embodiments, it will be understood that they are not intended to limit the invention to those embodiments. One skilled in the art will recognize many methods and materials similar or equivalent to those described herein, which could be used in the practice of the present invention. The present invention is in no way limited to the methods and materials herein described.

Features, integers and characteristics, described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Unless defined otherwise, all technical and scientific terms used herein have the same meanings as commonly understood by one of ordinary skill in the art to which this invention belongs.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting.

The terms "comprising", "having", and "including" are to be construed as open-ended terms (i.e., meaning "including, but not limited to,") unless otherwise noted.

The terms "individual," "subject" or "patient" are used herein interchangeably. In a preferred embodiment, the subject is a human.

The term "chiral" refers to molecules, which have the property of non-superimposability of the mirror image partner, while the term "achiral" refers to molecules, which are superimposable on their mirror image partner.

The term "stereoisomers" refers to compounds, which have identical chemical constitution, but differ with regard to the arrangement of the atoms or groups in space.

"Diastereomer" refers to a stereoisomer with two or more centers of chirality in which the compounds are not mirror images of one another. Diastereomers have different physical properties, e.g. melting points, boiling points, spectral properties, and chemical and biological reactivities. Mixtures of diastereomers may be separated under high resolution analytical procedures such as electrophoresis and chromatography.

"Enantiomers" refer to two stereoisomers of a compound which are non-superimposable mirror images of one another. Stereochemical definitions and conventions used herein generally follow S. P. Parker, Ed., *McRaw-Hiff Dictionary of Chemical Terms* (1984), McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric or a scalemic mixture. A 50:50 mixture of enantiomers is referred to as a racemic mixture or a racemate. The term "tautomer" or "tautomeric form" refers to structural isomers of different energies, which are interconvertible via a low energy barrier. For example, proton tautomers include interconversions via migration of a proton, such as keto-enol and imine-enamine isomerizations.

The phrase "pharmaceutically acceptable salt" as used herein, refers to pharmaceutically acceptable organic or inorganic salts of a compound of the invention, in particular acid addition salts. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate (mesylate), ethanesulfonate, benzenesulfonate, p-toluenesulfonate, and pamoate salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

The term "protecting group" refers to a substituent that is commonly employed to block or protect a particular functionality during the reaction of other functional groups on the compound. For example, an "amino-protecting group" is a substituent attached to an amino group that blocks or protects the amino functionality in the compound. Suitable amino-protecting groups include acetyl, trifluoroacetyl, tert-butoxycarbonyl (BOC), benzyloxycarbonyl and 9-fluorenyl-methylenoxycarbonyl (Fmoc). For a general description of protecting groups and their use, see T. W. Greene, Protective Groups in Organic Synthesis, John Wiley & Sons, New York, 1991.

The terms "compound of this invention" and "compounds of the present invention" and "compounds of formula (I)" include stereoisomers, geometric isomers, tautomers, solvates, pharmaceutically acceptable salts, and solvates of the salts thereof.

The term "skin lesion" as used herein refers to a skin lesion which may be a skin cancer, such as non-melanoma skin cancer (NMSC) or a pre-invasive neoplastic skin proliferation, such as cutaneous squamous cell carcinoma in situ (cSCCis or Bowen's disease) or actinic keratosis (AK, also called "solar keratosis" and "senile keratosis"). Bowen's disease is a neoplastic skin disease which can be considered as an early stage or intraepidermal form of squamous cell carcinoma. Actinic keratosis is characterized by pre-cancerous patches of thick, scaly, or crusty skin, which are usually formed when skin gets damaged by ultraviolet (UV) radiation from the sun or indoor tanning beds.

The terms "non-melanoma skin cancer" and "NMSC" are used herein interchangeably. The term "NMSC" refers to a group of diseases including actinic keratosis (AK), squamous cell carcinoma (SCC), Bowen's Disease (BD) and basal cell carcinoma (BCC).

The term "field cancerization" refers to premalignant field defects and is a biological process in which large areas of cells at a tissue surface or within an organ are affected by carcinogenic alterations. The process arises from exposure to an injurious environment, such as UV radiation, often over a lengthy period. The initial step in field cancerization is associated with various molecular lesions such as acquired genetic mutations and epigenetic changes, occurring over a widespread, multi-focal "field". The field is affected by subclinical (nonvisible, nonpalpable) AK lesions, early AK lesions, late AK lesions, and possibly even invasive cSCCs. The concept of field cancerization provides the rationale for field therapy, in which the entire field—rather than individual lesions—is treated. The goals of field therapy are to eliminate not only clinically visible lesions but also subclinical lesions and to prevent the development of invasive SCC.

The terms "cutaneous squamous cell carcinoma" and "cSCC" are used herein interchangeably. cSCC is a histologically distinct form of cancer. It arises from the uncontrolled multiplication of cells of epithelium, or cells showing particular cytological or tissue architectural characteristics of squamous-cell differentiation, such as the presence of keratin, tonofilament bundles, or desmosomes, structures involved in cell-to-cell adhesion.

The terms "treatment"/"treating" as used herein include: (1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (2) inhibiting the state, disorder or condition (e.g.

arresting, reducing or delaying the development of the disease, or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment. In one embodiment, the terms "treatment"/"treating" as used herein, refer to a therapeutic treatment. In another embodiment, the terms "treatment"/"treating" as used herein, refer to a prophylactic treatment.

The term "mammal" includes, but is not limited to, humans, mice, rats, guinea pigs, monkeys, dogs, cats, horses, cows, pigs, and sheep. The term "mammal", as used herein, preferably refers to humans.

With regard to actinic keratosis (AK) the term "treatment" as used herein comprises lesion-directed and field-directed therapies. Lesion-directed therapy may be useful in the treatment of discrete, solitary lesions. Other factors considered when deciding which treatment option to pursue are morphology and duration of lesions, preexisting skin cancer, and individual patient factors such as age, immune status, cosmesis, pain tolerance, and treatment adherence. Field-directed therapy is indicated when there are multiple lesions on a chronically photodamaged field or a history of multiple lesions. Lesion-directed and field-directed therapies can be used in combination. The advantage of combination therapy is enhanced therapeutic effect, especially in difficult-to-treat case.

As used herein, the term "systemic administration" refers to administration of a compound according to the invention, such that the compound becomes widely distributed in the body in significant amounts and has a biological effect, e.g. its desired effect, in the blood and/or reaches its desired site of action via the vascular system. Typical systemic routes of administration include administration by (1) introducing the compound directly into the vascular system or (2) oral, pulmonary, or intramuscular administration wherein the compound is adsorbed, enters the vascular system, and is carried to one or more desired site(s) of action via the blood.

The terms "oral", "orally", and "oral administration", as used herein, refer to orally ingesting a compound of the present invention.

The term "topical administration" is used in its broadest sense to include administration to a surface on the body that is generally open to the surroundings. This includes not only the skin but also the nasal and oral passages and the genitalia. Thus, topical administration can include application to the skin, application to the nasal passages, application to the oral cavity (including the upper throat), and application to the genitalia. Topical formulations have been available in a variety of forms, including creams, ointments, solutions, lotions, suspensions, pastes, emulsions, foams and the like. Water miscible creams have generally been employed for moist or weeping lesions, whereas ointments have been generally chosen for dry, lichenified or scaly lesions or where a more occlusive effect has been required. Lotions have generally been useful when minimal application to a large or hair-bearing area has been required or for the treatment of exudative lesions.

Skin lesions, such as cSCC, AK or cSCCis are usually diagnosed/assessed by physical examination, but can be confirmed by histological analysis.

The expression "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of NMSC or pre-invasive forms thereof, the effective amount of the drug may reduce the lesions or make them disappear. For therapy of NMSC or pre-invasive forms thereof, efficacy can be measured, for example, by either physically assessing the lesions or by histology.

The term "dual PI3K/mTOR" inhibitor as used herein refers to a compound capable of inhibiting a Type I PI3K kinase and mTOR kinase activity by at least 2 μM preferably by at least 1 μM.

The term "prodrug" as used in this application refers to a precursor or derivative form of a compound of the invention that may have improved properties such as better solubility, reduced cytotoxicity or increased bioavailability compared to the parent compound or drug and is capable of being activated or converted into the more active parent form. The prodrugs of this invention include, but are not limited to, derivatives of the amino group connected to the pyridine or pyrimidine nucleus in which one or two hydrogens are replaced by a suitable substituent, or derivatives of the ring amino function if $R^2$ is piperazin-1-yl. Examples of such prodrugs are compounds acylated by an amino acid selected from the 20 most often occurring natural L-alpha-amino acids, acylated by a dipeptide such as L-Ala-L-Ala, by carbonic acid, sulfuric acid or phosphoric acid, as well as pharmaceutically acceptable salts thereof.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. In particular, compounds of formula (I) as defined hereinbefore, which are oxygenated or hydroxylated at any one position in the morpholine, piperazine or thiomorpholine ring $R^1$ and/or $R^2$ are considered metabolites. Further metabolites considered are thiomorpholine S-oxides and thiomorpholine S,S-dioxides. Accordingly, the invention is also directed to metabolites of compounds of the invention, including compounds produced by a process comprising contacting a compound of this invention with a mammal for a period of time sufficient to yield a metabolic product thereof.

In a first aspect of the invention, there is provided a compound of formula (I),

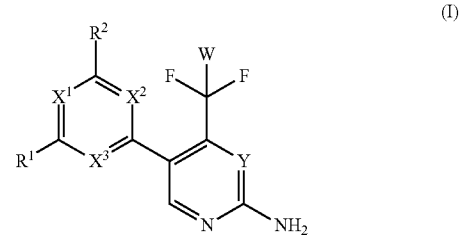

wherein
X$^1$, X$^2$ and X$^3$ are, independently of each other, N or CH; with the proviso that at least two of X$^1$, X$^2$ and X$^3$ are N;
Y is N or CH;
W is H or F; with the proviso that when W is F, then X$^1$, X$^2$ and X$^3$ are N;
R$^1$ and R$^2$ are independently of each other
(i) a morpholinyl of formula (II)

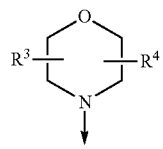

(II)

wherein the arrow denotes the bond in formula (I); and
wherein R$^3$ and R$^4$ are independently of each other H, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, CN, or C(O)O—C$_1$-C$_2$alkyl; or R$^3$ and R$^4$ form together a bivalent residue —R$^5$R$^6$— selected from C$_1$-C$_3$alkylene optionally substituted with 1 to 4 F, —CH$_2$—O—CH$_2$—, —CH$_2$—NH—CH$_2$—, or any of the structures

wherein the arrows denote the bonds in formula (II); or
(ii) a saturated 6-membered heterocyclic ring Z selected from thiomorpholinyl and piperazinyl, optionally substituted by 1 to 3 R$^7$; wherein R$^7$ is independently at each occurrence C$_1$-C$_3$alkyl optionally substituted with one or two OH, C$_1$-C$_2$fluoroalkyl, C$_1$-C$_2$alkoxyC$_1$-C$_3$alkyl, C$_3$-C$_6$cycloalkyl; or two R$^7$ substituents form together a bivalent residue —R$^8$R$^9$— selected from C$_1$-C$_3$alkylene optionally substituted with 1 to 4 F, —CH$_2$—O—CH$_2$— or —O—CH$_2$CH$_2$—O—;
with the proviso that at least one of R$^1$ and R$^2$ is a morpholinyl of formula II;
and prodrugs, metabolites, tautomers, solvates and pharmaceutically acceptable salts thereof, for use in the prevention or treatment of a skin lesion in a subject.

In another aspect, the invention provides for a compound of formula (I),

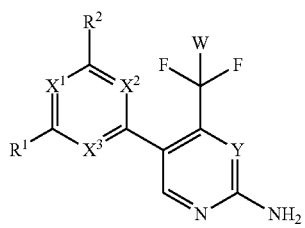

(I)

wherein
X$^1$, X$^2$ and X$^3$ are, independently of each other, N or CH; with the proviso that at least two of X$^1$, X$^2$ and X$^3$ are N; Y is N or CH; W is H or F; with the proviso that when W is F, then X$^1$, X$^2$ and X$^3$ are N;
R$^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and
R$^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, piperazin-1-yl, 4-methylpiperazin-1-yl, or 4-thiomorpholinyl; for use in the prevention or treatment of a skin lesion in a subject.

Each alkyl moiety either alone or as part of a larger group such as alkoxy is a straight or branched chain and is preferably C$_1$-C$_3$alkyl, more preferably C$_1$-C$_2$alkyl. Examples include in particular methyl, ethyl, n-propyl and prop-2-yl (iso-propyl). Examples of an alkoxy include in particular methoxy, ethoxy, n-propoxy and iso-propoxy. As described herein, alkoxy may include further substituents such as halogen atoms leading to haloalkoxy moieties.

The term "alkoxyalkyl" refers to an R—O—R' moiety in which the R and R' groups are alkyl groups as defined herein. Examples include methoxymethyl, methoxyethyl, ethoxyethyl and methoxypropyl.

Each alkylene moiety is a straight or branched chain and is, particularly for example, —CH$_2$—, —CH$_2$—CH$_2$—, —CH(CH$_3$)—, —CH$_2$—CH$_2$—CH$_2$—, —CH(CH$_3$)—CH$_2$—, or —CH(CH$_2$CH$_3$)—, preferably —CH$_2$—, —CH$_2$—CH$_2$— or —CH(CH$_3$)—.

Each haloalkyl moiety either alone or as part of a larger group such as haloalkoxy is an alkyl group substituted by one or more of the same or different halogen atoms. Haloalkyl moieties include for example 1 to 5 halo substituents, or 1 to 3 halo substituents. Examples include in particular fluoromethyl, difluoromethyl, trifluoromethyl, chlorodifluoromethyl and 2,2,2-trifluoro-ethyl.

Each haloalkenyl moiety either alone or as part of a larger group such as haloalkenyloxy is an alkenyl group substituted by one or more of the same or different halogen atoms. Examples include 2-difluoro-vinyl and 1,2-dichloro-2-fluoro-vinyl. Haloalkenyl moieties include for example 1 to 5 halo substituents, or 1 to 3 halo substituents.

Each cycloalkyl moiety can be in mono- or bi-cyclic form, typically and preferably in mono-cyclic form, and preferably contains 3 to 6 carbon atoms. Preferred examples of mono-cyclic cycloalkyl groups include in particular cyclopropyl, cyclobutyl, cyclopentyl and cyclohexyl.

The term "heterocyclic ring" refers to a saturated or partially unsaturated carbocyclic ring containing one to three heteroatoms selected from nitrogen, oxygen and sulfur as ring members. Such rings do not contain adjacent oxygen atoms, adjacent sulfur atoms, or adjacent oxygen and sulfur atoms within the ring. Preferred examples include in particular tetrahydrofuranyl, pyrrolidinyl, pyrazolidinyl, imidazolidinyl, piperidinyl, piperazinyl, dioxanyl, morpholinyl, oxazolidinyl and isoxazolidinyl.

Where a group is said to be optionally substituted, preferably there are optionally 1-3 substituents, more preferably optionally 1-2 substituents.

Certain compounds of formula (I) may contain one or two or more centers of chirality and such compounds may be provided as pure enantiomers or pure diastereoisomers as well as mixtures thereof in any ratio. The compounds of the invention also include all tautomeric forms of the compounds of formula (I).

In a preferred embodiment, the present invention provides for the compound of formula (I) as defined herein and tautomers, solvates and pharmaceutically acceptable salts thereof, for use in the prevention or treatment of a skin lesion in a subject.

In another preferred embodiment, the present invention provides for the compound of formula (I) for use in the prevention or treatment of a skin lesion in a subject, wherein $X^1$, $X^2$ and $X^3$ are N.

In another preferred embodiment, (i) said $X^1$ and said $X^2$ are N, and said $X^3$ is CH; (ii) said $X^1$ and said $X^3$ are N, and said $X^2$ is CH; or (iii) said $X^2$ and said $X^3$ are N, and said $X^1$ is CH, and preferably tautomers, solvates and pharmaceutically acceptable salts thereof. In another embodiment, (i) said $X^1$ and said $X^2$ are N, and said $X^3$ is CH; or (ii) said $X^2$ and said $X^3$ are N, and said $X^1$ is CH, and preferably tautomers, solvates and pharmaceutically acceptable salts thereof. In another preferred embodiment, said $X^1$ and said $X^3$ are N, and said $X^2$ is CH; and preferably tautomers, solvates and pharmaceutically acceptable salts thereof.

In another preferred embodiment, the present invention provides for the compound of formula (I) for use in the prevention or treatment of a skin lesion in a subject, wherein W is H.

In another preferred embodiment, the present invention provides for the compound of formula (I) for use in the prevention or treatment of a skin lesion in a subject, wherein W is F.

In another preferred embodiment, said Y is N, and preferably tautomers, solvates and pharmaceutically acceptable salts thereof. In another preferred embodiment, said Y is CH, and preferably tautomers, solvates and pharmaceutically acceptable salts thereof.

In another preferred embodiment, said $R^1$ and said $R^2$ are independently of each other selected from

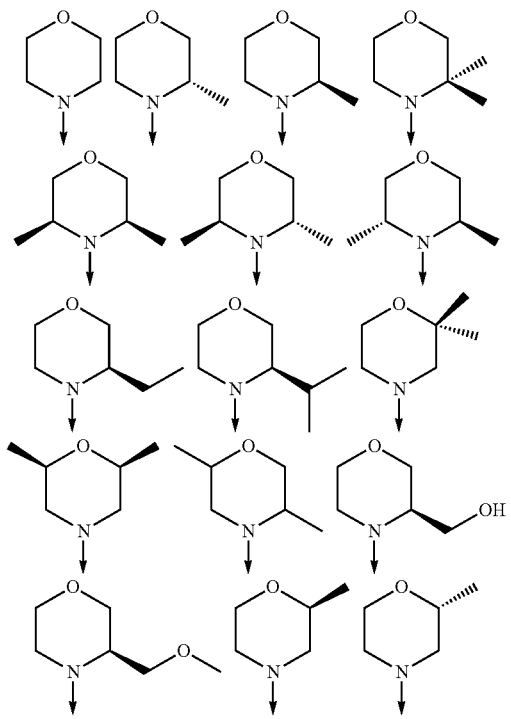

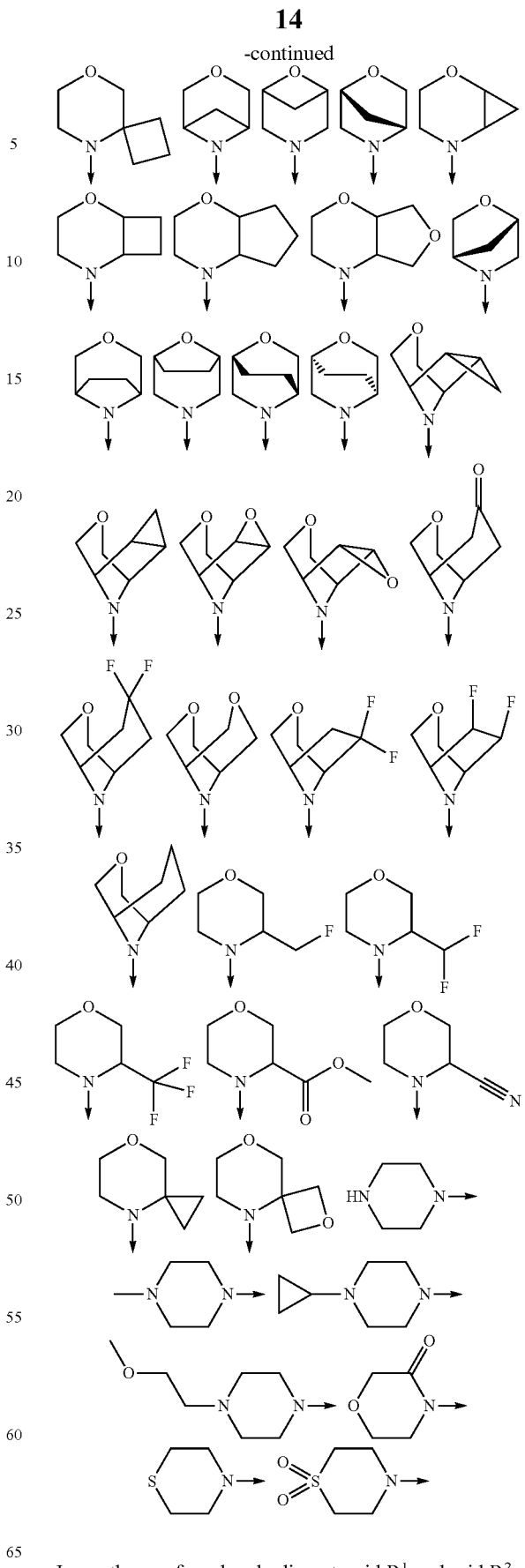

In another preferred embodiment, said $R^1$ and said $R^2$ are independently of each other selected from

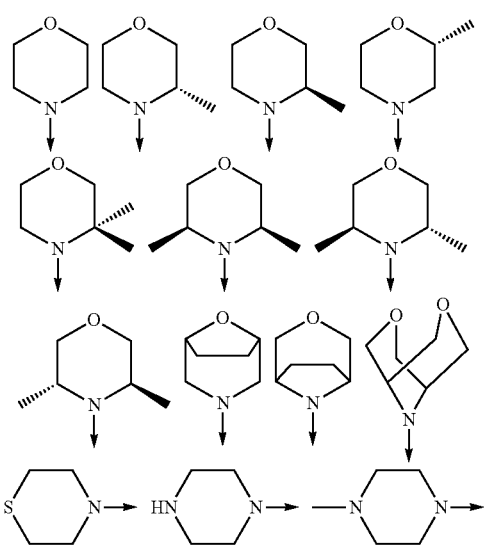

In another preferred embodiment, said R¹ and said R² are independently of each other selected from

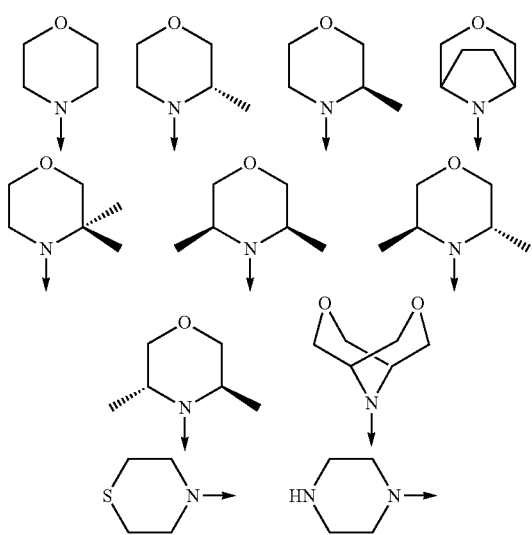

In another preferred embodiment, said compound is selected from
4-(difluoromethyl)-5-(4,6-dimorpholino-1,3,5-triazin-2-yl)pyridin-2-amine;
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyrimidin-2-amine;
5-(4,6-bis((S)-3-methylmorpholino)-1,3,5-triazin-2-yl)-4-(difluoromethyl)pyridin-2-amine;
5-(4,6-bis((S)-3-methylmorpholino)-1,3,5-triazin-2-yl)-4-(difluoromethyl)pyrimidin-2-amine;
(S)-4-(difluoromethyl)-5-(4-(3-methylmorpholino)-6-morpholino-1,3,5-triazin-2-yl)pyridin-2-amine;
(S)-4-(difluoromethyl)-5-(4-(3-methylmorpholino)-6-morpholino-1,3,5-triazin-2-yl)pyrimidin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyridin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine;
4-(difluoromethyl)-5-(4-morpholino-6-(piperazin-1-yl)-1,3,5-triazin-2-yl)pyridin-2-amine;
4-(difluoromethyl)-5-(4-morpholino-6-(piperazin-1-yl)-1,3,5-triazin-2-yl)pyrimidin-2-amine;
(S)-4-(difluoromethyl)-5-(4-(3-methylmorpholino)-6-(piperazin-1-yl)-1,3,5-triazin-2-yl)pyridin-2-amine;
(S)-4-(difluoromethyl)-5-(4-(3-methylmorpholino)-6-(piperazin-1-yl)-1,3,5-triazin-2-yl)pyrimidin-2-amine;
4-(difluoromethyl)-5-(2,6-dimorpholinopyrimidin-4-yl)pyridin-2-amine;
4'-(difluoromethyl)-2,6-dimorpholino-[4,5'-bipyrimidin]-2'-amine;
4-(difluoromethyl)-5-(4,6-dimorpholinopyrimidin-2-yl)pyridin-2-amine;
4'-(difluoromethyl)-4,6-dimorpholino-[2,5'-bipyrimidin]-2'-amine;
4-(difluoromethyl)-5-(4-morpholino-6-thiomorpholino-1,3,5-triazin-2-yl)pyridin-2-amine;
4-(difluoromethyl)-5-(4-morpholino-6-thiomorpholino-1,3,5-triazin-2-yl)pyrimidin-2-amine;
5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
5-(2-(3-oxa-8-azabicyclo[3.2.1]octan-8-yl)-6-morpholinopyrimidin-4-yl)-4-(difluoromethyl)pyridin-2-amine;
2-(3-oxa-8-azabicyclo[3.2.1]octan-8-yl)-4'-(difluoromethyl)-6-morpholino-[4,5'-bipyrimidin]-2'-amine;
5-(2,6-bis((S)-3-methylmorpholino)pyrimidin-4-yl)-4-(difluoromethyl)pyridin-2-amine;
4'-(difluoromethyl)-2,6-bis((S)-3-methylmorpholino)-[4,5'-bipyrimidin]-2'-amine;
(S)-4-(difluoromethyl)-5-(6-(3-methylmorpholino)-2-morpholinopyrimidin-4-yl)pyridin-2-amine;
(S)-4'-(difluoromethyl)-6-(3-methylmorpholino)-2-morpholino-[4,5'-bipyrimidin]-2'-amine;
5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine;
5-[4,6-bis(2,2-dimethylmorpholin-4-yl)-1,3,5-triazin-2-yl]-4-(difluoromethyl)pyridin-2-amine;
(S)-4-(difluoromethyl)-5-(2-(3-methylmorpholino)-6-morpholinopyrimidin-4-yl)pyridin-2-amine;
(S)-4'-(difluoromethyl)-2-(3-methylmorpholino)-6-morpholino-[4,5'-bipyrimidin]-2'-amine;
4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine;
5-[4,6-bis[(2R,6S)-2,6-dimethylmorpholin-4-yl]-1,3,5-triazin-2-yl]-4-(difluoromethyl)pyridin-2-amine;
5-[4,6-bis(3,7-dioxa-9-azabicyclo[3.3.1]nonan-9-yl)-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;
5-[4,6-bis(3,3-dimethylmorpholin-4-yl)-1,3,5-triazin-2-yl]-4-(difluoromethyl)pyridin-2-amine;
5-[4,6-bis[(3R,5S)-3,5-dimethylmorpholin-4-yl]-1,3,5-triazin-2-yl]-4-(difluoromethyl)pyridin-2-amine;

5-[4,6-bis[(3R)-3-methylmorpholin-4-yl]-1,3,5-triazin-2-yl]-4-(difluoromethyl)pyridin-2-amine;

4-(difluoromethyl)-5-[4-(3,3-dimethylmorpholin-4-yl)-6-morpholino-1,3,5-triazin-2-yl]pyridin-2-amine;

4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-(3,3-dimethylmorpholin-4-yl)-6-[(3R)-3-methylmorpholin-4-yl]-1,3,5-triazin-2-yl]pyridin-2-amine;

4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine;

4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine;

4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine;

4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine;

5-[4,6-bis[(3R)-3-ethylmorpholin-4-yl]-1,3,5-triazin-2-yl]-4-(difluoromethyl)pyridin-2-amine;

5-[4,6-bis(8-oxa-5-azaspiro[3.5]nonan-5-yl)-1,3,5-triazin-2-yl]-4-(difluoromethyl)pyridin-2-amine;

5-[4,6-bis[(3R)-3-isopropylmorpholin-4-yl]-1,3,5-triazin-2-yl]-4-(difluoromethyl)pyridin-2-amine 4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine;

4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine;

[(3R)-4-[4-[6-amino-4-(difluoromethyl)-3-pyridyl]-6-(3,3-dimethylmorpholin-4-yl)-1,3,5-triazin-2-yl]morpholin-3-yl]methanol;

4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine;

5-[4-(4-cyclopropylpiperazin-1-yl)-6-(3,3-dimethylmorpholin-4-yl)-1,3,5-triazin-2-yl]-4-(difluoromethyl)pyridin-2-amine;

4-(difluoromethyl)-5-[4-(3,3-dimethylmorpholin-4-yl)-6-[4-(2-methoxyethyl)piperazin-1-yl]-1,3,5-triazin-2-yl]pyridin-2-amine;

[(3R)-4-[4-[6-amino-4-(difluoromethyl)-3-pyridyl]-6-[(3R)-3-methylmorpholin-4-yl]-1,3,5-triazin-2-yl]morpholin-3-yl]methanol;

4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine;

4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-morpholino-6-(3-oxa-9-azabicyclo[3.3.1]nonan-9-yl)-1,3,5-triazin-2-yl]pyridin-2-amine;

4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;

5-[4,6-bis[(3S,5S)-3,5-dimethylmorpholin-4-yl]-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-morpholino-1,3,5-triazin-2-yl]pyridin-2-amine;

4-(difluoromethyl)-5-[4-[(3S)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine;

5-(4,6-dimorpholino-1,3,5-triazin-2-yl)-4-(trifluoromethyl)pyridin-2-amine;

5-(4,6-dimorpholino-1,3,5-triazin-2-yl)-4-(trifluoromethyl)pyrimidin-2-amine;

5-[4,6-bis[(3S)-3-methylmorpholin-4-yl]-1,3,5-triazin-2-yl]-4-(trifluoromethyl)pyridin-2-amine;

5-[4,6-bis[(3S)-3-methylmorpholin-4-yl]-1,3,5-triazin-2-yl]-4-(trifluoromethyl)pyrimidin-2-amine;

5-[4-[(3S)-3-methylmorpholin-4-yl]-6-morpholino-1,3,5-triazin-2-yl]-4-(trifluoromethyl)pyridin-2-amine;

5-[4-[(3S)-3-methylmorpholin-4-yl]-6-morpholino-1,3,5-triazin-2-yl]-4-(trifluoromethyl)pyrimidin-2-amine;

5-(4-morpholino-6-piperazin-1-yl-1,3,5-triazin-2-yl)-4-(trifluoromethyl)pyridin-2-amine;

5-(4-morpholino-6-piperazin-1-yl-1,3,5-triazin-2-yl)-4-(trifluoromethyl)pyrimidin-2-amine;

5-(4-morpholino-6-thiomorpholino-1,3,5-triazin-2-yl)-4-(trifluoromethyl)pyridin-2-amine;

5-(4-morpholino-6-thiomorpholino-1,3,5-triazin-2-yl)-4-(trifluoromethyl)pyrimidin-2-amine;

and tautomers, solvates and pharmaceutically acceptable salts thereof.

In another preferred embodiment, said compound is selected from 4-(difluoromethyl)-5-(4,6-dimorpholino-1,3,5-triazin-2-yl)pyridin-2-amine;

4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyrimidin-2-amine;

5-(4,6-bis((S)-3-methylmorpholino)-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;

(S)-4-(difluoromethyl)-5-(4-(3-methylmorpholino)-6-morpholino-1,3,5-triazin-2-yl)pyridin-2-amine;

(S)-4-(difluoromethyl)-5-(4-(3-methylmorpholino)-6-morpholino-1,3,5-triazin-2-yl)pyrimidin-2-amine;

5-(4-(3-oxa-8-azabicyclo[3.2.1]octan-8-yl)-6-((S)-3-methylmorpholino)-1,3,5-triazin-2-yl)-4-(difluoromethyl)pyridin-2-amine;

5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine;

4-(difluoromethyl)-5-(4-morpholino-6-(piperazin-1-yl)-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

(S)-4-(difluoromethyl)-5-(4-(3-methylmorpholino)-6-(piperazin-1-yl)-1,3,5-triazin-2-yl)pyridin-2-amine;
(S)-4-(difluoromethyl)-5-(4-(3-methylmorpholino)-6-(piperazin-1-yl)-1,3,5-triazin-2-yl)pyrimidin-2-amine;
4-(difluoromethyl)-5-(2,6-dimorpholinopyrimidin-4-yl) pyridin-2-amine;
4'-(difluoromethyl)-2,6-dimorpholino-[4,5'-bipyrimidin]-2'-amine;
4-(difluoromethyl)-5-(4,6-dimorpholinopyrimidin-2-yl) pyridin-2-amine;
4'-(difluoromethyl)-4,6-dimorpholino-[2,5'-bipyrimidin]-2'-amine;
4-(difluoromethyl)-5-(4-morpholino-6-thiomorpholino-1,3,5-triazin-2-yl)pyridin-2-amine;
4-(difluoromethyl)-5-(4-morpholino-6-thiomorpholino-1,3,5-triazin-2-yl)pyrimidin-2-amine;
5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
5-(2-(3-oxa-8-azabicyclo[3.2.1]octan-8-yl)-6-morpholinopyrimidin-4-yl)-4-(difluoromethyl)pyridin-2-amine;
2-(3-oxa-8-azabicyclo[3.2.1]octan-8-yl)-4'-(difluoromethyl)-6-morpholino-[4,5'-bipyrimidin]-2'-amine;
5-(2,6-bis((S)-3-methylmorpholino)pyrimidin-4-yl)-4-(difluoromethyl)pyridin-2-amine;
4'-(difluoromethyl)-2,6-bis((S)-3-methylmorpholino)-[4,5'-bipyrimidin]-2'-amine;
(S)-4-(difluoromethyl)-5-(6-(3-methylmorpholino)-2-morpholinopyrimidin-4-yl)pyridin-2-amine;
(S)-4'-(difluoromethyl)-6-(3-methylmorpholino)-2-morpholino-[4,5'-bipyrimidin]-2'-amine;
5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine;
5-[4,6-bis(2,2-dimethylmorpholin-4-yl)-1,3,5-triazin-2-yl]-4-(difluoromethyl)pyridin-2-amine;
(S)-4-(difluoromethyl)-5-(2-(3-methylmorpholino)-6-morpholinopyrimidin-4-yl)pyridin-2-amine;
(S)-4'-(difluoromethyl)-2-(3-methylmorpholino)-6-morpholino-[4,5'-bipyrimidin]-2'-amine;
4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine;
5-[4,6-bis[(2R,6S)-2,6-dimethylmorpholin-4-yl]-1,3,5-triazin-2-yl]-4-(difluoromethyl)pyridin-2-amine;
5-[4,6-bis(3,7-dioxa-9-azabicyclo[3.3.1]nonan-9-yl)-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;
5-[4,6-bis(3,3-dimethylmorpholin-4-yl)-1,3,5-triazin-2-yl]-4-(difluoromethyl)pyridin-2-amine;
5-[4,6-bis[(3R,5S)-3,5-dimethylmorpholin-4-yl]-1,3,5-triazin-2-yl]-4-(difluoromethyl)pyridin-2-amine;
5-[4,6-bis[(3R)-3-methylmorpholin-4-yl]-1,3,5-triazin-2-yl]-4-(difluoromethyl)pyridin-2-amine;
4-(difluoromethyl)-5-[4-(3,3-dimethylmorpholin-4-yl)-6-morpholino-1,3,5-triazin-2-yl]pyridin-2-amine;
4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;
4-(difluoromethyl)-5-[4-(3,3-dimethylmorpholin-4-yl)-6-[(3R)-3-methylmorpholin-4-yl]-1,3,5-triazin-2-yl]pyridin-2-amine;
4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;
4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;
4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;
5-[4,6-bis[(3S,5S)-3,5-dimethylmorpholin-4-yl]-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-morpholino-1,3,5-triazin-2-yl]pyridin-2-amine;
4-(difluoromethyl)-5-[4-[(3S)-3-ethylmorpholin-4-yl]-6-[(3R)-3-methylmorpholin-4-yl]-1,3,5-triazin-2-yl]pyridin-2-amine;
4-(difluoromethyl)-5-[4-[(3R)-3-ethylmorpholin-4-yl]-6-[(3R)-3-methylmorpholin-4-yl]-1,3,5-triazin-2-yl]pyridin-2-amine;
4-(difluoromethyl)-5-[4-[(3R)-3-methylmorpholin-4-yl]-6-(8-oxa-5-azaspiro[3.5]nonan-5-yl)-1,3,5-triazin-2-yl] pyridin-2-amine;
5-(4,6-dimorpholino-1,3,5-triazin-2-yl)-4-(trifluoromethyl) pyridin-2-amine;
5-(4,6-dimorpholino-1,3,5-triazin-2-yl)-4-(trifluoromethyl) pyrimidin-2-amine;
5-[4,6-bis[(3S)-3-methylmorpholin-4-yl]-1,3,5-triazin-2-yl]-4-(trifluoromethyl)pyridin-2-amine;
5-[4,6-bis[(3S)-3-methylmorpholin-4-yl]-1,3,5-triazin-2-yl]-4-(trifluoromethyl)pyridin-2-amine;
5-[4-[(3S)-3-methylmorpholin-4-yl]-6-morpholino-1,3,5-triazin-2-yl]-4-(trifluoromethyl)pyridin-2-amine;
5-[4-[(3S)-3-methylmorpholin-4-yl]-6-morpholino-1,3,5-triazin-2-yl]-4-(trifluoromethyl)pyridin-2-amine;
5-(4-morpholino-6-piperazin-1-yl-1,3,5-triazin-2-yl)-4-(trifluoromethyl)pyridin-2-amine;
5-(4-morpholino-6-piperazin-1-yl-1,3,5-triazin-2-yl)-4-(trifluoromethyl)pyrimidin-2-amine;
5-(4-morpholino-6-thiomorpholino-1,3,5-triazin-2-yl)-4-(trifluoromethyl)pyridin-2-amine;
5-(4-morpholino-6-thiomorpholino-1,3,5-triazin-2-yl)-4-(trifluoromethyl)pyrimidin-2-amine;
and tautomers, solvates and pharmaceutically acceptable salts thereof.

In another preferred embodiment, said compound is selected from
4-(difluoromethyl)-5-(4,6-dimorpholino-1,3,5-triazin-2-yl) pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4,6-bis((S)-3-methylmorpholino)-1,3,5-triazin-2-yl)-4-(difluoromethyl)pyrimidin-2-amine; (S)-4-(difluoromethyl)-5-(4-(3-methylmorpholino)-6-morpholino-1,3,5-triazin-2-yl)pyridin-2-amine;
4-(difluoromethyl)-5-(4-morpholino-6-(piperazin-1-yl)-1,3,5-triazin-2-yl)pyrimidin-2-amine;
4-(difluoromethyl)-5-(4,6-dimorpholino-1,3,5-triazin-2-yl) pyridin-2-amine; and
(S)-4-(difluoromethyl)-5-(4-(3-methylmorpholino)-6-morpholino-1,3,5-triazin-2-yl)pyrimidin-2-amine;
5-[4,6-bis(3,7-dioxa-9-azabicyclo[3.3.1]nonan-9-yl)-1,3,5-triazin-2-yl]-4-(difluoromethyl)pyrimidin-2-amine;
4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;

5-[4,6-bis(3,3-dimethylmorpholin-4-yl)-1,3,5-triazin-2-yl]-4-(difluoromethyl)pyridin-2-amine;

5-[4,6-bis[(3R,5S)-3,5-dimethylmorpholin-4-yl]-1,3,5-triazin-2-yl]-4-(difluoromethyl)pyridin-2-amine;

5-[4,6-bis[(3R)-3-methylmorpholin-4-yl]-1,3,5-triazin-2-yl]-4-(difluoromethyl)pyridin-2-amine;

4-(difluoromethyl)-5-[4-(3,3-dimethylmorpholin-4-yl)-6-morpholino-1,3,5-triazin-2-yl]pyridin-2-amine;

4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-(3,3-dimethylmorpholin-4-yl)-6-[(3R)-3-methylmorpholin-4-yl]-1,3,5-triazin-2-yl]pyridin-2-amine;

4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;

5-[4,6-bis[(3S,5S)-3,5-dimethylmorpholin-4-yl]-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-morpholino-1,3,5-triazin-2-yl]pyridin-2-amine;

4-(difluoromethyl)-5-[4-[(3S)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine;

5-(4,6-dimorpholino-1,3,5-triazin-2-yl)-4-(trifluoromethyl)pyridin-2-amine;

5-(4,6-dimorpholino-1,3,5-triazin-2-yl)-4-(trifluoromethyl)pyrimidin-2-amine;

5-[4,6-bis[(3S)-3-methylmorpholin-4-yl]-1,3,5-triazin-2-yl]-4-(trifluoromethyl)pyridin-2-amine;

5-[4,6-bis[(3S)-3-methylmorpholin-4-yl]-1,3,5-triazin-2-yl]-4-(trifluoromethyl)pyrimidin-2-amine;

5-[4-[(3S)-3-methylmorpholin-4-yl]-6-morpholino-1,3,5-triazin-2-yl]-4-(trifluoromethyl)pyridin-2-amine;

5-[4-[(3S)-3-methylmorpholin-4-yl]-6-morpholino-1,3,5-triazin-2-yl]-4-(trifluoromethyl)pyrimidin-2-amine;

5-(4-morpholino-6-piperazin-1-yl-1,3,5-triazin-2-yl)-4-(trifluoromethyl)pyridin-2-amine;

5-(4-morpholino-6-piperazin-1-yl-1,3,5-triazin-2-yl)-4-(trifluoromethyl)pyrimidin-2-amine;

5-(4-morpholino-6-thiomorpholino-1,3,5-triazin-2-yl)-4-(trifluoromethyl)pyridin-2-amine;

5-(4-morpholino-6-thiomorpholino-1,3,5-triazin-2-yl)-4-(trifluoromethyl)pyrimidin-2-amine;

and tautomers, solvates and pharmaceutically acceptable salts thereof.

In another preferred embodiment, said compound is selected from 4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine; (S)-4-(difluoromethyl)-5-(4-(3-methylmorpholino)-6-morpholino-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

4-(difluoromethyl)-5-(4,6-dimorpholino-1,3,5-triazin-2-yl)pyridin-2-amine; and (S)-4-(difluoromethyl)-5-(4-(3-methylmorpholino)-6-morpholino-1,3,5-triazin-2-yl)pyrimidin-2-amine;

5-[4,6-bis(3,7-dioxa-9-azabicyclo[3.3.1]nonan-9-yl)-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;

5-[4,6-bis(3,3-dimethylmorpholin-4-yl)-1,3,5-triazin-2-yl]-4-(difluoromethyl)pyridin-2-amine;

5-[4,6-bis[(3R,5S)-3,5-dimethylmorpholin-4-yl]-1,3,5-triazin-2-yl]-4-(difluoromethyl)pyridin-2-amine;

5-[4,6-bis[(3R)-3-methylmorpholin-4-yl]-1,3,5-triazin-2-yl]-4-(difluoromethyl)pyridin-2-amine;

4-(difluoromethyl)-5-[4-(3,3-dimethylmorpholin-4-yl)-6-morpholino-1,3,5-triazin-2-yl]pyridin-2-amine;

4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-(3,3-dimethylmorpholin-4-yl)-6-[(3R)-3-methylmorpholin-4-yl]-1,3,5-triazin-2-yl]pyridin-2-amine;

4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine;

5-[4,6-bis[(3S,5S)-3,5-dimethylmorpholin-4-yl]-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-morpholino-1,3,5-triazin-2-yl]pyridin-2-amine;

4-(difluoromethyl)-5-[4-[(3S)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-ethylmorpholin-4-yl]-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine;

and tautomers, solvates and pharmaceutically acceptable salts thereof.

In another preferred embodiment, said compound is selected from 4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;

(S)-4-(difluoromethyl)-5-(4-(3-methylmorpholino)-6-morpholino-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

4-(difluoromethyl)-5-(4,6-dimorpholino-1,3,5-triazin-2-yl)pyridin-2-amine; and (S)-4-(difluoromethyl)-5-(4-(3-methylmorpholino)-6-morpholino-1,3,5-triazin-2-yl)pyrimidin-2-amine;

5-(4,6-dimorpholino-1,3,5-triazin-2-yl)-4-(trifluoromethyl)pyridin-2-amine;

5-(4,6-dimorpholino-1,3,5-triazin-2-yl)-4-(trifluoromethyl)pyrimidin-2-amine;

5-[4,6-bis[(3S)-3-methylmorpholin-4-yl]-1,3,5-triazin-2-yl]-4-(trifluoromethyl)pyridin-2-amine;

5-[4,6-bis[(3S)-3-methylmorpholin-4-yl]-1,3,5-triazin-2-yl]-4-(trifluoromethyl)pyrimidin-2-amine;

5-[4-[(3S)-3-methylmorpholin-4-yl]-6-morpholino-1,3,5-triazin-2-yl]-4-(trifluoromethyl)pyridin-2-amine;

5-[4-[(3S)-3-methylmorpholin-4-yl]-6-morpholino-1,3,5-triazin-2-yl]-4-(trifluoromethyl)pyrimidin-2-amine;

5-(4-morpholino-6-piperazin-1-yl-1,3,5-triazin-2-yl)-4-(trifluoromethyl)pyridin-2-amine;

5-(4-morpholino-6-piperazin-1-yl-1,3,5-triazin-2-yl)-4-(trifluoromethyl)pyrimidin-2-amine;

5-(4-morpholino-6-thiomorpholino-1,3,5-triazin-2-yl)-4-(trifluoromethyl)pyridin-2-amine;

5-(4-morpholino-6-thiomorpholino-1,3,5-triazin-2-yl)-4-(trifluoromethyl)pyrimidin-2-amine;

and tautomers, solvates and pharmaceutically acceptable salts thereof.

In another preferred embodiment, said compound is selected from 4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;

(S)-4-(difluoromethyl)-5-(4-(3-methylmorpholino)-6-morpholino-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

4-(difluoromethyl)-5-(4,6-dimorpholino-1,3,5-triazin-2-yl)pyridin-2-amine; and (S)-4-(difluoromethyl)-5-(4-(3-methylmorpholino)-6-morpholino-1,3,5-triazin-2-yl)pyrimidin-2-amine;

and tautomers, solvates and pharmaceutically acceptable salts thereof.

In another preferred embodiment, said compound is selected from 4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

(S)-4-(difluoromethyl)-5-(4-(3-methylmorpholino)-6-morpholino-1,3,5-triazin-2-yl)pyridin-2-amine;

5-(4,6-dimorpholino-1,3,5-triazin-2-yl)-4-(trifluoromethyl)pyridin-2-amine;

5-(4,6-dimorpholino-1,3,5-triazin-2-yl)-4-(trifluoromethyl)pyrimidin-2-amine;

5-[4,6-bis[(3S)-3-methylmorpholin-4-yl]-1,3,5-triazin-2-yl]-4-(trifluoromethyl)pyridin-2-amine;

5-[4,6-bis[(3S)-3-methylmorpholin-4-yl]-1,3,5-triazin-2-yl]-4-(trifluoromethyl)pyrimidin-2-amine;

5-[4-[(3S)-3-methylmorpholin-4-yl]-6-morpholino-1,3,5-triazin-2-yl]-4-(trifluoromethyl)pyridin-2-amine;

5-[4-[(3S)-3-methylmorpholin-4-yl]-6-morpholino-1,3,5-triazin-2-yl]-4-(trifluoromethyl)pyrimidin-2-amine;

5-(4-morpholino-6-piperazin-1-yl-1,3,5-triazin-2-yl)-4-(trifluoromethyl)pyridin-2-amine;

5-(4-morpholino-6-piperazin-1-yl-1,3,5-triazin-2-yl)-4-(trifluoromethyl)pyrimidin-2-amine;

5-(4-morpholino-6-thiomorpholino-1,3,5-triazin-2-yl)-4-(trifluoromethyl)pyridin-2-amine;

5-(4-morpholino-6-thiomorpholino-1,3,5-triazin-2-yl)-4-(trifluoromethyl)pyrimidin-2-amine.

and tautomers, solvates and pharmaceutically acceptable salts thereof.

In another very preferred embodiment, said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof.

In another very preferred embodiment, said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

(S)-4-(difluoromethyl)-5-(4-(3-methylmorpholino)-6-morpholino-1,3,5-triazin-2-yl)pyridin-2-amine; and 5-(4,6-dimorpholino-1,3,5-triazin-2-yl)-4-(trifluoromethyl)pyridin-2-amine;

and tautomers, solvates and pharmaceutically acceptable salts thereof.

In another very preferred embodiment, said compound of formula (I) is 4-(difluoromethyl)-5-(4,6-dimorpholino-1,3,5-triazin-2-yl)pyrimidin-2-amine.

In another very preferred embodiment, said compound of formula (I) is 4-(difluoromethyl)-5-(4,6-dimorpholino-1,3,5-triazin-2-yl)pyrimidin-2-amine; and tautomers, solvates and pharmaceutically acceptable salts thereof.

In another very preferred embodiment, said compound of formula (I) is 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine.

In another very preferred embodiment, said compound of formula (I) is 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof.

In another very preferred embodiment, said compound of formula (I) is (S)-4-(difluoromethyl)-5-(4-(3-methylmorpholino)-6-morpholino-1,3,5-triazin-2-yl)pyridin-2-amine.

In another very preferred embodiment, said compound of formula (I) is (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof.

In another very preferred embodiment, said compound of formula (I) is 5-(4,6-dimorpholino-1,3,5-triazin-2-yl)-4-(trifluoromethyl)pyridin-2-amine.

In another very preferred embodiment, said compound of formula (I) is 5-(4,6-dimorpholino-1,3,5-triazin-2-yl)-4-(trifluoromethyl)pyridin-2-amine; and tautomers, solvates and pharmaceutically acceptable salts thereof.

In another preferred embodiment, said $R^1$ and $R^2$ are independently of each other a morpholinyl of formula (II). In one preferred embodiment, said $R^1$ is equal to $R^2$. In another preferred embodiment, said $R^1$ is not equal to $R^2$.

In another preferred embodiment, said W is H, and said $R^1$ and $R^2$ are independently of each other a morpholinyl of formula (II). In one preferred embodiment, said $R^1$ is equal to $R^2$.

In another preferred embodiment, said $R^1$ is not equal to $R^2$.

In another preferred embodiment, said W is F, said $R^1$ and $R^2$ are independently of each other a morpholinyl of formula (II). In one preferred embodiment, said $R^1$ is equal to $R^2$. In another preferred embodiment, said $R^1$ is not equal to $R^2$.

In another preferred embodiment, said $R^1$ and $R^2$ are independently of each other a morpholinyl of formula (II) and said saturated 6-membered heterocyclic ring Z.

In another preferred embodiment, said W is H, and said $R^1$ and $R^2$ are independently of each other a morpholinyl of formula (II) and said saturated 6-membered heterocyclic ring Z.

In another preferred embodiment, said W is F, and said $R^1$ and $R^2$ are independently of each other a morpholinyl of formula (II) and said saturated 6-membered heterocyclic ring Z.

In another preferred embodiment, within said morpholinyl of formula (II)

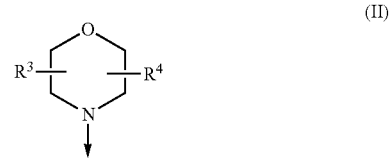

(II)

$R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

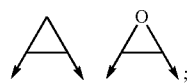

wherein the arrows denote the bonds in formula (II).

In the instance that R3 and R4 together form a bivalent residue and are bound to vicinal carbon atoms annulated morpholinyl substituents are formed. In the instance that R3 and R4 together form a bivalent residue and are spanning across the morpholine ring bridged morpholinyl substituents are formed. In the instance that R3 and R4 together form a bivalent residue and are bound to the same carbon atom of the morpholine, spiro morpholinyl substituents are formed.

In a preferred embodiment, $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

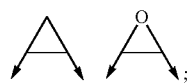

and forming a bridged morpholinyl substituent.

In another preferred embodiment, said $R^1$ and $R^2$ are independently of each other a morpholinyl of formula (II), wherein $R^3$ and $R^4$ form together a bivalent residue leading to a bridged morpholinyl, wherein $R^3$ and $R^4$ form together a bivalent residue —$R^5R^6$— selected from $C_1$-$C_3$alkylene, preferably $C_1$-$C_2$alkylene, —CH$_2$CF$_2$—, —CHFCHF—, —CH$_2$CF$_2$CH$_2$—, —CH$_2$—O—CH$_2$—, —CH$_2$—NH—CH$_2$—, or any of the structures

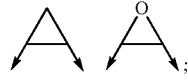

wherein the arrows denote the bonds in formula (II).

In a further preferred embodiment, said morpholinyl of formula (II)

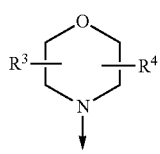

(II)

is independently of each other a morpholinyl of said formula (II), wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

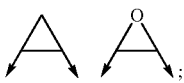

wherein the arrows denote the bonds in formula (II).

In a further preferred embodiment, said morpholinyl of formula (II) is independently of each other a morpholinyl of said formula (II), wherein $R^3$ and $R^4$ are independently of each other H or $CH_3$.

In a further preferred embodiment, said morpholinyl of formula (II) is independently of each other a morpholinyl of said formula (II), wherein $R^3$ and $R^4$ are independently of each other $C_2$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

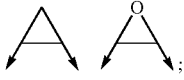

wherein the arrows denote the bonds in formula (II).

In a further preferred embodiment, said morpholinyl of formula (II) is independently of each other selected from

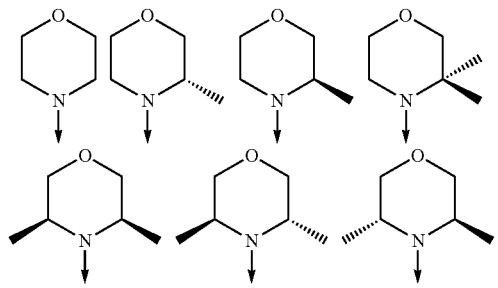

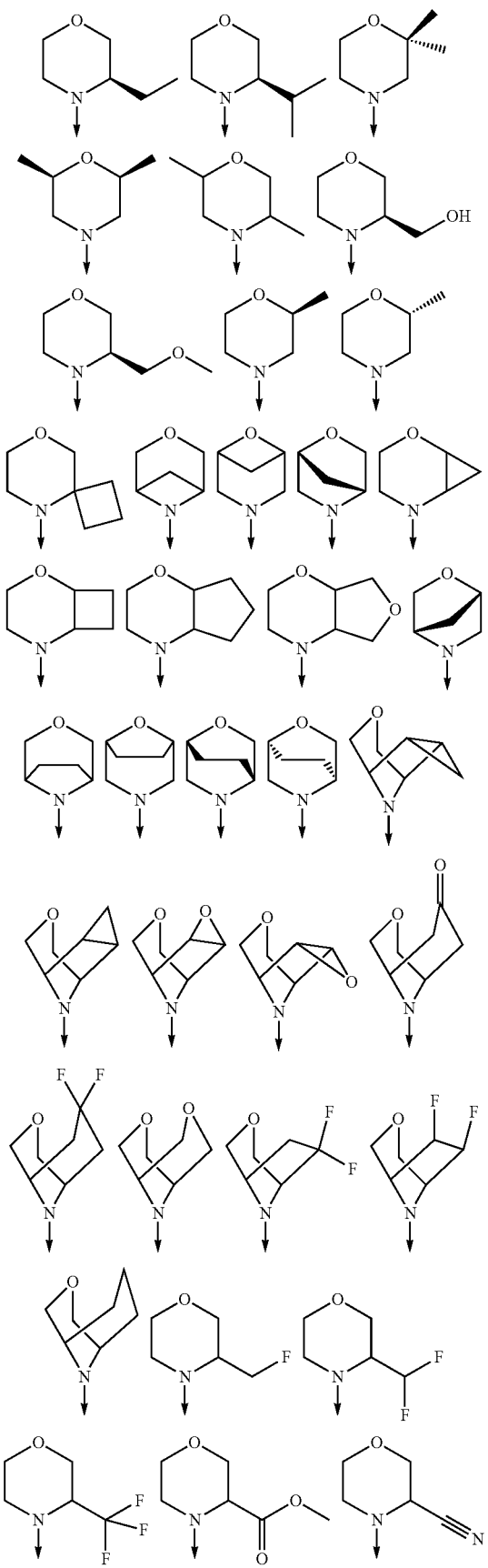

-continued

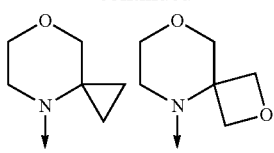

In a further preferred embodiment, said morpholinyl of formula (II) is independently of each other selected from

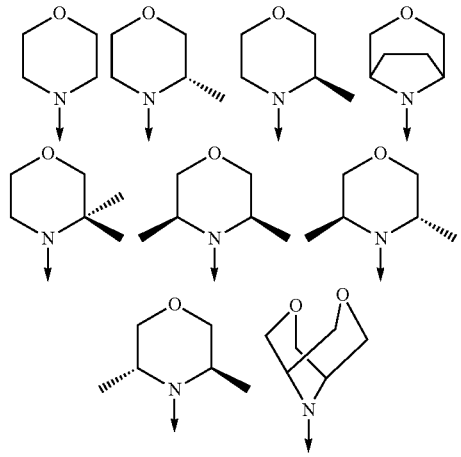

In a further preferred embodiment, said heterocyclic ring Z is a saturated 6-membered heterocyclic ring Z selected from thiomorpholinyl and piperazinyl, optionally substituted by 1 to 3 $R^7$; wherein $R^7$ is independently at each occurrence $C_1$-$C_3$alkyl, $CH_2OH$, $CH_2CH_2OH$, $CH_2F$, $CHF_2$, $CF_3$, $CH_2CF_3$, $C_1$-$C_2$alkoxy$C_1$-$C_3$alkyl, $C_3$-$C_6$cycloalkyl; or two $R^7$ substituents form together a bivalent residue —$R^8R^9$— selected from $C_1$-$C_3$alkylene optionally substituted with 1 to 4 F, —$CH_2$—O—$CH_2$— or —O—$CH_2CH_2$—O—;

In a further preferred embodiment, said heterocyclic ring Z is selected from

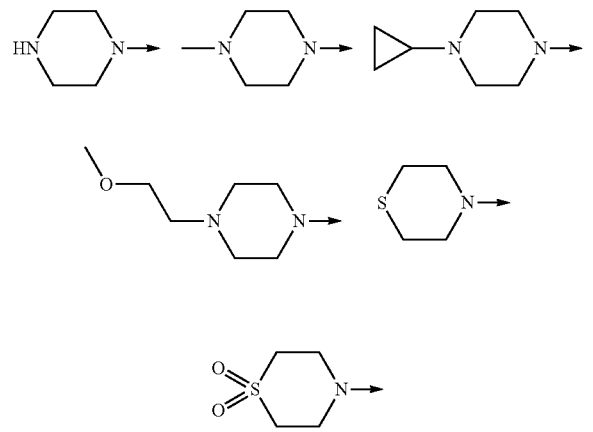

In another preferred embodiment of the present invention, said $R^1$ and said $R^2$ are independently of each other a morpholinyl of formula (II)

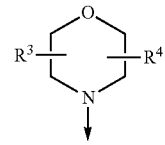

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

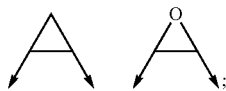

wherein the arrows denote the bonds in formula (II).

In a further preferred embodiment, said $R^1$ is equal to said $R^2$, and said $R^1$ and said $R^2$ are independently of each other a morpholinyl of formula (II)

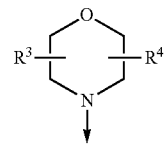

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

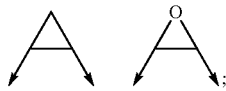

wherein the arrows denote the bonds in formula (II).

In a further preferred embodiment of the present invention, said $R^1$ and said $R^2$ are independently of each other a morpholinyl of formula (II)

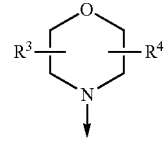

wherein the arrow denotes the bond in formula (I); and wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

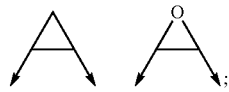
;

wherein the arrows denote the bonds in formula (II).

In a further preferred embodiment of the present invention, $R^1$ is equal to $R^2$, and said $R^1$ and said $R^2$ are a morpholinyl of formula (II)

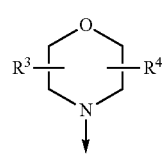
(II)

wherein the arrow denotes the bond in formula (I); and wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

;

wherein the arrows denote the bonds in formula (II).

In another aspect and preferred embodiment, the present invention provides for a compound of (I) for use in the prevention or treatment of a skin lesion in a subject,

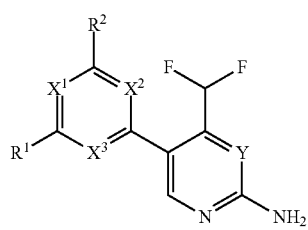
(I)

wherein
$X^1$, $X^2$ and $X^3$ are, independently of each other, N or CH; with the proviso that at least two of $X^1$, $X^2$ and $X^3$ are N; Y is N or CH; and wherein $R^1$ and $R^2$ are independently of each other a morpholinyl of formula (II)

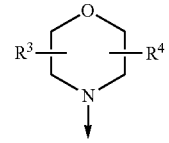
(II)

wherein the arrow denotes the bond in formula (I); and $R^1$ is not equal to $R^2$, and at least one of said $R^1$ and said $R^2$ are a morpholinyl of formula (II),

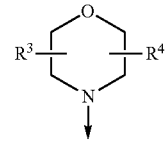
(II)

wherein $R^3$ and $R^4$ are independently of each other $C_2$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

;

wherein the arrows denote the bonds in formula (II).

Preferably, said $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

.

In another preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl.

In another preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$, $X^2$ and $X^3$ are N; and tautomers, solvates and pharmaceutically acceptable salts thereof. Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo [3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo [3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a further preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^3$ are N, and $X^2$ is CH; and tautomers, solvates and pharmaceutically acceptable salts thereof. Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo [3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^2$ are N, and $X^3$ is CH; and tautomers, solvates and pharmaceutically acceptable salts thereof. Preferably, Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo [3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^2$ and $X^3$ are N, and $X^1$ is CH; and tautomers, solvates and pharmaceutically acceptable salts thereof. Preferably, Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo [3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In one embodiment, there is provided a compound of formula (I) according to the invention for use in the prevention or treatment of a skin lesion in a subject, wherein said skin lesion is non-melanoma skin cancer (NMSC), a cutaneous lymphoma or a pre-invasive form thereof.

In a preferred embodiment of the present invention, said skin lesion is a pre-invasive form of non-melanoma skin cancer (NMSC).

In another preferred embodiment of the present invention, said skin lesion is a non-melanoma skin cancer (NMSC).

In another preferred embodiment of the present invention, said skin lesion is a cutaneous lymphoma.

In a further embodiment, there is provided the a compound of formula (I) according to the invention for use in the prevention or treatment of a non-melanoma skin cancer (NMSC) in a subject, wherein said non-melanoma skin cancer is a cutaneous squamous cell carcinoma (cSCC) or a basal cell carcinoma.

In a preferred embodiment, there is provided a compound of formula (I) according to the invention for use in the prevention or treatment of a cutaneous squamous cell carcinoma (cSCC) in a subject.

In a further embodiment, there is provided a compound of formula (I) according to the invention for use in the prevention or treatment of a cutaneous squamous cell carcinoma (cSCC) in a subject, wherein said cutaneous squamous cell carcinoma (cSCC) is an invasive cSCC.

In a further embodiment, there is provided the a compound of formula (I) according to the invention for use in the prevention or treatment of a cutaneous squamous cell carcinoma (cSCC) in a subject, wherein said cutaneous squamous cell carcinoma (cSCC) is a metastatic cSCC.

In one embodiment, there is provided a compound of formula (I) according to the invention for use in the prevention or treatment of a basal cell carcinoma in a subject.

In a further embodiment, there is provided a compound of formula (I) according to the invention for use in the prevention or treatment of a basal cell carcinoma in a subject, wherein said basal cell carcinoma is selected from the group consisting of superficial basal cell carcinoma (also known as "in situ basal cell carcinoma" or "superficial multicentric basal-cell carcinoma"), infiltrative basal cell carcinoma and nodular basal cell carcinoma.

In a preferred embodiment, there is provided a compound of formula (I) according to the invention for use in the prevention or treatment of a basal cell carcinoma in a subject, wherein said basal cell carcinoma is a superficial basal cell carcinoma (also known as "in situ basal cell carcinoma" or "superficial multicentric basal-cell carcinoma").

In a further preferred embodiment, there is provided a compound of formula (I) according to the invention for use in the prevention or treatment of a basal cell carcinoma in a subject, wherein said basal cell carcinoma is an infiltrative basal cell carcinoma.

In a further preferred embodiment, there is provided a compound of formula (I) according to the invention for use in the prevention or treatment of a basal cell carcinoma in a subject, wherein said basal cell carcinoma is a nodular basal cell carcinoma.

In one embodiment, there is provided a compound of formula (I) according to the invention for use in the prevention or treatment of a basal cell carcinoma in a subject, wherein said basal cell carcinoma is selected from the group consisting of cystic basal cell carcinoma, cicatricial basal cell carcinoma (also known as "morpheaform basal cell carcinoma" or "morphoeic basal cell carcinoma"), micronodular basal cell carcinoma, pigmented basal cell carcinoma, rodent ulcer (also known as "Jacob's ulcer"), fibroepithelioma of Pinkus, polypoid basal cell carcinoma, pore-like basal cell carcinoma and aberrant basal cell carcinoma.

In a further embodiment, there is provided a compound of formula (I) according to the invention for use in the prevention or treatment of a pre-invasive form of non-melanoma skin cancer (NMSC) in a subject, wherein said pre-invasive form is selected from the group consisting of cutaneous squamous cell carcinoma in situ (cSCCis, also known as "Bowen's disease"), precancerous actinic keratosis (AK) and chronic UV damage.

In a preferred embodiment, there is provided a compound of formula (I) according to the invention for use in the prevention or treatment of a pre-invasive form of non-melanoma skin cancer (NMSC), wherein said pre-invasive form is cutaneous squamous cell carcinoma in situ (cSCCis, also known as "Bowen's disease").

In a further preferred embodiment, there is provided a compound of formula (I) according to the invention for use in the prevention or treatment of a pre-invasive form of non-melanoma skin cancer (NMSC) in a subject, wherein said pre-invasive form is precancerous actinic keratosis (AK).

In a further preferred embodiment, there is provided a compound of formula (I) according to the invention for use in the prevention or treatment of a pre-invasive form of non-melanoma skin cancer (NMSC) in a subject, wherein said pre-invasive form is chronic UV damage.

In one embodiment, there is provided a compound of formula (I) according to the invention for use in the prevention or treatment of precancerous actinic keratosis (AK) in a subject, wherein said AK is a field cancerization.

In a preferred embodiment, there is provided a compound of formula (I) according to the invention for use in the prevention or treatment of a cutaneous lymphoma in a subject, wherein said cutaneous lymphoma is a cutaneous T-cell lymphoma (CTCL) or a cutaneous B-cell lymphoma (CBCL).

In another preferred embodiment, there is provided a compound of formula (I) according to the invention for use in the prevention or treatment of a cutaneous T-cell lymphoma (CTCL) in a subject.

In another preferred embodiment, there is provided a compound of formula (I) according to the invention for use in the prevention or treatment of a cutaneous lymphoma in a subject, wherein said cutaneous lymphoma is a cutaneous B-cell lymphoma (CBCL).

In one embodiment, there is provided a compound of formula (I) according to the invention for use in the prevention or treatment of a skin lesion in a subject, wherein said compound of formula (I) is administered topically to the subject.

In a further embodiment, there is provided a compound of formula (I) according to the invention for use in the prevention or treatment of a skin lesion in a subject, wherein said skin lesion is a non-melanoma skin cancer (NMSC) or a pre-invasive form thereof and wherein said compound of formula (I) is administered topically to the subject.

In a further embodiment, there is provided a compound of formula (I) according to the invention for use in the prevention or treatment of a non-melanoma skin cancer (NMSC) or a pre-invasive form thereof in a subject, wherein said non-melanoma skin cancer is cutaneous squamous cell carcinoma (cSCC) or a basal cell carcinoma and wherein said compound of formula (I) is administered topically to the subject.

In a further preferred embodiment, there is provided a compound of formula (I) according to the invention for use in the prevention or treatment of a non-melanoma skin cancer (NMSC) or a pre-invasive form thereof in a subject, wherein said pre-invasive form is precancerous actinic keratosis (AK) and wherein said compound of formula (I) is administered topically to the subject.

In one embodiment, there is provided a compound of formula (I) according to the invention for use in the prevention or treatment of a skin lesion in a subject, wherein said compound of formula (I) is administered systemically, preferably orally to the subject.

In a further embodiment, there is provided a compound of formula (I) according to the invention for use in the prevention or treatment of a skin lesion in a subject, wherein said skin lesion is a non-melanoma skin cancer (NMSC) or a pre-invasive form thereof and wherein said compound of formula (I) is administered systemically, preferably orally to the subject.

In a further embodiment, there is provided a compound of formula (I) according to the invention for use in the prevention or treatment of a non-melanoma skin cancer (NMSC) or a pre-invasive form thereof in a subject, wherein said non-melanoma skin cancer is cutaneous squamous cell carcinoma (cSCC) or a basal cell carcinoma and wherein said compound of formula (I) is administered systemically, preferably orally to the subject.

In a further preferred embodiment, there is provided a compound of formula (I) according to the invention for use in the prevention or treatment of a non-melanoma skin cancer (NMSC) or a pre-invasive form thereof in a subject, wherein said pre-invasive form is precancerous actinic keratosis (AK) and wherein said compound of formula (I) is administered systemically, preferably orally to the subject.

In a preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine;
5-(4,6-dimorpholino-1,3,5-triazin-2-yl)-4-(trifluoromethyl)pyridin-2-amine; and tautomers, solvates and pharmaceutically acceptable salts thereof,
for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof,
for use in the prevention or treatment of a skin lesion in a subject, wherein the skin lesion is cSCC, cSCCis, BCC, CTCL, CBCL or AK, preferably cSCC, cSCCis or AK.

In a further preferred embodiment, there is provided a compound of formula (I) according to the invention, wherein said compound is 5-(4,6-dimorpholino-1,3,5-triazin-2-yl)-4-(trifluoromethyl)pyridin-2-amine; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a further preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine;
5-(4,6-dimorpholino-1,3,5-triazin-2-yl)-4-(trifluoromethyl)pyridin-2-amine;
and tautomers, solvates and pharmaceutically acceptable salts thereof,
for use in the prevention or treatment of cSCC in a subject.

In a further preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof,
for use in the prevention or treatment of cSCC in a subject.

In a further preferred embodiment, there is provided a compound of formula (I) according to the invention, wherein said compound is 5-(4,6-dimorpholino-1,3,5-triazin-2-yl)-4-(trifluoromethyl)pyridin-2-amine; and tautomers, solvates and pharmaceutically acceptable salts thereof, for use in the prevention or treatment of cSCC in a subject.

In a preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine;
5-(4,6-dimorpholino-1,3,5-triazin-2-yl)-4-(trifluoromethyl)pyridin-2-amine;
and tautomers, solvates and pharmaceutically acceptable salts thereof,
for use in the prevention or treatment of cSCCis in a subject.

In a preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof,
for use in the prevention or treatment of cSCCis in a subject.

In a further preferred embodiment, there is provided a compound of formula (I) according to the invention, wherein said compound is 5-(4,6-dimorpholino-1,3,5-triazin-2-yl)-4-(trifluoromethyl)pyridin-2-amine; and tautomers, solvates and pharmaceutically acceptable salts thereof, for use in the prevention or treatment of cSCCis in a subject.

In a preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine;
5-(4,6-dimorpholino-1,3,5-triazin-2-yl)-4-(trifluoromethyl)pyridin-2-amine;
and tautomers, solvates and pharmaceutically acceptable salts thereof,
for use in the prevention or treatment of AK in a subject.

In a preferred embodiment, there is provided a compound of formula (I) according to the invention, wherein said compound is selected from:
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
(S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof,
for use in the prevention or treatment of AK in a subject.

In a further preferred embodiment, there is provided a compound of formula (I) according to the invention, wherein said compound is 5-(4,6-dimorpholino-1,3,5-triazin-2-yl)-4-(trifluoromethyl)pyridin-2-amine; and tautomers, solvates and pharmaceutically acceptable salts thereof, for use in the prevention or treatment of AK in a subject.

In a preferred embodiment, there is provided a compound of formula (I) according to the invention, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of cSCC in a subject.

In a preferred embodiment, there is provided a compound of formula (I) according to the invention, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of cSCCis in a subject.

In a preferred embodiment, there is provided a compound of formula (I) according to the invention, wherein said compound is selected from 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of AK in a subject.

In a preferred embodiment, there is provided the compound 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a particularly preferred embodiment, there is provided the compound 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof, for use in the prevention or treatment of cSCC in a subject.

In a further particularly preferred embodiment, there is provided the compound 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof, for use in the prevention or treatment of cSCCis in a subject.

In a further particularly preferred embodiment, there is provided the compound 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof, for use in the prevention or treatment of AK in a subject.

In a preferred embodiment, there is provided the compound (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a particularly preferred embodiment, there is provided the compound (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of cSCC in a subject.

In a further particularly preferred embodiment, there is provided the compound (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of cSCCis in a subject.

In a further particularly preferred embodiment, there is provided the compound (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof, for use in the prevention or treatment of AK in a subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein W is H, and wherein R1 and R2 are independently of each other a morpholinyl of formula (II); and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein W is H, and wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein W is F, and wherein R1 and R2 are independently of each other a morpholinyl of formula (II); and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein W is F, and wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in the prevention or treatment of cSCC in a subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in the prevention or treatment of cSCCis in a subject.

In a preferred embodiment, there is provided a compound of formula (I) according to the invention, wherein R1 and R2 are independently of each other a morpholinyl of formula (II); and tautomers, solvates and pharmaceutically acceptable salts thereof, for use in the prevention or treatment of AK in a subject.

In a preferred embodiment, there is provided a compound of formula (I) according to the invention, wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCC in a subject.

In a preferred embodiment, there is provided a compound of formula (I) according to the invention, wherein W is H, and wherein R1 and R2 are independently of each other a morpholinyl of formula (II); and tautomers, solvates and pharmaceutically acceptable salts thereof, for use in the prevention or treatment of cSCC in a subject.

In a preferred embodiment, there is provided a compound of formula (I) according to the invention, wherein W is H, and wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCC in a subject.

In a preferred embodiment, there is provided a compound of formula (I) according to the invention, wherein W is F, and wherein R1 and R2 are independently of each other a morpholinyl of formula (II); and tautomers, solvates and pharmaceutically acceptable salts thereof, for use in the prevention or treatment of cSCC in a subject.

In a preferred embodiment, there is provided a compound of formula (I) according to the invention, wherein W is F, and wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCC in a subject.

In a preferred embodiment, there is provided a compound of formula (I) according to the invention, wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCCis in a subject.

In a preferred embodiment, there is provided a compound of formula (I) according to the invention, wherein W is H, and wherein R1 and R2 are independently of each other a morpholinyl of formula (II); and tautomers, solvates and pharmaceutically acceptable salts thereof, for use in the prevention or treatment of cSCCis in a subject.

In a preferred embodiment, there is provided a compound of formula (I) according to the invention, wherein W is H, and wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCCis in a subject.

In a preferred embodiment, there is provided a compound of formula (I) according to the invention, wherein W is F, and wherein R1 and R2 are independently of each other a morpholinyl of formula (II); and tautomers, solvates and pharmaceutically acceptable salts thereof, for use in the prevention or treatment of cSCCis in a subject.

In a preferred embodiment, there is provided a compound of formula (I) according to the invention, wherein W is F, and wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCCis in a subject.

In a preferred embodiment, there is provided a compound of formula (I) according to the invention, wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCC or cSCCis in a subject.

In a preferred embodiment, there is provided a compound of formula (I) according to the invention, wherein W is H, and wherein R1 and R2 are independently of each other a morpholinyl of formula (II); and tautomers, solvates and pharmaceutically acceptable salts thereof, for use in the prevention or treatment of cSCC or cSCCis in a subject.

In a preferred embodiment, there is provided a compound of formula (I) according to the invention, wherein W is H, and wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCC or cSCCis in a subject.

In a preferred embodiment, there is provided a compound of formula (I) according to the invention, wherein W is F, and wherein R1 and R2 are independently of each other a morpholinyl of formula (II); and tautomers, solvates and pharmaceutically acceptable salts thereof, for use in the prevention or treatment of cSCC or cSCCis in a subject.

In a preferred embodiment, there is provided a compound of formula (I) according to the invention, wherein W is F, and wherein said $R^1$ and $R^2$ are independently of each other a morpholinyl of formula (II) and said saturated 6-membered heterocyclic ring Z; and tautomers, solvates and pharmaceutically acceptable salts thereof, for use in the prevention or treatment of cSCC or cSCCis in a subject.

In a preferred embodiment, there is provided a compound of formula (I) according to the invention, wherein R1 is equal to R2; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein R1 is equal to R2; and tautomers, solvates and pharmaceutically acceptable salts thereof, for use in the prevention or treatment of cSCC in a subject.

In a preferred embodiment, there is provided a compound of formula (I) according to the invention, wherein R1 is equal to R2; and tautomers, solvates and pharmaceutically acceptable salts thereof, for use in the prevention or treatment of cSCCis in a subject.

In a preferred embodiment, there is provided a compound of formula (I) according to the invention, wherein R1 is equal to R2; and tautomers, solvates and pharmaceutically acceptable salts thereof, for use in the prevention or treatment of AK in a subject.

In a preferred embodiment, there is provided a compound of formula (I) according to the invention, wherein R1 is not equal to R2; and tautomers, solvates and pharmaceutically acceptable salts thereof, for use in the prevention or treatment of a skin lesion in a subject, wherein the skin lesion is cSCC, cSCCis, BCC, CTCL, CBCL or AK, preferably cSCC, cSCCis or AK.

In a preferred embodiment, there is provided a compound of formula (I) according to the invention, wherein R1 is not equal to R2; and tautomers, solvates and pharmaceutically acceptable salts thereof, for use in the prevention or treatment of cSCC in a subject.

In a preferred embodiment, there is provided a compound of formula (I) according to the invention, wherein R1 is not equal to R2; and tautomers, solvates and pharmaceutically acceptable salts thereof, for use in the prevention or treatment of cSCCis in a subject.

In a preferred embodiment, there is provided a compound of formula (I) according to the invention, wherein R1 is not equal to R2; and tautomers, solvates and pharmaceutically acceptable salts thereof, for use in the prevention or treatment of AK in a subject.

In a further aspect of the invention, there is provided a method for treating or preventing a skin lesion in a subject, comprising administering an effective amount of a compound of formula (I) according to the invention to said subject.

In one embodiment, there is provided a method for treating or preventing a skin lesion in a subject, comprising administering an effective amount of a compound of formula (I) according to the invention to said subject, wherein said skin lesion is selected from the group consisting of a cutaneous lymphoma, a cutaneous squamous cell carcinoma (cSCC), a basal cell carcinoma, a cutaneous squamous cell carcinoma in situ (cSCCis, Bowen's disease) and precancerous actinic keratosis (AK).

In a particularly preferred embodiment, there is provided a method for treating or preventing a skin lesion in a subject, comprising administering an effective amount of a compound of formula (I) according to the invention to said subject, wherein said compound is selected from: 4-(difluoromethyl)-5-(4,6-dimorpholino-1,3,5-triazin-2-yl)pyrimidin-2-amine; 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof; and wherein the skin lesion is cSCC, cSCCis, BCC, CTCL, CBCL or AK, preferably cSCC, cSCCis or AK.

In yet a further aspect of the invention, there is provided the use of a compound of formula (I) according to the invention for treating or preventing a skin lesion in a subject.

In one embodiment, there is provided the use of a compound of formula (I) according to the invention for treating or preventing a skin lesion in a subject, wherein said skin lesion is selected from the group consisting of a cutaneous lymphoma, a cutaneous squamous cell carcinoma (cSCC), a basal cell carcinoma, a cutaneous squamous cell carcinoma in situ (cSCCis, Bowen's disease) and precancerous actinic keratosis (AK).

In a particularly preferred embodiment, there is provided the use of a compound of formula (I) according to the invention for treating or preventing a skin lesion in a subject, wherein said compound is selected from:

4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

(S)-4-(difluoromethyl)-5-(4-(3-methylmorpholino)-6-morpholino-1,3,5-triazin-2-yl)pyridin-2-amine;

5-(4,6-dimorpholino-1,3,5-triazin-2-yl)-4-(trifluoromethyl)pyridin-2-amine;

and tautomers, solvates and pharmaceutically acceptable salts thereof; and wherein the skin lesion is cSCC, cSCCis, BCC, CTCL, CBCL or AK, preferably cSCC, cSCCis or AK.

In yet a further aspect of the invention, there is provided the use of a compound of formula (I) according to the invention for the manufacture of a medicament for treating or preventing a skin lesion in a subject.

In one embodiment, there is provided the use of a compound of formula (I) according to the invention for the manufacture of a medicament for treating or preventing a skin lesion in a subject, wherein said skin lesion is selected from the group consisting of a cutaneous lymphoma, a cutaneous squamous cell carcinoma (cSCC), a basal cell carcinoma, a cutaneous squamous cell carcinoma in situ (cSCCis, Bowen's disease) and precancerous actinic keratosis (AK).

In a particularly preferred embodiment, there is provided the use of a compound of formula (I) according to the invention for the manufacture of a medicament for treating or preventing a skin lesion in a subject, wherein said compound is selected from:

4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

(S)-4-(difluoromethyl)-5-(4-(3-methylmorpholino)-6-morpholino-1,3,5-triazin-2-yl)pyridin-2-amine;

5-(4,6-dimorpholino-1,3,5-triazin-2-yl)-4-(trifluoromethyl)pyridin-2-amine;

and tautomers, solvates and pharmaceutically acceptable salts thereof; and wherein the skin lesion is cSCC, cSCCis, BCC, CTCL, CBCL or AK, preferably cSCC, cSCCis or AK.

Most preferred for the present invention are the following compounds shown by formula: (The names of the corresponding structures were produced using ChemDraw Ultra, version 13.0.1 as well as lower and upper software versions thereof, CambridgeSoft Corp., Cambridge MA).

Compound 1

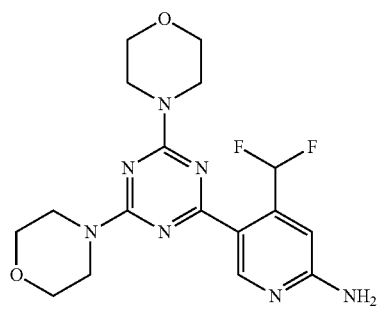

4-(difluoromethyl)-5-(4,6-dimorpholino-1,3,5-triazin-2-yl)pyridin-2-amine

Compound 1*

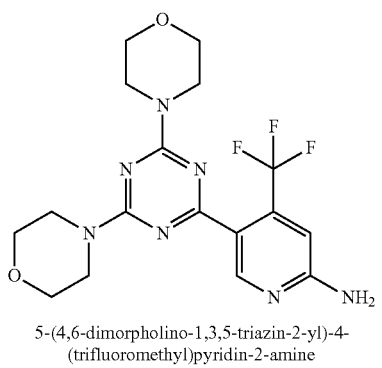

5-(4,6-dimorpholino-1,3,5-triazin-2-yl)-4-(trifluoromethyl)pyridin-2-amine

Compound 2

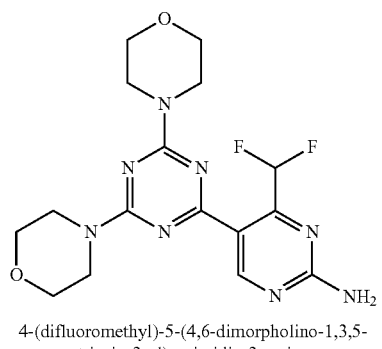

4-(difluoromethyl)-5-(4,6-dimorpholino-1,3,5-triazin-2-yl)pyrimidin-2-amine

Compound 2*

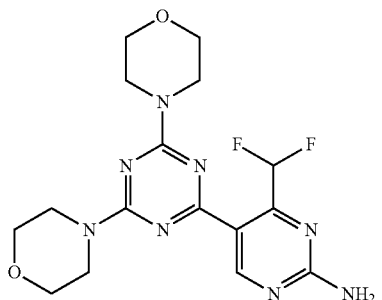

5-(4,6-dimorpholino-1,3,5-triazin-2-yl)-4-(trifluoromethyl)pyrimidin-2-amine

Compound 3

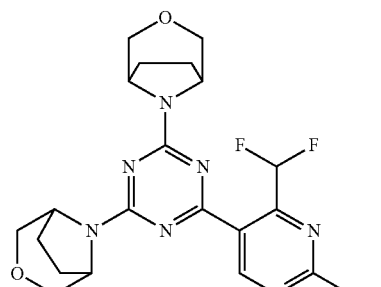

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine Compound 4

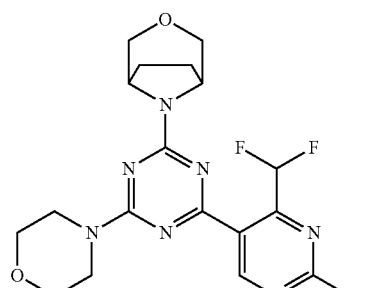

5-(4-(3-oxa-8-azabicyclo[3.2.1]octan-8-yl)-6-morpholino-1,3,5-triazin-2-yl)-4-(difluoromethyl)pyridin-2-amine Compound 5

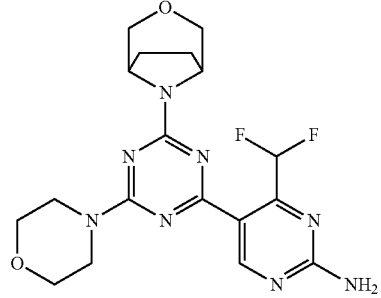

5-(4-(3-oxa-8-azabicyclo[3.2.1]octan-8-yl)-6-morpholino-1,3,5-triazin-2-yl)-4-(difluoromethyl)pyrimidin-2-amine Compound 6

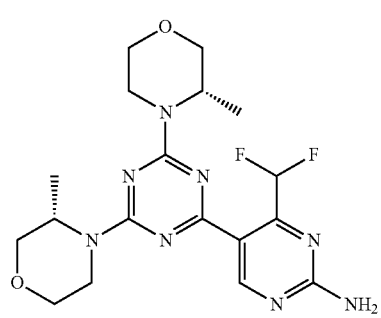

5-(4,6-bis((S)-3-methylmorpholino)-1,3,5-triazin-2-yl)-4-(difluoromethyl)pyridin-2-amine Compound 6*

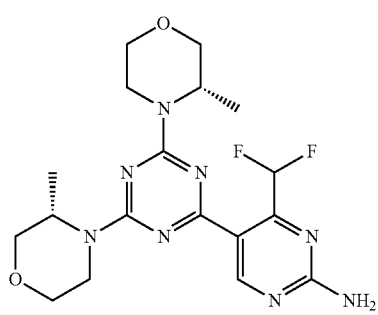

5-[4,6-bis[(3S)-3-methylmorpholin-4-yl]-1,3,5-triazin-2-yl]-4-(trifluormethyl)pyridin-2-amine Compound 7

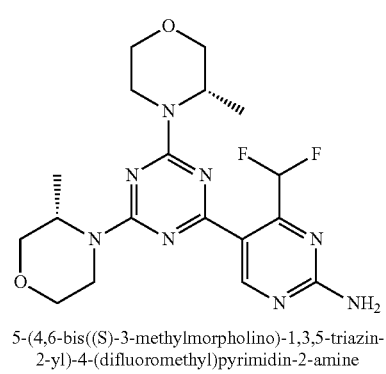

5-(4,6-bis((S)-3-methylmorpholino)-1,3,5-triazin-2-yl)-4-(difluoromethyl)pyrimidin-2-amine Compound 7*

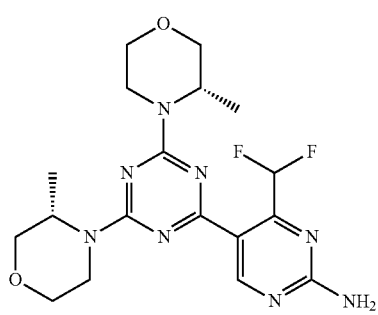

5-[4,6-bis[(3S)-3-methylmorpholin-4-yl]-1,3,5-triazin-2-yl]-4-(trifluormethyl)pyrimidin-2-amine Compound 8

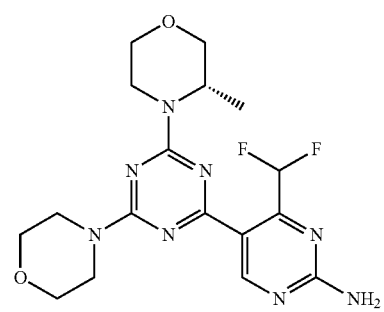

(S)-4-(difluoromethyl)-5-(4-(3-methylmorpholino)-6-morpholino-1,3,5-triazin-2-yl)pyridin-2-amine Compound 8*

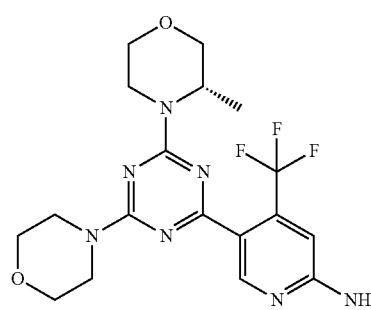

5-[4-[(3S)-3-methylmorpholin-4-yl]-6-morpholino-1,3,5-triazin-2-yl]-4-(trifluoromethyl)pyridin-2-amine Compound 9

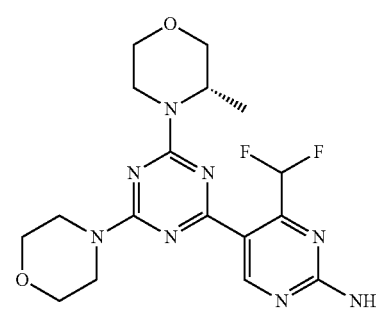

(S)-4-(difluoromethyl)-5-(4-(3-methylmorpholino)-6-morpholino-1,3,5-triazin-2-yl)pyrimidin-2-amine Compound 9*

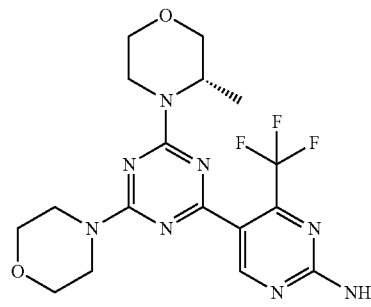

5-[4-[(3S)-3-methylmorpholin-4-yl]-6-morpholino-1,3,5-triazin-2-yl]-4-(trifluoromethyl)pyrimidin-2-amine Compound 10

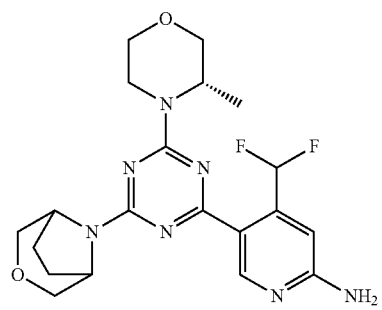

5-(4-(3-oxa-8-azabicyclo[3.2.1]octan-8-yl)-6-((S)-3-methylmorpholino)-1,3,5-triazin-2-yl)-4-(difluoromethyl)pyridin-2-amine Compound 11

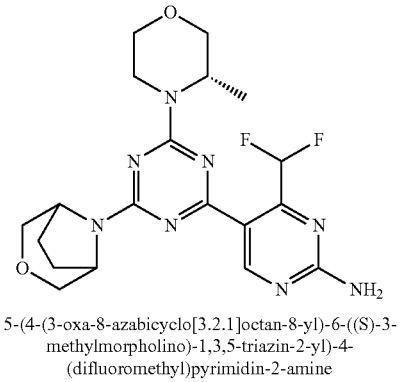

5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine Compound 12

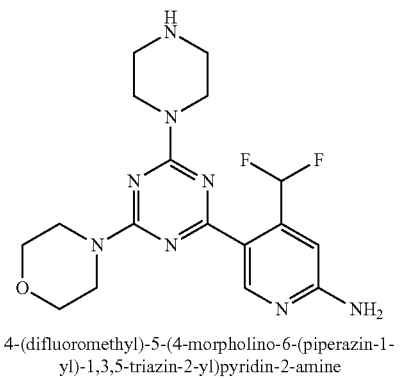

4-(difluoromethyl)-5-(4-morpholino-6-(piperazin-1-yl)-1,3,5-triazin-2-yl)pyridin-2-amine Compound 12*

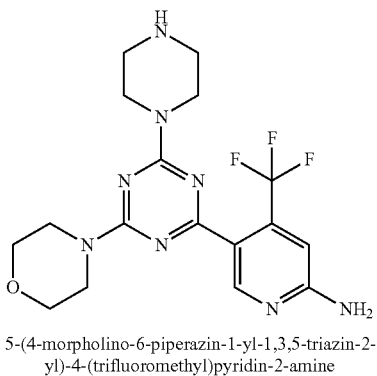

5-(4-morpholino-6-piperazin-1-yl-1,3,5-triazin-2-yl)-4-(trifluoromethyl)pyridin-2-amine Compound 13

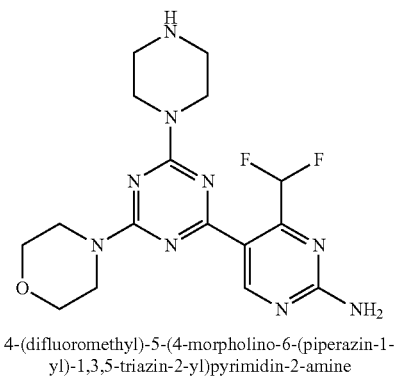

4-(difluoromethyl)-5-(4-morpholino-6-(piperazin-1-yl)-1,3,5-triazin-2-yl)pyrimidin-2-amine Compound 13*

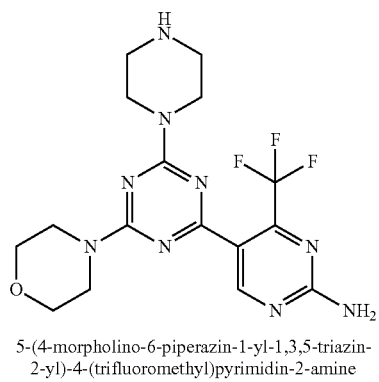

5-(4-morpholino-6-piperazin-1-yl-1,3,5-triazin-2-yl)-4-(trifluoromethyl)pyrimidin-2-amine Compound 14

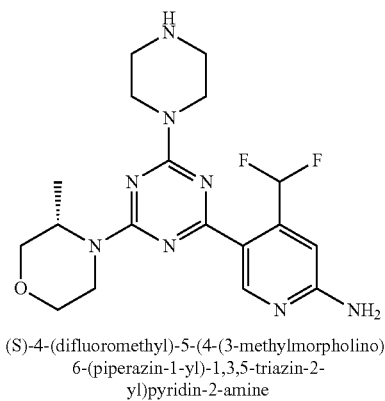

(S)-4-(difluoromethyl)-5-(4-(3-methylmorpholino)-6-(piperazin-1-yl)-1,3,5-triazin-2-yl)pyridin-2-amine Compound 15

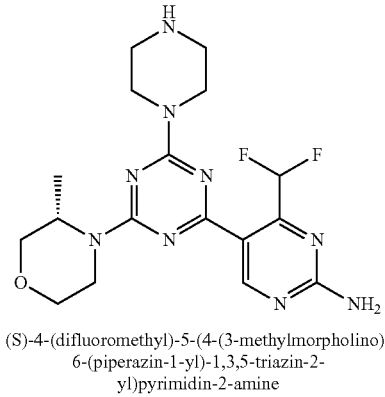

(S)-4-(difluoromethyl)-5-(4-(3-methylmorpholino)-6-(piperazin-1-yl)-1,3,5-triazin-2-yl)pyrimidin-2-amine Compound 16

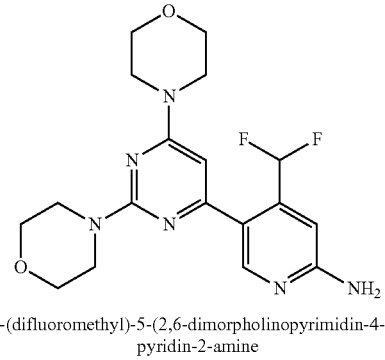

4-(difluoromethyl)-5-(2,6-dimorpholinopyrimidin-4-yl)pyridin-2-amine

Compound 17

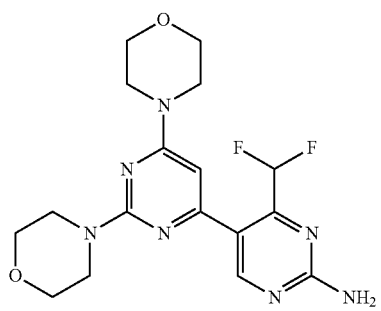

4'-(difluoromethyl)-2,6-dimorpholino-[4,5'-bipyrimidin]-2'-amine

Compound 18

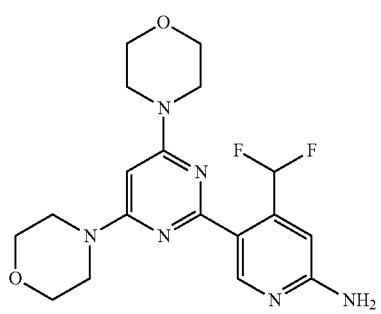

4-(difluoromethyl)-5-(4,6-dimorpholinopyrimidin-2-yl)pyridin-2-amine

Compound 19

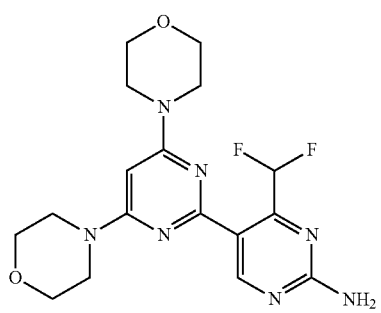

4'-(difluoromethyl)-4,6-dimorpholino-[2,5'-bipyrimidin]-2'-amine

Compound 20

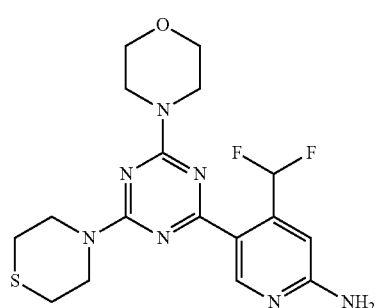

4-(difluoromethyl(-5-(4-morpholino-6-thiomorpholino-1,3,5-triazin-2-yl)pyridin-2-amine Compound 20*

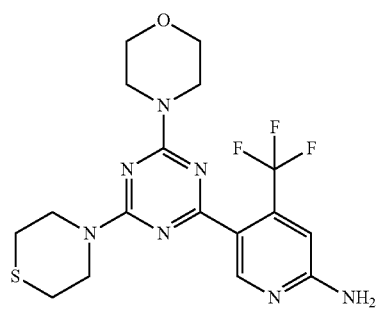

5-(4-morpholino-6-thiomorpholino-1,3,5-triazin-2-yl)-4-(trifluoromethyl)pyridin-2-amine Compound 21

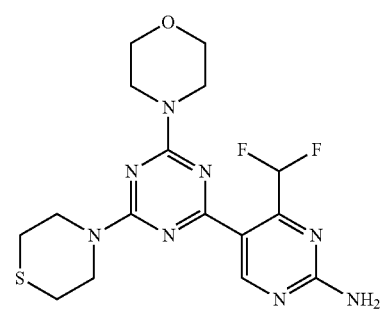

4-(difluoromethyl)-5-(4-morpholino-6-thiomorpholino-1,3,5-triazin-2-yl)pyrimidin-2-amine Further preferred are the following compounds Compound 21*

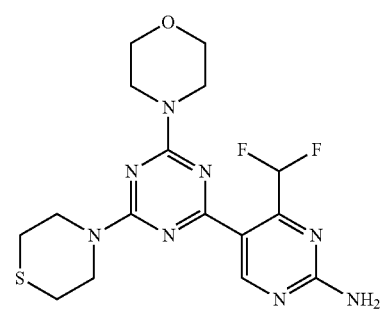

5-(4-morpholino-6-thiomorpholino-1,3,5-triazin-2-yl)-4-(trifluoromethyl)pyrimidin-2-amine Compound 22

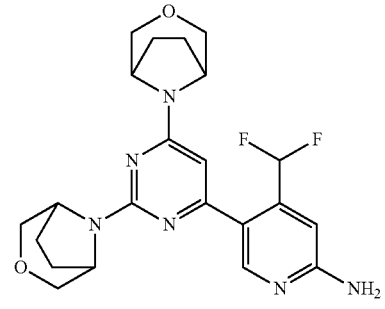

5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine Compound 23

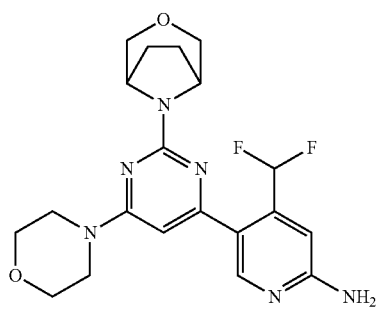

5-(2-(3-oxa-8-azabicyclo[3.2.1]octan-8-yl)-6-morpholinopyrimidin-4-yl)-4-(difluoromethyl)pyridin-2-amine Compound 24

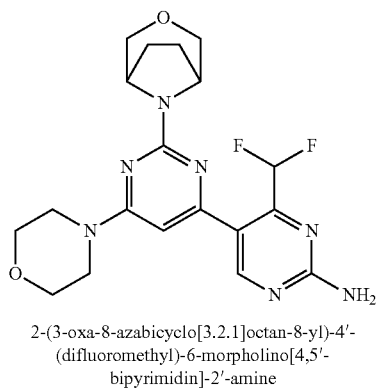

2-(3-oxa-8-azabicyclo[3.2.1]octan-8-yl)-4'-(difluoromethyl)-6-morpholino[4,5'-bipyrimidin]-2'-amine Compound 25

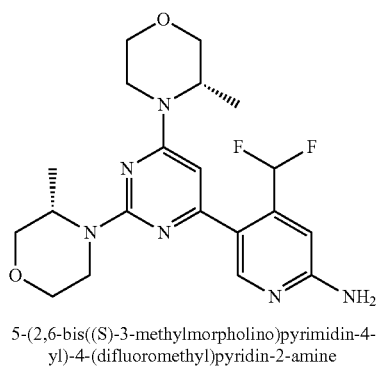

5-(2,6-bis((S)-3-methylmorpholino)pyrimidin-4-yl)-4-(difluoromethyl)pyridin-2-amine Compound 26

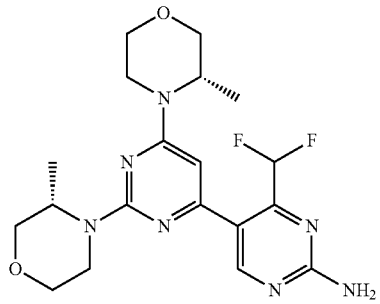

4'-(difluoromethyl)-2,6-bis((S)-3-methylmorpholino)-[4,5'-bipyrimidin]-2'-amine

Compound 27

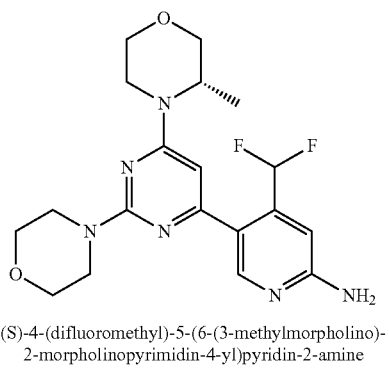

(S)-4-(difluoromethyl)-5-(6-(3-methylmorpholino)-2-morpholinopyrimidin-4-yl)pyridin-2-amine Compound 28

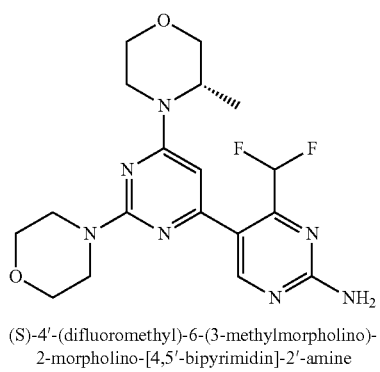

(S)-4'-(difluoromethyl)-6-(3-methylmorpholino)-2-morpholino-[4,5'-bipyrimidin]-2'-amine Compound 29

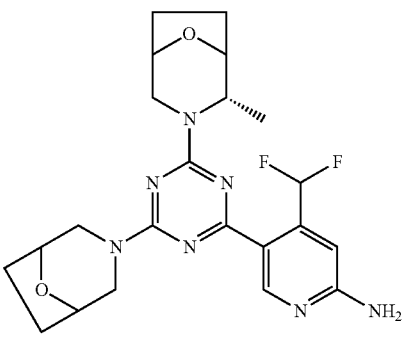

5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine Compound 30

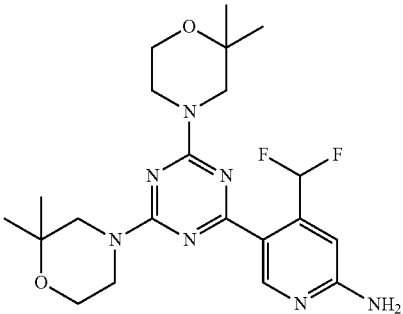

5-[4,6-bis(2,2-dimethylmorpholin-4-yl)-1,3,5-triazin-2-yl]-4-(difluoromethyl)pyridin-2-amine Compound 31

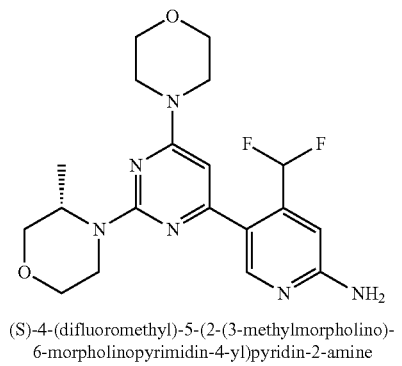

(S)-4-(difluoromethyl)-5-(2-(3-methylmorpholino)-
6-morpholinopyrimidin-4-yl)pyridin-2-amine Compound 32

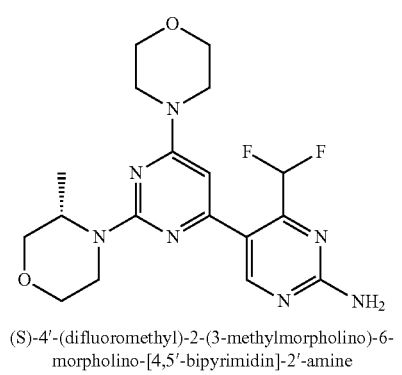

(S)-4'-(difluoromethyl)-2-(3-methylmorpholino)-6-
morpholino-[4,5'-bipyrimidin]-2'-amine Compound 33

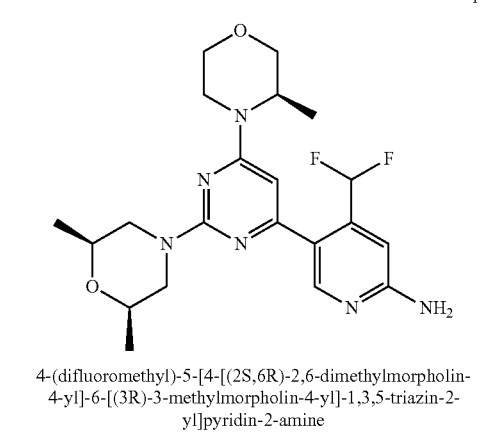

4-(difluoromethyl)-5-[4-[(2S,6R)-2,6-dimethylmorpholin-
4-yl]-6-[(3R)-3-methylmorpholin-4-yl]-1,3,5-triazin-2-
yl]pyridin-2-amine Compound 34

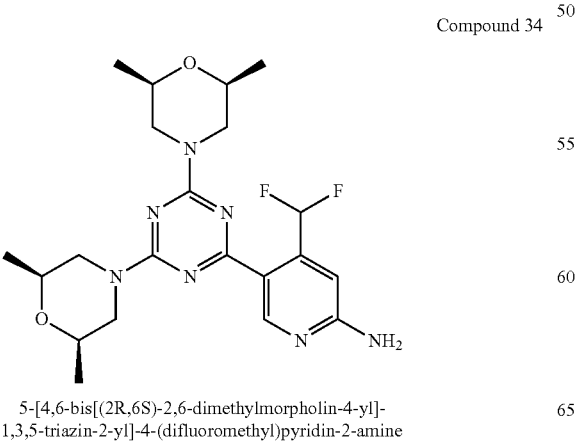

5-[4,6-bis[(2R,6S)-2,6-dimethylmorpholin-4-yl]-
1,3,5-triazin-2-yl]-4-(difluoromethyl)pyridin-2-amine Compound 37

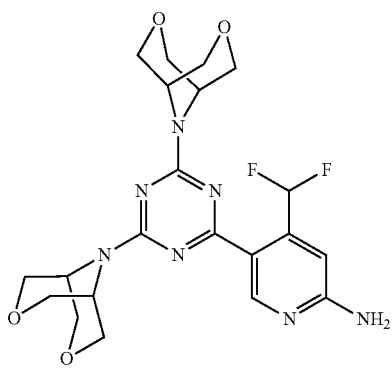

5-[4,6-bis(3,7-dioxa-9-azabicyclo[3.3.1]nonan-9-yl)-
1,3,5-triazin-2-yl]-4-(difluoromethyl)pyridin-2-amine Compound 38

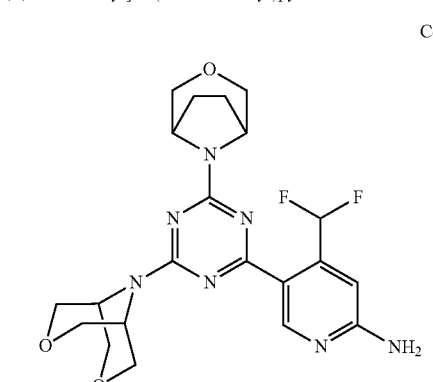

4-(difluoromethyl)-5-[4-(3,7-dioxa-9-azabicyclo[3.3.1]nonan-
9-yl)-6-(3-oxa-8-azabicyclo[3.2.1]octan-8-yl)-
1,3,5-triazin-2-yl]pyridin-2-amine Compound 39

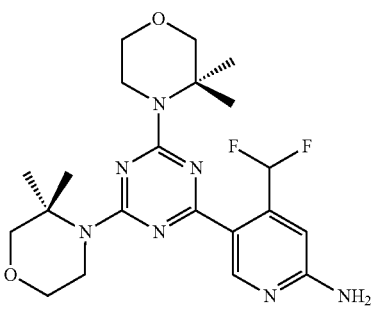

5-[4,6-bis(3,3-dimethylmorpholin-4-yl)-1,3,5-
triazin-2-yl]-4-(difluoromethyl)pyridin-2-amine Compound 40

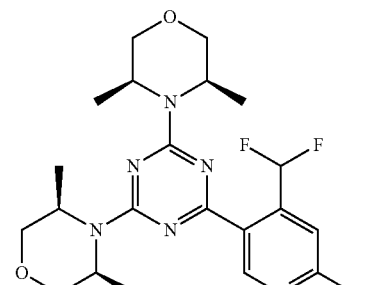

5-[4,6-bis[(3R,5S)-3,5-dimethylmorpholin-4-yl]-
1,3,5-triazin-2-yl]-4-(difluoromethyl)pyridin-2-amine Compound 41

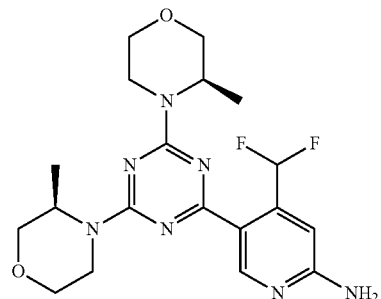

5-[4,6-bis[(3R)-3-methylmorpholin-4-yl]-1,3,5-triazin-2-yl]-
4-(difluoromethyl)pyridin-2-amine Compound 42

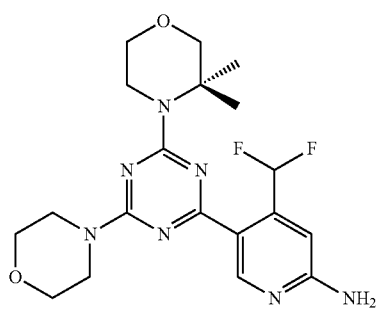

4-(difluoromethyl)-5-[4-(3,3-dimethylmorpholin-
4-yl)-6-morpholino-1,3,5-triazin-2-yl]pyridin-2-amine Compound 44

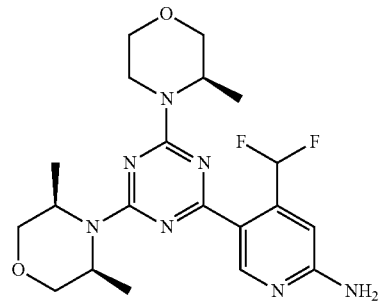

4-(difluoromethyl)-5-[4-[(3R,5S)-3,5-dimethylmorpholin-
4-yl]-6-[(3R)-3-methylmorpholin-4-yl]-
1,3,5-triazin-2-yl]pyridin-2-amine Compound 45

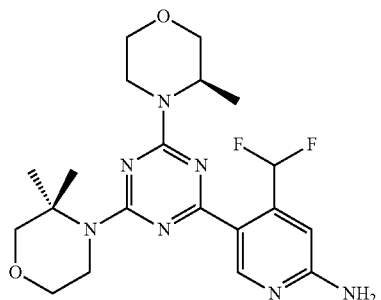

4-(difluoromethyl)-5-[4-(3,3-dimethylmorpholin-
4-yl)-6-[(3R)-3-methylmorpholin-4-yl]-1,3,5-
triazin-2-yl]pyridin-2-amine Compound 46

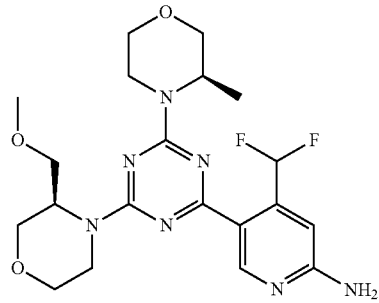

4-(difluoromethyl)-5-[4-[(3R)-3-(methoxymethyl)
morpholin-4-yl]-6-[(3R)-3-methylmorpholin-4-yl]-
1,3,5-triazin-2-yl]pyridin-2-amine Compound 47

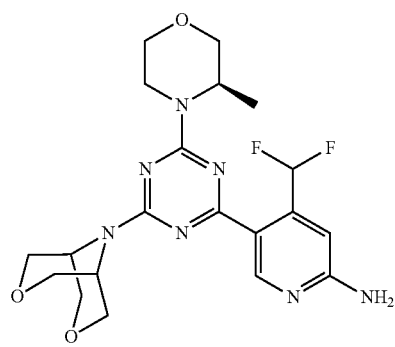

4-(difluoromethyl)-5-[4-(3,7-dioxa-9-azabicyclo
[3.3.1]nonan-9-yl)-6-[(3R)-3-
methylmorpholin-4-yl]-1,3,5-triazin-2-yl]pyridin-2-amine Compound 50

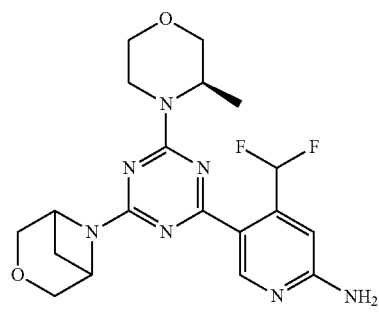

4-(difluoromethyl)-5-[4-[(3R)-3-methylmorpholin-
4-yl]-6-(3-oxa-6-azabicyclo[3.1.1]heptan-
6-yl)-1,3,5-triazin-2-yl]pyridin-2-amine Compound 51

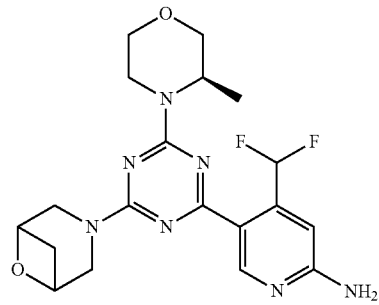

4-(difluoromethyl)-5-[4-[(3R)-3-methylmorpholino-
4-yl]-6-(6-oxa-3-azabicyclo[3.1.1]heptan-3-yl)-
1,3,5-triazin-2-yl]pyridin-2-amine -continued Compound 52

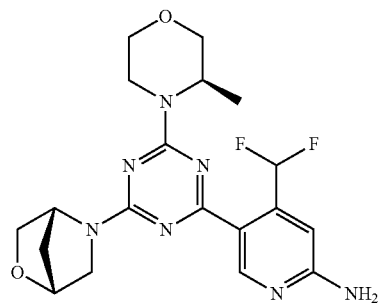

4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine Compound 53

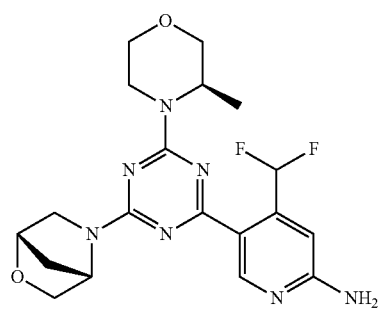

4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine Compound 54

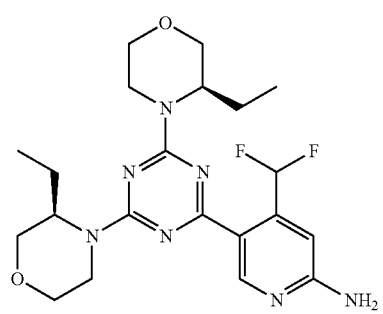

5-[4,6-bis[(3R)-3-ethylmorpholin-4-yl]-1,3,5-triazin-2-yl]-4-(difluoromethyl)pyridin-2-amine Compound 55

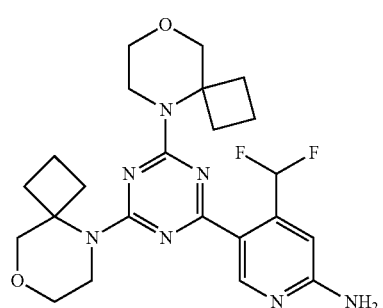

5-[4,6-bis(8-oxa-5-azaspiro[3.5]nonan-5-yl)-1,3,5-triazin-2-yl]-4-(difluoromethyl)pyridin-2-amine Compound 56

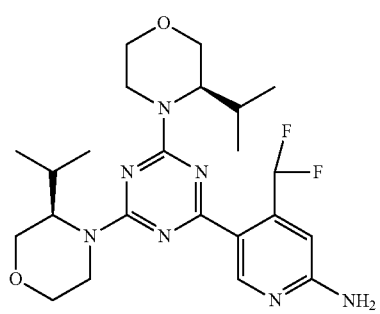

5-[4,6-bis[(3R)-3-isopropylmorpholin-4-yl]-1,3,5-triazin-2-yl]-4-(difluoromethyl)pyridin-2-amine Compound 66

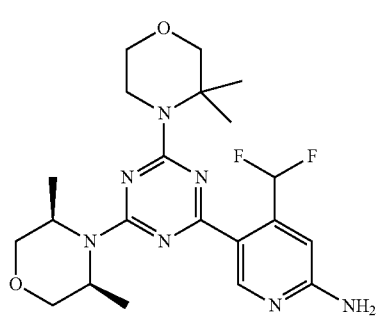

4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine Compound 67

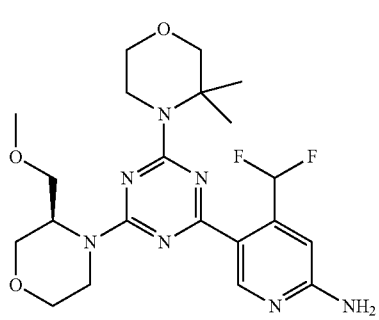

4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine Compound 68

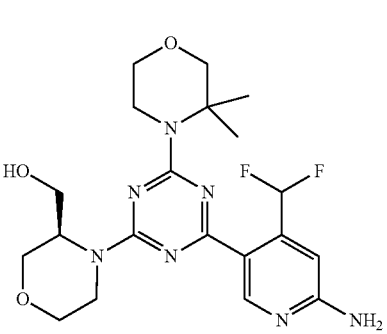

[(3R)-4-[4-[6-amino-4-(difluoromethyl)-3-pyridyl]-6-(3,3-dimethylmorpholin-4-yl)-1,3,5-triazin-2-yl]morpholin-3-yl]methanol -continued Compound 69

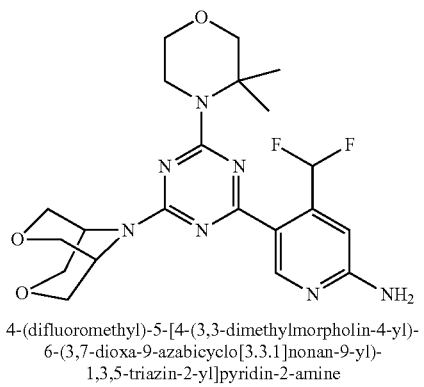

4-(difluoromethyl)-5-[4-(3,3-dimethylmorpholin-4-yl)-
6-(3,7-dioxa-9-azabicyclo[3.3.1]nonan-9-yl)-
1,3,5-triazin-2-yl]pyridin-2-amine Compound 70

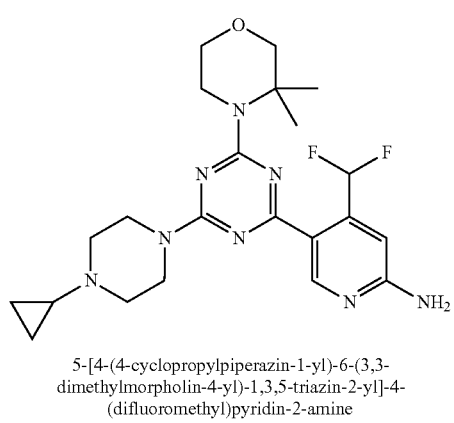

5-[4-(4-cyclopropylpiperazin-1-yl)-6-(3,3-
dimethylmorpholin-4-yl)-1,3,5-triazin-2-yl]-4-
(difluoromethyl)pyridin-2-amine Compound 71

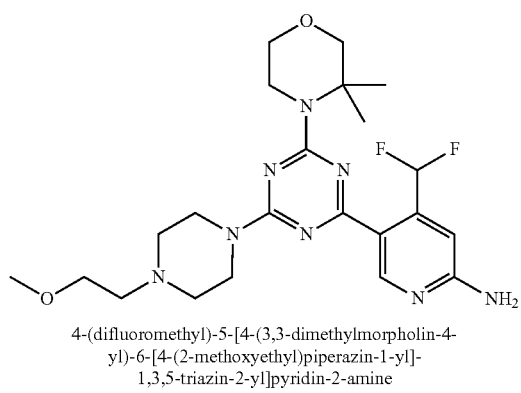

4-(difluoromethyl)-5-[4-(3,3-dimethylmorpholin-4-
yl)-6-[4-(2-methoxyethyl)piperazin-1-yl]-
1,3,5-triazin-2-yl]pyridin-2-amine Compound 77

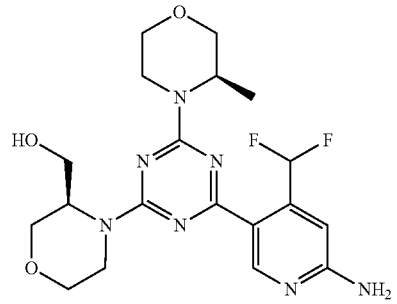

[(3R)-4-[4-[6-amino-4-(difluoromethyl)-3-pyridyl]-6-
[(3R)-3-methylmorpholin-4-yl]-1,3,5-triazin-
2-yl]morpholin-3-yl]methanol -continued Compound 78

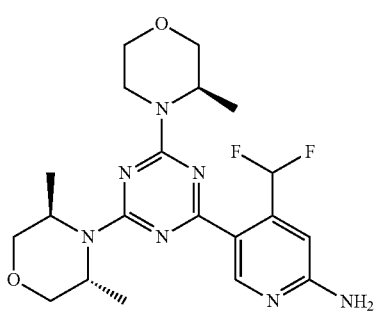

4-(difluoromethyl)-5-[4-[(3R,5R)-3,5-
dimethylmorpholin-4-yl]-6-[(3R)-3-
methylmorpholin-4-yl]-1,3,5-triazin-2-yl]pyridin-2-amine Compound 79

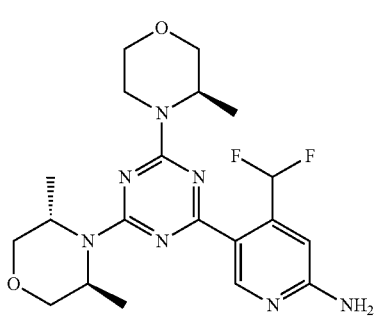

4-(difluoromethyl)-5-[4-[(3S,5S)-3,5-
dimethylmorpholin-4-yl]-6-[(3R)-3-
methylmorpholin-4-yl]-1,3,5-triazin-2-yl]pyridin-2-amine Compound 80

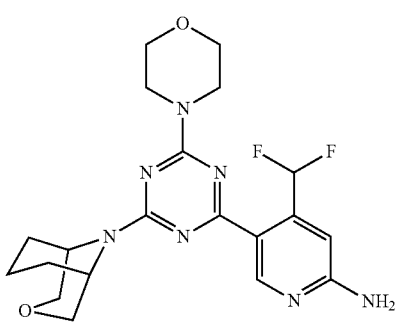

4-(difluoromethyl)-5-[4-morpholino-6-(3-oxa-9-
azabicyclo[3.3.1]nonan-9-yl)-1,3,5-triazin-2-
yl]pyridin-2-amine Compound 82

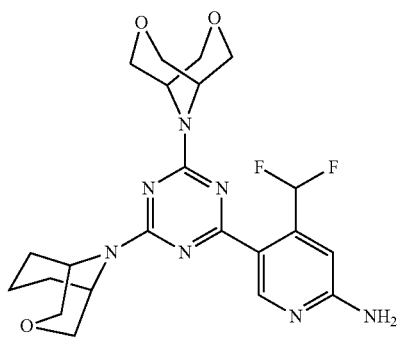

4-(difluoromethyl)-5-[4-(3,7-dioxa-9-azabicyclo[3.3.1]
nonan-9-yl)-6-(3-oxa-9-azabicyclo[3.3.1]nonan-9-yl)-
1,3,5-triazin-2-yl]pyridin-2-amine Compound 83

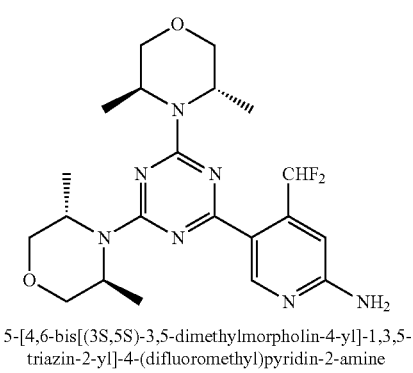

5-[4,6-bis[(3S,5S)-3,5-dimethylmorpholin-4-yl]-1,3,5-
triazin-2-yl]-4-(difluoromethyl)pyridin-2-amine Compound 84

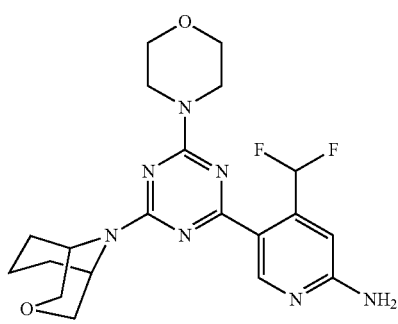

4-(difluoromethyl)-5-[4-(3,7-dioxa-9-azabicyclo[3.3.1]
nonan-9-yl)-6-morpholino-1,3,5-triazin-2-yl]
pyridin-2-amine Compound 85

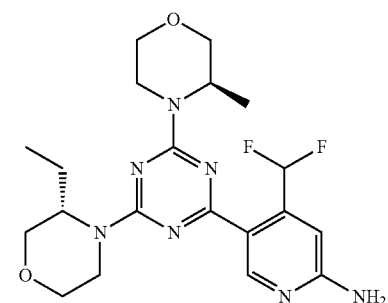

4-(difluoromethyl)-5-[4-[(3S)-3-ethylmorpholin-
4-yl]-6-[(3R)-3-methylmorpholin-4-yl]-
1,3,5-triazin-2-yl]pyridin-2-amine Compound 86

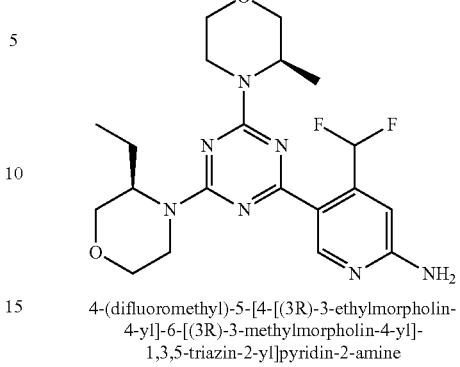

4-(difluoromethyl)-5-[4-[(3R)-3-ethylmorpholin-
4-yl]-6-[(3R)-3-methylmorpholin-4-yl]-
1,3,5-triazin-2-yl]pyridin-2-amine Compound 88

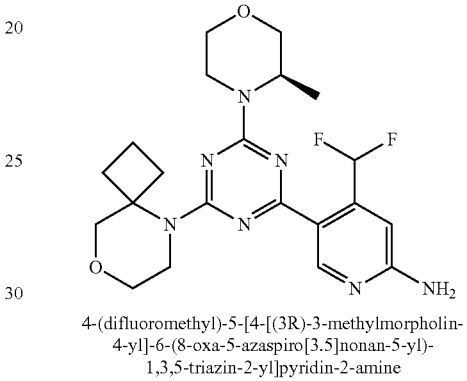

4-(difluoromethyl)-5-[4-[(3R)-3-methylmorpholin-
4-yl]-6-(8-oxa-5-azaspiro[3.5]nonan-5-yl)-
1,3,5-triazin-2-yl]pyridin-2-amine Preparation of Compounds of the Invention The compounds of the invention may be synthesized by synthetic routes that include processes analogous to those well known in the chemical arts, particularly in light of the description contained herein. The starting materials are generally available from commercial sources or are readily prepared using methods well known to those skilled in the art.

In preparing compounds of the invention, protection of remote functionality (e.g., primary or secondary amine) of intermediates may be necessary. The need for such protection will vary depending on the nature of the remote functionality and the conditions of the preparation methods. Suitable amino-protecting groups include tert-butyloxycarbonyl (BOC), bis-tert-butyloxycarbonyl or dimethylaminomethylenyl. The need for such protection is readily determined by one skilled in the art. For a general description of protecting groups and their use, see T. W. Greene, *Protective Groups in Organic Synthesis*, John Wiley & Sons, New York, 1991.

Methods of Separation

In the methods of preparing the compounds of this invention, it may be advantageous to separate reaction products from one another and/or from starting materials. The desired products of each step or series of steps are separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; high, medium and low pressure liquid chromatography methods and apparatus; small scale analytical; and preparative thin or thick layer chromatography, as well as techniques of small scale thin layer and flash chromatography.

Selection of appropriate methods of separation depends on the nature of the materials involved, for example, presence or absence of polar functional groups in chromatography, stability of materials in acidic and basic media in multiphase extraction, and the like. One skilled in the art will apply techniques most likely to achieve the desired separation.

EXAMPLES

The Examples are intended to illustrate the present invention without restricting it.

The chemical reactions described in the Examples may be readily adapted to prepare a number of other lipid kinase inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

As a rule, $^1$H NMR and mass spectra have been obtained for the compounds prepared. In the Examples described below, unless otherwise indicated, all temperatures are set forth in degrees Celsius (° C.). Reagents were purchased from commercial suppliers such as Sigma Aldrich, Fluorochem, Acros, Lancaster, TCI or Maybridge, and were used without further purification unless otherwise indicated. The reactions set forth below were done generally under a positive pressure of nitrogen or with a drying tube (unless otherwise stated) in anhydrous solvents, and the reaction flasks were typically fitted with rubber septa for the introduction of substrates and reagents via syringe. Glassware was oven dried. Column chromatography was performed using Merck silica gel. $^1$H NMR spectra were recorded on a Bruker instrument operating at 400 MHz. $^1$H NMR spectra were obtained for solutions in various deuterated solvents such as CDCl$_3$, (CD$_3$)$_2$SO, CD$_3$OD or (CD$_3$)$_2$CO. The chemical shift δ values were reported in ppm and corrected to the signal of the deuterated solvents (7.26 ppm for CDCl$_3$) or TMS (0 ppm). $^{19}$F NMR spectra were calibrated relative to CFCl$_3$ (δ=0 ppm) as external standard. $^{19}$F NMR spectra were recorded $^1$H-decoupled. When peak multiplicities are reported, the following abbreviations are used: s (singlet), d (doublet), t (triplet), m (multiplet), quint (quintet), br (broadened). Coupling constants, when given, are reported in Hertz (Hz). MALDI-ToF Mass spectra (MS) have been obtained on a Voyager-De™ Pro measured in m/z.

The following abbreviations are used hereinafter: BSA (bovine serum albumin), DMSO (dimethyl sulfoxide), ESI (electronspray ionization), HCl (hydrochloric acid), M (molar), MALDI (Matrix-assisted Laser Desorption/Ionization), MS (mass spectrometry), PBS (phosphate buffered saline), TLC (thin layer chromatography), nd (not determined).

Example 1

Preparation of Intermediate Compounds and of Compounds of the Invention

Preparation of Intermediate Compounds

The following methods were used to prepare the intermediates compounds used to produce compounds of formula (I).

Method 1: 8-(4-(3-oxa-8-azabicyclo[3.2.1]octan-8-yl)-6-chloro-1,3,5-triazin-2-yl)-3-oxa-8-azabicyclo[3.2.1]octane (i1)

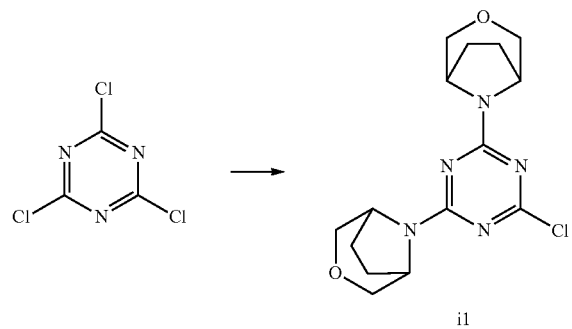 [SMILES: Clc1nc(Cl)nc(Cl)n1 ; Clc1nc(N2C3CCC2COC3)nc(N2C3CCC2COC3)n1]

3-Oxa-8-azabicyclo[3.2.1]octane-HCl (Advanced ChemBlocks Inc, product number A-861, 2.00 g, 13.4 mmol, 2.0 eq.) and N,N-diisopropylethylamine (4.80 mL, 27.6 mmol, 4.1 eq.) are charged into a flask and dissolved in dichloromethane (20 mL). The flask is placed in an ice bath and the solution subsequently cooled down to 0° C. This solution is then added dropwise to a solution of cyanuric chloride in dichloromethane (20 mL) at 0° C. The resulting reaction mixture is stirred overnight, while it is allowed to warm up to room temperature. Additional dichloromethane (100 mL) is added and the organic layer is washed with a saturated aqueous solution of sodium bisulfate. The organic layer is then dried over anhydrous sodium sulfate, filtered and the solvent is evaporated under reduced pressure. Purification by flash chromatography (cyclohexane/ethyl acetate 4:1) gives the desired intermediate i1 as a colorless solid (79% yield). $^1$H NMR (400 MHz, CDCl$_3$): δ 4.70-4.54 (m, 4H), 3.80-3.58 (m, 8H), 2.14-1.89 (m, 8H); MS (MALDI): m/z=338.4 ([M+H]$^+$).

Method 1 is also used for the preparation of the following intermediate compounds i2 to i10, and intermediates i79 to i81 and i90.

| Reagent | Structure | NMR | MS |
|---|---|---|---|
| i2 | (morpholine) / 2-chloro-4,6-di(morpholin-4-yl)-1,3,5-triazine | ¹H NMR (400 MHz, CDCl₃): δ 3.78 (m, 8 H), 3.70 (m, 8 H). | MS (MALDI): m/z = 285.9 ([M + H]⁺). |
| i3 | (3S)-3-methylmorpholine / 2-chloro-4,6-bis[(3S)-3-methylmorpholin-4-yl]-1,3,5-triazine | ¹H NMR (400 MHz, CDCl₃): δ 4.75-4.56 (m, 2 H), 4.34-4.30 (m, 2 H), 3.94 (dd, $^2J_{H,H}$ = 12.0 Hz, $^3J_{H,H}$ = 4.0 Hz, 2 H), 3.74 (d, $^2J_{H,H}$ = 12.0 Hz, 2 H), 3.63 (dd, $^2J_{H,H}$ = 12.0 Hz, $^3J_{H,H}$ = 4.0 Hz, 2 H), 3.49 (dt, $^2J_{H,H}$ = 12.0 Hz, $^3J_{H,H}$ = 4.0 Hz, 2 H), 3.25 (dt, $^2J_{H,H}$ = 12.0 Hz, $^3J_{H,H}$ = 4.0 Hz, 2 H), 1.31 (d, $^3J_{H,H}$ = 8.0 Hz, 6 H). | MS (MALDI): m/z = 314.4 ([M + H]⁺). |
| i4 | 3,3-dimethylmorpholine / 2-chloro-4,6-bis(3,3-dimethylmorpholin-4-yl)-1,3,5-triazine | ¹H NMR (400 MHz, CDCl₃): δ 3.81-3.72 (m, 8 H), 3.43 (s, 4 H), 1.43 (br s, 12 H). | MS (MALDI): m/z = 342.5 ([M + H]⁺). |
| i5 | (3R)-3-methylmorpholine / 2-chloro-4,6-bis[(3R)-3-methylmorpholin-4-yl]-1,3,5-triazine | ¹H NMR (400 MHz, CDCl₃): δ 4.75-4.56 (m, 2 H), 4.34-4.30 (m, 2 H), 3.94 (dd, $^2J_{H,H}$ = 12.0 Hz, $^3J_{HH}$ = 4.0 Hz, 2 H), 3.74 (d, $^2J_{H,H}$ = 12.0 Hz, 2 H), 3.63 (dd, $^2J_{H,H}$ = 12.0 Hz, $^3J_{H,H}$ = 4.0 Hz, 2 H), 3.49 (dt, $^2J_{H,H}$ = 12.0 Hz, $^3J_{H,H}$ = 4.0 Hz, 2 H), 3.25 (dt, $^2J_{H,H}$ = 12.0 Hz, $^3J_{H,H}$ = 4.0 Hz, 2 H), 1.31 (d, $^3J_{H,H}$ = 8.0 Hz, 6 H). | MS (MALDI): m/z = 314.3 ([M + H]⁺). |
| i6 | (3R,5S)-3,5-dimethylmorpholine / 2-chloro-4,6-bis[(3R,5S)-3,5-dimethylmorpholin-4-yl]-1,3,5-triazine | ¹H NMR (400 MHz, CDCl₃): δ 4.40-4.37 (m, 4 H), 3.74 (d, $^3J_{H,H}$ = 11.6 Hz, 4 H), 3.53 (dd, $^3J_{H,H}$ = 11.6 Hz, $^2J_{H,H}$ = 4.0 Hz, 4 H), 1.26 (d, $^3J_{H,H}$ = 6.9 Hz, 12 H). | MS (MALDI): m/z = 342.8 ([M + H]⁺). |

-continued

| Reagent | Structure | NMR | MS |
|---|---|---|---|
| i7 | 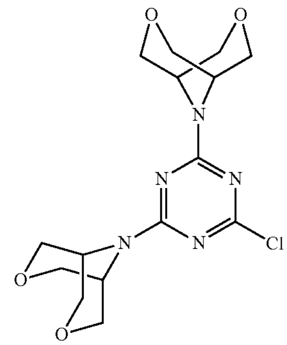 [SMILES: Clc1nc(N2C3COCC2COC3)nc(N2C3COCC2COC3)n1] | ¹H NMR (400 MHz, CDCl₃): δ 4.53 (br s, 2 H), 4.36 (br s, 2 H), 4.12-4.06 (m, 8 H), 3.92-3.83 (m, 8 H). | MS (MALDI): m/z = 370.3 ([M + H]⁺). |
| i8 | 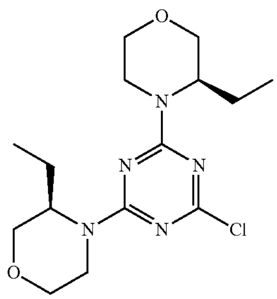 [SMILES: CC[C@@H]1COCCN1c1nc(Cl)nc(N2CCOC[C@H]2CC)n1] | ¹H NMR (400 MHz, (CD₃)₂SO): δ 4.36-4.21 (m, 4 H), 3.85-3.75 (m, 4 H), 3.48-3.45 (m, 2 H), 3.40-3.34 (m, 2 H), 3.14-3.09 (m, 2 H), 1.72 (m, 4 H), 0.82 (m, 6 H). | MS (MALDI): m/z = 342.3 ([M]⁺). |
| i9 | 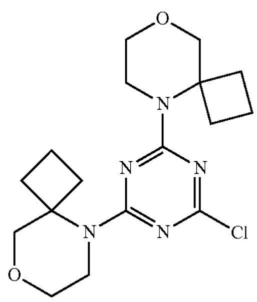 [SMILES: Clc1nc(N2CCOCC23CCC3)nc(N2CCOCC23CCC3)n1] | ¹H NMR (400 MHz, (CD₃)₂SO): δ 3.64 (m, 8 H), 3.351-3.48 (m, 4 H), 2.46-2.38 (m, 4 H), 2.20-2.16 (m, 4 H), 1.73-1.66 (m, 4 H). | MS (MALDI): m/z = 366.7 ([M + H]⁺). |
| i10 | 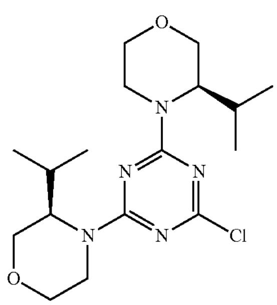 [SMILES: CC(C)[C@@H]1COCCN1c1nc(Cl)nc(N2CCOC[C@H]2C(C)C)n1] | ¹H NMR (400 MHz, (CD₃)₂SO): δ 4.40-4.25 (m, 2 H), 4.20-4.05 (m, 2 H), 4.08 (m, 2 H), 3.95 (m, 2 H), 3.83 (m, 4 H), 3.08 (m, 2 H), 2.30 (m, 2 H), 0.98 (m, 6 H), 0.48 (m, 6 H). | MS (MALDI): m/z = 370.4 ([M + H]⁺). |
| i79 | 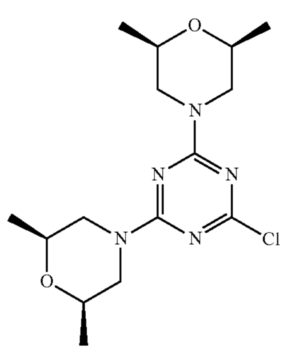 | ¹H NMR (400 MHz, CDCl₃): δ 4.59-4.31 (m, 4 H), 3.66-3.46 (m, 4 H), 2.70 (m, 4 H), 1.14 (m, 12 H). | MS (MALDI): m/z = 342.4 ([M + H]⁺). |

| Reagent | Structure | NMR | MS |
|---|---|---|---|
| i80 | 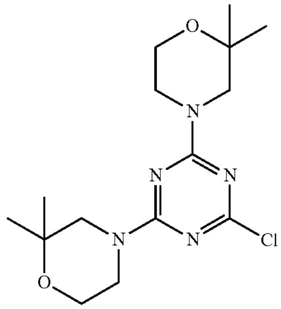 | $^1$H NMR (400 MHz, CDCl$_3$): δ 3.73-3.64 (m, 8 H), 3.57 (s, 2 H), 3.51 (s, 2 H), 1.14 (s, 12 H). | MS (MALDI): m/z = 342.3 ([M + H]$^+$). |
| i81 | 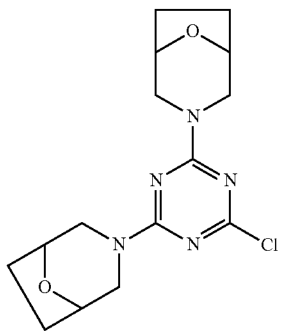 [SMILES: Clc1nc(N2CC3CCC(C2)O3)nc(N2CC3CCC(C2)O3)n1] | $^1$H NMR (400 MHz, CDCl$_3$): δ 4.41 (br s, 4 H), 4.32-4.16 (m, 4 H), 3.24-3.10 (m, 4 H), 1.99-1.84 (m, 4 H), 1.84-1.67 (m, 4 H). | MS (MALDI): m/z = 338.4 ([M + H]$^+$). |
| i90 | 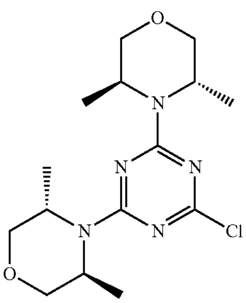 [SMILES: C[C@H]1COC[C@H](C)N1c1nc(Cl)nc(N2[C@@H](C)COC[C@@H]2C)n1] | $^1$H NMR (400 MHz, CDCl$_3$): δ 4.20 (m, 4 H), 4.10 (m, 4 H), 3.66 (m, 4 H), 1.35 (d, $^3J_{H,H}$ = 6.9 Hz, 12 H) | MS (MALDI): m/z = 342.8 ([M + H]$^+$) |

Method 2: 2,4-dichloro-6-morpholino-1,3,5-triazine (i11)

To a solution of cyanuric chloride (18.1 g, 0.100 mol, 1.0 eq.) in dichloromethane (200 mL) is dropwise added a solution of morpholine (17.4 g, 0.200 mol, 2.0 eq.) at −78° C. over 2 hours. The resulting mixture is allowed to warm to 0° C. with stirring and mixed with an ice cold saturated solution of sodium bisulfate in water. The phases are separated and the organic phase is washed with half concentrated brine dried over sodium sulfate and evaporated to yield the title compound i11 as a colorless solid. $^1$H NMR (400 MHz, CDCl$_3$): δ 3.90-3.86 (m, 4H), 3.77-3.72 (m, 4H).

Method 3: 8-(4-chloro-6-morpholino-1,3,5-triazin-2-yl)-3-oxa-8-azabicyclo-[3.2.1]octane (i12)

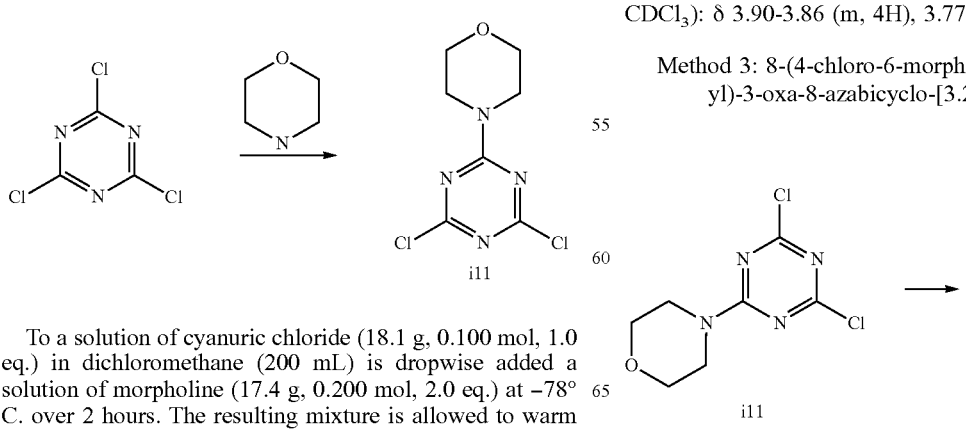

-continued

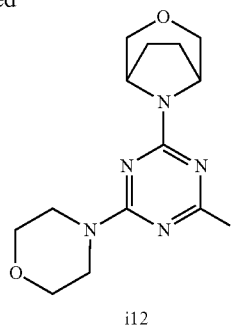

i12

3-Oxa-8-azabicyclo[3.2.1]octane-HCl (Advanced Chem-Blocks Inc, product number A-861, 200 mg, 1.34 mmol, 1.1 eq.) and N,N-diisopropylethylamine (470 μL, 2.69 mmol, 2.1 eq.) are charged in a flask and dissolved in ethanol (3 mL). The flask is placed in an ice bath. A solution of compound i11 (300 mg, 1.28 mmol, 1.0 eq.) in ethanol (2 mL) is added to the above solution at 0° C. The resulting mixture is stirred overnight, while allowing it to warm up to room temperature. Deionized water (20 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 9:1→8:2) gives the desired intermediate i12 as a colorless solid (78% yield). $^1$H NMR (400 MHz, CDCl$_3$): δ 4.69-4.56 (m, 2H), 3.86-3.59 (m, 12H), 2.12-1.91 (m, 4H); MS (MALDI): m/z=312.7 ([M+H]$^+$).

Method 3 is also used for the preparation of the following intermediate compounds i13 to i16, and intermediates i87 and i91.

| | Reagent | Structure | NMR |
|---|---|---|---|
| i13 | ![morpholine with methyl] | ![triazine product i13] | $^1$H NMR (400 MHz, CDCl$_3$): δ 4.71-4.61 (m, 1 H), 4.34-4.31 (m, 1 H), 3.96-3.92 (m, 1 H), 3.79-3.70 (m, 9 H), 3.65-3.61 (m, 1 H), 3.51-3.45 (m, 1 H), 3.29-3.21 (m, 1 H), 1.36-1.30 (d, $^3J_{H,H}$ = 6.9 Hz, 3 H). |
| i14 | ![Boc-piperazine] | ![triazine product i14] | $^1$H NMR (400 MHz, CDCl$_3$): δ 3.79-3.71 (m, 12 H), 3.46 (m, 4 H), 1.48 (s, 9 H). |
| i15 | ![thiomorpholine] | ![triazine product i15] | $^1$H NMR (400 MHz, CDCl$_3$): δ 4.12-3.98 (m, 4 H), 3.84-3.70 (m, 4 H), 3.70-3.62 (m, 4 H), 2.66-2.56 (m, 4 H). |

-continued
| Reagent | Structure | NMR |
|---|---|---|
| i16 | 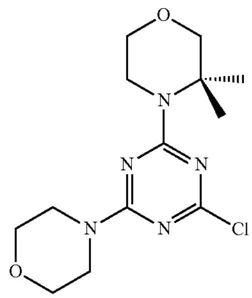 | $^1$H NMR (400 MHz, CDCl$_3$): δ 3.77 (m, 4 H), 3.68-3.63 (m, 8 H), 3.44 (s, 2 H), 1.44 (s, 6 H). |
| i87 | 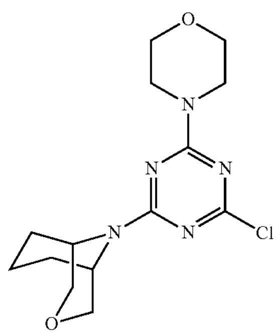 [SMILES: Clc1nc(N2CCOCC2)nc(N2C3CCCC2COC3)n1] | $^1$H NMR (400 MHz, CDCl$_3$): δ 4.52 (m, 1 H), 4.43 (m, 1 H), 3.93 (m, 2 H), 3.65 (m, 10 H), 2.48 (m, 1 H), 1.88-1.72 (m, 4 H), 1.57 (m, 1 H) |
| i91 | 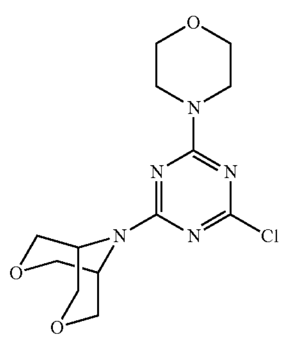 [SMILES: Clc1nc(N2CCOCC2)nc(N2C3COCC2COC3)n1] | $^1$H NMR (400 MHz, CDCl$_3$): δ 4.44 (m, 1 H), 4.32 (m, 1 H), 4.00 (m, 4 H), 3.74-3.65 (m, 12 H); |
Method 4: (S)-4-(4,6-dichloro-1,3,5-triazin-2-yl)-3-methylmorpholine (i7)
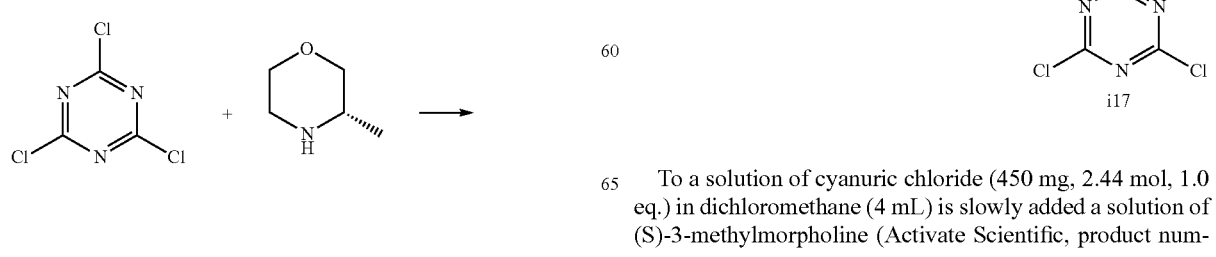
-continued
To a solution of cyanuric chloride (450 mg, 2.44 mol, 1.0 eq.) in dichloromethane (4 mL) is slowly added a solution of (S)-3-methylmorpholine (Activate Scientific, product number AS3424, 0.28 mL, 2.44 mol, 1.0 eq.) and triethylamine (0.35 mL, 2.51 mol, 1.02 eq.) in dichloromethane (2 mL) at −50° C. The resulting mixture is stirred for 2 hours at −50° C., then allowed to warm to 0° C. with stirring and mixed with an ice cold saturated solution of sodium bisulfate in water. The phases are separated and the organic phase is washed with brine dried over sodium sulfate and evaporated to yield the title compound i17 as a colorless solid (95% yield). $^1$H NMR (400 MHz, CDCl$_3$): δ 4.78-4.69 (m, 1H), 4.43-4.39 (m, 1H), 3.98-3.96 (m, 1H), 3.78-3.76 (m, 1H), 3.67-3.65 (m, 1H), 3.51-3.47 (m, 1H), 3.40-3.37 (m, 1H), 1.36 (m, 3H).

Method 5: 8-(4-chloro-6-((S)-3-methylmorpholino)-1,3,5-triazin-2-yl)-3-oxa-8-azabicyclo[3.2.1]octane (i18)

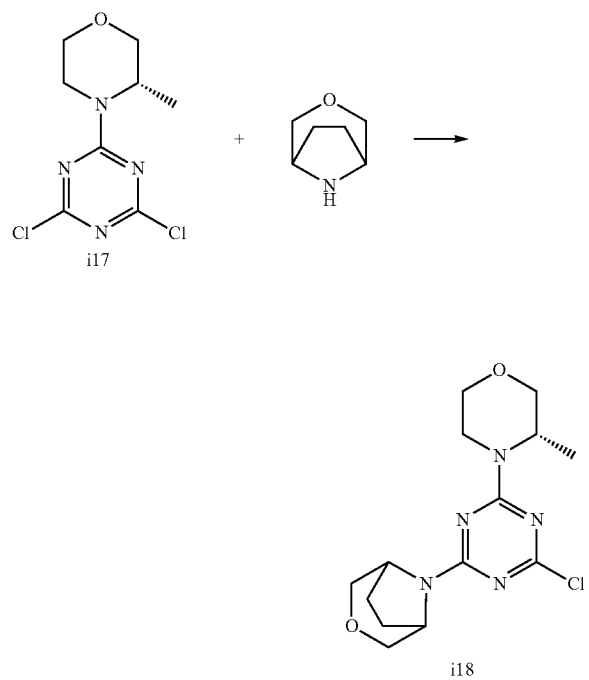

3-Oxa-8-azabicyclo[3.2.1]octane-HCl (Advanced ChemBlocks Inc, product number A-861, 383 mg, 2.55 mmol, 1.1 eq.) and N,N-diisopropylethylamine (1.0 mL, 5.60 mmol, 2.4 eq.) are charged in a flask and dissolved in ethanol (4 mL). The flask is placed in an ice bath. A solution of compound i17 (580 mg, 2.33 mmol, 1.0 eq.) in ethanol (2 mL) is added to the above solution at 0° C. The resulting mixture is stirred for 4 hours, while allowing it to warm up to room temperature. Deionized water (20 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 9:1→8:2) gives the desired intermediate i18 as a colorless solid (88% yield). $^1$H NMR (400 MHz, CDCl$_3$): δ 4.75-4.52 (m, 3H), 4.37-4.24 (m, 1H), 3.95-3.92 (m, 1H), 3.73-3.70 (m, 3H), 3.64-3.61 (m, 3H), 3.52-3.42 (m, 1H), 3.29-3.17 (m, 1H), 2.11-1.89 (m, 4H), 1.31 (m, 3H).

Method 6: tert-butyl 4-(4,6-dichloro-1,3,5-triazin-2-yl)piperazine-1-carboxylate (i19)

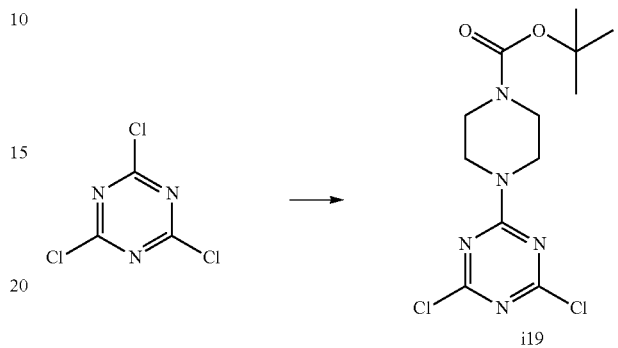

To a cooled (−50° C.) solution of cyanuric chloride (1.0 g, 5.42 mmol, 1.0 eq.) in dichloromethane (4 mL) is added dropwise a solution of tert-butyl piperazine-1-carboxylate (Sigma, product number 343536, 1.02 g, 5.48 mmol, 1.01 eq.) and triethylamine (0.767 mL, 5.53 mmol, 1.02 eq.) in dichloromethane (2 mL). The resulting reaction mixture is stirred at −50° C. for 4 hours. A saturated aqueous solution of sodium bisulfate (10 mL) and dichloromethane (20 mL) are added. The mixture is transferred to a separating funnel. The organic layer is separated, washed with a saturated aqueous solution of sodium bisulfate (20 mL), dried over anhydrous sodium sulfate, filtered and then the solvent is evaporated under reduced pressure to give pure intermediate i19 (80% yield). $^1$H NMR (400 MHz, CDCl$_3$): δ 3.88-3.85 (m, 4H), 3.53-3.51 (m, 4H), 1.49 (m, 9H).

Method 7: tert-butyl 4-(4-(3-oxa-8-azabicyclo[3.2.1]octan-8-yl)-6-chloro-1,3,5-triazin-2-yl)piperazine-1-carboxylate (i20)

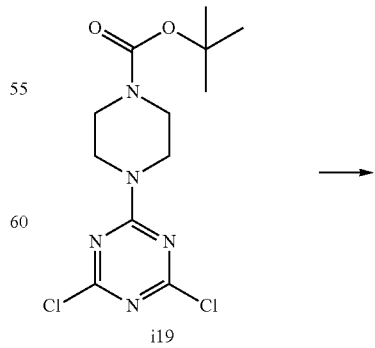

79

-continued

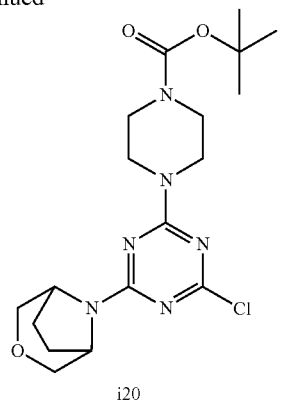

i20

3-Oxa-8-azabicyclo[3.2.1]octane-HCl (Advanced ChemBlocks Inc, product number A-861, 235 mg, 1.57 mmol, 1.0 eq.) and N,N-diisopropylethylamine (592 µL, 3.14 mmol, 2.1 eq.) are charged in a flask and dissolved in ethanol (6 mL). The flask is placed in an ice bath. A solution of compound i19 (500 mg, 1.5 mmol, 1.0 eq.) in ethanol (2 mL) is added to the above solution at 0° C. The resulting mixture is stirred overnight, while allowed to warm up to room temperature. Deionized water (10 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 8:2) gave the desired intermediate i20 as a colorless solid (77% yield). $^1$H NMR (400 MHz, CDCl$_3$): δ 4.68-4.60 (m, 2H), 3.76-3.70 (m, 6H), 3.64-3.62 (m, 2H), 3.47-3.45 (m, 4H), 2.08-1.95 (m, 4H), 1.48 (br s, 9H); MS (MALDI): m/z=411.8 ([M+H]$^+$).

Method 7 is also used for the preparation of the following intermediate compound i21.

80

Method 8: 4,4'-(6-chloropyrimidine-2,4-diyl)dimorpholine (i22) and 4,4'-(2-chloropyrimidine-4,6-diyl)dimorpholine (i23)

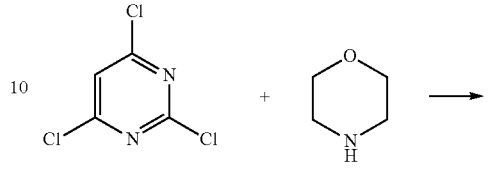

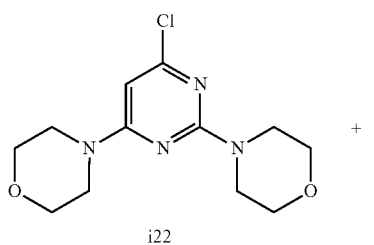

i22

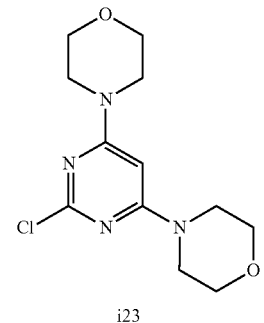

i23

2,4,6-Trichloropyrimidine (Manchester Organics, product number Y17832, 11.2 g, 61 mmol, 1.0 eq.), N,N-diisopropylethylamine (23.3 mL, 134.2 mmol, 2.2 eq.) and morpholine (11.7 mL, 134.2 mmol, 2.2 eq.) are charged in a flask and dissolved in ethanol (120 mL). The flask is equipped

| Reagent | Structure | NMR | MS |
|---|---|---|---|
| i21 | | $^1$H NMR (400 MHz, CDCl$_3$): δ 4.76-4.61 (m, 1 H), 4.35-4.30 (m, 1 H), 3.94 (dd, $^2J_{H,H}$ = 12 Hz, $^3J_{H,H}$ = 4.0 Hz, 1 H), 3.76-3.72 (m, 5 H), 3.65 (dd, $^2J_{H,H}$ = 12 Hz, $^3J_{H,H}$ = 4.0 Hz, 1 H), 3.51-3.44 (m, 5 H), 3.25 (dt, $^2J_{H,H}$ = 12 Hz, $^3J_{H,H}$ = 4.0 Hz, 1 H), 1.48 (s, 9 H), 1.30 (d, $^3J_{H,H}$ = 8.0 Hz, 3 H). | MS (MALDI): m/z = 399.1 ([M + H]$^+$). | with a refluxed condenser and placed in an oil bath preheated at 100° C. The reaction mixture is stirred at this temperature for 18 hours. After this time, the reaction mixture is cooled down to room temperature and volatiles are removed under reduced pressure. The resulting mixture is dissolved in dichloromethane (100 mL) and washed twice with an aqueous solution of sodium bisulfate (2×80 mL). The organic layer is dried over anhydrous sodium sulfate, filtered and concentrated under reduced pressure using a rotary evaporator. Products i22 and i23 are isolated by flash chromatography on silica gel (cyclohexane/ethyl acetate 3:1 to 1:1). The product fractions are pooled and evaporated to yield i22 as a colorless powder (13.8 g, 80%) and i23 as a colorless powder (2.2 g, 13% yield).

4,4'-(6-chloropyrimidine-2,4-diyl)dimorpholine (i22): $^1$H NMR (400 MHz, CDCl$_3$): δ 5.85 (s, 1H), 3.71-3.75 (m, 12H), 3.52-3.55 (m, 4H); MS (MALDI): m/z: 285.4 ([M+H]$^+$).

4,4'-(2-chloropyrimidine-4,6-diyl)dimorpholine (i23): $^1$H NMR (400 MHz, CDCl$_3$): δ 5.38 (s, 1H), 3.73-3.76 (m, 8H), 3.52-3.54 (m, 8H); MS (MALDI): m/z: 285.2 ([M+H]$^+$).

Method 9: 8-(4-(3-oxa-8-azabicyclo[3.2.1]octan-8-yl)-6-chloropyrimidin-2-yl)-3-oxa-8-azabicyclo[3.2.1]octane (i24)

A solution of 2,4,6-trichloropyrimidine (0.676 mL, 5.88 mmol, 1.0 eq.), 3-oxa-8-azabicyclo[3.2.1]octane hydrochloride (1.76 g, 11.8 mmol, 2.0 eq.), and N,N-diisopropylethylamine (4.10 mL, 23.5 mmol, 4.0 eq.) in ethyl acetate (18 volumes) is heated for 16 hours (100° C.). Then, the solvent is removed under reduced pressure and the residue is dissolved in dichloromethane (60 volumes) and washed with a saturated aqueous sodium bisulfate (3×60 volumes). The organic layer is dried over anhydrous sodium sulfate, filtered and concentrated under reduced pressure. Purification by column chromatography on silica gel (cyclohexane/ethyl acetate 3:1 to 1:1) affords the desired intermediate i24 as a colorless solid (1.23 g, 62%). $^1$H NMR (400 MHz, CDCl$_3$): δ 5.80 (s, 1H), 4.59 (s, 2H), 4.35 (m, 2H), 3.76 (t, $^2J_{H,H}$=10.8 Hz, 4H), 3.59 (d, $^2J_{H,H}$=10.8 Hz, 4H), 2.03 (m, 8H); MS (MALDI): m/z=337.7 ([M+H]$^+$).

Method 9 is also used for the preparation of the following intermediate compound i25.

| Reagent | Structure | NMR | MS |
|---|---|---|---|
| i25 | 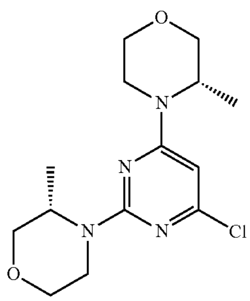 [SMILES: C[C@H]1COCCN1c1cc(Cl)nc(N2CCOC[C@@H]2C)n1] | $^1$H NMR (400 MHz, CDCl$_3$): δ 5.83 (s, 1 H), 4.64-4.57 (m, 1 H), 4.27 (dd, $^3J_{H,H}$ = 2.4 Hz, $^2J_{H,H}$ = 13.5 Hz, 1 H), 4.20-4.11 (m, 1 H), 3.97-3.87 (m, 3 H), 3.77-3.63 (m, 4 H), 3.56-3.46 (m, 2 H), 3.26-3.15 (m, 2 H), 1.28 (d, $^3J_{H,H}$ = 3.2 Hz, 3 H), 1.27 (d, $^3J_{H,H}$ = 3.2 Hz, 3 H). | MS (MALDI): m/z = 313.6 ([M + H]$^+$). |

Method 10: 4-(4,6-dichloropyrimidin-2-yl)morpholine (i26) and 4-(2,6-dichloropyrimidin-4-yl)morpholine (i27)

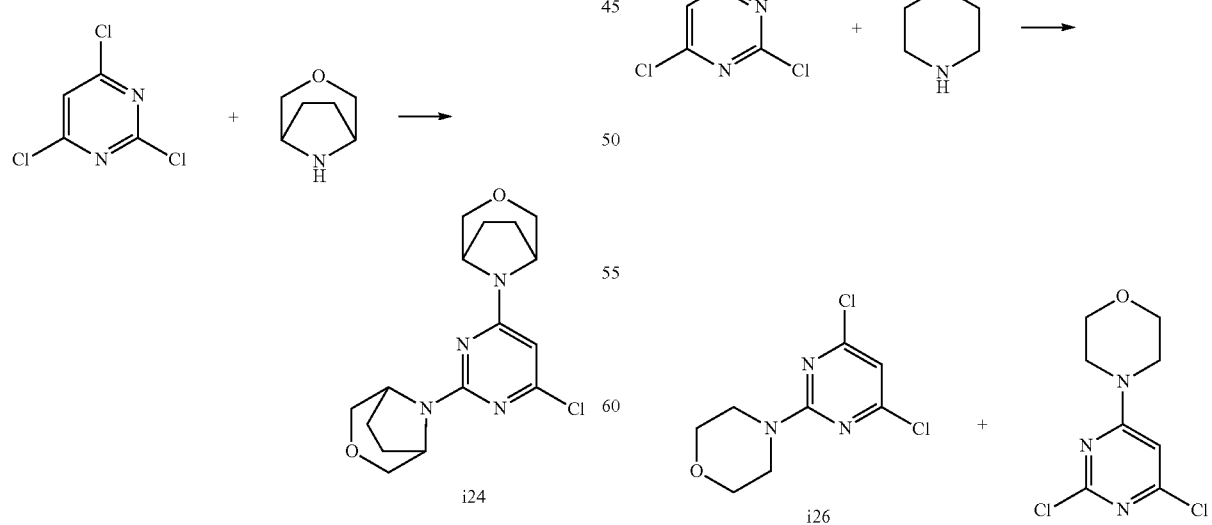

To a solution of 2,4,6-trichloropyrimidine (14.0 mL, 122 mmol, 1.0 eq.) in EtOH (150 mL) is added a solution of morpholine (11.2 mL, 256 mmol, 2.1 eq.) and N,N-diisopropylethylamine (44.6 mL, 256 mmol, 2.1 eq.) in EtOH (150 mL) dropwise at 0° C. The reaction mixture is stirred overnight at room temperature and the solvent is removed under reduced pressure. The crude product is extracted with dichloromethane (3×100 mL) and the organic phase is successively washed with saturated aqueous sodium bisulfate (3×400 mL). The combined organic layers are dried over anhydrous sodium sulfate, filtered and evaporated under reduced pressure. The crude mixture is purified by flash column chromatography (SiO$_2$, cyclohexane/ethyl acetate 9:1 to 3:1) to yield i26 (5.02 g, 18%) and i27 (16.7 g, 59%), both as colorless solids.

4-(4,6-dichloropyrimidin-2-yl)morpholine (i26): $^1$H NMR (400 MHz, CDCl$_3$): δ 6.56 (s, 1H), 3.78 (m, 4H) 3.74 (m, 4H).

4-(2,6-dichloropyrimidin-4-yl)morpholine (i27): $^1$H NMR (400 MHz, CDCl$_3$): δ 6.41 (s, 1H), 3.78 (m, 4H), 3.65 (m, 4H).

Method 11: (S)-4-(2-chloro-6-morpholinopyrimidin-4-yl)-3-methylmorpholine (i28)

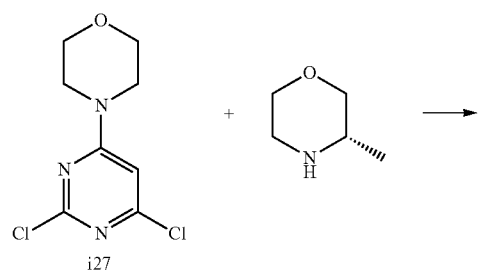

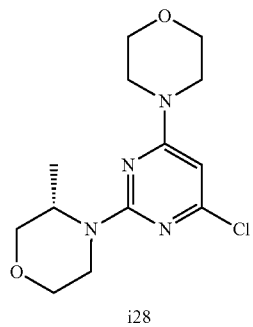

i28

A solution of i27 (694 mg, 2.97 mmol, 1.0 eq.), (S)-3-methylmorpholine (0.500 mL, 4.46 mmol, 1.5 eq.) and N,N-diisopropylethylamine (1.29 mL, 7.43 mmol, 2.5 eq.) in EtOH (5.0 mL) is heated to reflux for 3 days. Then, the solvent is removed under reduced pressure. The residue is dissolved in dichloromethane (60 volumes) and washed with saturated aqueous sodium bisulfate (3×60 volumes). The organic layer is dried over anhydrous sodium sulfate, filtered and concentrated under reduced pressure. The crude mixture is purified by flash chromatography (SiO$_2$, cyclohexane/ethyl acetate 3:1 to 1:1) to afford the title compound (S)-4-(2-chloro-6-morpholinopyrimidin-4-yl)-3-methylmorpholine (i28) as a colorless solid (425 mg, 48%). $^1$H NMR (400 MHz, CDCl$_3$): δ 5.85 (s, 1H), 4.62 (dd, 2J$_{H,H}$=3.6 Hz, $^3$J$_{H,H}$=2.9 Hz, 1H), 4.25 (dd, $^2$J$_{H,H}$=13.6 Hz, 3J$_{H,H}$=2.9 Hz, 1H), 3.93 (dd, $^2$J$_{H,H}$=11.4 Hz, $^3$J$_{H,H}$=3.8 Hz, 1H), 3.75, (t, $^3$J$_{H,H}$=5.0 Hz, 4H), 3.71 (s, 1H), 3.66 (dd, $^2$J$_{H,H}$=11.3 Hz, $^3$J$_{H,H}$=3.2 Hz, 1H), 3.53 (m, 5H), 3.23 (m, 1H), 1.26 (d, $^2$J$_{H,H}$=11.3 Hz, 3H); MS (MALDI): m/z=299.4 ([M+H]$^+$).

Method 11 is also used for the preparation of the following intermediate compound i29.

| Reagent | Structure | NMR | MS |
|---|---|---|---|
| i29 | 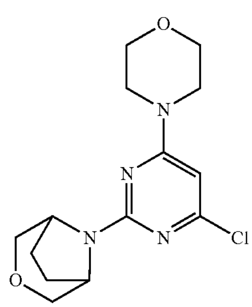 [SMILES: Clc1cc(N2CCOCC2)nc(N2C3CCC2COC3)n1] | $^1$H NMR (400 MHz, CDCl$_3$): δ 5.86 (s, 1 H), 4.60 (br s, 2 H) 3.80-3.72 (m, 6 H), 3.62-3.56 (m, 2 H), 3.56-3.50 (m, 4 H), 2.08-1.90 (m, 4 H). | MS (MALDI): m/z = 309.6 ([M + H]$^+$). |

Method 12: (S)-4-(6-chloro-2-morpholinopyrimidin-4-yl)-3-methylmorpholine (i30)

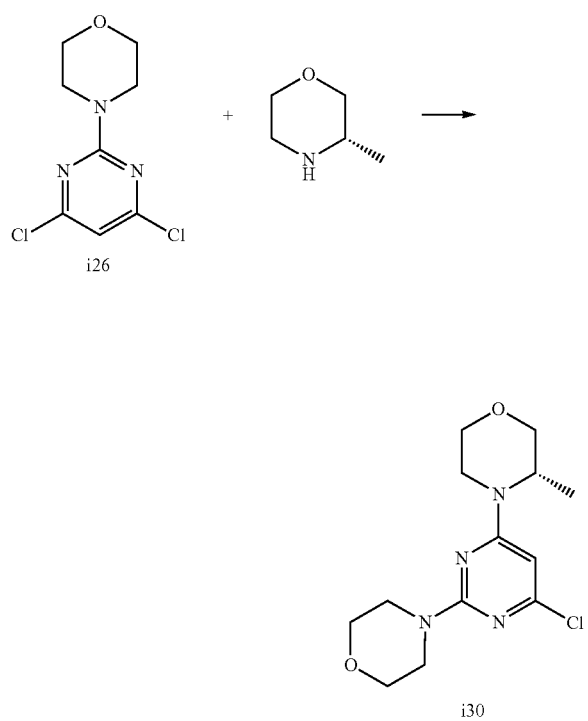

i26 i30

A solution of (S)-3-methylmorpholine (194 mg, 1.32 mmol, 1.5 eq.), i26 (300 mg, 1.28 mmol, 1.0 eq.) and N,N-diisopropylethylamine (3.0 eq.) in DMF (17 volumes) is heated for 16 hours (130° C.). Then, the solvent is removed under reduced pressure. The residue is dissolved in dichloromethane (100 volumes) and washed with saturated aqueous sodium bisulfate (3×100 volumes). The organic layer is dried over anhydrous sodium sulfate, filtered and concentrated under reduced pressure. The crude mixture is purified by flash chromatography (SiO$_2$, cyclohexane/ethyl acetate 5:1) to afford the title compound i30 as a colorless solid (257 mg, 67%). $^1$H NMR (400 MHz, CDCl$_3$): δ 5.84 (s, 1H), 4.18 (m, 1H), 3.94 (m, 2H), 3.71 (m, 10H), 3.53, (dt, $^2J_{H,H}$=12.0 Hz, $^3J_{H,H}$=3.1 Hz, 1H), 3.20 (dt, $^2J_{H,H}$=12.8 Hz, $^3J_{H,H}$=3.8 Hz, 1H), 1.27 (d, $^3J_{H,H}$=6.8 Hz, 3H); MS (MALDI): m/z=298.4 ([M]$^+$).

Method 14: 8-(4,6-dichloro-1,3,5-triazin-2-yl)-3-oxa-8-azabicyclo[3.2.1]octane (i32)

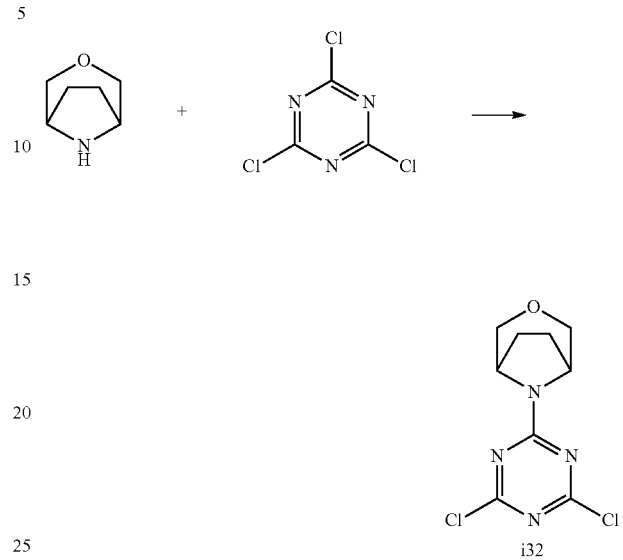

i32

A solution of cyanuric chloride (1.97 g, 10.7 mmol, 1.0 eq.) in dichloromethane (10 mL) is cooled to −50° C. A solution of 3-oxa-8-azabicyclo[3.2.1]octane hydrochloride (1.60 g, 10.7 mmol, 1.0 eq.) and N,N-diisopropylethylamine (3.73 mL, 21.4 mmol, 2.0 eq.) in dichloromethane (40 mL) is slowly added over a period of 5 hours. The mixture is stirred for another 5 hours at this temperature. Then, dichloromethane (20 mL) and saturated aqueous sodium bisulfate (50 mL) are added and the mixture is allowed to warm to room temperature. The layers are separated and the organic layer is washed with saturated aqueous sodium bisulfate (2×50 mL). The organic layer is dried over anhydrous sodium sulfate and the solvent is removed under reduced pressure. The crude mixture is recrystallized from n-heptane/dichloromethane (20 mL/13 mL) to afford the title compound 8-(4,6-dichloro-1,3,5-triazin-2-yl)-3-oxa-8-azabicyclo[3.2.1]octane (i32) as a colorless solid (2.47 g, 47%). $^1$H NMR (400 MHz, CDCl$_3$): δ 4.74 (m, 2H), 3.72 (d, $^3J_{H,H}$=1.5 Hz, 4H), 2.08 (m, 4H). Method 14 is also used for the preparation of the following intermediate compounds i33 and i34.

| Reagent | | Structure | NMR |
|---|---|---|---|
| i33 | (S)-3-methylmorpholine structure | triazine product structure | $^1$H NMR (400 MHz, CDCl$_3$): δ 4.54-4.60 (m, 1 H), 4.20 (dd, $^3J_{H,H}$ = 2.9 Hz, $^2J_{H,H}$ = 14 Hz, 1 H), 3.92 (dd, $^3J_{H,H}$ = 3.4 Hz, $^2J_{H,H}$ = 12 Hz, 1 H), 3.71 (d, $^2J_{H,H}$ = 12 Hz, 1 H), 3.57 (dd, $^3J_{H,H}$ = 3.2 Hz, $^2J_{H,H}$ = 12 Hz, 1 H), 3.42 (m, 1 H), 3.32 (m, 1 H), 1.27 (d, $^3J_{H,H}$ = 6.9 Hz, 3H). |

| Reagent | Structure | NMR |
|---|---|---|
| i34 | 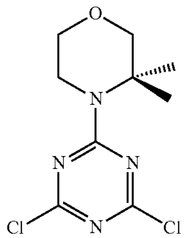 | $^1$H NMR (400 MHz, (CD$_3$)$_2$SO): δ 3.88-3.81 (m, 4 H), 3.51 (s, 2 H), 1.46 (s, 6 H). |

Method 15: 9-(4-(3-oxa-8-azabicyclo[3.2.1]octan-8-yl)-6-chloro-1,3,5-triazin-2-yl)-3,7-dioxa-9-azabicyclo[3.3.1]nonane (i35)

Method 16: 9-(4-chloro-6-((R)-3-methylmorpholino)-1,3,5-triazin-2-yl)-3,7-dioxa-9-azabicyclo[3.3.1]nonane (i36)

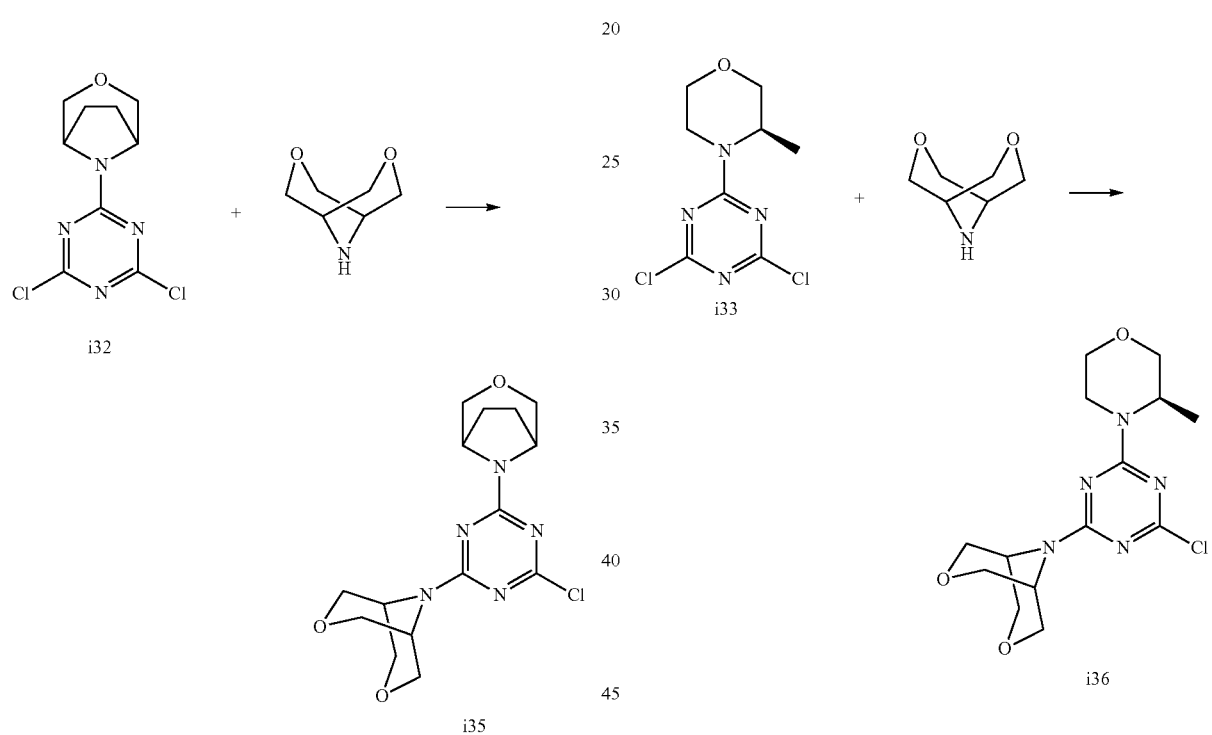

To a solution of 3,7-dioxa-9-azabicyclo[3.3.1]nonane (184 mg, 0.700 mmol, 1.0 eq.) and N,N-diisopropylethylamine (0.170 mL, 0.970 mmol, 1.4 eq.) in 1,4-dioxane (1.0 mL) a solution of i32 (100 mg, 0.770 mmol, 1.1 eq.) in 1,4-dioxane (2.0 mL) is added. The resulting mixture is heated for 1 hour at 70° C. Then, dichloromethane (50 mL) and water (50 mL) are added. The aqueous layer is extracted with dichloromethane (3×50 mL), the combined organic layers are dried over anhydrous sodium sulfate and the solvent is evaporated. The crude mixture is purified by automated flash chromatography on silica gel (cyclohexane/ethyl acetate 2:1 to 0:1) to afford the title compound 9-(4-(3-oxa-8-azabicyclo[3.2.1]octan-8-yl)-6-chloro-1,3,5-triazin-2-yl)-3,7-dioxa-9-azabicyclo[3.3.1]nonane (i35) as a colorless solid (192 mg, 77%). $^1$H NMR (400 MHz, (CD$_3$)$_2$SO): δ 4.70 (m, 1H), 4.55 (m, 2H), 4.44 (m, 1H), 4.12 (m, 4H), 3.90 (m, 4H), 3.72 (m, 2H), 3.64 (m, 2H), 2.08 (m, 2H), 1.97 (m, 2H); MS (MALDI): m/z=354.3 ([M]$^+$).

To a solution of 3,7-dioxa-9-azabicyclo[3.3.1]nonane (173 mg, 1.27 mmol, 1.05 eq.) and N,N-diisopropylethylamine (0.50 mL, 2.52 mmol, 2.1 eq.) in tetrahydrofuran (5 mL) a solution of i33 (300 mg, 2.52 mmol, 2.1 eq.) in 1,4-dioxane (2.0 mL) is added. The resulting mixture is heated for 2 hours (70° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO$_2$, cyclohexane/ethyl acetate 2:1 to 0:1) to afford the title compound i36 as a colorless solid (316 mg, 76%). $^1$H NMR (400 MHz, (CD$_3$)$_2$SO): δ 4.55-4.53 (m, 1H), 4.42 (m, 1H), 4.32 (m, 1H), 4.25-4.16 (m, 1H), 4.01-3.97 (m, 4H), 3.87 (dd, $^3J_{H,H}$=3.8 Hz, $^2J_{H,H}$=11.2 Hz, 1H), 3.73-3.65 (m, 5H), 3.53 (dd, $^3J_{H,H}$=3.0 Hz, $^2J_{H,H}$=11.6 Hz, 1H), 3.38 (m, 1H), 3.15 (m, 1H), 1.20 (d, $^3J_{H,H}$=6.9 Hz, 3H).

Method 16 is also used for the preparation of the following intermediate compounds i37 to i53, intermediate i82 and intermediates i85, i86, i92, i93, i94.

| Reagent | Structure | NMR | MS |
|---|---|---|---|
| i37 | 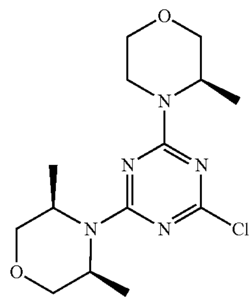 [SMILES: C[C@@H]1COCCN1c1nc(Cl)nc(N2[C@H](C)COC[C@@H]2C)n1] | $^1$H NMR (400 MHz, (CD$_3$)$_2$SO): δ 4.58-4.50 (m, 1 H), 4.44-4.35 (m, 2 H), 4.25-4.12 (m, 1 H), 3.90-3.86 (m, 1 H), 3.75-3.65 (m, 3 H), 3.56-3.49 (m, 3 H), 3.38 (m, 1 H), 3.16 (m, 1 H), 1.25 (d, $^3J_{H,H}$ = 6.9 Hz, 6 H), 1.19 (d, $^3J_{H,H}$ = 6.9 Hz, 3 H). | MS (MALDI): m/z = 328.2 ([M + H]$^+$). |
| i38 | 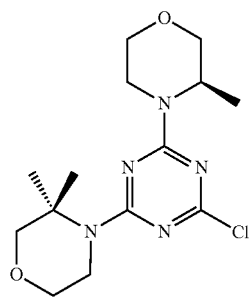 | $^1$H NMR (400 MHz, (CD$_3$)$_2$SO): δ 4.54-4.46 (m, 1 H), 4.18-4.13 (m, 1 H), 3.88 (m, 1 H), 3.80-3.65 (m, 5 H), 3.54 (m, 1 H), 3.44-3.36 (m, 3 H), 3.18 (m, 1 H), 1.44 (s, 6 H), 1.21 (d, $^3J_{H,H}$ = 6.9 Hz, 3 H). | |
| i39 | 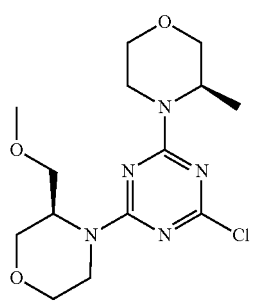 [SMILES: COC[C@@H]1COCCN1c1nc(Cl)nc(N2CCOC[C@H]2C)n1] | $^1$H NMR (400 MHz, (CD$_3$)$_2$SO): δ 4.65-4.51 (m, 2 H), 4.31-4.20 (m, 2 H), 3.66 (m, 3 H), 3.69-3.56 (m, 2 H), 3.54-3.48 (m, 3 H), 3.42-3.35 (m, 2 H), 3.31 (s, 3 H), 3.21-3.13 (m, 2 H), 1.21 (d, $^3J_{H,H}$ = 6.9 Hz, 3 H). | MS (MALDI): m/z = 344.2 ([M + H]$^+$). |
| i40 | 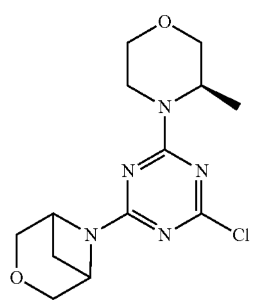 [SMILES: C[C@@H]1COCCN1c1nc(Cl)nc(N2C3COCC2C3)n1] | $^1$H NMR (400 MHz, (CD$_3$)$_2$SO): δ 4.55-4.51 (m, 1 H), 4.42-4.35 (m, 2 H), 4.12-4.25 (m, 2 H), 4.04-4.07 (m, 1 H), 3.86-3.88 (m, 1 H), 3.78-3.75 (m, 2 H), 3.69-3.65 (m, 1 H), 3.55-3.51 (m, 1 H), 3.38 (m, 1 H), 3.20-3.13 (m, 1 H), 2.68 (m, 1 H), 1.81 (m, 1 H), 1.20 (d, $^3J_{H,H}$ = 6.9 Hz, 3 H). | |
| i41 | 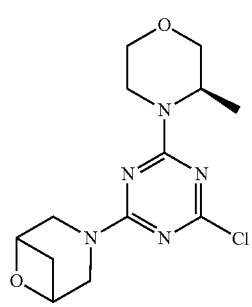 [SMILES: C[C@@H]1COCCN1c1nc(Cl)nc(N2CC3CC(C2)O3)n1] | $^1$H NMR (400 MHz, (CD$_3$)$_2$SO): δ 4.69-4.53 (m, 3 H), 4.31-4.15 (m, 1 H), 3.93-3.78 (m, 3 H), 3.71-3.53 (m, 4 H), 3.42-3.35 (m, 1 H), 3.22-3.16 (m, 1 H), 3.12-3.08 (m, 1 H), 1.81 (m, 1 H), 1.21 (d, $^3J_{H,H}$ = 6.9 Hz, 3 H). | |

-continued

| Reagent | Structure | NMR | MS |
|---|---|---|---|
| i42 | 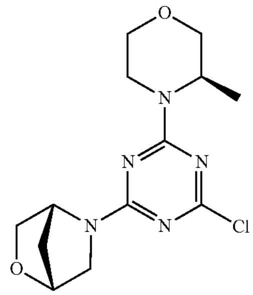 [SMILES: C[C@@H]1COCCN1c1nc(Cl)nc(N2C[C@H]3C[C@@H]2CO3)n1] | $^1$H NMR (400 MHz, (CD$_3$)$_2$SO): δ 4.95-4.88 (m, 1 H), 4.64 (m, 1 H), 4.54 (m, 1 H), 4.31-4.09 (m, 1 H), 3.89-3.85 (m, 1 H), 3.75-3.73 (m, 1 H), 3.66-3.63 (m, 2 H), 3.52 (m, 1 H), 3.45-3.32 (m, 3 H), 3.18-3.12 (m, 1 H), 1.90-1.83 (m, 2 H), 1.21 (d, $^3J_{H,H}$ = 6.9 Hz, 3 H). | MS (MALDI): m/z = 312.2 ([M + H]$^+$). |
| i43 | 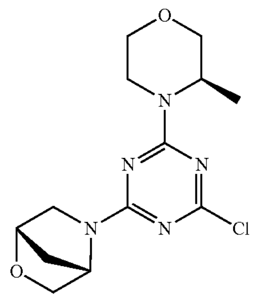 [SMILES: C[C@@H]1COCCN1c1nc(Cl)nc(N2C[C@@H]3C[C@H]2CO3)n1] | $^1$H NMR (400 MHz, (CD$_3$)$_2$SO): δ 4.94-4.88 (m, 1 H), 4.64 (m, 1 H), 4.54 (m, 1 H), 4.29-4.12 (m, 1 H), 3.89-3.85 (m, 1 H), 3.75-3.73 (m, 2 H), 3.66-3.63 (m, 2 H), 3.52 (m, 1 H), 3.45-3.32 (m, 2 H), 3.18-3.12 (m, 1 H), 1.90-1.83 (m, 2 H), 1.21 (d, $^3J_{H,H}$ = 6.9 Hz, 3 H). | MS (MALDI): m/z = 312.2 ([M + H]$^+$). |
| i53 | 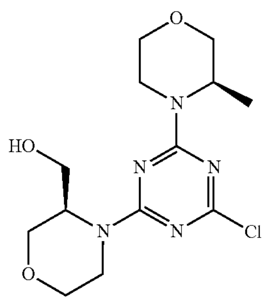 [SMILES: C[C@@H]1COCCN1c1nc(Cl)nc(N2CCOC[C@H]2CO)n1] | $^1$H NMR (400 MHz, (CD$_3$)$_2$SO): δ 4.65 (m, 1 H), 4.55 (m, 1 H), 4.32 (m, 1 H), 4.22 (m, 2 H), 3.98 (m, 1 H), 3.86 (m, 2 H), 3.63 (m, 2 H), 3.55 (m, 1 H), 3.49-3.34 (m, 4 H), 3.17 (m, 1 H), 3.12 (m, 1 H), 1.21 (d, $^3J_{H,H}$ = 6.9 Hz, 3 H). | MS (MALDI): m/z = 330.1 ([M + H]$^+$). |
| i82 | 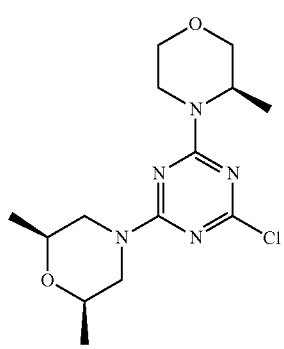 | $^1$H NMR (400 MHz, (CD$_3$)$_2$SO): δ 4.67-4.53 (m, 1 H), 4.45-4.34 (m, 2 H), 4.31-4.09 (m, 1 H), 3.88 (m, 1 H), 3.68 (m, 1 H), 3.55 (m, 3 H), 3.38 (m, 1 H), 3.13 (m, 1 H), 2.55 (m, 2 H), 1.20 (d, $^3J_{H,H}$ = 6.9 Hz, 3 H), 1.19 (d, $^3J_{H,H}$ = 6.9 Hz, 6 H). | MS (MALDI): m/z = 328.3 ([M + H]$^+$). |
| i85 | 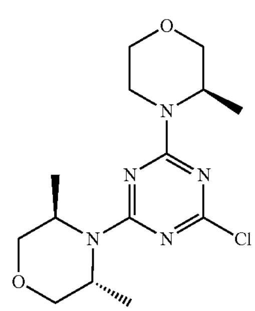 [SMILES: C[C@@H]1COCCN1c1nc(Cl)nc(N2[C@H](C)COC[C@H]2C)n1] | $^1$H NMR (400 MHz, (CD$_3$)$_2$SO): δ 4.53 (m, 1 H), 4.22 (m, 3 H), 4.11-4.08 (m, 2 H), 3.88 (m, 1 H), 3.66 (m, 3 H), 3.54 (m, 1 H), 3.36 (m, 1 H), 3.18 (m, 1 H), 1.33 (m, 6 H), 1.22 (d, $^3J_{H,H}$ = 6.9 Hz, 3 H) | MS (MALDI): m/z = 328.2 ([M + H]$^+$) |

-continued
| Reagent | Structure | NMR | MS |
|---|---|---|---|
| i86 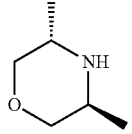 | 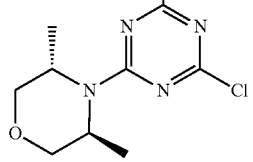 | ¹H NMR (400 MHz, (CD₃)₂SO): δ 4.55 (m, 1 H), 4.22-4.07 (m, 5 H), 3.88 (m, 1 H), 3.70-3.63 (m, 3 H), 3.54 (m, 1 H), 3.38 (m, 1 H), 3.19 (m, 1 H), 1.33 (m, 6 H), 1.21 (d, $^3J_{H,H}$ = 6.9 Hz, 3 H) | MS (MALDI): m/z = 328.5 ([M + H]⁺). |
| i92 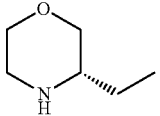 | 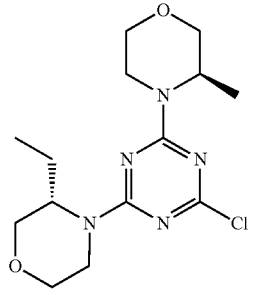 [SMILES: CC[C@H]1COCCN1c1nc(Cl)nc(N2CCOC[C@H]2C)n1] | ¹H NMR (400 MHz, (CD₃)₂SO): δ 4.54-4.15 (m, 4 H), 3.86 (m, 2 H), 3.77 (m, 1 H), 3.66 (m, 2 H), 3.55-3.46 (m, 2 H), 3.38 (m, 1 H), 3.14 (m, 2 H), 1.70 (m, 2 H), 1.22 (d, $3J_{H,H}$ = 6.9 Hz, 3 H), 0.86 (m, 3 H) | MS (MALDI): m/z = 328.6 ([M + H]⁺). |
| i93 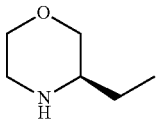 | 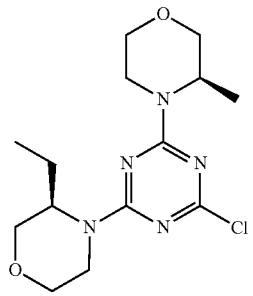 [SMILES: CC[C@@H]1COCCN1c1nc(Cl)nc(N2CCOC[C@H]2C)n1] | ¹H NMR (400 MHz, (CD₃)₂SO): δ 4.54-4.15 (m, 4 H), 3.86 (m, 2 H), 3.77 (m, 1 H), 3.66 (m, 2 H), 3.55-3.46 (m, 2 H), 3.38 (m, 1 H), 3.14 (m, 2 H), 1.70 (m, 2 H), 1.22 (d, $^3J_{H,H}$ = 6.9 Hz, 3H), 0.86 (m, 3 H) | MS (MALDI): m/z = 328.1 ([M + H]⁺). |
| i94 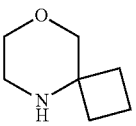 | 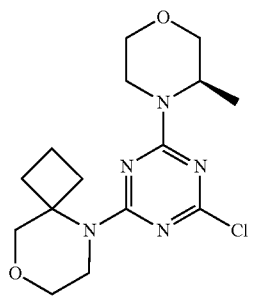 [SMILES: C[C@@H]1COCCN1c1nc(Cl)nc(N2CCOCC23CCC3)n1] | ¹H NMR (400 MHz, (CD₃)₂SO): δ 4.45 (m, 1 H), 4.11 (m, 1 H), 3.87 (m, 1 H), 3.66 (m, 5 H), 3.50 (m, 3 H), 3.38 (m, 1 H), 3.15 (m, 1 H), 2.44 (m, 2 H), 2.21 (m, 2 H), 1.70 (m, 2 H), 1.19 (d, $^3J_{H,H}$ = 6.9 Hz, 3 H) | MS (MALDI): m/z = 340.6 ([M + H]⁺). |

Method 17: 9-(4-chloro-6-(3,3-dimethylmor-pholino)-1,3,5-triazin-2-yl)-3,7-dioxa-9-azabicyclo[3.3.1]nonane (i54)

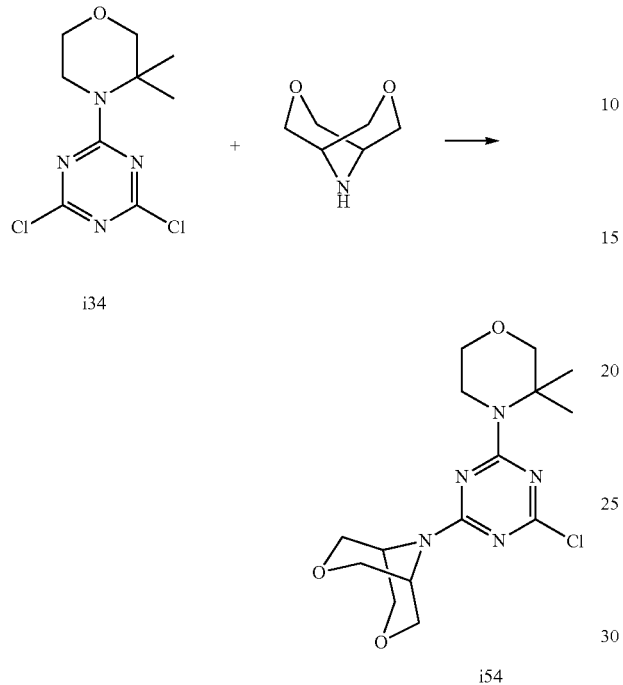

i34 i54

To a solution of 3,7-dioxa-9-azabicyclo[3.3.1]nonane (155 mg, 1.20 mmol, 1.05 eq.) and N,N-diisopropylethyl-amine (0.42 mL, 2.40 mmol, 2.1 eq.) in 1,4-dioxane (5 mL) a solution of i34 (300 mg, 1.14 mmol, 1 eq.) in 1,4-dioxane (1 mL) is added. The resulting mixture is heated for 2 hours (70° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO$_2$, cyclohexane/ethyl acetate 2:1 to 0:1) to afford the title compound i54 as a colorless solid (178 mg, 44%). $^1$H NMR (400 MHz, (CD$_3$)$_2$SO): δ 4.32 (m, 2H), 4.05-3.98 (m, 4H), 3.77 (m, 4H), 3.71 (m, 4H), 3.44 (m, 2H), 1.41 (s, 6H). MS (MALDI): m/z=356.3 ([M+H]$^+$).

Method 17 is also used for the preparation of the following intermediate compounds i55 to i64.

| | Reagent | Structure | NMR | MS |
|---|---|---|---|---|
| i55 | ![structure] | ![structure] | $^1$H NMR (400 MHz, (CD$_3$)$_2$SO): δ 4.36 (m, 2 H), 3.77-3.74 (m, 6 H), 3.55 (m, 2 H), 3.44 (m, 2 H), 1.44 (s, 6 H), 1.26 (d, $^3J_{H,H}$ = 6.9 Hz, 6 H). | MS (MALDI): m/z = 342.9 ([M + H]$^+$). |
| i56 | ![structure] | ![structure] | $^1$H NMR (400 MHz, (CD$_3$)$_2$SO): δ 4.52 (m, 1 H), 4.20 (m, 1 H), 3.90 (m, 2 H), 3.77 (m, 4 H), 3.65 (m, 1 H), 3.51-3.41 (m, 5 H), 3.28 (s, 3 H), 3.12 (m, 1 H), 1.44 (s, 3 H), 1.43 (s, 3 H). | |

| Reagent | Structure | NMR | MS |
|---|---|---|---|
| i57 | 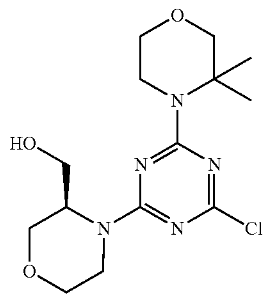 [SMILES: CC1(C)COCCN1c1nc(Cl)nc(N2CCOC[C@H]2CO)n1] | ¹H NMR (400 MHz, (CD₃)₂SO): δ 4.98 (m, 1 H), 4.35 (m, 1 H), 4.18 (m, 1 H), 4.00 (m 1 H), 3.87 (m, 1 H), 3.81-3.65 (m, 5 H), 3.51-3.35 (m, 5 H), 3.21-3.04 (m, 1 H), 1.44 (s, 3 H), 1.45 (s, 3 H). | MS (MALDI): m/z = 344.2 ([M + H]⁺). |
| i58 | 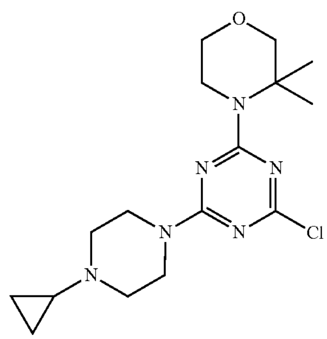 [SMILES: CC1(C)COCCN1c1nc(Cl)nc(N2CCN(C3CC3)CC2)n1] | ¹H NMR (400 MHz, (CD₃)₂SO): δ 3.77 (m, 4 H), 3.65 (m, 4 H), 3.44 (m, 2 H), 2.56 (m, 4 H), 1.64 (m, 1 H), 1.44 (s, 6 H), 0.44 (m, 2 H), 0.35 (m, 2 H). | MS (MALDI): m/z = 353.0 ([M + H]⁺). |
| i59 | 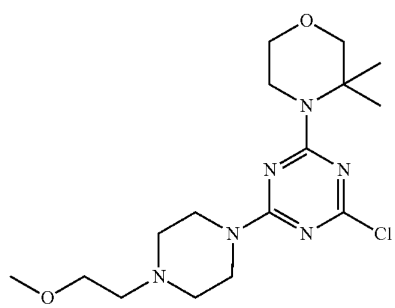 | ¹H NMR (400 MHz, (CD₃)₂SO): δ 3.76 (m, 4 H), 3.68 (m, 4 H), 3.47-3.44 (m, 4 H), 3.24 (m, 3 H), 2.52-2.45 (m, 6 H), 1.44 (s, 6 H). | MS (MALDI): m/z = 371.1 ([M + H]⁺). |

Method 18: 4-(difluoromethyl)pyridin-2-amine (i65)

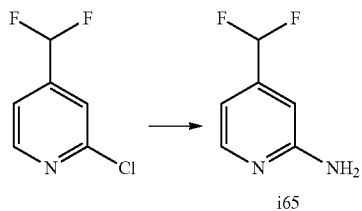

Palladium acetate (275 mg, 1.22 mmol, 0.05 eq.) and 2-dicyclohexylphosphino-2',4',6'-triisopropylbiphenyl (Sigma-Aldrich, product number 638064, 1.17 g, 2.45 mmol, 0.10 eq.) are dissolved in 1,4-dioxane (10 mL) under nitrogen atmosphere, and the resulting mixture is allowed to stir at room temperature for 45 minutes. This solution is then added to a mixture of tert-butylcarbamate (Sigma, product number 167398, 4.30 g, 36.7 mmol, 1.5 eq.), Cs₂CO₃ (15.9 g, 48.8 mmol, 2.0 eq.) and 2-chloro-4-difluoromethyl-pyridine (Manchester Organics, product number U15343, 4.00 g, 24.5 mmol, 1.0 eq.) in 1,4-dioxane (80 mL) under nitrogen atmosphere. The resulting reaction mixture is then heated at 90° C. for 3 hours, during which it turned brownish. After this time, the mixture is allowed to cool to room temperature. It is then diluted with ethyl acetate, washed with an aqueous saturated solution of ammonium chloride (2×30 mL) and deionized water. The organic layer is dried over anhydrous sodium sulfate, filtered and the solvent is evaporated under reduced pressure. The brownish residue is mixed with 4 M HCl in dioxane (50 mL, excess) and methanol (20 mL), and then heated at 80° C. for 45 minutes. Deionized water is added and the aqueous layer is washed with ethyl acetate (3×). The aqueous layer is then basified to pH=9, with solid sodium hydroxide. The aqueous layer is extracted with ethyl acetate (3×). The combined organic layer is dried over anhydrous sodium sulfate, filtered and concentrated to dryness under reduced pressure. The desired product i65 is obtained as a colorless solid, which is used in the next step without further purification (98% yield). ¹H NMR (400 MHz, CDCl₃): δ 8.16 (d, ²$J_{H,H}$=5.2 Hz, 1H), 6.74 (d, ²$J_{H,H}$=4.8 Hz, 1H), 6.59 (s, 1H), 6.51 (t, ²$J_{H,F}$=56 Hz, 1H), 4.61 (br s, 2H); ¹⁹F NMR (376 MHz, CDCl₃): δ −116.0 (s, 2 F).

Method 19: 5-bromo-4-(difluoromethyl)pyridin-2-amine (i66)

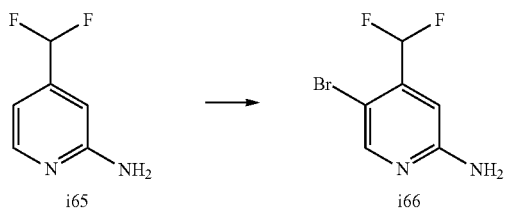 [SMILES: Nc1cc(C(F)F)ccn1 ; Nc1cc(C(F)F)c(Br)cn1]

To a solution of compound i65 (3.00 g, 20.8 mmol, 1.0 eq.) in tetrahydrofuran (60 mL) is added N-bromosuccinimide (3.89 g, 21.9 mmol, 1.05 eq.) at 0° C. in an ice bath. The resulting mixture is stirred overnight, while it is allowed to warm up to room temperature. Ethyl acetate is added and the organic layer is washed with aqueous sodium carbonate (8%). The organic layer is then separated and acidified with an aqueous 3 M HCl-solution. The aqueous layer is washed with ethyl acetate (3×50 mL) and then basified to pH=10, with solid sodium hydroxide. The aqueous layer is extracted with ethyl acetate (3×50 mL). The combined organic layer is dried over anhydrous sodium sulfate, filtered and concentrated to dryness under reduced pressure. The desired product i66 is obtained as a brownish solid, which is used in the next step without further purification (79% yield). $^1$H NMR (400 MHz, CDCl$_3$): δ 8.20 (s, 1H), 6.75 (s, 1H), 6.71 (t, $^2J_{H,F}$=54 Hz, 1H); 4.62 (br s, 2H); $^{19}$F NMR (376 MHz, CDCl$_3$): 5-118.9 (s, 2 F).

Method 20: N'-(5-bromo-4-(difluoromethyl)pyridin-2-yl)-N,N-dimethylformimidamide (i67)

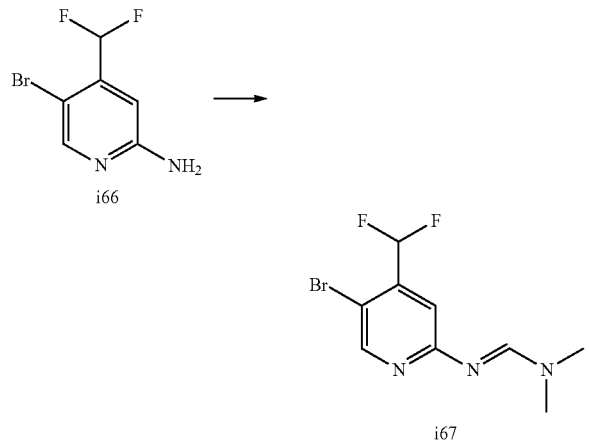

To a solution of compound i66 (3.68 g, 16.5 mmol, 1.0 eq.) in tetrahydrofuran (50 mL) is added N,N-dimethylformamide dimethyl acetal (Manchester Organics, product number 005030, 3.30 mL, 24.8 mmol, 1.5 eq.) and the resulting mixture is stirred at 60° C. for 3 hours. The mixture is allowed to cool to room temperature and the solvent is evaporated under reduced pressure. The crude product is purified by column chromatography on silica gel (cyclohexane/ethyl acetate 1:1) to afford the desired product i67 as a yellowish solid (82% yield). $^1$H NMR (400 MHz, CDCl$_3$): 38.43 (s, 1H), 8.34 (br s, 1H), 7.17 (s, 1H), 6.73 (t, $^2J_{H,F}$=54 Hz, 1H), 3.12 (s, 3H), 3.10 (s, 3H); $^{19}$F NMR (376 MHz, CDCl$_3$): δ –118.6 (s, 2 F); MS (MALDI): m/z=278.5 ([M+H]$^+$).

Method 21: N'-(4-(difluoromethyl)-5-(4,4,5,5-tetramethyl-1,3,2-dioxaborolan-2-yl)pyridin-2-yl)-N,N-dimethylformimidamide (i68)

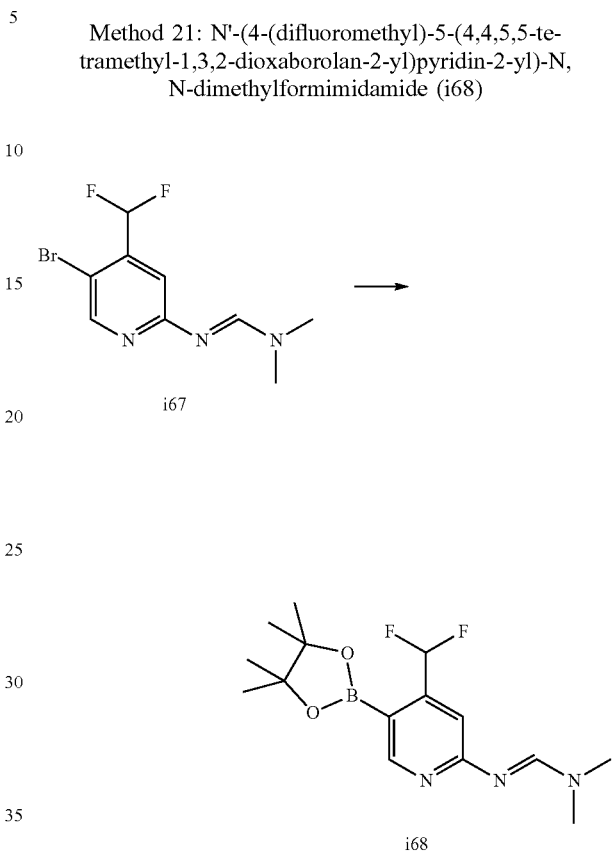

To a 2 M solution of isopropylmagnesium chloride (Sigma, product number 230111, 3.10 mL, 6.20 mmol, 1.15 eq.) in tetrahydrofuran (6 mL) is slowly added a solution of compound i67 (1.50 g, 5.39 mmol, 1.0 eq.) in tetrahydrofuran (5 mL) at 0° C. The resulting brownish mixture is stirred at 0° C. for 45 minutes and then at room temperature for 15 minutes. After this time, TLC monitoring (cyclohexane/ethyl acetate 1:1) showed complete consumption of starting material. 2-Isopropoxy-4,4,5,5-tetramethyl-1,3,2-dioxaborolane (Manchester Organics, product number W23343, 1.43 mL, 7.00 mmol, 1.3 eq.) is added and the mixture is heated at 60° C. for 3 hours. The mixture is then placed in an Erlenmeyer flask, cooled to 0° C. with an ice bath and quenched with a 15% aqueous solution of ammonium chloride. The layers are separated and the aqueous layer is extracted with ethyl acetate (3×40 mL). The combined organic layers are dried over anhydrous sodium sulfate, filtered and the solvent is evaporated under reduced pressure. Heptane is added and the organic layer is washed with a saturated aqueous solution of sodium bicarbonate, dried over anhydrous sodium sulfate, filtered and then concentrated to dryness under reduced pressure. The desired product i68 is obtained as a brownish oil, which is used in the next step without further purification (94% yield). $^1$H NMR (400 MHz, CDCl$_3$): δ 8.66 (s, 1H), 8.51 (s, 1H), 7.34-7.04 (m, 2H), 3.12 (s, 3H), 3.12 (s, 3H), 1.34 (s, 12H); $^{19}$F NMR (376 MHz, CDCl$_3$): δ –115.6 (s, 2 F); MS (MALDI): m/z=326.0 ([M+H]$^+$).

Method 22: 4-(difluoromethyl)pyrimidin-2-amine (i69)

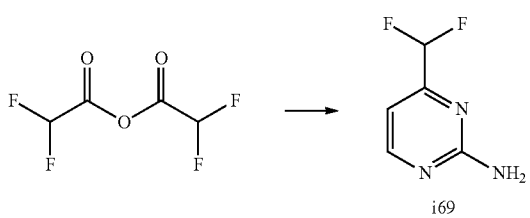 [SMILES: O=C(OC(=O)C(F)F)C(F)F ; Nc1nccc(C(F)F)n1]

To a solution of ethyl vinyl ether (4.00 mL, 41.8 mmol, 1.0 eq.) in a mixture of pyridine (4.10 mL, 50.7 mmol, 1.2 eq.) and dichloromethane (40 mL), is added dropwise a solution of 2,2-difluoroacetic anhydride (Manchester Organics, (product number L24754, 5.90 mL, 50.1 mmol, 1.2 eq.) in dichloromethane (5 mL) at −70° C. in a dry ice/isopropanol bath. The resulting solution is allowed to warm up to room temperature overnight. The mixture is then washed with deionized water, dried over anhydrous sodium sulfate, filtered and the solvent is evaporated under reduced pressure to afford an orange oil.

At the same time, a suspension of guanidine·HCl (Sigma, product number 50940, 4.80 g, 50.2 mmol, 1.2 eq.) in ethanol (20 mL) is stirred at room temperature for 1 hour. To this solution are added sodium hydroxide pellets (2.00 g, 50.0 mmol, 1.2 eq.) in one portion. The resulting suspension is stirred at room temperature overnight.

The orange oil is diluted with dichloromethane (20 mL) and added dropwise over 1 hour to the ethanol suspension. The resulting suspension is stirred at room temperature for 2 hours. Dichloromethane is evaporated under reduced pressure. Deionized water (25 mL) is added to the residue. The resulting mixture is stirred vigorously for 2 hours and is then allowed to stand at room temperature overnight. The formed solid is filtered off, washed with deionized water (2×) and heptane (1×) and then dried in vacuo. The desired product i69 is obtained as a colorless solid (65% yield). $^1$H NMR (400 MHz, CDCl$_3$): δ 8.43 (d, $^2J_{H,H}$=4.8 Hz, 1H), 7.02 (br s, 2H), 6.76 (d, $^2J_{H,H}$=5.2 Hz, 1H), 6.67 (t, $^2J_{H,F}$=55 Hz, 1H); $^{19}$F NMR (376 MHz, CDCl$_3$): δ −120.5 (s, 2 F).

Method 23: 5-bromo-4-(difluoromethyl)pyrimidin-2-amine (i70)

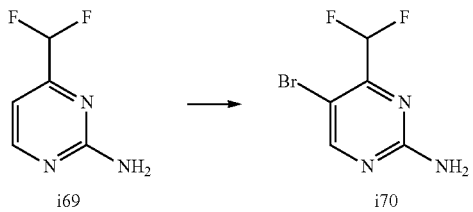 [SMILES: Nc1nccc(C(F)F)n1 ; Nc1ncc(Br)c(C(F)F)n1]

To a solution of compound i69 (3.00 g, 20.7 mmol, 1.0 eq.) in tetrahydrofuran (90 mL) is added N-bromosuccinimide (3.86 g, 21.7 mmol, 1.0 eq.) portionwise at 0° C. The reaction mixture is allowed to warm up to room temperature overnight. After this time, the solvent is evaporated under reduced pressure. The residue is taken up in ethyl acetate (200 mL), washed with an aqueous saturated solution of sodium carbonate (4×), dried over anhydrous sodium sulfate, filtered and then concentrated to dryness under reduced pressure. The desired product i70 is obtained as a yellowish solid, which is used in the next step without further purification (98% yield). $^1$H NMR (400 MHz, (CD$_3$)$_2$SO): δ 8.50 (s, 1H), 7.30 (br s, 2H), 6.87 (t, $^2J_{H,F}$=53 Hz, 1H); $^{19}$F NMR (376 MHz, (CD$_3$)$_2$SO): δ −121.4 (s, 2 F).

Method 24: N-tert-butyl carboxylate-N-(5-bromo-4-(difluoromethyl)pyrimidin-2-yl)-carbamate (i71)

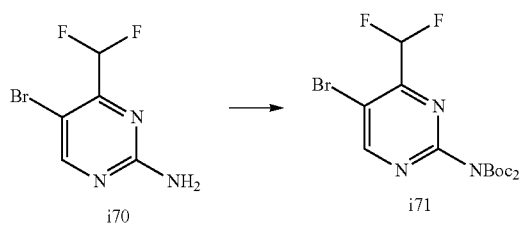

Compound i70 (4.35 g, 19.4 mmol, 1.0 eq.) and 4-(dimethylamino)pyridine (480 mg, 3.92 mmol, 0.20 eq.) are dissolved in tetrahydrofuran (50 mL). N,N-Diisopropylethylamine (7.50 mL, 42.1 mmol, 2.2 eq.) and di-tert-butyl dicarbonate (9.33 g, 42.7 mmol, 2.2 eq.) are then added at 0° C. and the resulting solution is allowed to warm up to room temperature overnight. The solvent is evaporated under reduced pressure. The crude product is purified by column chromatography on silica gel (cyclohexane/ethyl acetate 9:1→4:1) to afford the desired product i71 as a colorless solid (85% yield).

$^1$H NMR (400 MHz, CDCl$_3$): δ 8.92 (s, 1H), 6.73 (t, $^2J_{H,F}$=53 Hz, 1H), 1.47 (s, 18H); $^{19}$F NMR (376 MHz, CDCl$_3$): δ −120.4 (s, 2 F).

General Procedure 1:

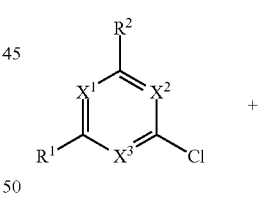

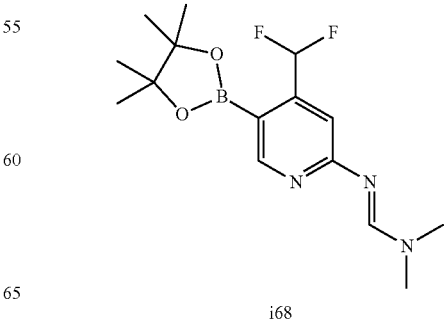

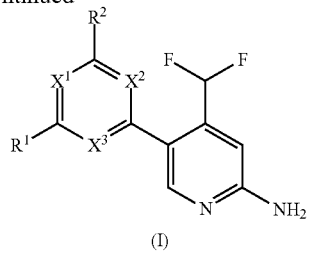

Substituted monochloro-triazine or substituted monochloro-pyrimidine (1.0 eq.), compound i68 (1.1 eq.), potassium phosphate tribasic (2.0 eq.) and chloro(2-dicyclohexylphosphino-2',4',6'-triisopropyl-1,1'-biphenyl) [2-(2'-amino-1,1'-biphenyl)]-palladium(II) (Sigma-Aldrich, product number 741825, 0.05 eq.) are charged in a flask. Under nitrogen atmosphere, 1,4-dioxane (30 volumes) and deionized water (1.5 volume) are added and the resulting mixture is then directly placed into an oil bath pre-heated at 95° C. The reaction mixture is stirred at this temperature for 2 hours. A 5 M aqueous HCl-solution (20 eq.) is added. The resulting mixture is heated to 60° C. overnight. The pH of the resulting mixture is adjusted to 8-9 by addition of a 2 M aqueous solution of sodium hydroxide, the mixture is then extracted with ethyl acetate (3×20 volumes). The combined organic layers are dried over anhydrous sodium sulfate, filtered and the solvent is evaporated under reduced pressure. Purification by flash chromatography affords the desired products of structure (I).

General Procedure 2:

Compound i71 (1.0 eq.), 4,4,4',4',5,5,5',5'-octamethyl-2,2'-bi(1,3,2-dioxaborolane) (Manchester Organics, product number M23170, 1.5 eq.), potassium acetate (3.0 eq.) and [1,1'-bis(diphenylphosphino)-ferrocene]-dichloropalladium (II) (Sigma-Aldrich, product number 697230, 0.099 eq.) are dissolved in 1,4-dioxane (12.5 volumes) under nitrogen atmosphere. The resulting mixture is heated at 100° C. for 15 minutes (solution turned black). TLC monitoring (cyclohexane/ethyl acetate 3:1) is used to show complete consumption of starting material.

To the resulting mixture, substituted chloro-triazine or substituted chloropyrimidine (1.1 eq.), an aqueous solution of potassium carbonate (2 M, 3.0 eq.) and a previously mixed solution of triphenylphosphine (0.12 eq.) and palladium acetate (0.04 eq.) in tetrahydrofuran (100 volumes) are added. The resulting mixture is heated at 60° C. for 2 hours and subsequently allowed to cool to room temperature.

A 5 M aqueous HCl-solution (20 eq.) is added. The resulting mixture is heated to 60° C. overnight. The pH of the resulting mixture is adjusted to 8-9 by addition of a 2 M aqueous solution of sodium hydroxide, the mixture is then extracted with ethyl acetate (3×20 volumes). The combined organic layers are dried over anhydrous sodium sulfate, filtered and the solvent is evaporated under reduced pressure. Purification by flash chromatography affords the desired products.

Method 27: tert-butyl N-tert-butoxycarbonyl-N-(5-(4-chloro-6-morpholino-1,3,5-triazin-2-yl)-4-(difluoromethyl)pyrimidin-2-yl)carbamate (i74)

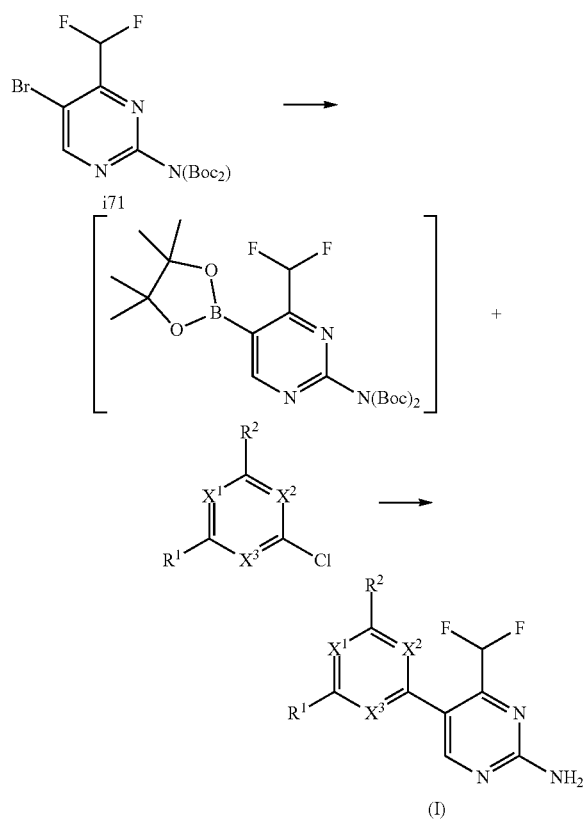

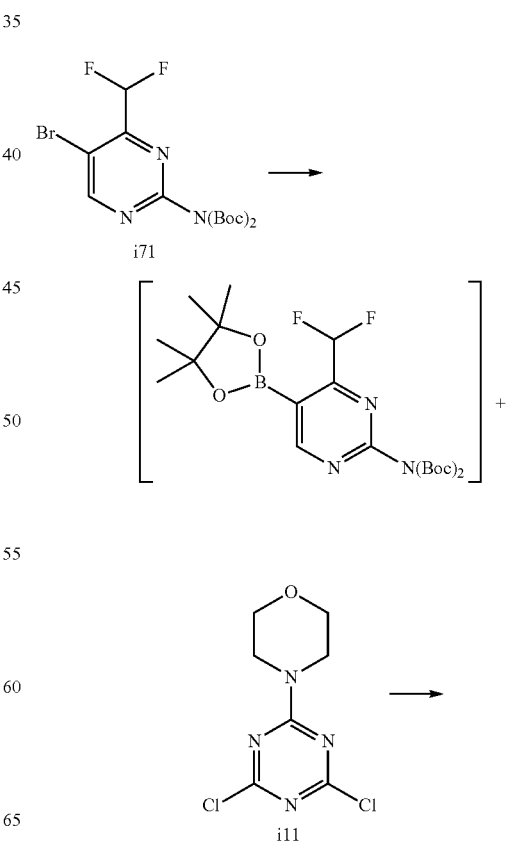

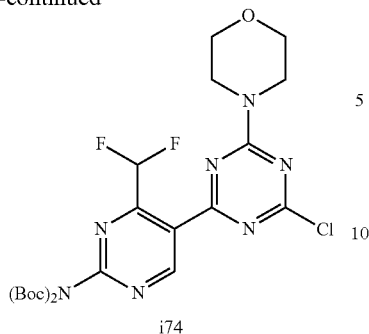

Intermediate i71 (2.00 g, 4.71 mmol, 1.0 eq.), bis(pinacolato)diboron (1.80 g, 7.09 mmol, 1.5 eq.), KOAc (1.60 g, 16.3 mmol, 3.4 eq.) and [1,1'-bis(diphenylphosphino)ferrocene]-dichloropalladium(II) (350 mg, 478 µmol, 0.10 eq.) are mixed in 1,4-dioxane under nitrogen atmosphere and heated at 95° C. for 45 minutes. A pre-catalyst solution of palladium(II) acetate (43.0 mg, 192 µmol, 0.04 eq.) and triphenylphosphine 148 mg, 564 µmol, 0.12 eq.) in tetrahydrofuran (2 mL) is also prepared and stirred at room temperature for 1 hour. This solution is then added to the cooled above solution at room temperature, followed by the addition of 4-(4,6-dichloro-1,3,5-triazin-2-yl)morpholine i11 (1.65 g, 7.05 mmol, 1.5 eq.) and aqueous $K_2CO_3$-solution (2.4 M, 5.90 mL, 14.2 mmol, 3.0 eq.). The resulting mixture is heated at 55° C. overnight. After this time, the mixture is poured onto an aqueous $NH_4Cl$-solution (15%) and extracted with ethyl acetate (3×). The combined organic layer is dried over anhydrous sodium sulfate, filtered and concentrated under reduced pressure. Purification by column chromatography on silica gel (cyclohexane/ethyl acetate 1:0 to 4:1) gives product i74 as a colorless solid (36% yield).

$^1$H NMR (400 MHz, CDCl$_3$): δ 9.57 (s, 1H), 7.55 (t, $^2J_{H,F}$=54 Hz, 1H), 3.99-3.91 (m, 4H), 3.84-3.76 (m, 4H), 1.49 (s, 18H); $^{19}$F NMR (376 MHz, CDCl$_3$): δ -121.0 (s, 2 F).

Method 32: (E)-4-ethoxy-1,1-difluoro-but-3-en-2-one (i83)

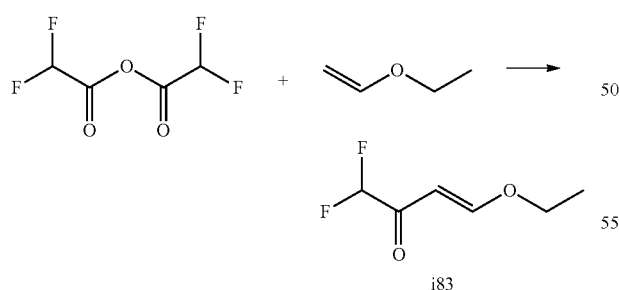

To a cooled (-70° C.) solution of pyridine (61.5 mL, 760.5 mmol, 1.2 eq) in dichloromethane (500 mL) is added ethyl vinyl ether (60 mL, 626.5 mmol, 1 eq), followed by a solution of difluoroacetic anhydride (88.5 mL, 760.5 mmol, 1.2 eq) in dichloromethane (75 mL). Then the mixture is slowly warmed to room temperature overnight. The mixture is transferred into a separating funnel and the organic layer is washed with water (6×800 mL) until the pH of the aqueous layer becomes neutral. The organic layer is dried over sodium sulfate and solvent is removed under reduced pressure to afford the desired product i83 as an orange oil (76.7 g, 81%). $^1$H NMR (400 MHz, (CD$_3$)$_2$SO): δ 7.92 (d, $^3J_{H,H}$=12.5 Hz, 1H), 6.34 (t, $^2J_{H,F}$=53.6 Hz, 1H), 5.87 (d, $^3J_{H,H}$=12.5 Hz, 1H), 4.14 (q, $^3J_{H,H}$=7.1 Hz, 2H), 1.28 (t, $^3J_{H,H}$=7.1 Hz, 3H); $^{19}$F NMR (400 MHz, (CD$_3$)$_2$SO): δ -127.39 (s, 2F).

Method 33: (E)-3-(difluoromethyl)-5-ethoxy-3-hydroxy-pent-4-enenitrile (i84)

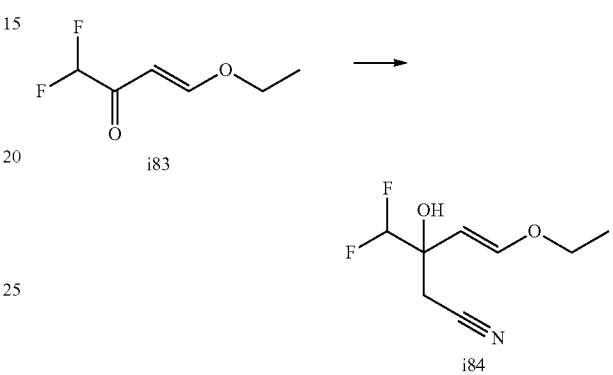

To a cooled (-70° C.) solution of n-butyl lithium 2.5M (102.9 mL, 256.7 mmol, 1 eq) in tetrahydrofuran (435 mL) is added acetonitrile (13.4 mL, 256.7 mmol, 1 eq). A white suspension is formed and is stirred at -70° C. for 1.5 hours. A solution of (E)-4-ethoxy-1,1-difluoro-but-3-en-2-one (i83) (38.5 g, 256.7 mmol, 1 eq) in tetrahydrofuran (65 mL) is added to the white suspension (mixture becomes an orange solution). The mixture is stirred at -70° C. for 1 hour and slowly warmed to room temperature. Water (400 mL) is added. Then ethyl acetate (600 mL) is added. Layers are separated and aqueous layer is extracted with ethyl acetate (3×600 mL). Combined organic layers are dried over sodium sulfate and solvent is evaporated under reduced pressure. Filtration on a short pad of silica gel, using a mixture of cyclohexane/ethyl acetate (3:1) as eluent, gives the desired product i84 as a dark orange oil (43.4 g, 88%). $^1$H NMR (400 MHz, (CD$_3$)$_2$SO): δ 6.66 (d, $^3J_{H,H}$=12.8 Hz, 1H), 6.20 (s, 1H), 5.79 (t, $^2J_{H,F}$=55.8 Hz, 1H), 4.75 (d, $^3J_{H,H}$=12.8 Hz, 1H), 3.74 (q, $^3J_{H,H}$=7.0 Hz, 2H), 2.88 (d, $^3J_{H,H}$=16.8 Hz, 1H), 2.81 (d, $^3J_{H,H}$=16.8 Hz, 1H), 1.21 (t, $^3J_{H,H}$=7.0 Hz, 3H); $^{19}$F NMR (400 MHz, (CD$_3$)$_2$SO): δ -129.32 (d, $^2J_{F,F}$=311.2 Hz, 1F), -130.05 (d, $^2J_{F,F}$=311.2 Hz, 1F).

Method 34: 4-(difluoromethyl)pyridin-2-amine (i65)

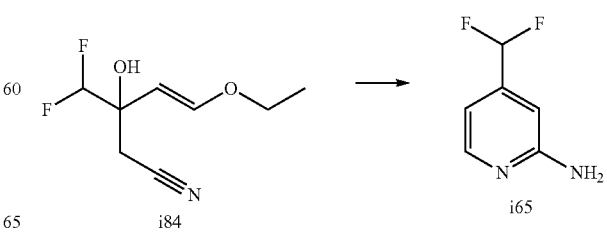

To a solution of (E)-3-(difluoromethyl)-5-ethoxy-3-hydroxy-pent-4-enenitrile (i84) (8.1 g, 42.4 mmol, 1 eq) in acetic acid (80 mL) is added O-methylhydroxylamine hydrochloride (Fluorochem, product number 078603) (10.6 g, 127.2 mmol, 3 eq). Mixture is stirred at 50° C. for 7 hours. Then reaction mixture is cooled down to room temperature and hydrobromic acid in acetic acid (33%) (14.2 mL, 84.8 mmol, 2 eq) is added. Reaction mixture is stirred at 90° C. overnight. Reaction mixture is degassed and placed under nitrogen. Reaction mixture is maintained at room temperature with a water bath with ice while zinc powder (8.12 g, 127.2 mmol, 3 eq) is added portionwise. Reaction mixture is stirred 3 h at room temperature. Mixture is filtered over a short pad of celite and the cake is washed with ethyl acetate. Then the major part of the solvent is removed under reduced pressure. 60 mL of aqueous ammonium hydroxide (28%) is added. Aqueous layer is extracted with dichloromethane (3×150 mL). Combined organic layers are dried over sodium sulfate. Compound i65 is recrystallized from dichloromethane and heptane as anti-solvent (solvent switch at the rotavap). Compound i65 is collected, as a light yellow solid, by filtration (5.12 g, 84%).

Method 35: 9-[4-chloro-6-(3-oxa-9-azabicyclo[3.3.1]nonan-9-yl)-1,3,5-triazin-2-yl]-3,7-dioxa-9-azabicyclo[3.3.1]nonane (i89)

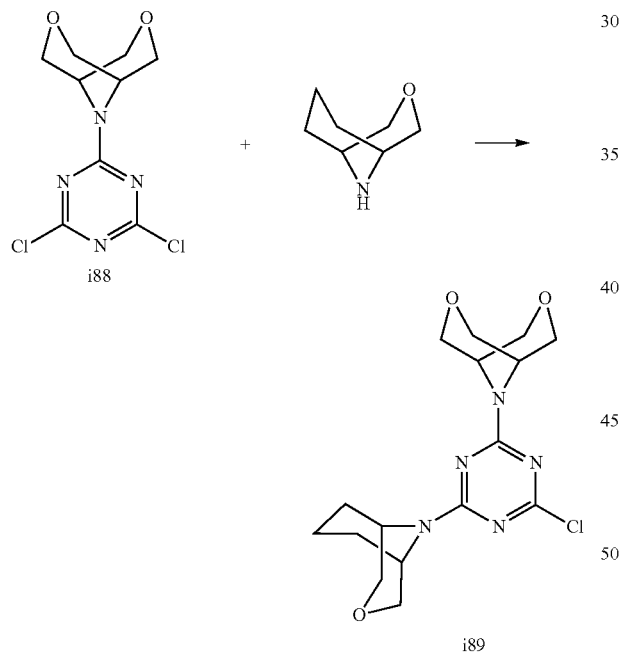

To a solution of 3-oxa-9-azabicyclo[3.3.1]nonane hydrochloride (176 mg, 1.20 mmol, 1.05 eq.) and N,N-diisopropylethylamine (0.42 mL, 2.40 mmol, 2.1 eq.) in 1,4-dioxane (5 mL) a solution of i88 (300 mg, 1.14 mmol, 1 eq.) in 1,4-dioxane (1 mL) is added. The resulting mixture is heated for 3 hours (75° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO$_2$, cyclohexane/ethyl acetate 2:1 to 0:1) to afford the title compound i89 as a colorless solid (297 mg, 75%). $^1$H NMR (400 MHz, (CD$_3$)$_2$SO): δ 4.58 (m, 1H), 4.44 (m, 1H), 4.40 (m, 1H), 4.32 (m, 1H), 4.00-3.97 (m, 4H), 3.94-3.90 (m, 2H), 3.72-3.64 (m, 6H), 2.46 (m, 1H), 1.90-1.70 (m, 4H), 1.53 (m, 1H). MS (MALDI): m/z=368.0 ([M+H]$^+$).

Preparation of Compounds of the Invention

Compound 1: 4-(difluoromethyl)-5-(4,6-dimorpholino-1,3,5-triazin-2-yl)pyridin-2-amine (1)

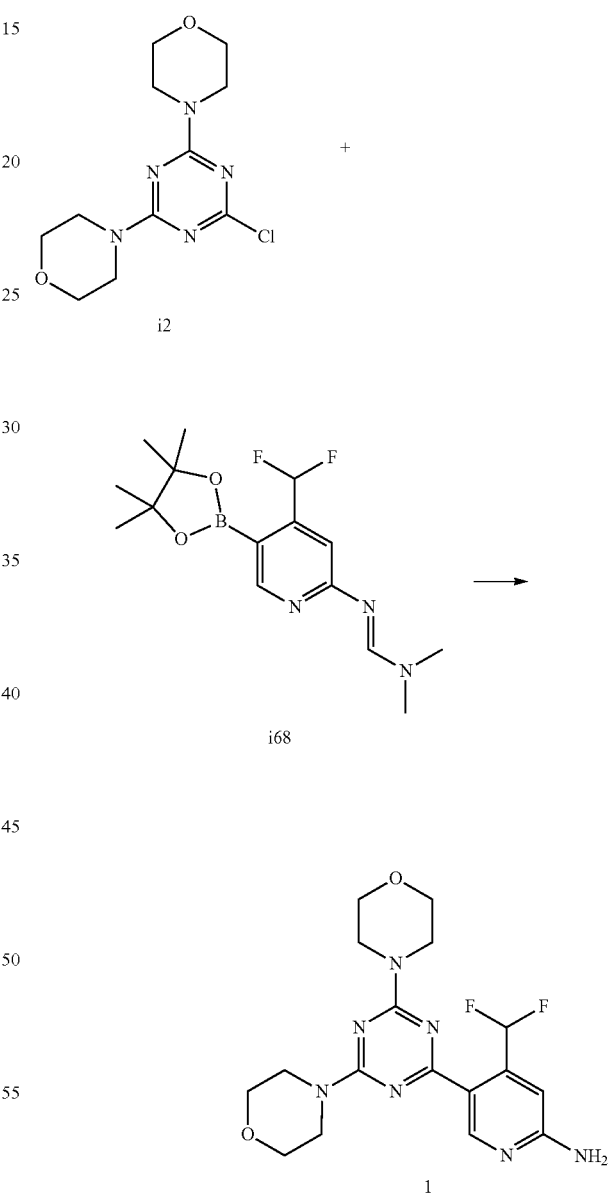

According to general procedure 1, compound 1 is obtained from starting materials i2 and i68 in 73% yield as a colorless solid. $^1$H NMR (400 MHz, CDCl$_3$): δ 9.02 (s, 1H), 7.65 (t, $^2$J$_{H,F}$=55 Hz, 1H), 6.83 (s, 1H), 4.85 (br s, 2H), 3.89-3.79 (m, 8H), 3.77-3.72 (m, 8H); $^{19}$F NMR (376 MHz, CDCl$_3$): δ −115.9 (s, 2 F); MS (MALDI): m/z=393.9 ([M+H]$^+$).

Compound 2: 4-(difluoromethyl)-5-(4,6-dimorpholino-1,3,5-triazin-2-yl)pyrimidin-2-amine (2)

Compound 3: 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine (3)

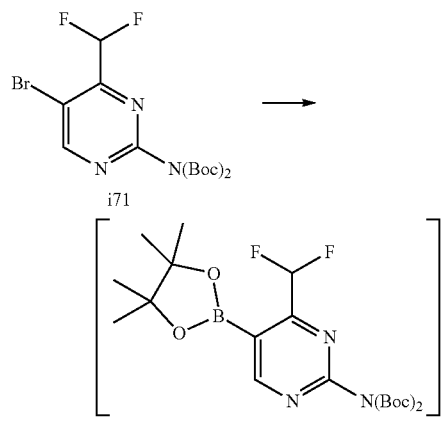

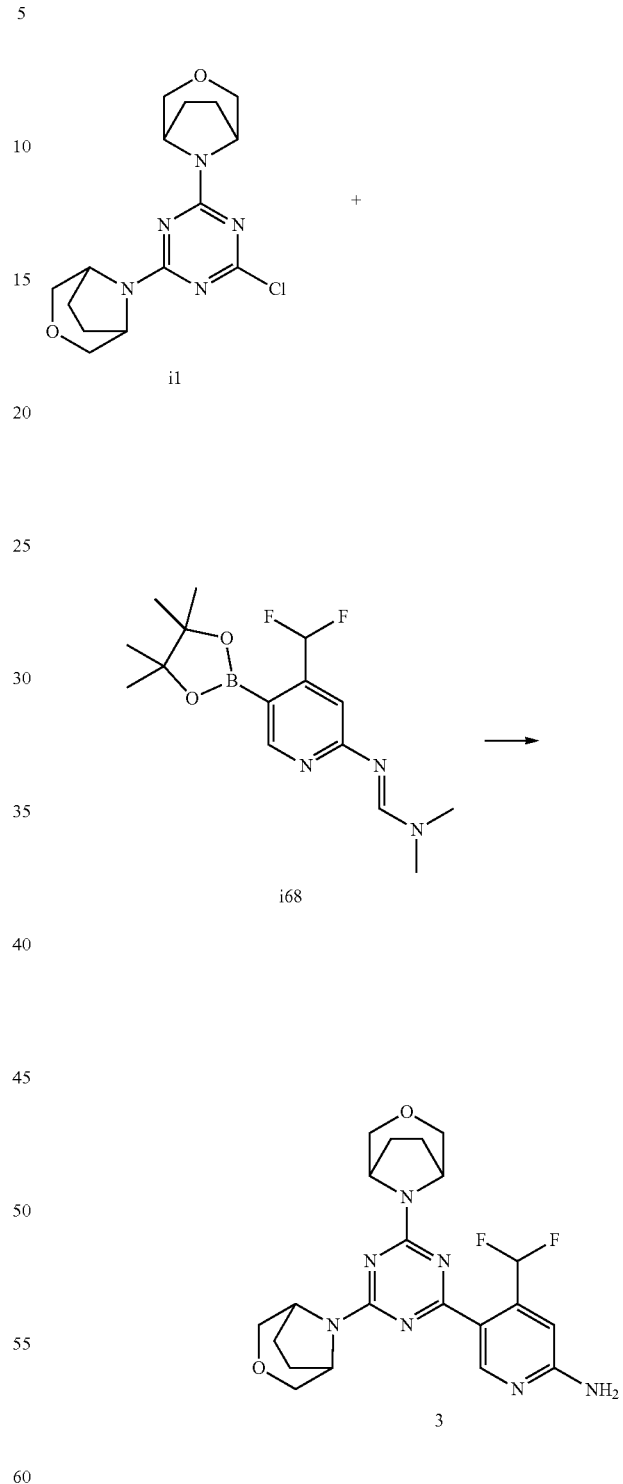

According to general procedure 2, compound 2 is obtained from starting materials i2 and i71 in 74% yield as a colorless solid. $^1$H NMR (400 MHz, CDCl$_3$): δ 9.20 (s, 1H), 7.62 (t, $^2J_{H,F}$=54 Hz, 1H), 5.97 (br s, 2H), 3.91-3.68 (m, 16H); $^{19}$F NMR (376 MHz, CDCl$_3$): δ −121.5 (s, 2 F); MS (MALDI): m/z=395.2 ([M+H]$^+$).

According to general procedure 1, compound 3 is obtained from starting materials i1 and 168 in 75% yield as a colorless solid. $^1$H NMR (400 MHz, CDCl$_3$): δ 9.04 (s, 1H), 7.71 (t, $^2J_{H,F}$=55 Hz, 1H), 6.83 (s, 1H), 4.89 (br s, 2H), 4.71-4.64 (m, 4H), 3.79-3.76 (m, 4H), 3.67-3.62 (m, 4H), 2.09-1.98 (m, 8H); $^{19}$F NMR (376 MHz, CDCl$_3$): δ −115.4 (−117.3) (m, 2 F); MS (MALDI): m/z=446.3 ([M+H]$^+$).

111

Compound 4: 5-(4-(3-oxa-8-azabicyclo[3.2.1]octan-8-yl)-6-morpholino-1,3,5-triazin-2-yl)-4-(difluoromethyl)pyridin-2-amine (4)

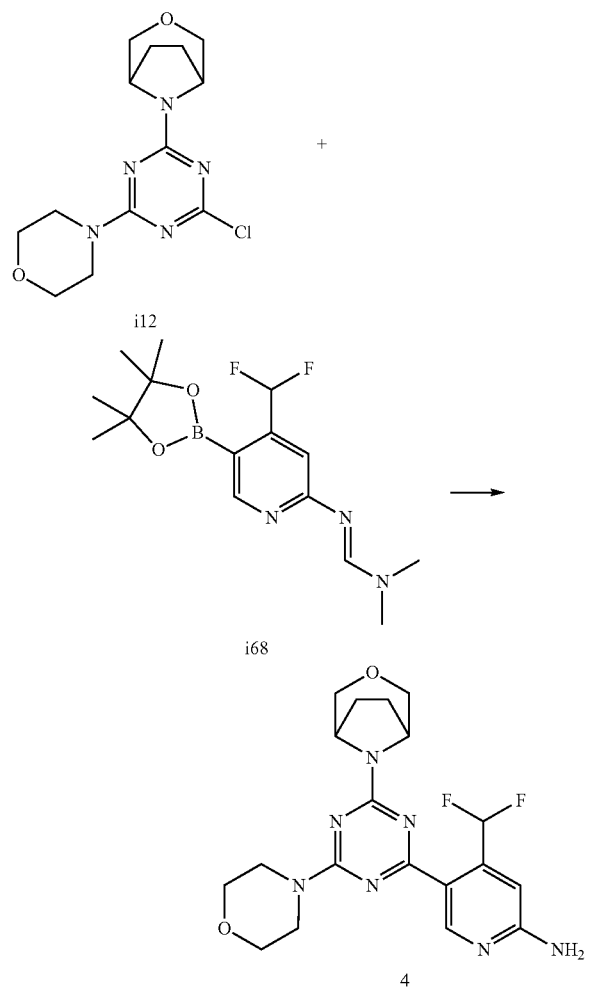

According to general procedure 1, compound 4 is obtained from starting materials i12 and i68 in 57% yield as a colorless solid. $^1$H NMR (400 MHz, CDCl$_3$): δ 9.03 (s, 1H), 7.68 (m, 1H), 6.83 (s, 1H), 4.94 (br s, 2H), 4.70-4.65 (m, 2H), 3.93-3.57 (m, 12H), 2.14-1.92 (m, 4H); $^{19}$F NMR (376 MHz, CDCl$_3$): δ −116.0 (−116.2) (m, 2 F); MS (MALDI): m/z=420.6 ([M+H]$^+$).

Compound 5: 5-(4-(3-oxa-8-azabicyclo[3.2.1]octan-8-yl)-6-morpholino-1,3,5-triazin-2-yl)-4-(difluoromethyl)pyrimidin-2-amine (5)

112

-continued

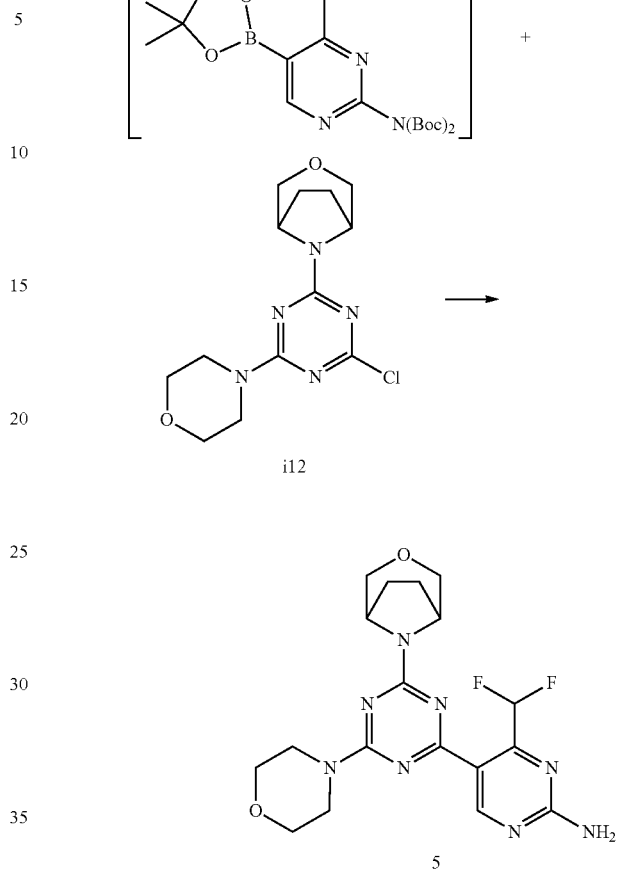

According to general procedure 2, compound 5 is obtained from starting materials i71 and i12 in 50% yield as a colorless solid. $^1$H NMR (400 MHz, CDCl$_3$): δ 9.23 (s, 1H), 7.65 (t, $^2J_{H,F}$=54 Hz, 1H), 5.66 (br s, 2H), 4.68 (m, 2H), 3.90-3.61 (m, 12H), 2.13-1.92 (4H); $^{19}$F NMR (376 MHz, CDCl$_3$): δ −120.4 (−121.5) (m, 2 F); MS (MALDI): m/z=420.9 ([M+H]$^+$).

Compound 6: 5-(4,6-bis((S)-3-methylmorpholino)-1,3,5-triazin-2-yl)-4-(difluoromethyl)pyridin-2-amine (6)

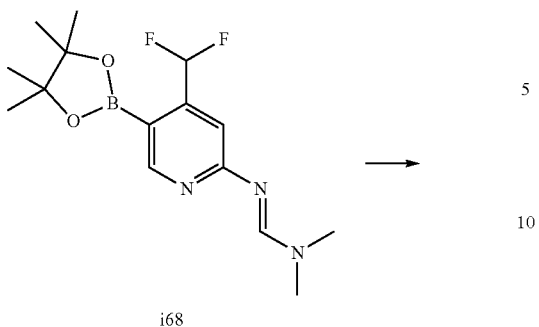

i68

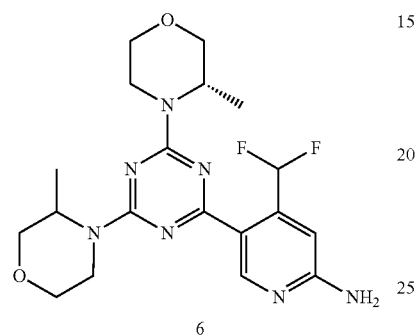

6

According to general procedure 1, compound 6 is obtained from starting materials i3 and i68 in 79% yield as a colorless solid. $^1$H NMR (400 MHz, CDCl$_3$): δ 8.87 (s, 1H), 7.70 (t, $^2J_{H,F}$=55 Hz, 1H), 6.86 (s, 1H), 5.48 (br s, 2H), 4.73-4.72 (m, 2H), 4.41-4.38 (m, 2H), 3.98 (dd, $J_{H,H}$=11.6, 3.8 Hz, 2H), 3.78 (d, $J_{H,H}$=12 Hz, 2H), 3.67 (dd, $J_{H,H}$=12, 3.2 Hz, 2H), 3.52 (td, $J_{H,H}$=12, 3.0 Hz, 2H), 3.27 (td, $J_{H,H}$=13, 3.8 Hz, 2H), 1.33 (d, $^3J_{H,H}$=6.8 Hz, 6H); $^{19}$F NMR (376 MHz, CDCl$_3$): δ −115.4 (−116.2) (m, 2 F); MS (MALDI): m/z=421.9 ([M+H]$^+$).

Compound 7: 5-(4,6-bis((S)-3-methylmorpholino)-1,3,5-triazin-2-yl)-4-(difluoromethyl)pyrimidin-2-amine (7)

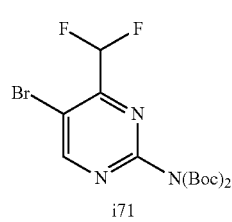

i71

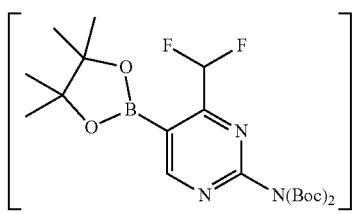

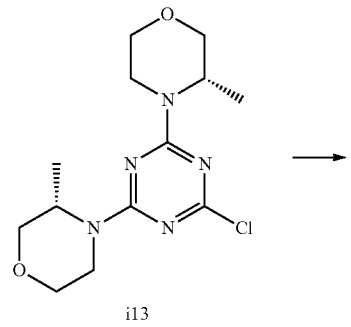

i13

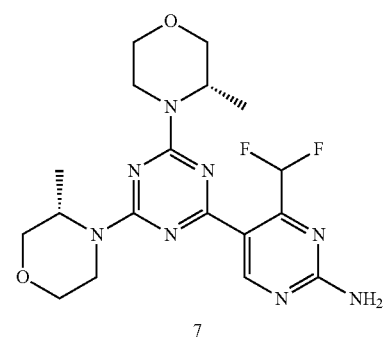

7

According to general procedure 2, compound 7 is obtained from starting materials i71 and i3 in 52% yield as a colorless solid. $^1$H NMR (400 MHz, CDCl$_3$): δ 9.24 (s, 1H), 7.66 (t, $^2J_{H,F}$=54 Hz, 1H), 5.77 (br s, 2H), 4.73 (br s, 2H), 4.45-4.32 (m, 2H), 3.98 (dd, $J_{H,H}$=12, 3.6 Hz, 2H), 3.78 (d, $J_{H,H}$=12 Hz, 2H), 3.67 (dd, $J_{H,H}$=11, 2.8 Hz, 2H), 3.52 (td, $J_{H,H}$=12, 2.8 Hz, 2H), 3.27 (td, $J_{H,H}$=13, 3.2 Hz, 2H), 1.33 (d, $^3J_{H,H}$=6.8 Hz, 6H); $^{19}$F NMR (376 MHz, CDCl$_3$): δ −120.5 (−122.7) (m, 2 F); MS (MALDI): m/z=423.3 ([M+H]$^+$).

Compound 8: (S)-4-(difluoromethyl)-5-(4-(3-methylmorpholino)-6-morpholino-1,3,5-triazin-2-yl)pyridin-2-amine (8)

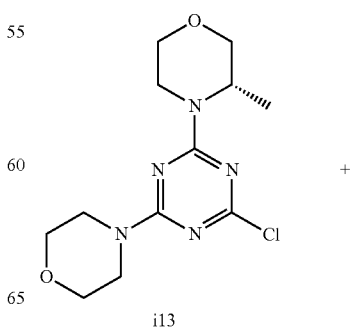

i13

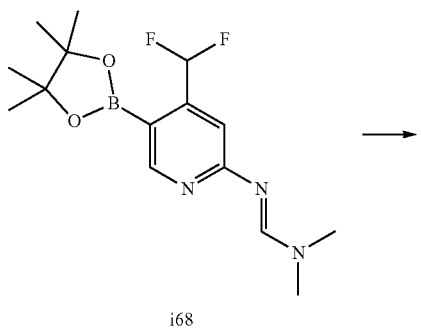

i68

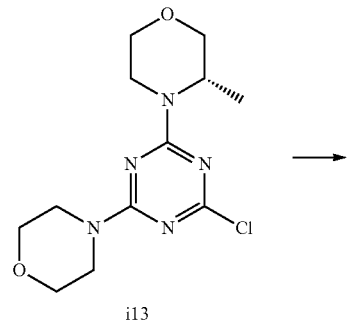

i13

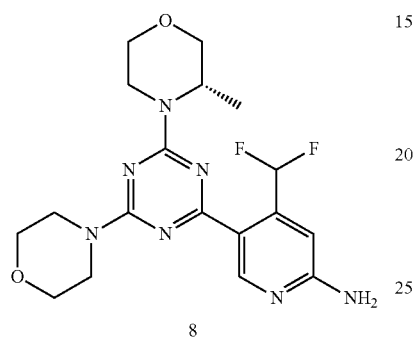

8

According to general procedure 1, compound 8 is obtained from starting materials i13 and i68 in 47% yield as a colorless solid. $^1$H NMR (400 MHz, CDCl$_3$): δ 9.03 (s, 1H), 7.70 (t, $^2J_{H,F}$=55 Hz, 1H), 6.84 (s, 1H), 4.78 (br s, 2H), 4.75 (m, 1H), 4.42-4.38 (m, 1H), 4.00-3.96 (m, 1H), 3.84-3.66 (m, 10H), 3.55-3.50 (m, 1H), 3.30-3.25 (m, 1H), 1.33 (d, $^3J_{H,H}$=6.8 Hz, 3H); $^{19}$F NMR (376 MHz, CDCl$_3$): δ −116.1 (−115.9) (m, 2 F); MS (MALDI): m/z=408.9 ([M+H]$^+$).

Compound 9: (S)-4-(difluoromethyl)-5-(4-(3-methylmorpholino)-6-morpholino-1,3,5-triazin-2-yl)pyrimidin-2-amine (9)

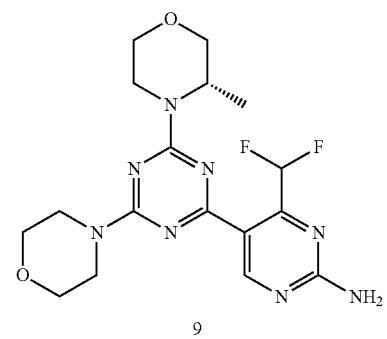

9

According to general procedure 2, compound 9 is obtained from starting materials i71 and i13 in 60% yield as a colorless solid. $^1$H NMR (400 MHz, CDCl$_3$): δ 9.24 (s, 1H), 7.66 (t, $^2J_{H,F}$=54 Hz, 1H), 5.67 (br s, 2H), 4.74 (m, 1H), 4.41-4.38 (m, 1H), 4.00-3.97 (m, 1H), 3.90-3.72 (m, 9H), 3.68-3.36 (m, 1H), 3.56-3.49 (m, 1H), 3.32-3.25 (m, 1H), 1.33 (d, $^3J_{H,H}$=6.9 Hz, 3H); $^{19}$F NMR (376 MHz, CDCl$_3$): δ −121.3 (−121.6)(m, 2F); MS (MALDI): m/z=409.4 ([M+H]$^+$).

Compound 10: 5-(4-(3-oxa-8-azabicyclo[3.2.1]octan-8-yl)-6-((S)-3-methylmorpholino)-1,3,5-triazin-2-yl)-4-(difluoromethyl)pyridin-2-amine (10)

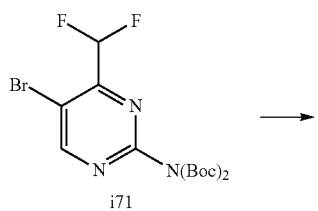

i71

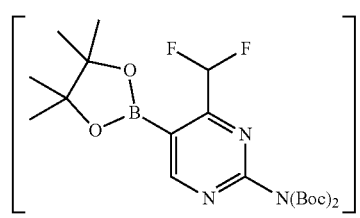

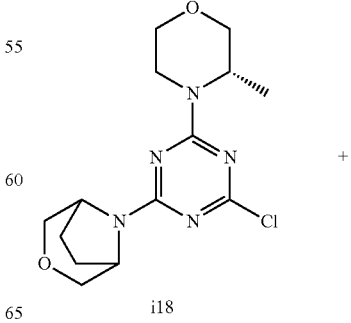

i18

+

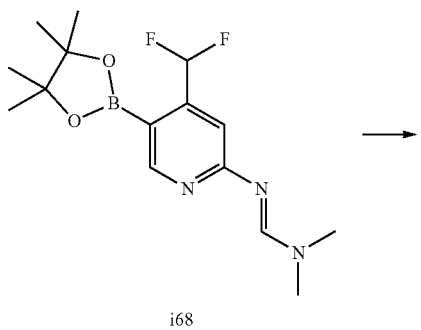

i68

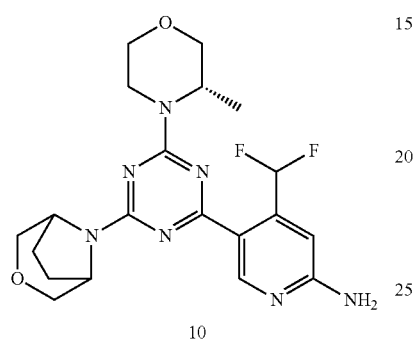

10

According to general procedure 1, compound 10 is obtained from starting materials i18 and i68 in 42% yield as a colorless solid. $^1$H NMR (400 MHz, CDCl$_3$): δ 9.04 (s, 1H), 7.69 (t, $^2J_{H,F}$=55 Hz, 1H), 6.84 (s, 1H), 4.85 (br s, 2H), 4.71-4.65 (m, 3H), 4.42-4.39 (m, 1H), 3.98-3.95 (m, 1H), 3.79-3.76 (m, 3H), 3.70-3.65 (m, 3H), 3.56-3.53 (m, 1H), 3.30-3.27 (m, 1H), 2.10-1.99 (m, 4H), 1.33 (m, 3H); $^{19}$F NMR (376 MHz, CDCl$_3$): δ −115.9 (−116.2) (m, 2 F); MS (MALDI): m/z=434.2 ([M+H]$^+$).

Compound 11: 5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine (11)

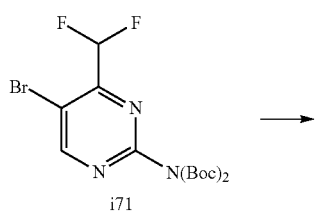

i71

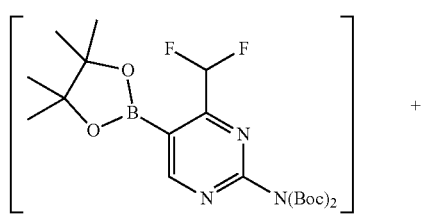

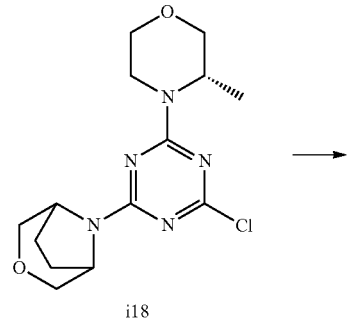

i18

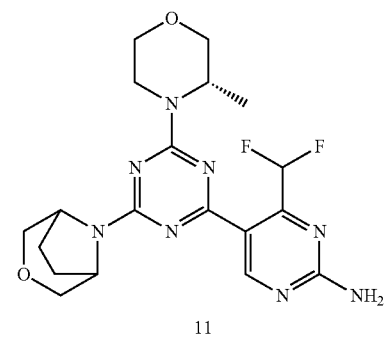

11

According to general procedure 2, compound 11 is obtained from starting materials i71 and i18 in 46% yield as a colorless solid. $^1$H NMR (400 MHz, CDCl$_3$): δ 9.25 (s, 1H), 7.68 (t, $^2J_{H,F}$=55 Hz, 1H), 5.81 (br s, 2H), 4.71-4.65 (m, 3H), 4.42-4.38 (m, 1H), 4.00-3.96 (m, 1H), 3.81-3.60 (m, 6H), 3.55-3.50 (m, 1H), 3.31-3.24 (m, 1H), 2.11-2.00 (m, 4H), 1.37-1.28 (m, 3H); $^{19}$F NMR (376 MHz, CDCl$_3$): δ −121.5 (−121.7) (m, 2 F); MS (MALDI): m/z=434.6 ([M+H]$^+$).

Compound 12: 4-(difluoromethyl)-5-(4-morpholino-6-(piperazin-1-yl)-1,3,5-triazin-2-yl)pyridin-2-amine (12)

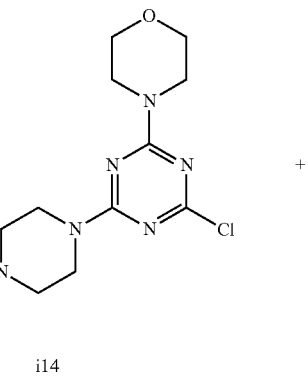

i14

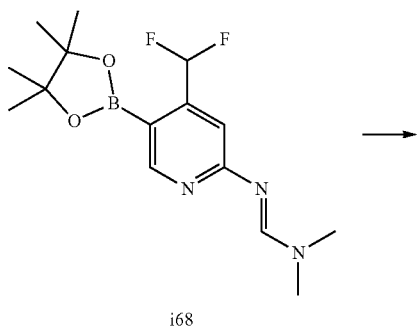

i68

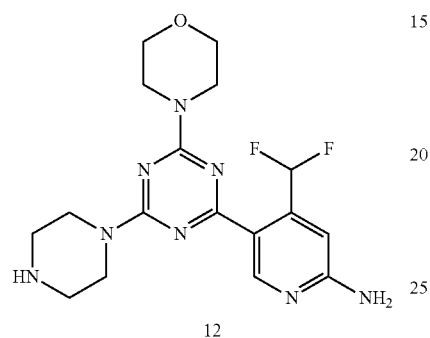

12

According to general procedure 1, compound 12 is obtained from starting materials i68 and i14 in 86% yield as a colorless solid. $^1$H NMR (400 MHz, (CD$_3$)$_2$SO): δ 8.85 (s, 1H), 7.74 (t, $^2J_{H,F}$=55 Hz, 1H), 6.84 (s, 2H), 6.75 (s, 1H), 3.82-3.70 (m, 8H), 3.69-3.60 (m, 4H), 2.88-2.80 (m, 4H); $^{19}$F NMR (376 MHz, (CD$_3$)$_2$SO): δ −115.4 (s, 2 F); MS (MALDI): m/z=393.8 ([M+H]$^+$).

Compound 13: 4-(difluoromethyl)-5-(4-morpholino-6-(piperazin-1-yl)-1,3,5-triazin-2-yl)pyrimidin-2-amine (13)

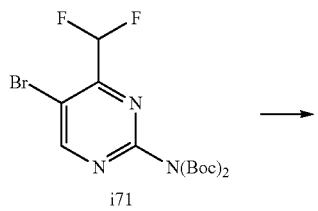

i71

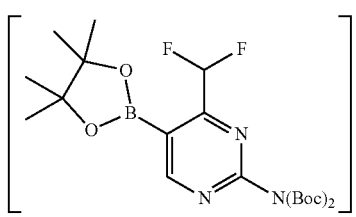

+

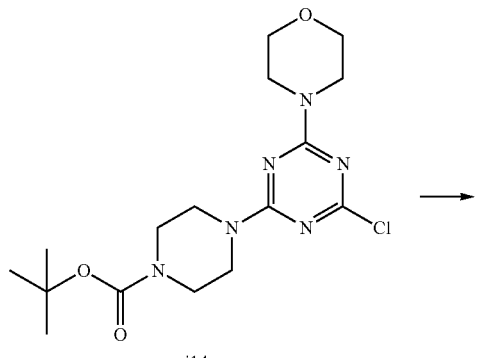

i14

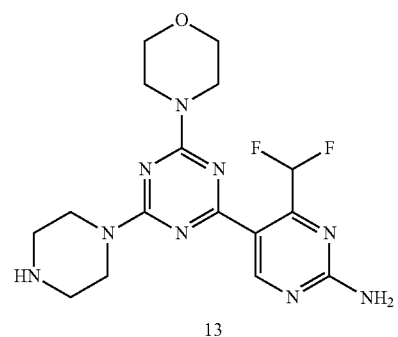

13

According to general procedure 2, compound 13 is obtained from starting materials i71 and i14 in 55% yield as a colorless solid. $^1$H NMR (400 MHz, CDCl$_3$): δ 9.23 (s, 1H), 7.64 (t, $^2J_{H,F}$=55 Hz, 1H), 5.60 (br s, 2H), 3.83-3.75 (m, 12H), 2.94-2.88 (m, 4H); $^{19}$F NMR (376 MHz, CDCl$_3$): δ −111.4 (s, 2 F); MS (MALDI): m/z=394.1 ([M+H]$^+$).

Compound 14: (S)-4-(difluoromethyl)-5-(4-(3-methylmorpholino)-6-(piperazin-1-yl)-1,3,5-triazin-2-yl)pyridin-2-amine (14)

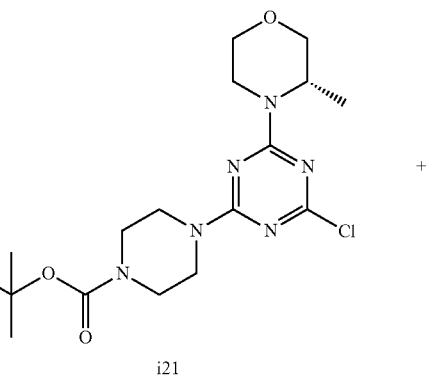

i21

+

121
-continued

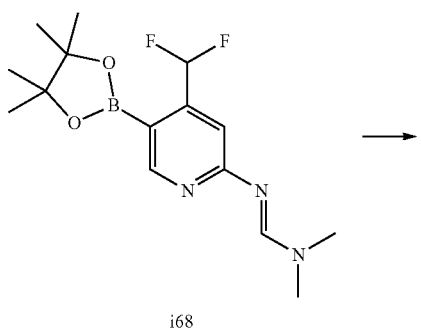
i68

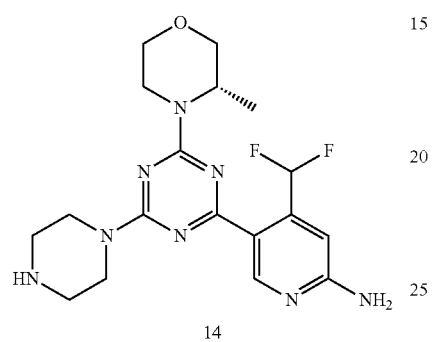
14

According to general procedure 1, compound 14 is obtained from starting materials i21 and i68 in 47% yield as a colorless solid. $^1$H NMR (400 MHz, CDCl$_3$): δ 9.02 (s, 1H), 7.67 (t, $^2J_{H,F}$=56 Hz, 1H), 6.84 (s, 1H), 4.90 (br s, 2H), 4.74 (s, 1H), 4.40 (d, $J_{H,H}$=16 Hz, 1H), 3.98 (dd, $J_{H,H}$=4.0 Hz, 12 Hz, 1H), 3.91 (m, 4H), 3.78 (d, $J_{H,H}$=12 Hz, 1H), 3.68 (dd, $J_{H,H}$=4.0, 12 Hz, 1H), 3.56 (t, $J_{H,H}$=4.0 Hz, 1H), 3.26 (dt, $J_{H,H}$=4.0, 12 Hz, 1H), 2.99 (t, $J_{H,H}$=4.0 Hz, 4H), 1.32 (d, $J_{H,H}$=8.0 Hz, 3H); $^{19}$F NMR (376 MHz, CDCl$_3$): δ −115.9 (s, 2 F); MS (MALDI): m/z=407.2 ([M+H]$^+$).

Compound 15: (S)-4-(difluoromethyl)-5-(4-(3-methylmorpholino)-6-(piperazin-1-yl)-1,3,5-triazin-2-yl)pyrimidin-2-amine (15)

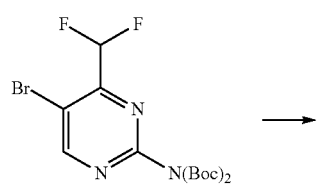

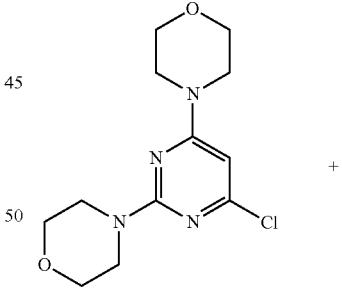

122
-continued

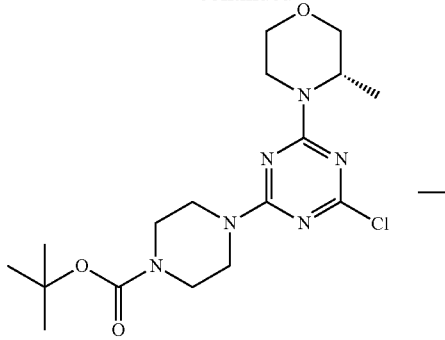

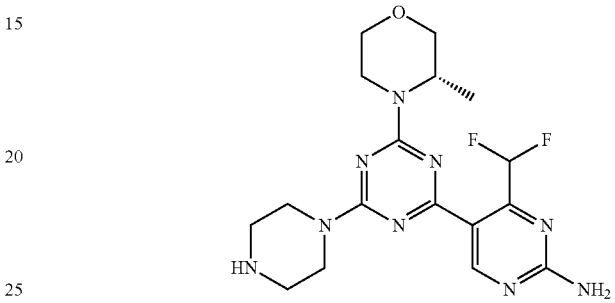

According to general procedure 2, compound 15 is obtained from starting materials i71 and i21 in 30% yield as a colorless solid. $^1$H NMR (400 MHz, CDCl$_3$): δ 9.24 (s, 1H), 7.66 (t, $^2J_{H,F}$=56 Hz, 1H), 5.69 (br s, 2H), 4.74 (s, 1H), 4.40 (d, $J_{H,H}$=16 Hz, 1H), 4.38 (dd, $J_{H,H}$=4.0, 12 Hz, 1H), 3.83 (m, 4H), 3.78 (d, $J_{H,H}$=12 Hz, 1H), 3.68 (dd, $J_{H,H}$=4.0, 12 Hz, 1H), 3.54 (dt, $J_{H,H}$=4.0, 12 Hz, 1H), 3.28 (dt, $J_{H,H}$=4.0, 12 Hz, 1H), 2.92 (t, $J_{H,H}$=8.0 Hz, 4H), 1.33 (t, $J_{H,H}$=8.0 Hz, 3H); $^{19}$F NMR (376 MHz, CDCl$_3$): δ −121.4 (s, 2 F); MS (MALDI): m/z=408.7 ([M+H]$^+$).

Compound 16: 4-(difluoromethyl)-5-(2,6-dimorpholinopyrimidin-4-yl)pyridin-2-amine (16)

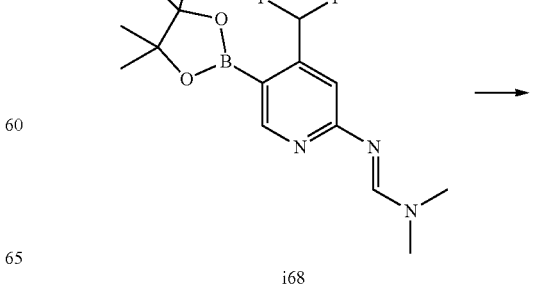

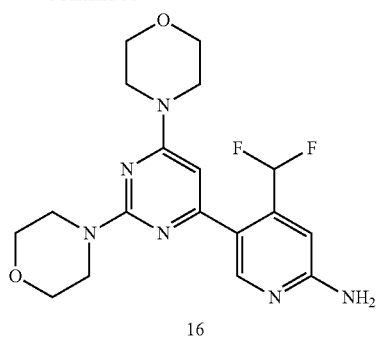

16

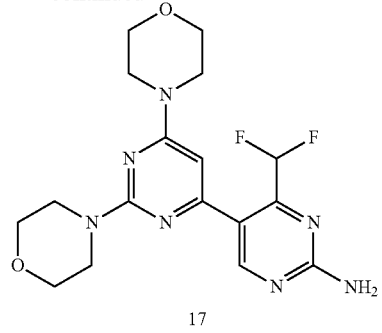

17

According to general procedure 1, compound 16 is obtained from starting materials i22 and i68 in 73% yield as a colorless solid. $^1$H NMR (400 MHz, CDCl$_3$): δ 8.31 (s, 1H), 7.30 (t, $^2J_{H,F}$=55 Hz, 1H), 6.85 (s, 1H), 6.04 (s, 1H), 4.73 (br s, 2H), 3.81-3.72 (m, 12H), 3.65-3.59 (m, 4H); $^{19}$F NMR (376 MHz, CDCl$_3$): δ −115.1 (s, 2 F); MS (MALDI): m/z=393.3 ([M+H]$^+$).

Compound 17: 4'-(difluoromethyl)-2,6-dimorpholino-[4,5'-bipyrimidin]-2'-amine (17)

According to general procedure 2, compound 17 is obtained from starting materials i71 and i22 in 7% yield as a colorless solid. $^1$H NMR (400 MHz, CDCl$_3$): δ 8.60 (s, 1H), 7.11 (t, $^2J_{H,F}$=55 Hz, 1H), 6.02 (s, 1H), 5.46 (br s, 2H), 3.80-3.74 (m, 12H), 3.64-3.60 (m, 4H); $^{19}$F NMR (376 MHz, CDCl$_3$): δ −119.5 (s, 2 F); MS (MALDI): m/z=394.3 ([M+H]$^+$).

Compound 18: 4-(difluoromethyl)-5-(4,6-dimorpholinopyrimidin-2-yl)pyridin-2-amine (18)

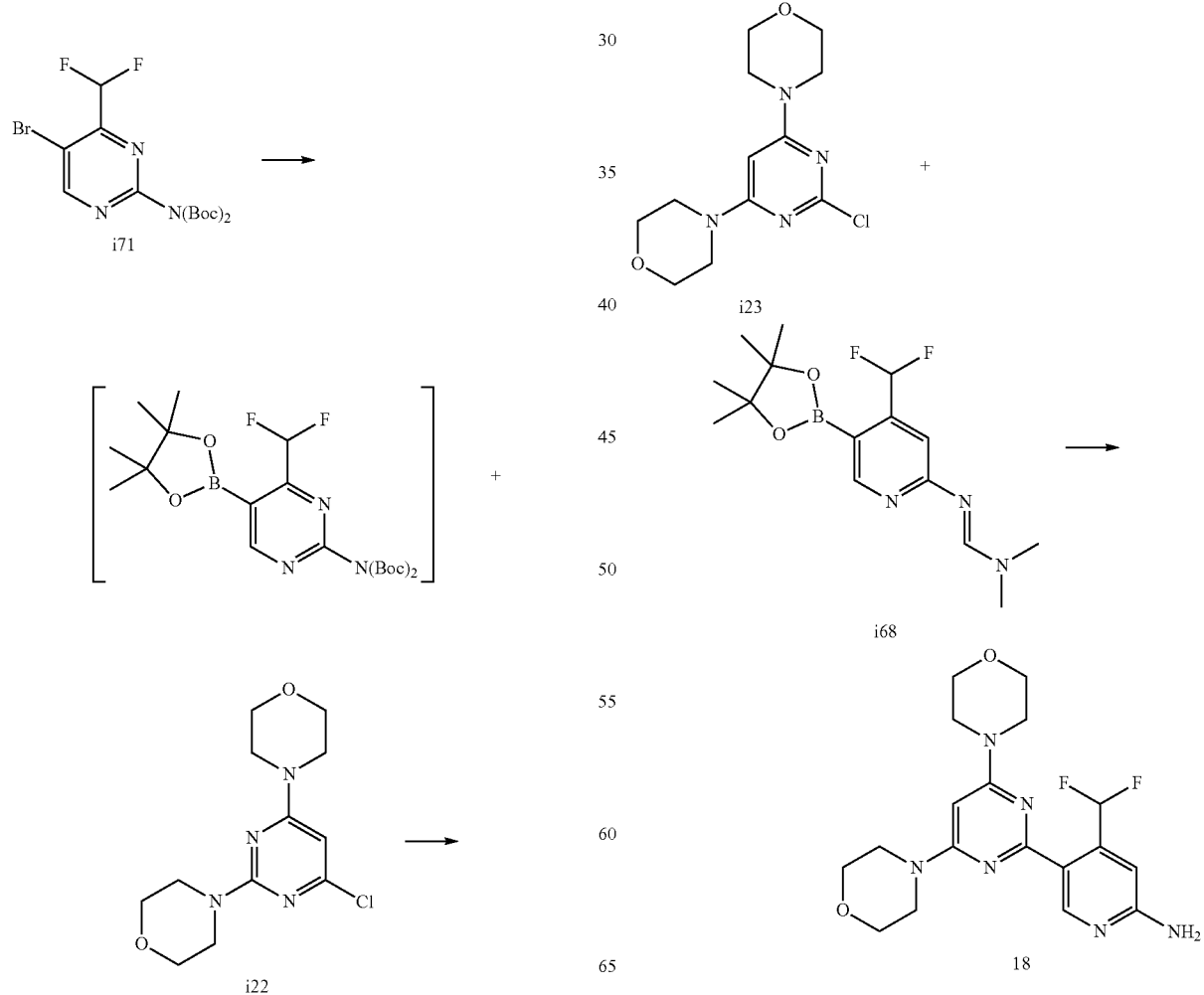

According to general procedure 1, compound 18 is obtained from starting materials i23 and i68 in 89% yield as a colorless solid. $^1$H NMR (400 MHz, CDCl$_3$): δ 8.94 (s, 1H), 7.61 (t, $^2J_{H,F}$=55 Hz, 1H), 6.83 (s, 1H), 5.50 (s, 1H), 4.74 (br s, 2H), 3.82-3.78 (m, 8H), 3.61-3.57 (m, 8H); $^{19}$F NMR (376 MHz, CDCl$_3$): δ −115.4 (s, 2 F); MS (MALDI): m/z=393.3 ([M+H]$^+$).

Compound 19: 4'-(difluoromethyl)-4,6-dimorpholino-[2,5'-bipyrimidin]-2'-amine (19)

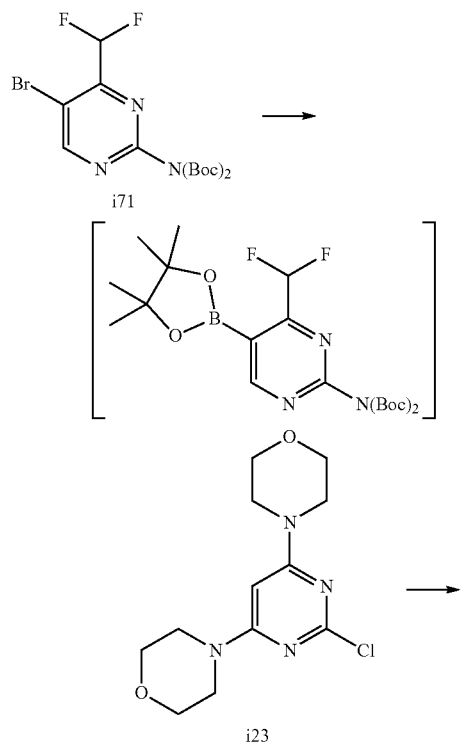

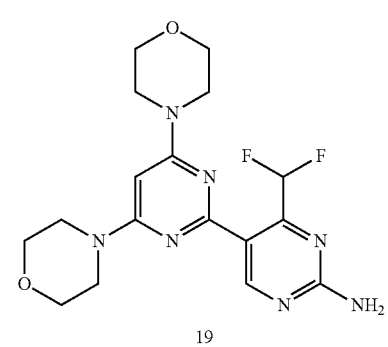

According to general procedure 2, compound 19 is obtained from starting materials i71 and i23 in 7% yield as a colorless solid. $^1$H NMR (400 MHz, CDCl$_3$): δ 9.16 (s, 1H), 7.58 (t, $^2J_{H,F}$=55 Hz, 1H), 5.75 (br s, 2H), 5.50 (s, 1H), 3.82-3.79 (m, 8H), 3.61-3.58 (m, 8H); $^{19}$F NMR (376 MHz, CDCl$_3$): δ −121.1 (s, 2 F); MS (MALDI): m/z=395.3 ([M+H]$^+$).

Compound 20: 4-(difluoromethyl)-5-(4-morpholino-6-thiomorpholino-1,3,5-triazin-2-yl)-pyridin-2-amine (20)

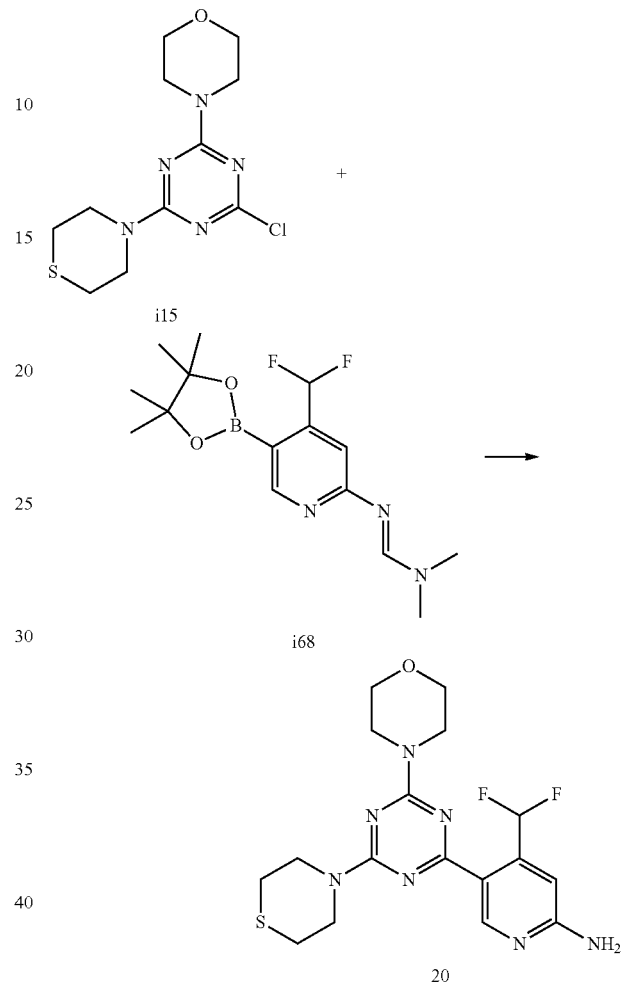

According to general procedure 1, compound 20 is obtained from starting materials i15 and i68 in 77% yield as a colorless solid. $^1$H NMR (400 MHz, CDCl$_3$): δ 9.02 (s, 1H), 7.65 (t, $^2J_{H,F}$=55 Hz, 1H), 6.84 (s, 1H), 4.83 (br s, 2H), 4.23-4.07 (m, 4H), 3.90-3.79 (m, 4H), 3.79-3.71 (m, 4H), 2.71-2.62 (m, 4H); $^{19}$F NMR (376 MHz, CDCl$_3$): δ −116.0 (s, 2 F); MS (MALDI): m/z=410.3 ([M+H]$^+$).

Compound 21: 4-(difluoromethyl)-5-(4-morpholino-6-thiomorpholino-1,3,5-triazin-2-yl)-pyrimidin-2-amine (21)

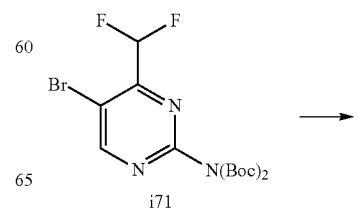

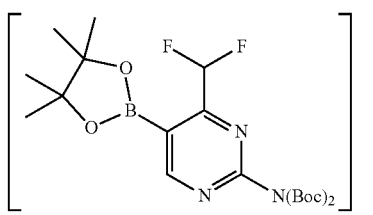

i15

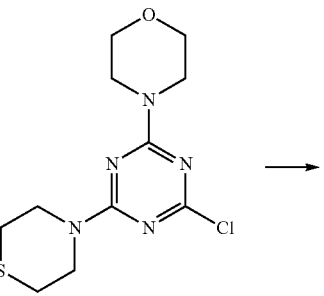

21

According to general procedure 2, compound 21 is obtained from starting materials i71 and i15 in 70% yield as a colorless solid. $^1$H NMR (400 MHz, CDCl$_3$): δ 9.21 (s, 1H), 7.60 (t, $^2J_{H,F}$=54 Hz, 1H), 5.90 (br s, 2H), 4.22-4.06 (m, 4H), 3.91-3.78 (m, 4H), 3.78-3.71 (m, 4H), 2.71-2.62 (m, 4H); $^{19}$F NMR (376 MHz, CDCl$_3$): δ −120.5 (−121.5) (m, 2 F); MS (MALDI): m/z=411.2 ([M+H]$^+$).

Compound 22: 5-(6-(3-oxa-8-azabicyclo[3.2.1]oc-tan-8-yl)-2-(3-oxa-8-azabicyclo[3.2.1]octan-8-yl) pyrimidin-4-yl)-4-(difluoromethyl)pyridin-2-amine (22)

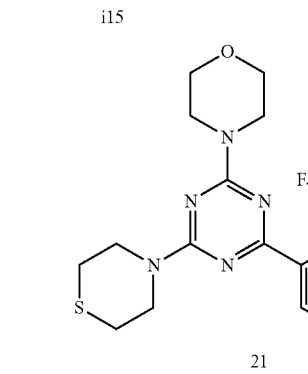

i24

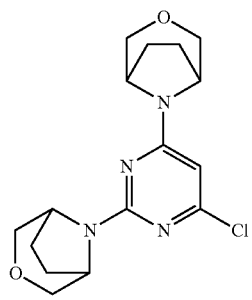

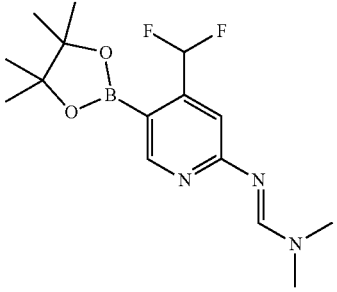

i68

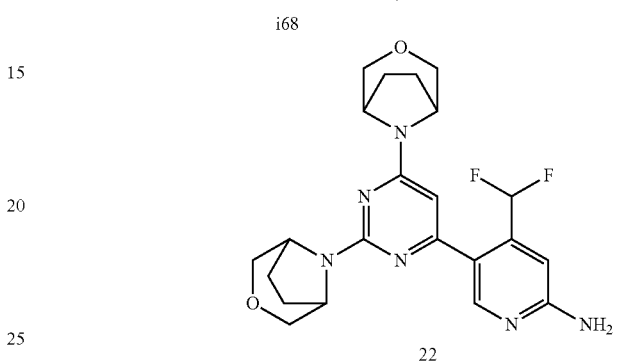

22

According to general procedure 1, compound 22 is obtained from starting materials i24 and i68 in 61% yield as a colorless solid. 1H NMR (400 MHz, (CD$_3$)$_2$SO): δ 8.34 (s, 1H), 7.55 (t, $^2J_{H,F}$=55 Hz, 1H), 6.76 (s, 1H), 6.60 (br s, 2H), 6.36 (s, 1H), 4.64-4.47 (m, 4H), 3.67-3.49 (m, 4H), 3.56-3.49 (m, 4H), 1.98-1.79 (m, 8H); $^{19}$F NMR (376 MHz, (CD$_3$)$_2$SO): δ −114.9 (−115.2) (m, 2 F); MS (MALDI): m/z=445.3 ([M+H]$^+$).

Compound 23: 5-(2-(3-oxa-8-azabicyclo[3.2.1]oc-tan-8-yl)-6-morpholinopyrimidin-4-yl)-4-(difluo-romethyl)pyridin-2-amine (23)

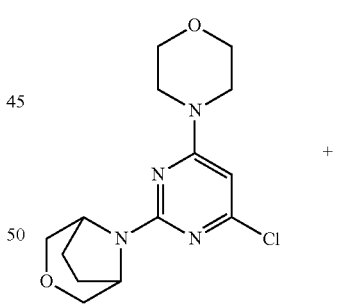

i29

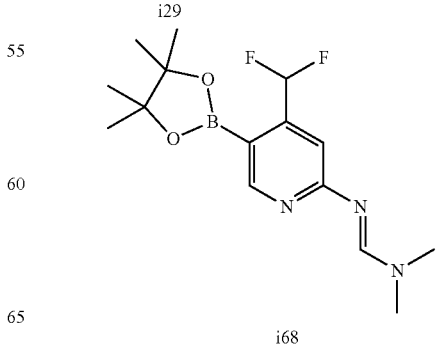

i68

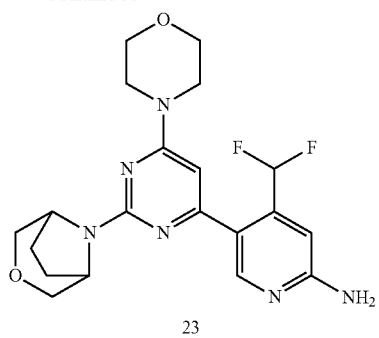

23

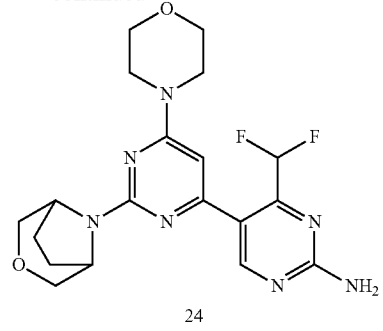

24

According to general procedure 1, compound 23 is obtained from starting materials i29 and i68 in 54% yield as a colorless solid. $^{1}$H NMR (400 MHz, CDCl$_{3}$): δ 8.30 (s, 1H), 7.30 (t, $^{2}J_{H,F}$=55 Hz, 1H), 6.84 (s, 1H), 6.04 (s, 1H), 4.85 (br s, 2H), 4.62 (br s, 2H), 3.82-3.74 (m, 6H), 3.65-3.56 (m, 6H), 2.09-2.00 (m, 2H), 2.00-1.91 (m, 2H); $^{19}$F NMR (376 MHz, CDCl$_{3}$): δ −115.2 (−116.2) (m, 2 F); MS (MALDI): m/z=419.0 ([M+H]$^{+}$).

Compound 24: 2-(3-oxa-8-azabicyclo[3.2.1]octan-8-yl)-4'-(difluoromethyl)-6-morpholino-[4,5'-bipyrimidin]-2'-amine (24)

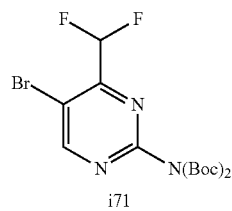

i71

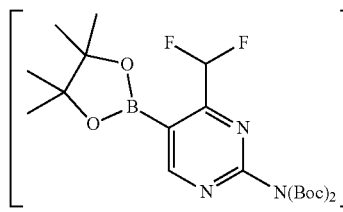

+

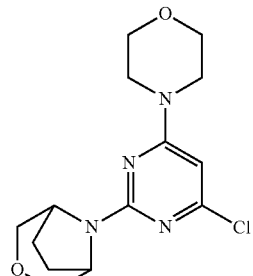

i29

According to general procedure 2, compound 24 is obtained from starting materials i29 and i71 in 72% yield as a colorless solid. $^{1}$H NMR (400 MHz, (CD$_{3}$)$_{2}$SO): δ 8.71 (s, 1H), 7.35 (s, 2H), 7.32 (t, $^{2}J_{H,F}$=54 Hz, 1H), 6.45 (s, 1H), 4.54 (br s, 2H), 3.71-3.50 (m, 12H), 1.95-1.78 (m, 4H); $^{19}$F NMR (376 MHz, (CD$_{3}$)$_{2}$SO): δ −119.2 (s, 2 F); MS (MALDI): m/z=420.6 ([M+H]$^{+}$).

Compound 25: 5-(2,6-bis((S)-3-methylmorpholino)pyrimidin-4-yl)-4-(difluoromethyl)pyridin-2-amine (25)

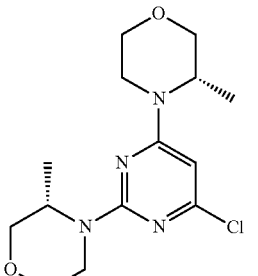

i25

+

i68

25

According to general procedure 1, compound 25 is obtained from starting materials i25 and i68 in 57% yield as a colorless solid. ¹H NMR (400 MHz, (CD$_3$)$_2$SO): δ 8.31 (s, 1H), 7.52 (t, ²J$_{H,F}$=55 Hz, 1H), 6.76 (s, 1H), 6.59 (br s, 2H), 6.30 (s, 1H), 4.60-4.50 (m, 1H), 4.44-4.33 (m, 1H), 4.24-4.15 (m, 1H), 4.12-4.04 (m, 1H), 3.94-3.83 (m, 2H), 3.74-3.64 (m, 2H), 3.59-3.51 (m, 2H), 3.45-3.35 (m, 2H), 3.14-3.02 (m, 2H), 1.18 (t, ³J$_{H,H}$=7.2 Hz, 6H); ¹⁹F NMR (376 MHz, (CD$_3$)$_2$SO): δ −113.7 (−115.9) (m, 2 F); MS (MALDI): m/z=421.1 ([M+H]⁺).

Compound 26: 4'-(difluoromethyl)-2,6-bis((S)-3-methylmorpholino)-[4,5'-bipyrimidin]-2'-amine (26)

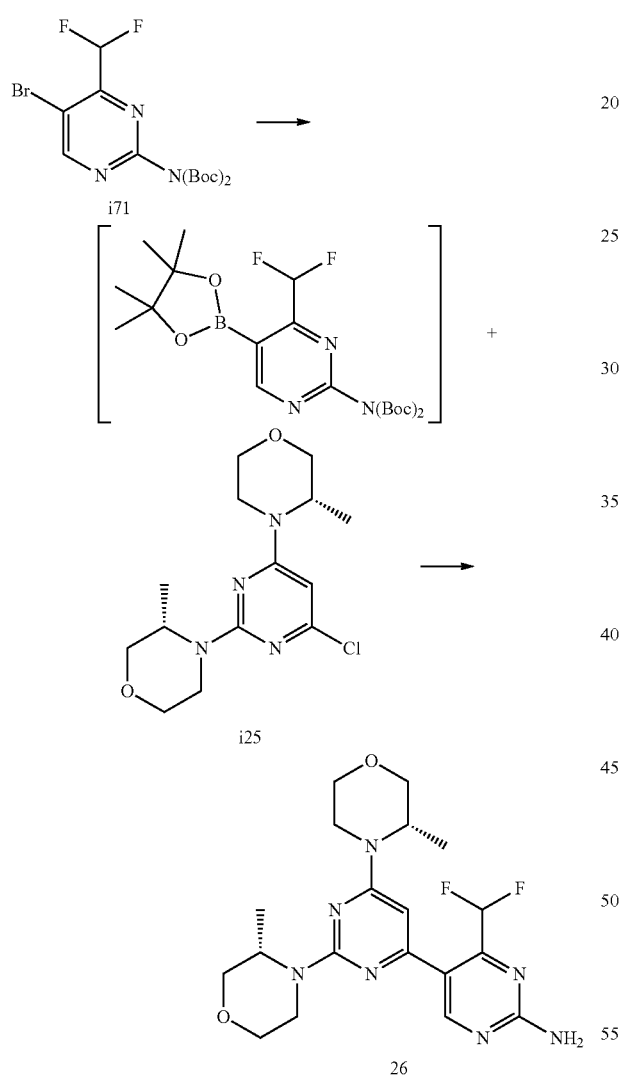

According to general procedure 2, compound 26 is obtained from starting materials i25 and i71 in 56% yield as a colorless solid. ¹H NMR (400 MHz, CDCl$_3$): δ 8.60 (s, 1H), 7.14 (t, ²J$_{H,F}$=54 Hz, 1H), 5.98 (s, 1H), 5.48 (br s, 2H), 4.71-4.62 (m, 1H), 4.34-4.23 (m, 2H), 4.08-3.92 (m, 3H), 3.83-3.65 (m, 4H), 3.61-3.49 (m, 2H), 3.25 (dt, ²J$_{H,H}$=13 Hz, ³J$_{H,H}$=3.6 Hz, 2H), 1.33-1.27 (m, 6H); ¹⁹F NMR (376 MHz, CDCl$_3$): δ −119.5 (s, 1 F), 119.7 (m, 1 F); MS (MALDI): m/z=422.2 ([M+H]⁺).

Compound 27: (S)-4-(difluoromethyl)-5-(6-(3-methylmorpholino)-2-morpholinopyrimidin-4-yl)pyridin-2-amine (27)

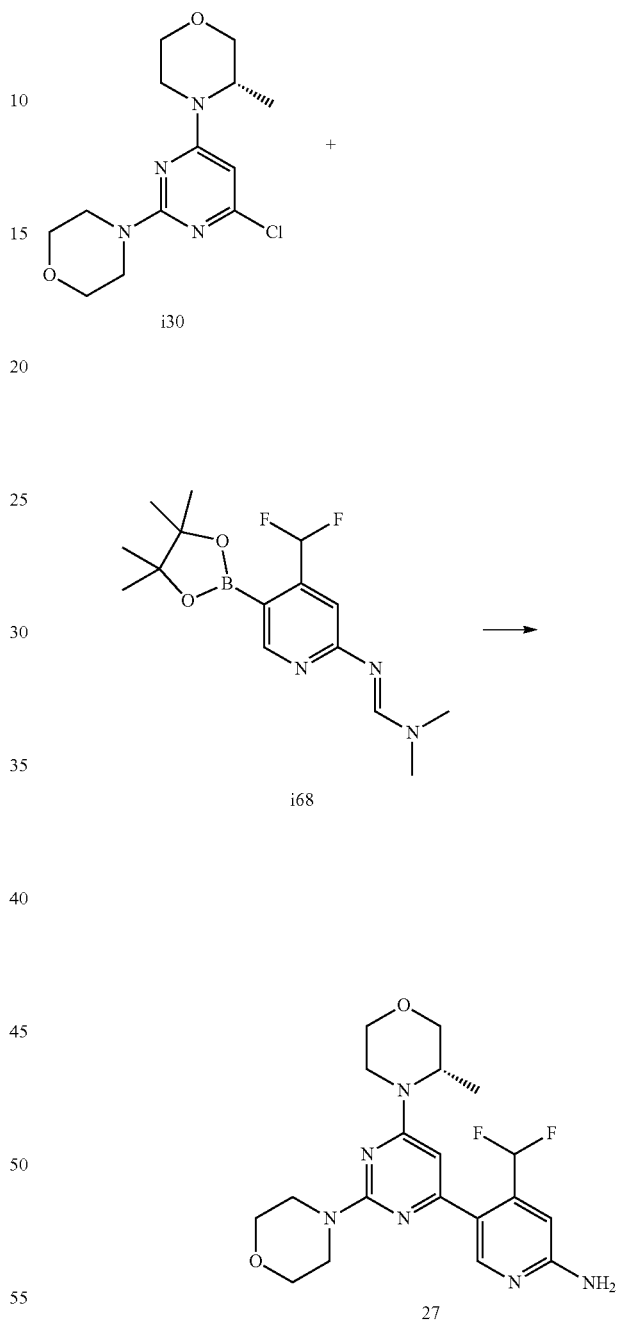

According to general procedure 1, compound 27 is obtained from starting materials i30 and i68 in 74% yield as a colorless solid. ¹H NMR (400 MHz, CDCl$_3$): δ 8.31 (s, 1H), 7.30 (t, ²J$_{H,F}$=55 Hz, 1H), 6.85 (s, 1H), 6.02 (s, 1H), 4.75 (br s, 2H), 4.35-4.25 (m, 1H), 4.06-3.96 (m, 2H), 3.83-3.69 (m, 10H), 3.58 (dt, ²J$_{H,H}$=12 Hz, ³J$_{H,H}$=3.2 Hz, 1H), 3.25 (dt, 2J$_{H,H}$=13 Hz, ³J$_{H,H}$=3.8 Hz, 1H), 1.31 (d, ³J$_{H,H}$=6.8 Hz, 3H); ¹⁹F NMR (376 MHz, CDCl$_3$): δ −114.9 (−115.0) (m, 2 F); MS (MALDI): m/z=407.1 ([M+H]⁺).

Compound 28: (S)-4'-(difluoromethyl)-6-(3-methyl-morpholino)-2-morpholino-[4,5'-bipyrimidin]-2'-amine (28)

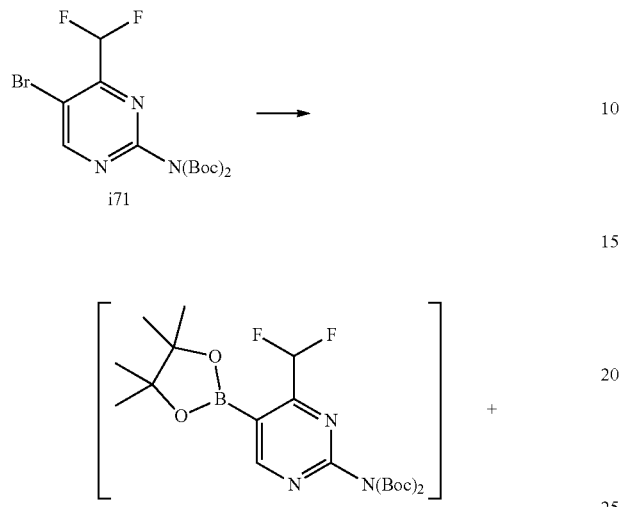

Compound 29: 5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine (29)

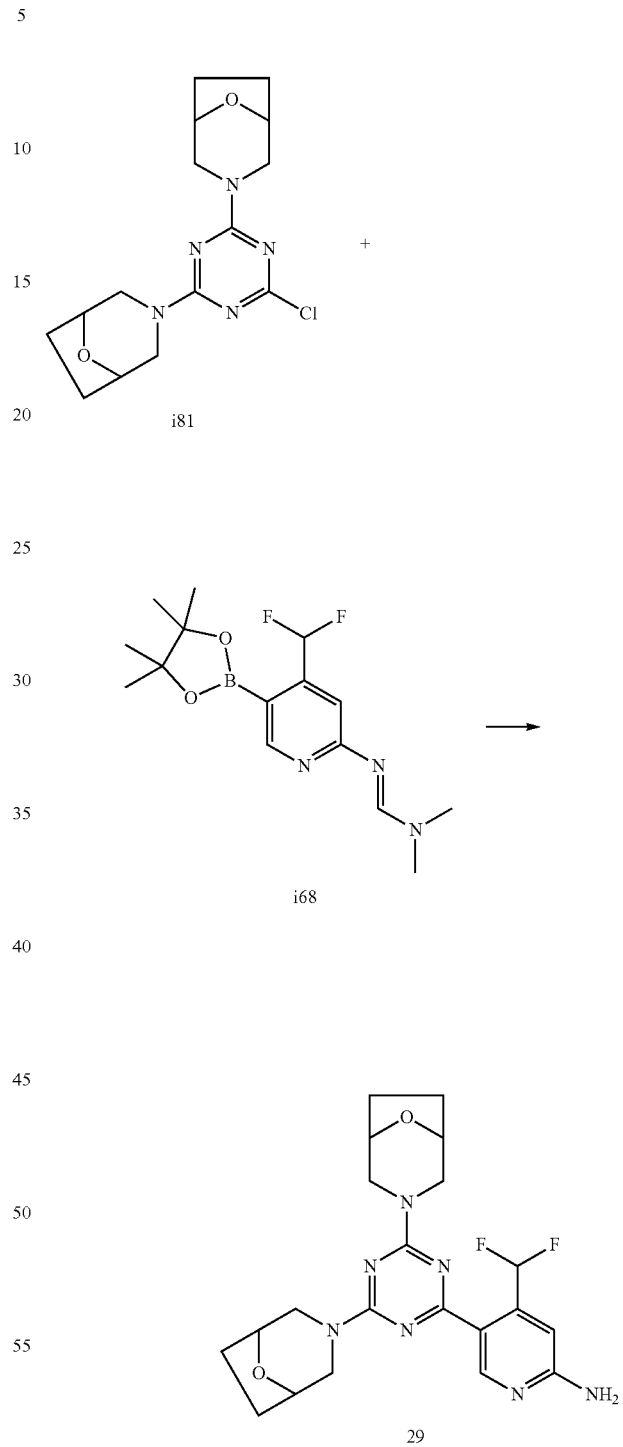

According to general procedure 2, compound 28 is obtained from starting materials i30 and i71 in 53% yield as a colorless solid. $^1$H NMR (400 MHz, CDCl$_3$): δ 8.60 (s, 1H), 7.13 (t, $^2J_{H,F}$=54 Hz, 1H), 6.01 (s, 1H), 5.47 (br s, 2H), 4.71-4.63 (m, 1H), 4.31 (dd, $^2J_{H,H}$=14 Hz, $^3J_{H,H}$=2.4 Hz, 1H), 3.97 (dd, $^2J_{H,H}$=11 Hz, $^3J_{H,H}$=3.4 Hz, 1H), 3.79 (t, $^3J_{H,H}$=4.6 Hz, 4H), 3.72-3.66 (m, 2H), 3.65-3.58 (m, 3H), 3.58-3.50 (m, 2H), 3.30-3.21 (m, 1H), 1.30 (d, $^3J_{H,H}$=6.8 Hz, 3H); $^{19}$F NMR (376 MHz, CDCl$_3$): δ −119.7 (br s, 2 F); MS (MALDI): m/z=408.9 ([M+H]$^+$).

According to general procedure 1, compound 29 is obtained from starting materials i68 and i81 in 89% yield as a colorless solid. $^1$H NMR (400 MHz, CDCl$_3$): δ 9.03 (s, 1H), 7.69 (t, $^2J_{H,F}$=55 Hz, 1H), 6.83 (s, 1H), 4.85 (br s, 2H), 4.50-4.24 (m, 8H), 3.28-3.12 (m, 4H), 1.94 (br s, 4H), 1.86-1.71 (m, 4H); $^{19}$F NMR (376 MHz, CDCl$_3$): δ −115.1 (−117.2) (m, 2 F); MS (MALDI): m/z=446.3 ([M+H]$^+$).

Compound 30: 5-[4,6-bis(2,2-dimethylmorpholin-4-yl)-1,3,5-triazin-2-yl]-4-(difluoromethyl)pyridin-2-amine (30)

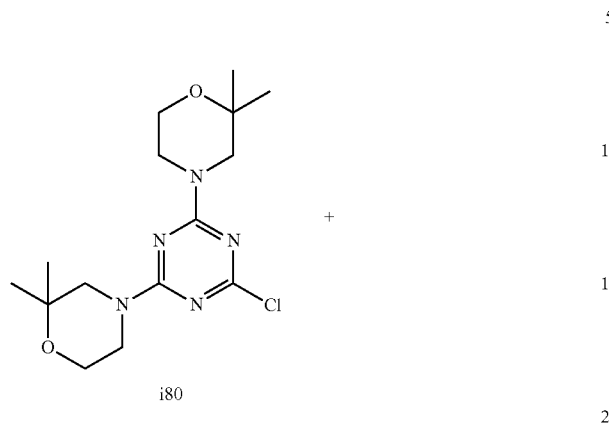

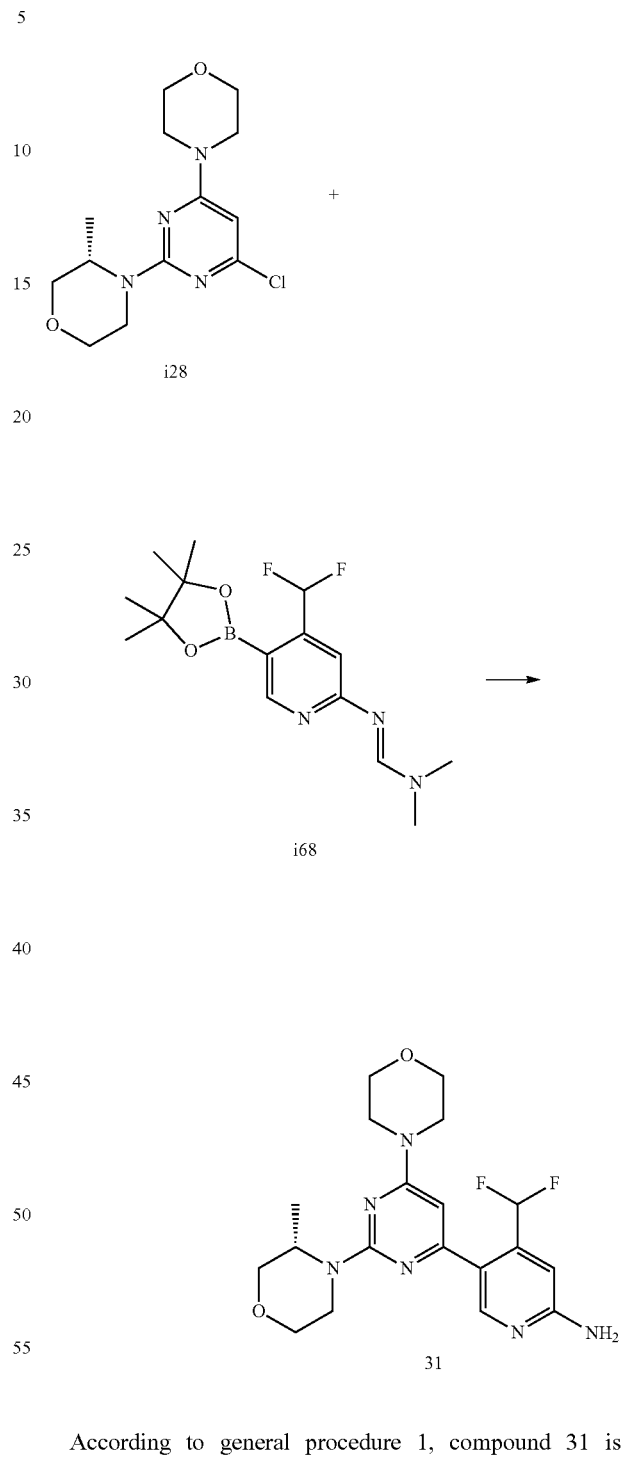

According to general procedure 1, compound 30 is obtained from starting materials i68 and i80 in 63% yield as a colorless solid. $^1$H NMR (400 MHz, $(CD_3)_2SO$): δ 8.86 (s, 1H), 7.71 (t, $^2J_{H,F}$=55 Hz, 1H), 6.84 (br s, 2H), 6.76 (s, 1H), 3.81-3.56 (m, 12H), 1.14 (s, 12H); MS (MALDI): m/z=450.0 ([M+H]$^+$).

Compound 31: (S)-4-(difluoromethyl)-5-(2-(3-methylmorpholino)-6-morpholinopyrimidin-4-yl)pyridin-2-amine (31)

According to general procedure 1, compound 31 is obtained from starting materials i28 and i68 in 58% yield as a colorless solid. $^1$H NMR (400 MHz, $(CD_3)_2SO$): δ 8.31 (s, 1H), 7.52 (t, $^2J_{H,F}$=55 Hz, 1H), 6.74 (s, 1H), 6.59 (br s, 2H), 6.35 (s, 1H), 4.59-4.51 (m, 1H), 4.22-4.14 (m, 1H), 3.91-3.84 (m, 1H), 3.72-3.50 (m, 10H), 3.44-3.35 (m, 1H), 3.14-3.03 (m, 1H), 1.16 (d, $^3J_{H,H}$=6.7 Hz, 3H); $^{19}$F NMR (376 MHz, $(CD_3)_2SO$): δ −113.7 (−115.3) (m, 2 F); MS (MALDI): m/z=407.1 ([M+H]$^+$).

Compound 32: (S)-4'-(difluoromethyl)-2-(3-methyl-morpholino)-6-morpholino-[4,5'-bipyrimidin]-2'-amine (32)

Compound 33: 4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine (33)

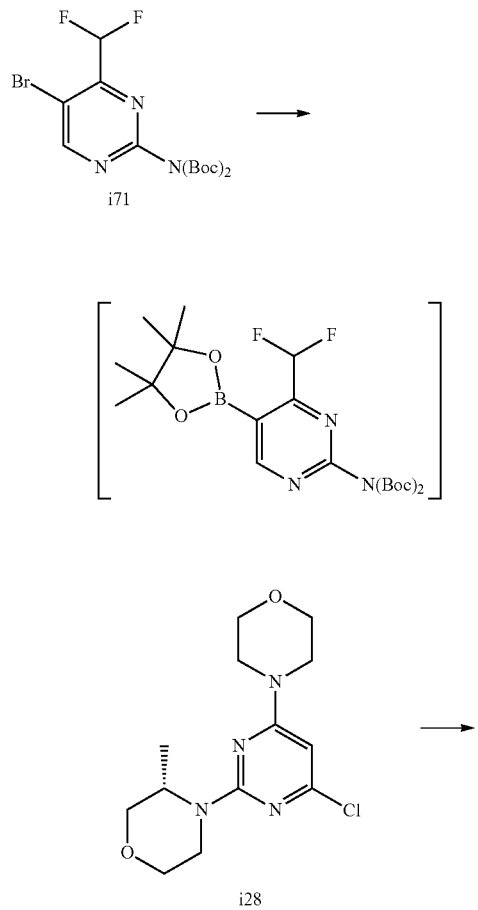

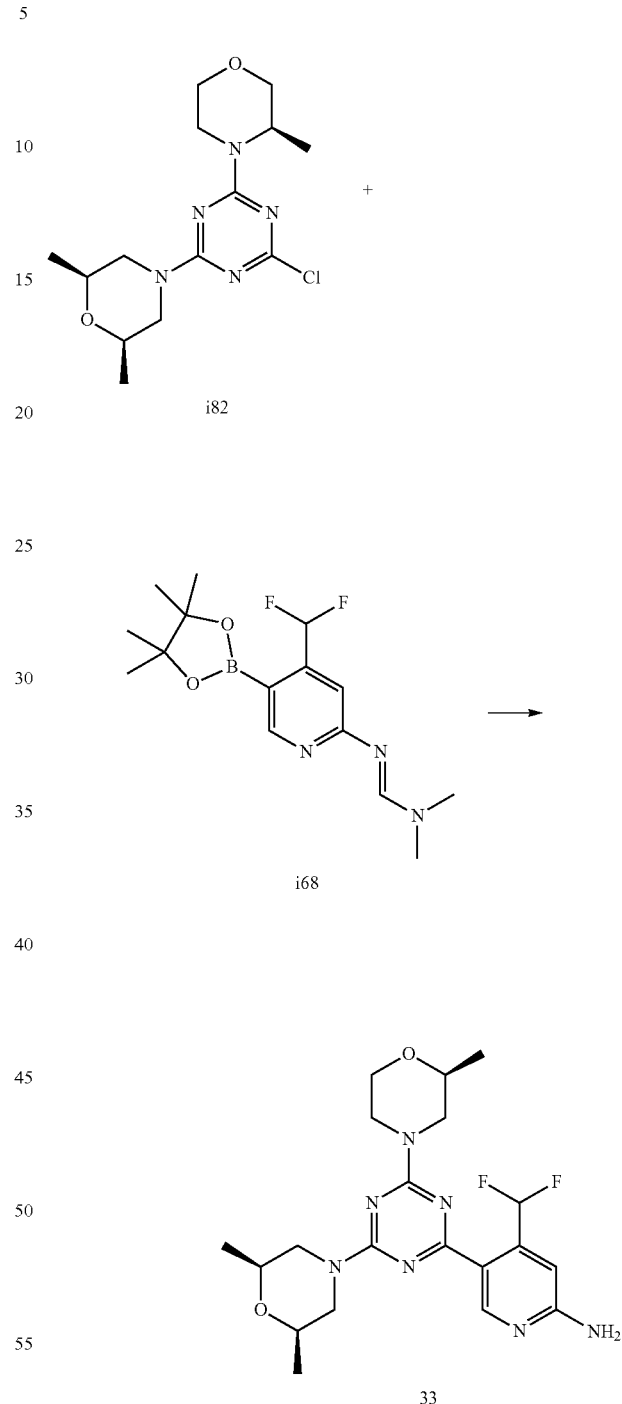

According to general procedure 2, compound 32 is obtained from starting materials i28 and i71 in 63% yield as a colorless solid. $^1$H NMR (400 MHz, CDCl$_3$): δ 8.60 (s, 1H), 7.13 (t, $^2J_{H,F}$=54 Hz, 1H), 5.99 (s, 1H), 5.46 (br s, 2H), 4.34-4.25 (m, 1H), 4.06-3.97 (m, 2H), 3.82-3.68 (m, 10H), 3.58 (dt, $^2J_{H,H}$, =12 Hz, $^3J_{H,H}$=3.2 Hz, 1H), 3.26 (dt, $^2J_{H,H}$=13 Hz, $^3J_{H,H}$=3.7 Hz, 1H), 1.31 (d, $^3J_{H,H}$=6.8 Hz, 3H); $^{19}$F NMR (376 MHz, (CD$_3$)$_2$SO): δ −119.5 (s, 2 F); MS (MALDI): m/z=408.7 ([M+H]$^+$).

According to general procedure 1, compound 33 is obtained from starting materials i68 and i82 in 71% yield as a colorless solid. $^1$H NMR (400 MHz, (CD$_3$)$_2$SO): δ 8.87 (s, 1H), 7.74 (t, $^2J_{H,F}$=55 Hz, 1H), 6.83 (br s, 2H), 6.76 (s, 1H), 4.71-4.62 (m, 1H), 4.45-4.34 (m, 2H), 4.31-4.09 (m, 1H), 3.90 (m, 1H), 3.71 (m, 1H), 3.55 (m, 3H), 3.38 (m, 1H), 3.13 (m, 1H), 2.55 (m, 2H), 1.20 (d, $^3J_{H,H}$=6.9 Hz, 3H), 1.19 (d, $^3J_{H,H}$=6.9 Hz, 6H); MS (MALDI): m/z=436.1 ([M+H]$^+$).

139

Compound 34: 5-[4,6-bis[(2R,6S)-2,6-dimethylmorpholin-4-yl]-1,3,5-triazin-2-yl]-4-(difluoromethyl)pyridin-2-amine (34)

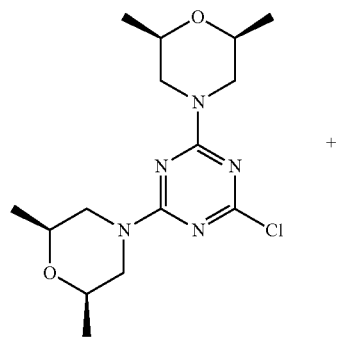

i79

+

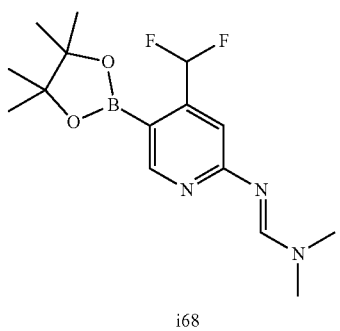

i68

→

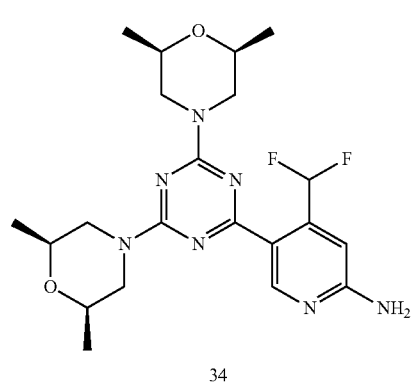

34

According to general procedure 1, compound 34 is obtained from starting materials i68 and i79 in 75% yield as a colorless solid. $^1$H NMR (400 MHz, (CD$_3$)$_2$SO): δ 8.86 (s, 1H), 7.71 (t, $^2J_{H,F}$=55 Hz, 1H), 6.83 (br s, 2H), 6.76 (s, 1H), 4.64-4.46 (m, 4H), 3.60-3.48 (m, 4H), 2.63 (m, 4H), 1.14 (m, 12H); MS (MALDI): m/z=450.0 ([M+H]$^+$).

140

Compound 37: 5-[4,6-bis(3,7-dioxa-9-azabicyclo[3.3.1]nonan-9-yl)-1,3,5-triazin-2-yl]-4-(difluoromethyl)pyridin-2-amine (37)

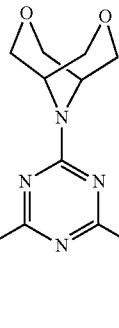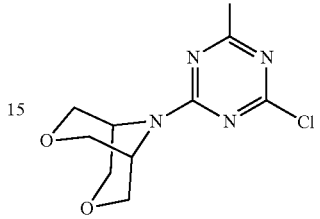

i7

+

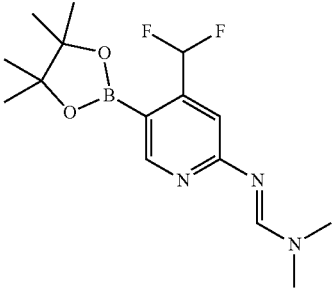

i68

→

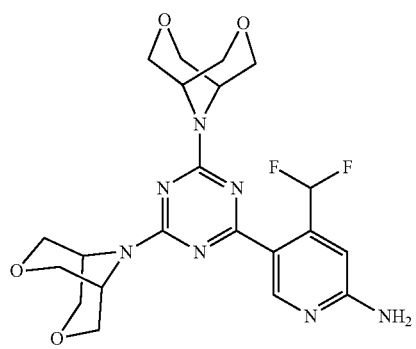

37

According to general procedure 1, compound 37 is obtained from starting materials i7 and i68 in 39% yield as a colorless solid. $^1$H NMR (400 MHz, (CD$_3$)$_2$SO): δ 8.85 (s, 1H), 7.68 (t, $^3J_{H,F}$=55 Hz, 1H), 6.87 (br s, 2H), 6.74 (s, 1H), 4.51 (br s, 2H), 4.45 (br s, 2H), 4.07-3.93 (m, 8H), 3.79-3.67 (m, 8H); $^{19}$F NMR (376 MHz, (CD$_3$)$_2$SO): δ −115.8 (s, 2 F); MS (MALDI): m/z=478.1 ([M+H]$^+$).

Compound 38: 4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine (38)

Compound 39: 5-[4,6-bis(3,3-dimethylmorpholin-4-yl)-1,3,5-triazin-2-yl]-4-(difluoromethyl)pyridin-2-amine (39)

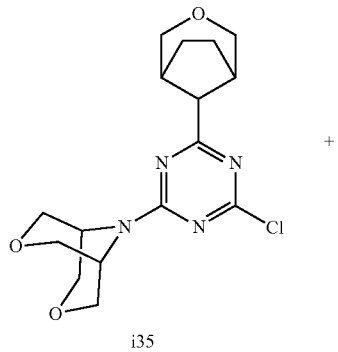
i35

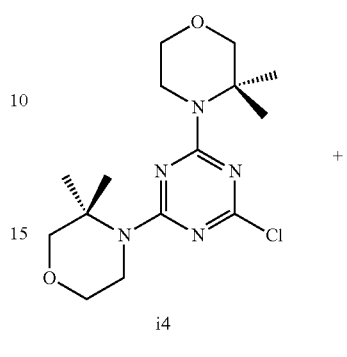
i4

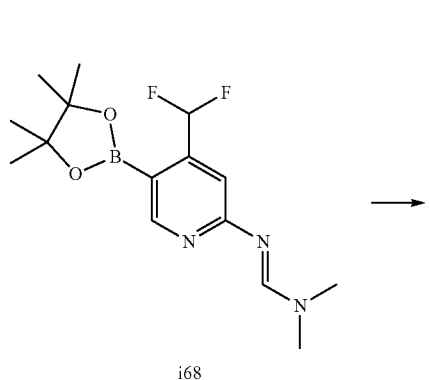
i68

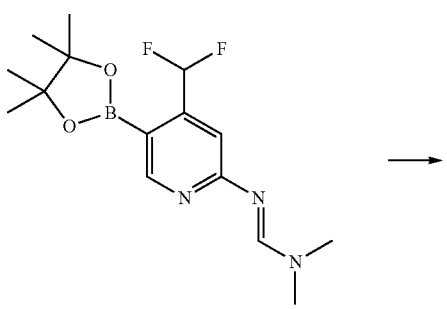
i68

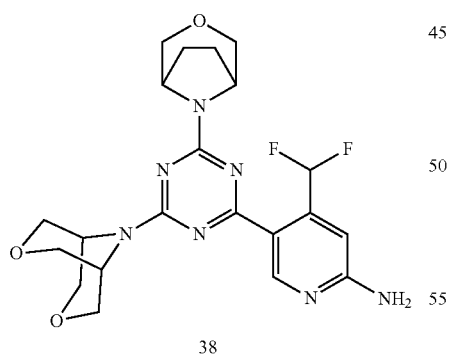
38

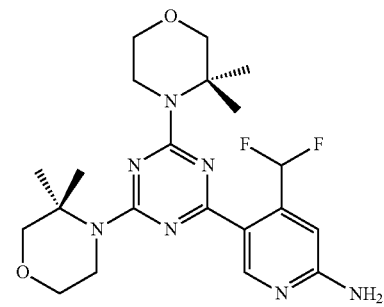
39

According to general procedure 1, compound 38 is obtained from starting materials i35 and i68 in 67% yield as a colorless solid. $^{1}$H NMR (400 MHz, (CD$_3$)$_2$SO): δ 8.87 (s, 1H), 7.73 (t, $^{3}J_{H,F}$=55 Hz, 1H), 6.87 (br s, 2H), 6.75 (s, 1H), 4.70-4.54 (m, 2H), 4.53-4.43 (m, 2H), 4.05-3.97 (m, 4H), 3.79-3.67 (m, 4H), 3.63-3.55 (m, 4H) 2.00-1.83 (m, 4H); $^{19}$F NMR (376 MHz, (CD$_3$)$_2$SO): δ −115.8 (s, 1 F), −115.9 (s, 1 F); MS (MALDI): m/z=462.1 ([M+H]$^{+}$).

According to general procedure 1, compound 39 is obtained from starting materials i4 and i68 in 28% yield as a colorless solid. $^{1}$H NMR (400 MHz, (CD$_3$)$_2$SO): δ 8.78 (s, 1H), 7.70 (t, $^{2}J_{H,F}$=55 Hz, 1H), 6.82 (br s, 2H), 6.77 (s, 1H), 3.87-3.75 (m, 8H), 3.45 (br s, 4H), 1.49 (s, 12H); $^{19}$F NMR (376 MHz, (CD$_3$)$_2$SO): δ −114.9 (−115.1) (m, 2 F); MS (MALDI): m/z=450.1 ([M+H]$^{+}$).

Compound 40: 5-[4,6-bis[(3R,5S)-3,5-dimethylmorpholin-4-yl]-1,3,5-triazin-2-yl]-4-(difluoromethyl)pyridin-2-amine (40)

Compound 41: 5-[4,6-bis[(3R)-3-methylmorpholin-4-yl]-1,3,5-triazin-2-yl]-4-(difluoromethyl)pyridin-2-amine (41)

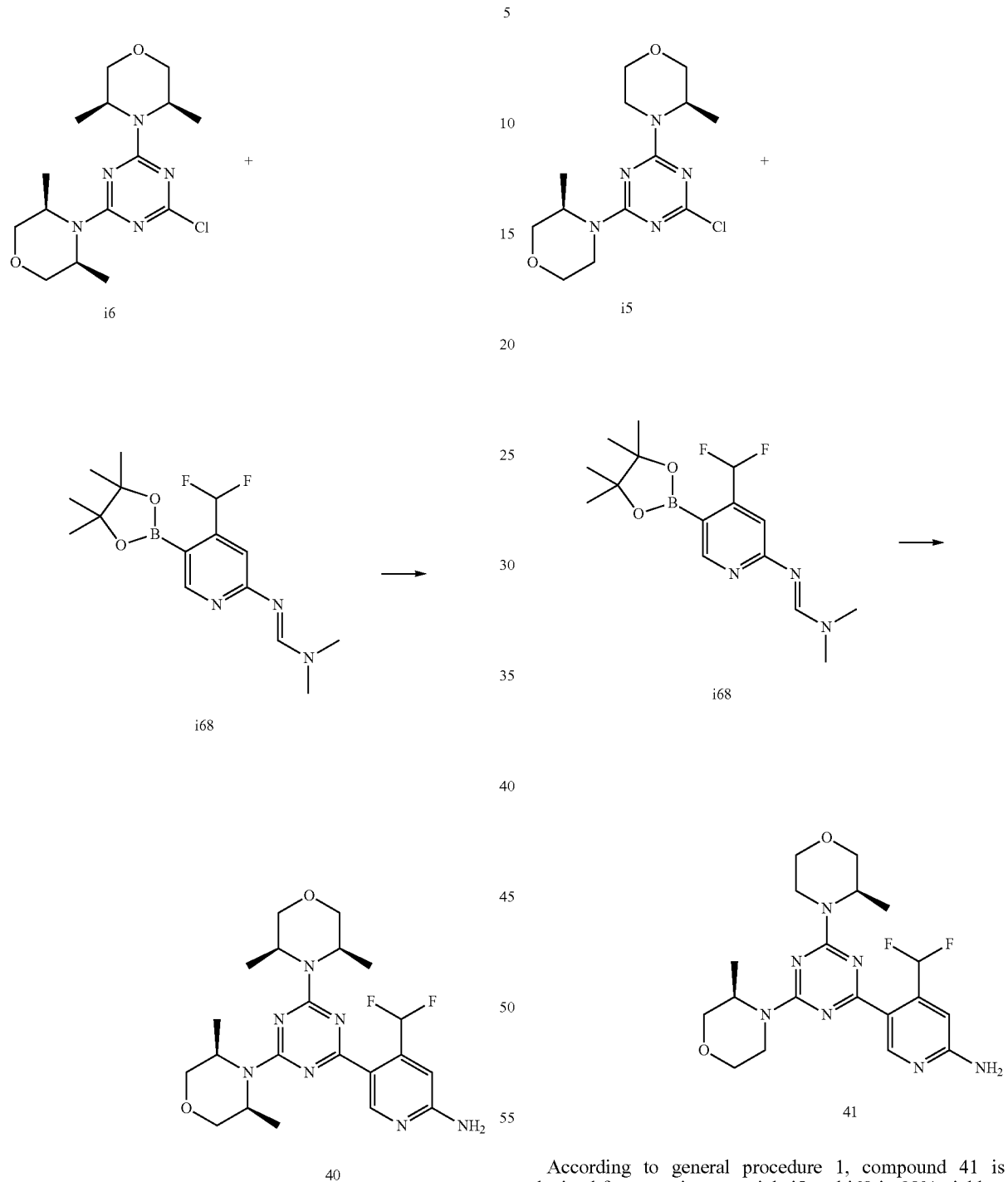

According to general procedure 1, compound 40 is obtained from starting materials i6 and i68 in 42% yield as a colorless solid. $^1$H NMR (400 MHz, (CD$_3$)$_2$SO): δ 8.90 (s, 1H), 7.82 (t, $^2J_{H,F}$=55 Hz, 1H), 6.84 (br s, 2H), 6.77 (s, 1H), 4.59-4.43 (m, 4H), 3.82-3.73 (m, 4H), 3.60-3.51 (m, 4H), 1.29 (d, $^2J_{H,H}$=6.9 Hz, 12H); $^{19}$F NMR (376 MHz, (CD$_3$)$_2$SO): δ −114.9 (−115.0) (m, 2 F); MS (MALDI): m/z=450.2 ([M+H]$^+$).

According to general procedure 1, compound 41 is obtained from starting materials i5 and i68 in 98% yield as a colorless solid. $^1$H NMR (400 MHz, CDCl$_3$): δ 9.04 (s, 1H), 7.70 (t, $^2J_{H,F}$=52.0 Hz, 1H), 6.84 (s, 1H), 4.88 (br s, 2H), 4.77-4.72 (m, 2H), 4.41 (d, $^2J_{H,H}$=12.0 Hz, 2H), 3.98 (dd, $^2J_{H,H}$=12.0 Hz, $^3J_{H,H}$=4.0 Hz, 2H), 3.78 (d, $^2J_{H,H}$=12.0 Hz, 2H), 3.68 (dd, $^2J_{H,H}$=12.0 Hz, $^3J_{H,H}$=4.0 Hz, 2H), 3.53 (dt, 2$J_{H,H}$=12.0 Hz, $^3J_{H,H}$=4.0 Hz, 2H), 3.28 (dt, $^2J_{H,H}$=12.0 Hz, $^3J_{H,H}$=4.0 Hz, 2H), 1.33 (d, $^2J_{H,H}$=8.0 Hz, 6H); $^{19}$F NMR (376 MHz, CDCl$_3$): δ −115.9 (s, 1 F), −116.0 (s, 1 F); MS (MALDI): m/z=421.7 ([M+H]$^+$).

Compound 42: 4-(difluoromethyl)-5-[4-(3,3-dimethylmorpholin-4-yl)-6-morpholino-1,3,5-triazin-2-yl]pyridin-2-amine (42)

Compound 44: 4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine (44)

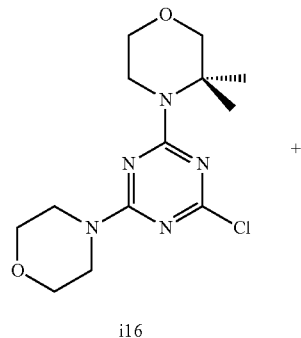

i16

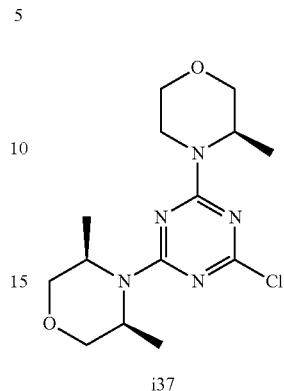

i37

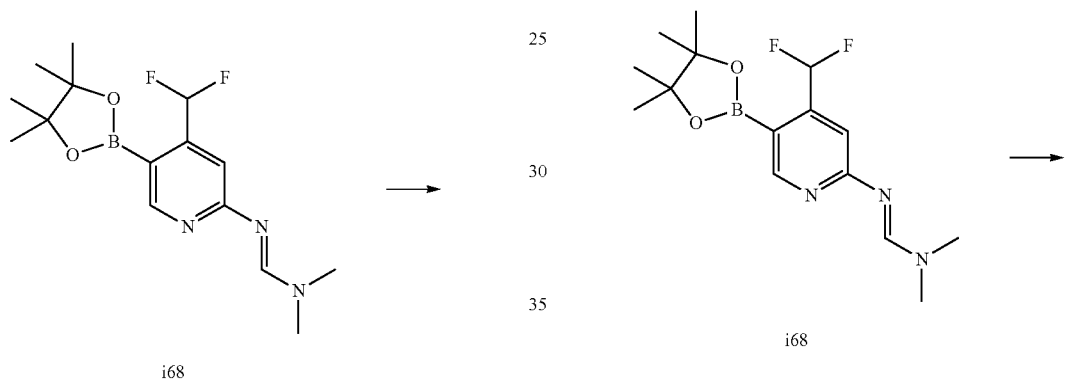

i68

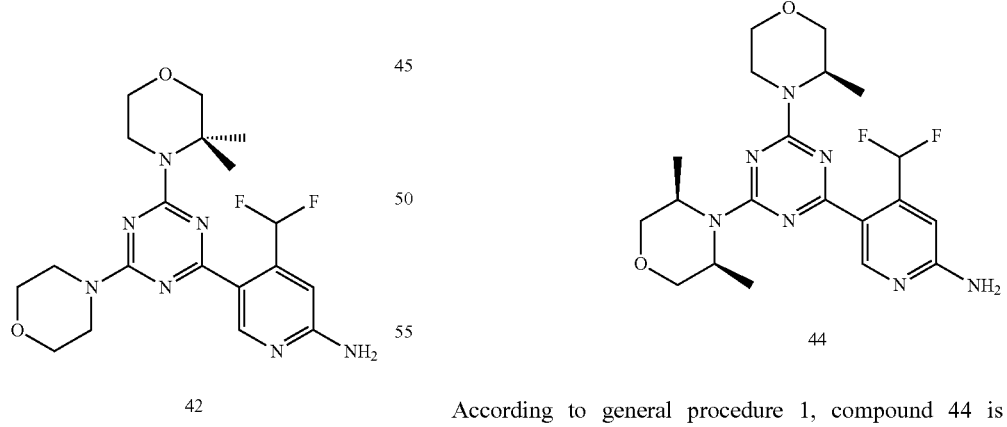

42

44

According to general procedure 1, compound 42 is obtained from starting materials i16 and i68 in 35% yield as a colorless solid. $^1$H NMR (400 MHz, $(CD_3)_2SO$): δ 8.83 (s, 1H), 7.73 (t, $^2J_{H,F}$=55 Hz, 1H), 6.84 (br s, 2H), 6.76 (s, 1H), 3.85-3.76 (m, 4H), 3.76-3.63 (m, 8H), 3.45 (br s, 2H), 1.49 (s, 6H); $^{19}$F NMR (376 MHz, $(CD_3)_2SO$): δ −116 (s, 2 F); MS (MALDI): m/z=422.1 ([M+H]$^+$).

According to general procedure 1, compound 44 is obtained from starting materials i37 and i68 in 75% yield as a colorless solid. $^1$H NMR (400 MHz, $(CD_3)_2SO$): δ 8.89 (s, 1H), 7.79 (t, $^2J_{H,F}$=55 Hz, 1H), 6.83 (br s, 2H), 6.76 (s, 1H), 4.65 (br s, 1H), 4.50 (br s, 2H), 4.37-4.25 (m, 1H), 3.93 (dd, $^3J_{H,H}$=11 Hz, $^3J_{H,H}$=3.2 Hz, 1H), 3.79-3.67 (m, 3H), 3.59-3.51 (m, 3H), 3.45-3.36 (m, 1H), 3.22-3.11 (m, 1H), 1.30 (d, $^3J_{H,H}$=6.7 Hz, 6H), 1.24 (d, $^3J_{H,H}$=6.7 Hz, 3H); $^{19}$F NMR (376 MHz, $(CD_3)_2SO$): δ −115.0 (br s, 2 F); MS (MALDI): m/z=436.1 ([M+H]$^+$).

Compound 45: 4-(difluoromethyl)-5-[4-(3,3-dimethylmorpholin-4-yl)-6-[(3R)-3-methylmorpholin-4-yl]-1,3,5-triazin-2-yl]pyridin-2-amine (45)

Compound 46: 4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine (46)

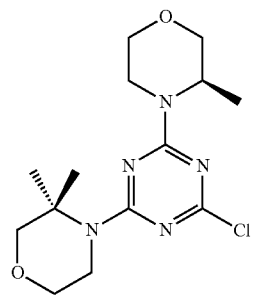

i38

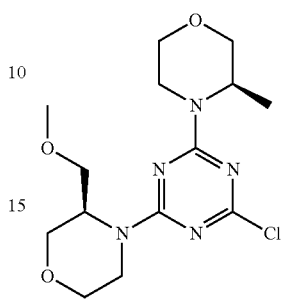

i39

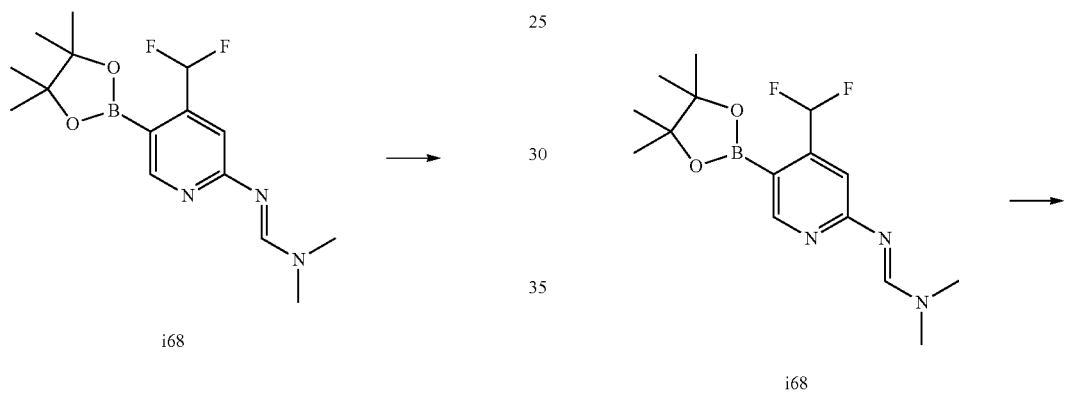

i68 i68

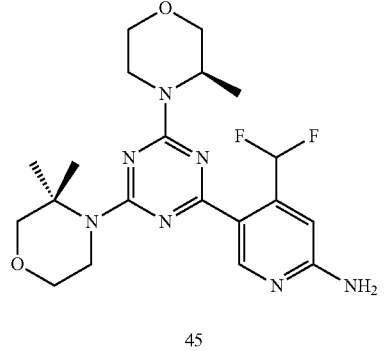

45

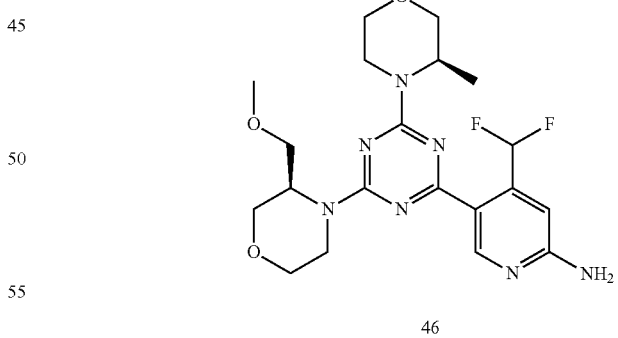

46

According to general procedure 1, compound 45 is obtained from starting materials i38 and i68 in 71% yield as a colorless solid. $^1$H NMR (400 MHz, (CD$_3$)$_2$SO): δ 8.84 (s, 1H), 7.74 (t, $^2J_{H,F}$=55 Hz, 1H), 6.83 (br s, 2H), 6.76 (s, 1H), 4.58 (br s, 1H), 4.31-4.19 (m, 1H), 3.93 (dd, $^2J_{H,H}$=12 Hz, $^3J_{H,H}$=3.9 Hz, 1H), 3.84-3.81 (m, 4H), 3.76-3.69 (m, 1H), 3.58 (dd, $^2J_{H,H}$=11 Hz, $^3J_{H,H}$=3.2 Hz, 1H), 3.46-3.38 (m, 3H), 3.23-3.13 (m, 1H), 1.50 (br s, 6H), 1.23 (d, $^3J_{H,H}$=6.7 Hz, 3H); $^{19}$F NMR (376 MHz, (CD$_3$)$_2$SO): δ −114.8 (−115.5) (m, 2 F); MS (MALDI): m/z=436.0 ([M+H]$^+$).

According to general procedure 1, compound 46 is obtained from starting materials i39 and i68 in 67% yield as a colorless solid. $^1$H NMR (400 MHz, (CD$_3$)$_2$SO): δ 8.87 (s, 1H), 7.77 (t, $^2J_{H,F}$=55 Hz, 1H), 6.84 (br s, 2H), 6.76 (s, 1H), 4.67 (br s, 2H), 4.44-4.24 (m, 2H), 3.96-3.83 (m, 3H), 3.75-3.63 (m, 2H), 3.60-3.36 (m, 5H), 3.31 (s, 3H), 3.21-3.04 (m, 2H), 1.23 (d, $^3J_{H,H}$=6.7 Hz, 3H); $^{19}$F NMR (376 MHz, (CD$_3$)$_2$SO): δ −115.0 (br s, 2 F); MS (MALDI): m/z=452.3 ([M+H]$^+$).

Compound 47: 4-(difluoromethyl)-5-[4-(3,7-dioxa-9-azabicyclo[3.3.1]nonan-9-yl)-6-[(3R)-3-methyl-morpholin-4-yl]-1,3,5-triazin-2-yl]pyridin-2-amine (47)

Compound 50: 4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine (50)

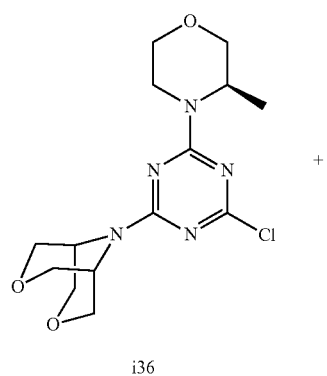
i36

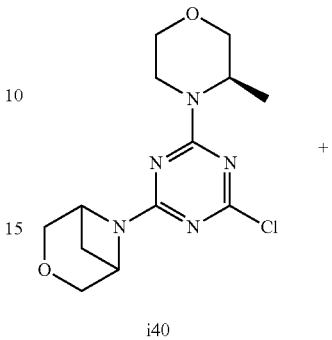
i40

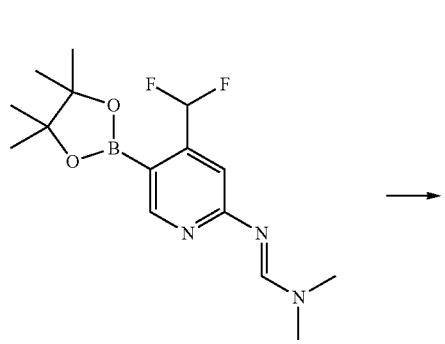
i68

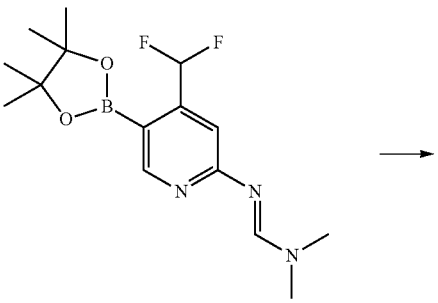
i68

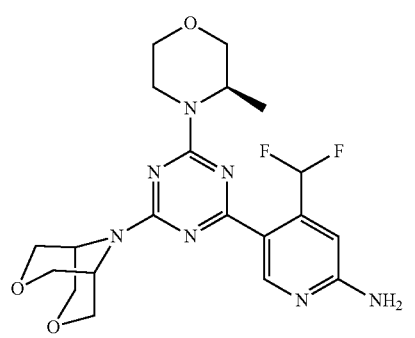
47

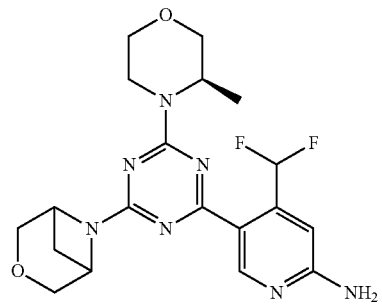
50

According to general procedure 1, compound 47 is obtained from starting materials i36 and i68 in 85% yield as a colorless solid. $^1$H NMR (400 MHz, (CD$_3$)$_2$SO): δ 8.86 (s, 1H), 7.72 (t, $^2J_{H,F}$=55 Hz, 1H), 6.84 (br s, 2H), 6.75 (s, 1H), 4.64 (br s, 1H), 4.53-4.42 (m, 2H), 4.37-4.25 (m, 1H), 4.05-3.96 (m, 4H), 3.92-3.84 (m, 1H), 3.77-3.66 (m, 5H), 3.60-3.52 (m, 1H), 3.44-3.35 (m, 1H), 3.22-3.10 (m, 1H), 1.23 (d, $^3J_{H,H}$=6.7 Hz, 3H); $^{19}$F NMR (376 MHz, (CD$_3$)$_2$SO): δ −114.9 (−117.1) (m, 2 F); MS (MALDI): m/z=450.0 ([M+H]$^+$).

According to general procedure 1, compound 50 is obtained from starting materials i40 and i68 in 52% yield as a colorless solid. $^1$H NMR (400 MHz, (CD$_3$)$_2$SO): δ 8.90 (s, 1H), 7.82 (t, $^2J_{H,F}$=55 Hz, 1H), 6.87 (br s, 2H), 6.76 (s, 1H), 4.55-4.51 (m, 1H), 4.34-4.14 (m, 3H), 4.12-4.25 (m, 2H), 3.92-3.80 (m, 1H), 3.76-3.68 (m, 3H), 3.55-3.51 (m, 1H), 3.38 (m, 1H), 3.20-3.13 (m, 1H), 2.68 (m, 1H), 1.78 (m, 1H), 1.20 (d, $^3J_{H,H}$=6.9 Hz, 3H); $^{19}$F NMR (376 MHz, (CD$_3$)$_2$SO): δ −115.0 (br s, 2 F); MS (MALDI): m/z=420.6 ([M+H]$^+$).

Compound 51: 4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine (51)

Compound 52: 4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine (52)

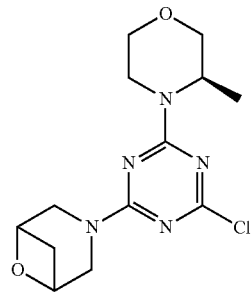

i41

i42

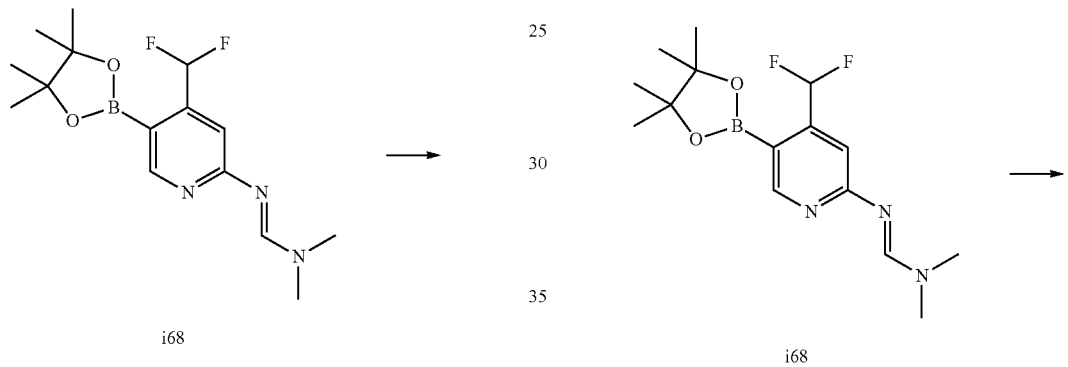

i68 i68

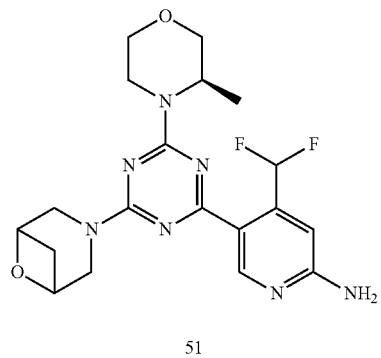

51

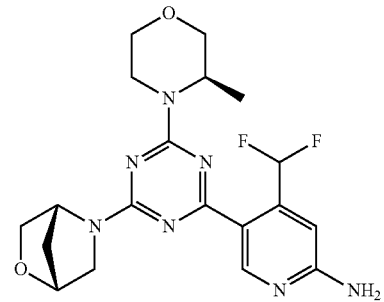

52

According to general procedure 1, compound 51 is obtained from starting materials i41 and i68 in 36% yield as a colorless solid. $^1$H NMR (400 MHz, (CD$_3$)$_2$SO): δ 8.99 (s, 1H), 7.89 (t, $^2J_{H,F}$=55 Hz, 1H), 6.84 (br s, 2H), 6.77 (s, 1H), 4.69 (m, 3H), 4.37 (m, 1H), 3.91-3.85 (m, 3H), 3.75-3.53 (m, 4H), 3.42-3.35 (m, 1H), 3.22-3.15 (m, 1H), 3.12-3.08 (m, 1H), 1.85 (m, 1H), 1.24 (d, $^3J_{H,H}$=6.9 Hz, 3H); $^{19}$F NMR (376 MHz, (CD$_3$)$_2$SO): δ −116.0 (br s, 2 F); MS (MALDI): m/z=420.6 ([M+H]$^+$).

According to general procedure 1, compound 52 is obtained from starting materials i42 and i68 in 44% yield as a colorless solid (1:1 mixture of rotamers). $^1$H NMR (400 MHz, (CD$_3$)$_2$SO): δ 8.89 (m, 1H), 7.77 (m, 1H), 6.84 (br s, 2H), 6.76 (s, 1H), 5.02-4.97 (m, 1H), 4.68-4.66 (m, 2H), 4.31 (m, 1H), 3.89-3.85 (m, 1H), 3.79-3.57 (m, 3H), 3.57-3.44 (m, 4H), 3.22 (m, 1H), 1.90-1.83 (m, 2H), 1.21 (d, $^3J_{H,H}$=6.9 Hz, 3H); $^{19}$F NMR (376 MHz, (CD$_3$)$_2$SO): δ −115.5 (br s, 2 F); MS (MALDI): m/z=420.2 ([M+H]$^+$).

Compound 53: 4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine (53)

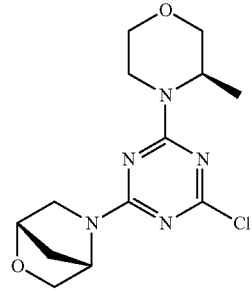

i43

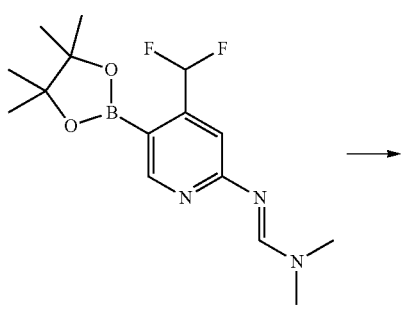

i68

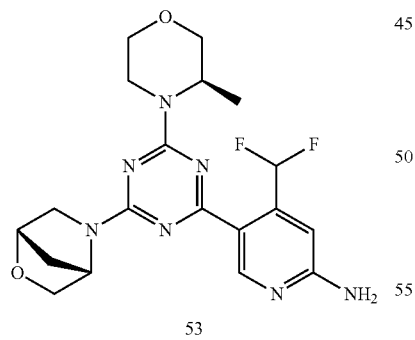

53

Compound 54: 5-[4,6-bis[(3R)-3-ethylmorpholin-4-yl]-1,3,5-triazin-2-yl]-4-(difluoromethyl)pyridin-2-amine (54)

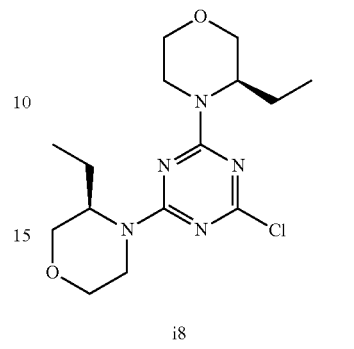

i8

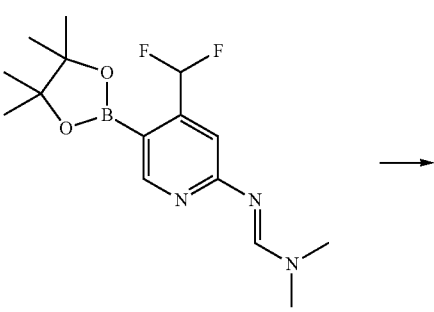

i68

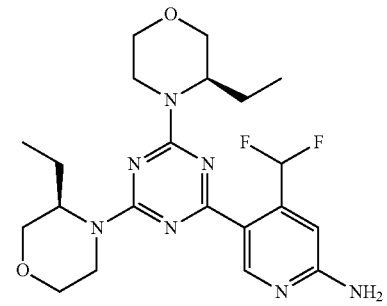

54

According to general procedure 1, compound 53 is obtained from starting materials i43 and i68 in 53% yield as a colorless solid (1:1 mixture of rotamers). $^1$H NMR (400 MHz, (CD$_3$)$_2$SO): δ 8.90 (m, 1H), 7.77 (m, 1H), 6.84 (br s, 2H), 6.76 (s, 1H), 5.02-4.96 (m, 1H), 4.68-4.62 (m, 2H), 3.90 (m, 1H), 3.80 (m, 1H), 3.70 (m, 2H), 3.57 (m, 2H), 3.45 (m, 3H), 3.20 (m, 1H), 1.90-1.83 (m, 2H), 1.21 (d, $^3J_{H,H}$=6.9 Hz, 3H); $^{19}$F NMR (376 MHz, (CD$_3$)$_2$SO): δ −115.0 (br s, 2 F); MS (MALDI): m/z=420.2 ([M+H]$^+$).

According to general procedure 1, compound 54 is obtained from starting materials i8 and i68 in 61% yield as a colorless solid. $^1$H NMR (400 MHz, (CD$_3$)$_2$SO): δ 8.87 (s, 1H), 7.77 (t, $^2J_{H,F}$=55 Hz, 1H), 6.83 (br s, 2H), 6.76 (s, 1H), 4.47 (m, 4H), 3.89-3.81 (m, 4H), 3.51-3.34 (m, 4H), 3.12 (m, 2H), 1.71 (m, 4H), 0.86 (m, 6H). $^{19}$F NMR (376 MHz, (CD$_3$)$_2$SO): δ −115.0 (br s, 2 F); MS (MALDI): m/z=450.3 ([M+H]$^+$).

155

Compound 55: 5-[4,6-bis(8-oxa-5-azaspiro[3.5]nonan-5-yl)-1,3,5-triazin-2-yl]-4-(difluoromethyl)pyridin-2-amine (55)

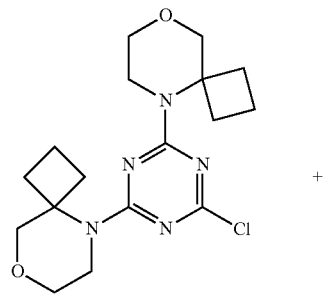

156

Compound 56: 5-[4,6-bis[(3R)-3-isopropylmorpholin-4-yl]-1,3,5-triazin-2-yl]-4-(difluoromethyl)pyridin-2-amine (56)

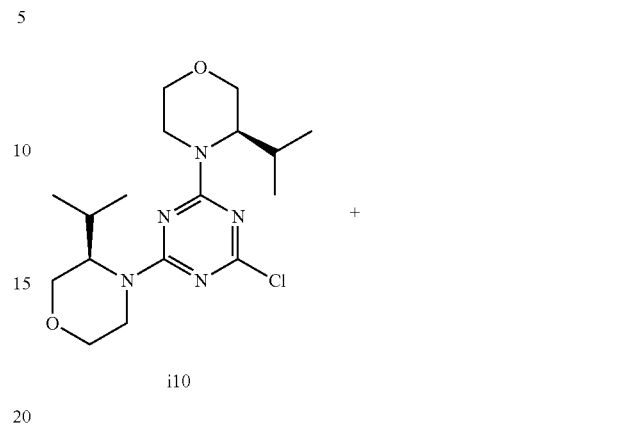

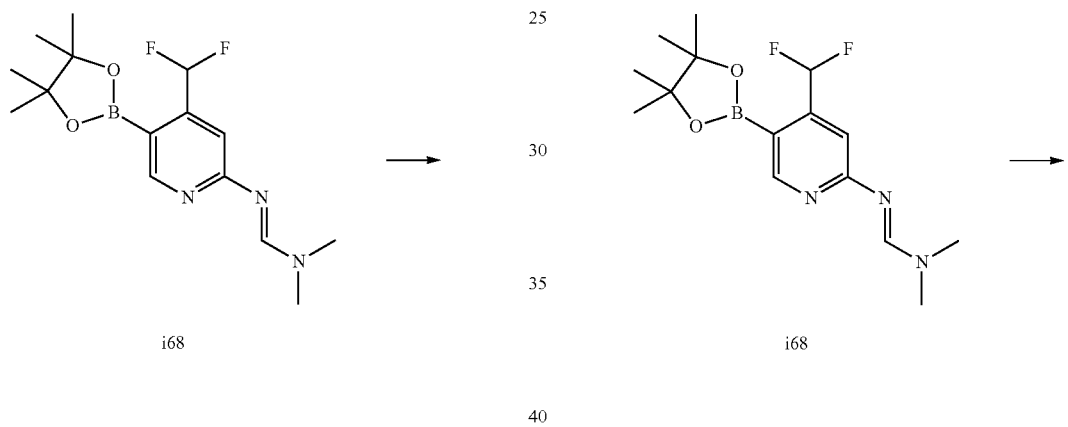

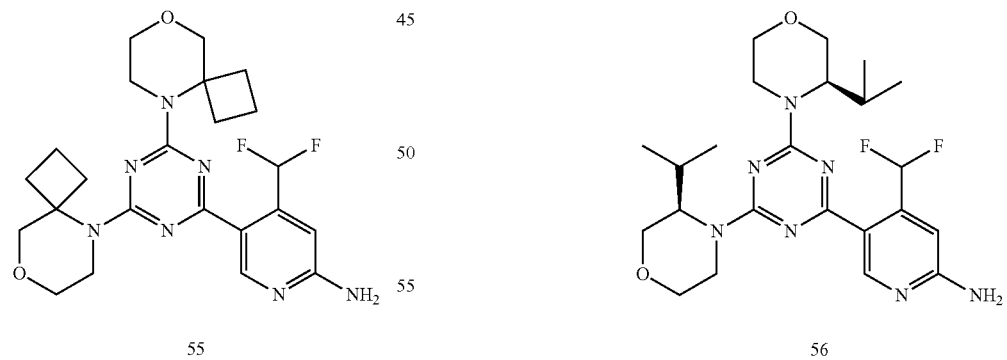

According to general procedure 1, compound 55 is obtained from starting materials i9 and i68 in 59% yield as a colorless solid. $^1$H NMR (400 MHz, (CD$_3$)$_2$SO): δ 8.74 (s, 1H), 7.65 (t, $^2J_{H,F}$=55 Hz, 1H), 6.81 (br s, 2H), 6.75 (s, 1H), 3.68 (m, 8H), 3.49 (m, 4H), 2.46-2.38 (m, 4H), 2.25-2.16 (m, 4H), 1.72-1.66 (m, 4H); $^{19}$F NMR (376 MHz, (CD$_3$)$_2$SO): δ −115.5 (br s, 2 F); MS (MALDI): m/z=474.3 ([M+H]$^+$).

According to general procedure 1, compound 56 is obtained from starting materials i10 and i68 in 59% yield as a colorless solid. $^1$H NMR (400 MHz, (CD$_3$)$_2$SO): δ 8.87 (s, 1H), 7.76 (t, $^2J_{H,F}$=55 Hz, 1H), 6.82 (br s, 2H), 6.76 (s, 1H), 4.50 (m, 2H), 4.29 (m, 2H), 4.02-3.84 (m, 4H), 3.40 (m, 4H), 3.08 (m, 2H), 2.34 (m, 2H), 1.02 (m, 6H), 0.77 (m, 6H); $^{19}$F NMR (376 MHz, (CD$_3$)$_2$SO): δ −115.0 (br s, 2 F); MS (MALDI): m/z=478.4 ([M+H]$^+$).

Compound 66: 4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine (66)

Compound 67: 4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine (67)

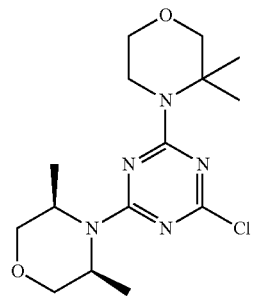

i55

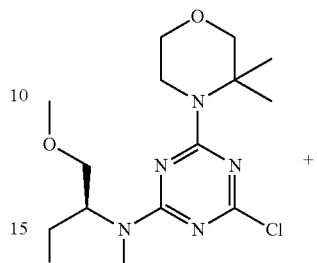

i56

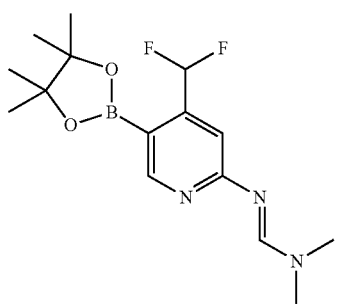

i68

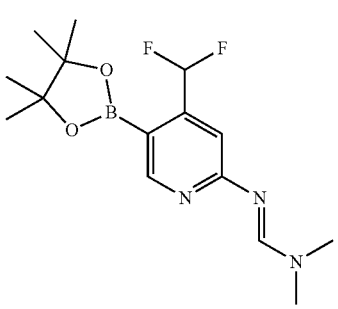

i68

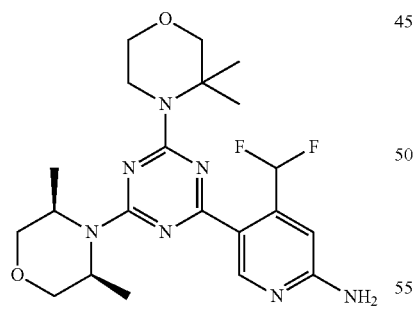

66

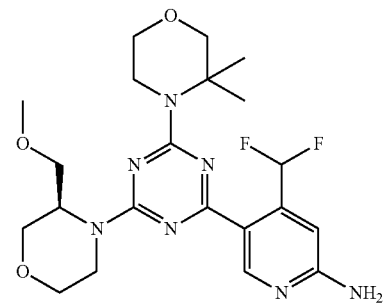

67

According to general procedure 1, compound 66 is obtained from starting materials i55 and i68 in 61% yield as a colorless solid. $^1$H NMR (400 MHz, (CD$_3$)$_2$SO): δ 8.87 (s, 1H), 7.77 (t, $^2J_{H,F}$=55 Hz, 1H), 6.83 (br s, 2H), 6.76 (s, 1H), 4.46 (m, 2H), 3.81-3.77 (m, 6H), 3.55 (m, 2H), 3.44 (m, 2H), 1.49 (s, 6H), 1.28 (d, $^3J_{H,H}$=6.9 Hz, 6H); $^{19}$F NMR (376 MHz, (CD$_3$)$_2$SO): δ −115.0 (br s, 2 F); MS (MALDI): m/z=450.4 ([M+H]$^+$).

According to general procedure 1, compound 67 is obtained from starting materials i56 and i68 in 37% yield as a colorless solid. $^1$H NMR (400 MHz, (CD$_3$)$_2$SO): δ 8.84 (s, 1H), 7.89 (t, $^2J_{H,F}$=55 Hz, 1H), 6.85 (br s, 2H), 6.76 (s, 1H), 4.60 (m, 1H), 4.31 (m, 1H), 3.92 (m, 2H), 3.83 (m, 4H), 3.65 (m, 1H), 3.51-3.41 (m, 5H), 3.28 (s, 3H), 3.12 (m, 1H), 1.49 (s, 3H), 1.48 (s, 3H); $^{19}$F NMR (376 MHz, (CD$_3$)$_2$SO): δ −115.5 (br s, 2 F); MS (MALDI): m/z=466.4 ([M+H]$^+$).

Compound 68: [(3R)-4-[4-[6-amino-4-(difluoromethyl)-3-pyridyl]-6-(3,3-dimethylmorpholin-4-yl)-1,3,5-triazin-2-yl]morpholin-3-yl]methanol (68)

Compound 69: 4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine (69)

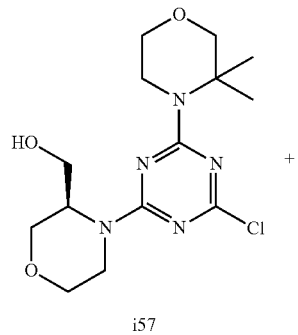

i57

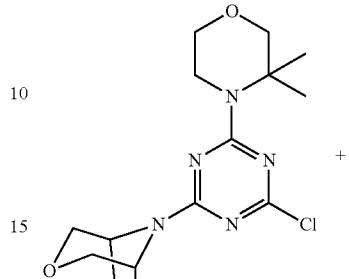

i54

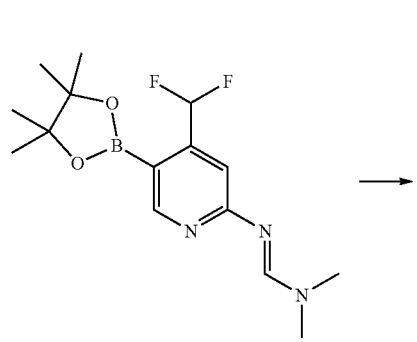

i68

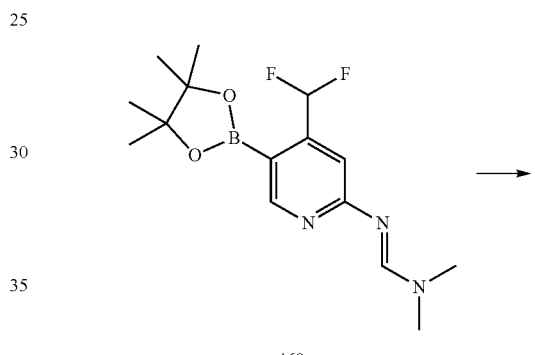

i68

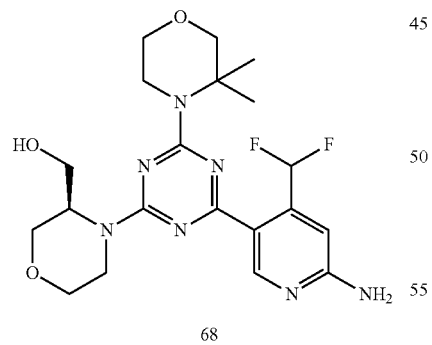

68

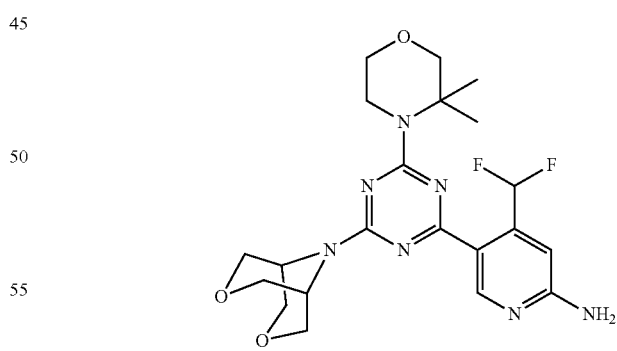

69

According to general procedure 1, compound 68 is obtained from starting materials i57 and i68 in 58% yield as a colorless solid. $^1$H NMR (400 MHz, (CD$_3$)$_2$SO): δ 8.83 (s, 1H), 7.77 (m, 1H), 6.84 (br s, 2H), 6.76 (s, 1H), 4.91 (m, 1H), 4.35 (m, 2H), 4.05 (m, 1H), 3.97-3.70 (m, 6H), 3.54-3.38 (m, 5H), 3.12 (m, 1H), 1.49 (s, 3H), 1.48 (s, 3H); $^{19}$F NMR (376 MHz, (CD$_3$)$_2$SO): δ −115.5 (br s, 2 F); MS (MALDI): m/z=452.2 ([M+H]$^+$).

According to general procedure 1, compound 69 is obtained from starting materials i54 and i68 in 57% yield as a colorless solid. $^1$H NMR (400 MHz, (CD$_3$)$_2$SO): δ 8.83 (s, 1H), 7.69 (t, $^2J_{H,F}$=55 Hz, 1H), 6.85 (br s, 2H), 6.76 (s, 1H), 4.47-4.37 (m, 2H), 4.01 (m, 4H), 3.80-3.71 (m, 8H), 3.45 (m, 2H), 1.48 (s, 6H); $^{19}$F NMR (376 MHz, (CD$_3$)$_2$SO): δ −115.7 (br s, 2 F); MS (MALDI): m/z=464.3 ([M+H]$^+$).

Compound 70: 5-[4-(4-cyclopropylpiperazin-1-yl)-6-(3,3-dimethylmorpholin-4-yl)-1,3,5-triazin-2-yl]-4-(difluoromethyl)pyridin-2-amine (70)

Compound 71: 4-(difluoromethyl)-5-[4-(3,3-dimethylmorpholin-4-yl)-6-[4-(2-methoxyethyl)piperazin-1-yl]-1,3,5-triazin-2-yl]pyridin-2-amine (71)

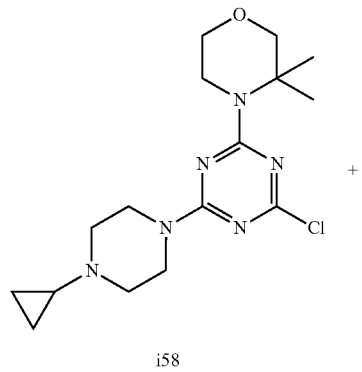

i58

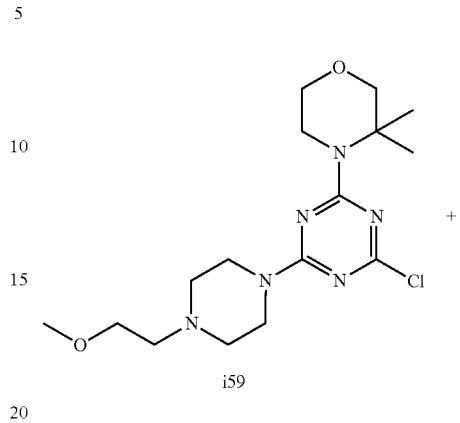

i59

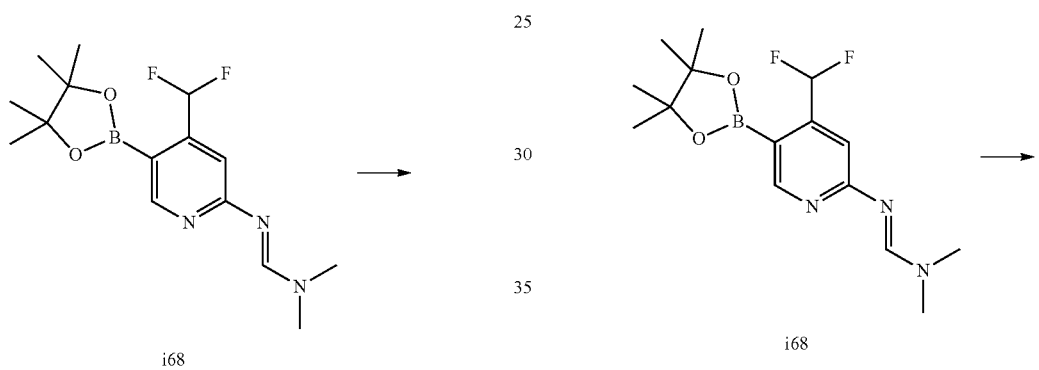

i68

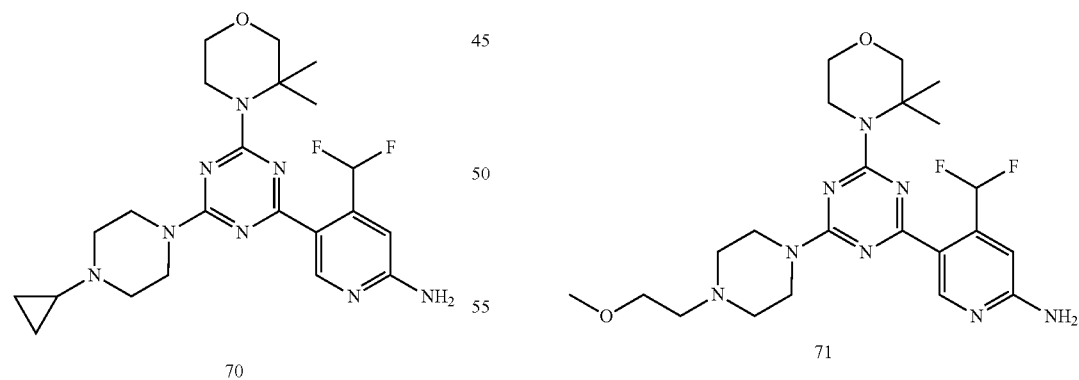

70

71

According to general procedure 1, compound 70 is obtained from starting materials i58 and i68 in 12% yield as a colorless solid. $^1$H NMR (400 MHz, (CD$_3$)$_2$SO): δ 8.82 (s, 1H), 7.72 (t, $^2J_{H,F}$=55 Hz, 1H), 6.83 (br s, 2H), 6.76 (s, 1H), 3.82 (m, 4H), 3.71 (m, 4H), 3.44 (m, 2H), 2.58 (m, 4H), 1.64 (m, 1H), 1.44 (s, 6H), 0.45 (m, 2H), 0.36 (m, 2H); $^{19}$F NMR (376 MHz, (CD$_3$)$_2$SO): δ −115.4 (br s, 2 F); MS (MALDI): m/z=460.4 ([M]$^+$).

According to general procedure 1, compound 71 is obtained from starting materials i59 and i68 in 42% yield as a colorless solid. $^1$H NMR (400 MHz, (CD$_3$)$_2$SO): δ 8.82 (s, 1H), 7.73 (t, $^2J_{H,F}$=55 Hz, 1H), 6.83 (br s, 2H), 6.76 (s, 1H), 3.88-3.69 (m, 10H), 3.47-3.44 (m, 4H), 3.24 (m, 3H), 2.52-2.45 (m, 4H), 1.44 (s, 6H); $^{19}$F NMR (376 MHz, (CD$_3$)$_2$SO): δ −115.4 (br s, 2 F); MS (MALDI): m/z=478.4 ([M]$^+$).

Compound 77: [(3R)-4-[4-[6-amino-4-(difluoromethyl)-3-pyridyl]-6-[(3R)-3-methylmorpholin-4-yl]-1,3,5-triazin-2-yl]morpholin-3-yl]methanol (77)

Compound 78: 4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine (78)

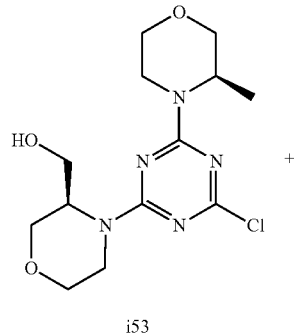

i53

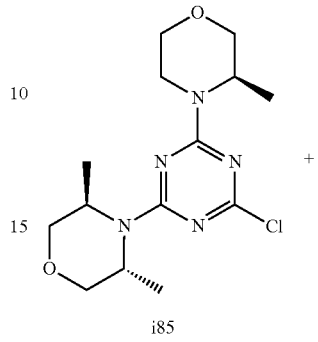

i85

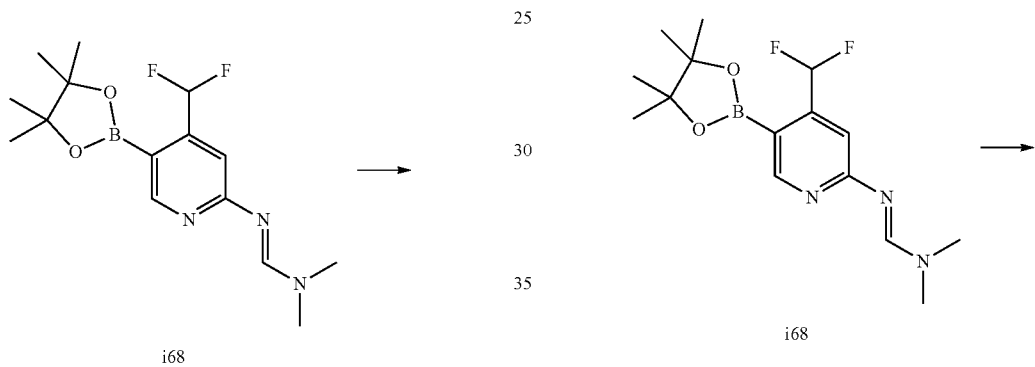

i68

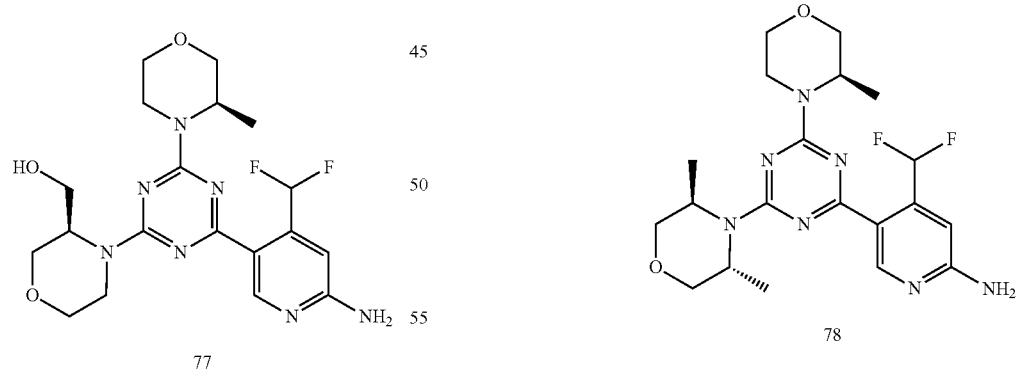

According to general procedure 1, compound 77 is obtained from starting materials i53 and i68 in 31% yield as a colorless solid. $^1$H NMR (400 MHz, (CD$_3$)$_2$SO): δ 8.88 (s, 1H), 7.78 (t, $^2J_{H,F}$=55 Hz, 1H), 6.84 (br s, 2H), 6.76 (s, 1H), 4.96 (m, 1H), 4.73 (m, 1H), 4.58-4.24 (m, 3H), 4.05 (m, 1H), 3.90 (m, 2H), 3.72 (m, 2H), 3.59 (m, 1H), 3.51-3.36 (m, 4H), 3.23-3.02 (m, 2H), 1.23 (d, $^3J_{H,H}$=6.9 Hz, 3H); MS (MALDI): m/z=438.3 ([M+H]$^+$).

According to general procedure 1, compound 78 is obtained from starting materials i85 and i68 in 71% yield as a colorless solid. $^1$H NMR (400 MHz, (CD$_3$)$_2$SO): δ 8.90 (s, 1H), 7.82 (t, $^2J_{H,F}$=55 Hz, 1H), 6.84 (br s, 2H), 6.76 (s, 1H), 4.66 (m, 1H), 4.32 (m, 3H), 4.15-4.11 (m, 2H), 3.92 (m, 1H), 3.70 (m, 3H), 3.57 (m, 1H), 3.40 (m, 1H), 3.18 (m, 1H), 1.37 (m, 6H), 1.24 (d, $^3J_{H,H}$=6.9 Hz, 3H); $^{19}$F NMR (376 MHz, (CD$_3$)$_2$SO): δ −114.9 (br s, 2 F); MS (MALDI): m/z=435.4 ([M]$^+$).

Compound 79: 4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine (79)

Compound 80: 4-(difluoromethyl)-5-[4-morpholino-6-(3-oxa-9-azabicyclo[3.3.1]nonan-9-yl)-1,3,5-triazin-2-yl]pyridin-2-amine (80)

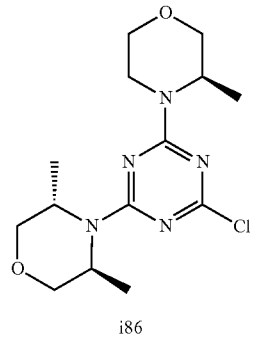

i86

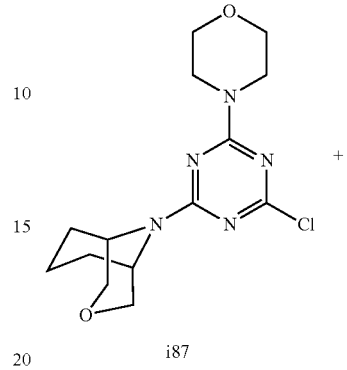

i87

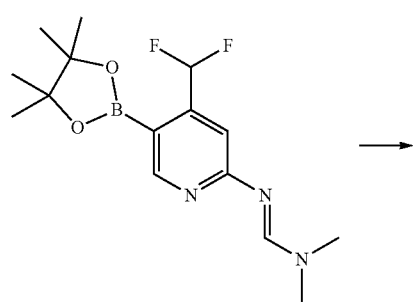

i68

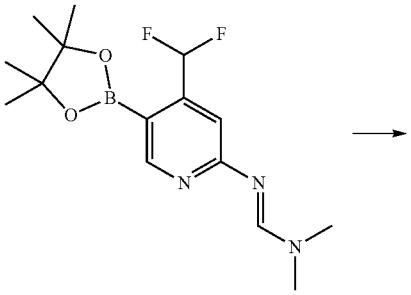

i68

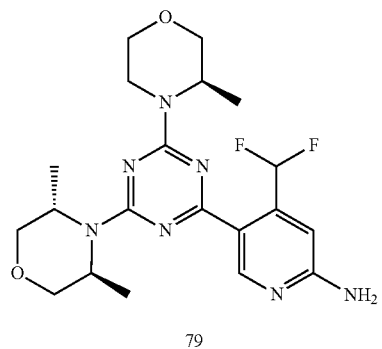

79

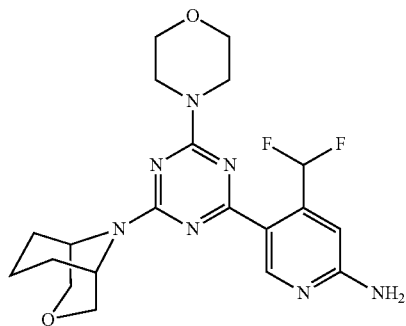

80

According to general procedure 1, compound 79 is obtained from starting materials i86 and i68 in 65% yield as a colorless solid. $^1$H NMR (400 MHz, (CD$_3$)$_2$SO): δ 8.91 (s, 1H), 7.82 (t, $^2J_{H,F}$=55 Hz, 1H), 6.85 (br s, 2H), 6.76 (s, 1H), 4.66 (m, 1H), 4.32 (m, 3H), 4.15-4.11 (m, 2H), 3.92 (m, 1H), 3.70 (m, 3H), 3.57 (m, 1H), 3.40 (m, 1H), 3.19 (m, 1H), 1.37 (m, 6H), 1.24 (d, $^3J_{H,H}$=6.9 Hz, 3H); $^{19}$F NMR (376 MHz, (CD$_3$)$_2$SO): δ −114.9 (br s, 2 F); MS (MALDI): m/z=434.3 ([M]$^+$).

According to general procedure 1, compound 80 is obtained from starting materials i87 and i68 in 57% yield as a colorless solid. $^1$H NMR (400 MHz, (CD$_3$)$_2$SO): δ 8.85 (s, 1H), 7.73 (t, $^2J_{H,F}$=55 Hz, 1H), 6.84 (br s, 2H), 6.75 (s, 1H), 4.61-4.57 (m, 2H), 3.95 (m, 2H), 3.75-3.65 (m, 10H), 2.48 (m, 1H), 1.88-1.72 (m, 4H), 1.57 (m, 1H); $^{19}$F NMR (376 MHz, (CD$_3$)$_2$SO): δ −115.4 (m, 2 F); MS (MALDI): m/z=434.3 ([M+H]$^+$).

Compound 82: 4-(difluoromethyl)-5-[4-(3,7-dioxa-9-azabicyclo[3.3.1]nonan-9-yl)-6-(3-oxa-9-azabicyclo[3.3.1]nonan-9-yl)-1,3,5-triazin-2-yl]pyridin-2-amine (82)

Compound 83: 5-[4,6-bis[(3S,5S)-3,5-dimethylmorpholin-4-yl]-1,3,5-triazin-2-yl]-4-(difluoromethyl)pyridin-2-amine (83)

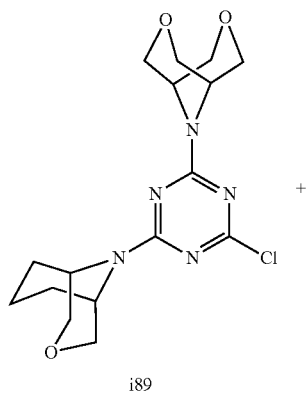

i89

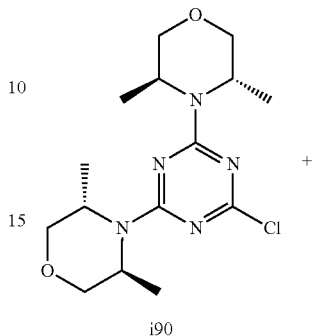

i90

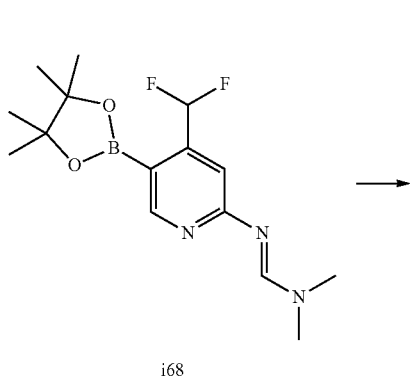

i68

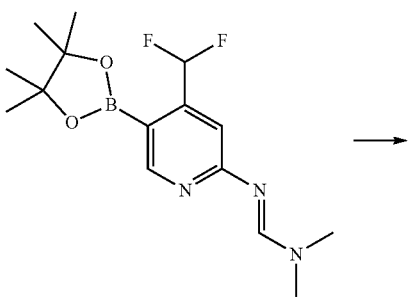

i68

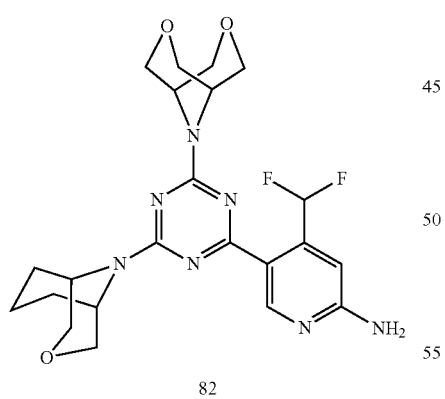

82

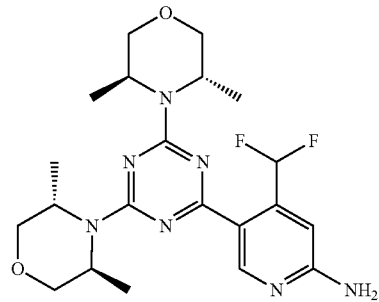

83

According to general procedure 1, compound 82 is obtained from starting materials i89 and i68 in 51% yield as a colorless solid. $^1$H NMR (400 MHz, (CD$_3$)$_2$SO): δ 8.84 (s, 1H), 7.70 (t, $^2J_{H,F}$=55 Hz, 1H), 6.85 (br s, 2H), 6.75 (s, 1H), 4.62 (m, 1H), 4.54 (m, 1H), 4.52 (m, 1H), 4.44 (m, 1H), 4.04-3.92 (m, 6H), 3.75-3.62 (m, 6H), 2.45 (m, 1H), 1.89-1.75 (m, 4H), 1.57 (m, 1H); $^{19}$F NMR (376 MHz, (CD$_3$)$_2$SO): δ −115.7 (m, 2 F); MS (MALDI): m/z=476.2 ([M+H]$^+$).

According to general procedure 1, compound 83 is obtained from starting materials i90 and i68 in 56% yield as a colorless solid. $^1$H NMR (400 MHz, (CD$_3$)$_2$SO): δ 8.92 (s, 1H), 7.87 (t, $^2J_{H,F}$=55 Hz, 1H), 6.84 (br s, 2H), 6.77 (s, 1H), 4.32 (m, 4H), 4.14 (m, 4H), 3.70 (m, 4H), 1.39 (d, $^3J_{H,H}$=6.9 Hz, 12H); $^{19}$F NMR (376 MHz, (CD$_3$)$_2$SO): δ −115.5 (br s, 2 F); MS (MALDI): m/z=448.3 ([M]$^+$).

Compound 84: 4-(difluoromethyl)-5-[4-(3,7-dioxa-9-azabicyclo[3.3.1]nonan-9-yl)-6-morpholino-1,3,5-triazin-2-yl]pyridin-2-amine (84)

Compound 85: 4-(difluoromethyl)-5-[4-[(3S)-3-ethylmorpholin-4-yl]-6-[(3R)-3-methylmorpholin-4-yl]-1,3,5-triazin-2-yl]pyridin-2-amine (85)

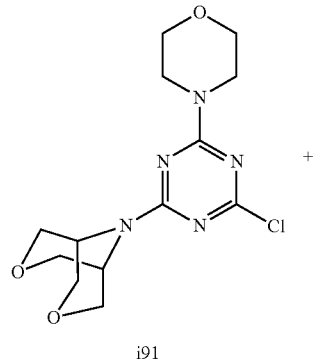

i91

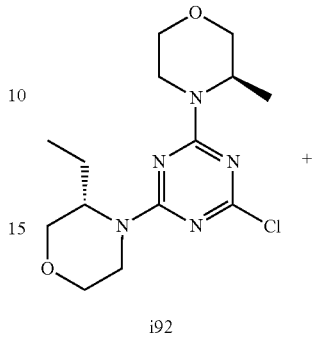

i92

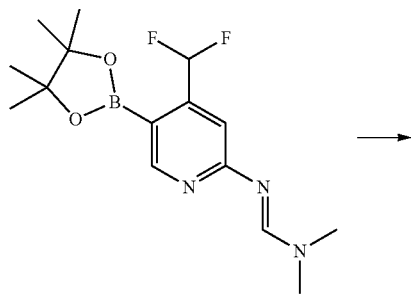

i68

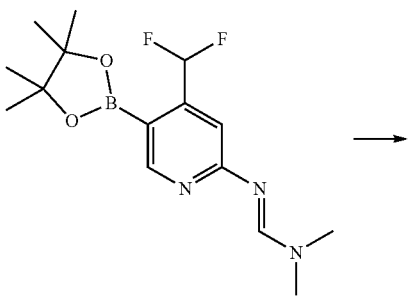

i68

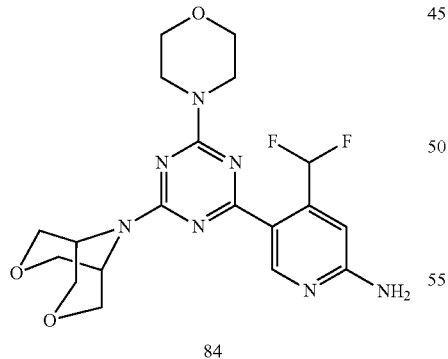

84

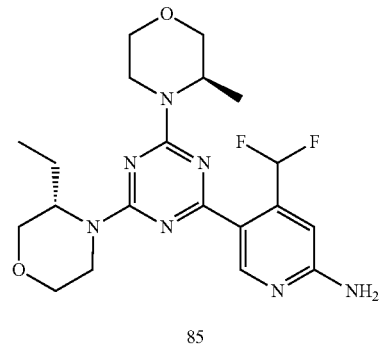

85

According to general procedure 1, compound 84 is obtained from starting materials i91 and i68 in 63% yield as a colorless solid. $^{1}$H NMR (400 MHz, (CD$_3$)$_2$SO): δ 8.86 (s, 1H), 7.71 (t, $^{2}J_{H,F}$=55 Hz, 1H), 6.87 (br s, 2H), 6.75 (s, 1H), 4.49 (m, 2H), 4.02 (m, 4H), 3.74-3.65 (m, 12H); $^{19}$F NMR (376 MHz, (CD$_3$)$_2$SO): δ −115.6 (br s, 2 F); MS (MALDI): m/z=436.4 ([M+H]$^+$).

According to general procedure 1, compound 85 is obtained from starting materials i92 and i68 in 52% yield as a colorless solid. $^{1}$H NMR (400 MHz, (CD$_3$)$_2$SO): δ 8.88 (s, 1H), 7.77 (t, $^{2}J_{H,F}$=55 Hz, 1H), 6.85 (br s, 2H), 6.76 (s, 1H), 4.70-4.25 (m, 4H), 3.90 (m, 3H), 3.72 (m, 1H), 3.60-3.45 (m, 4H), 3.16 (m, 2H), 1.73 (m, 2H), 1.22 (d, $^{3}J_{H,H}$=6.9 Hz, 3H), 0.86 (m, 3H); $^{19}$F NMR (376 MHz, (CD$_3$)$_2$SO): δ −114.9 (br s, 2 F); MS (MALDI): m/z=436.9 ([M+H]$^+$).

171

Compound 86: 4-(difluoromethyl)-5-[4-[(3R)-3-ethylmorpholin-4-yl]-6-[(3R)-3-methylmorpholin-4-yl]-1,3,5-triazin-2-yl]pyridin-2-amine (86)

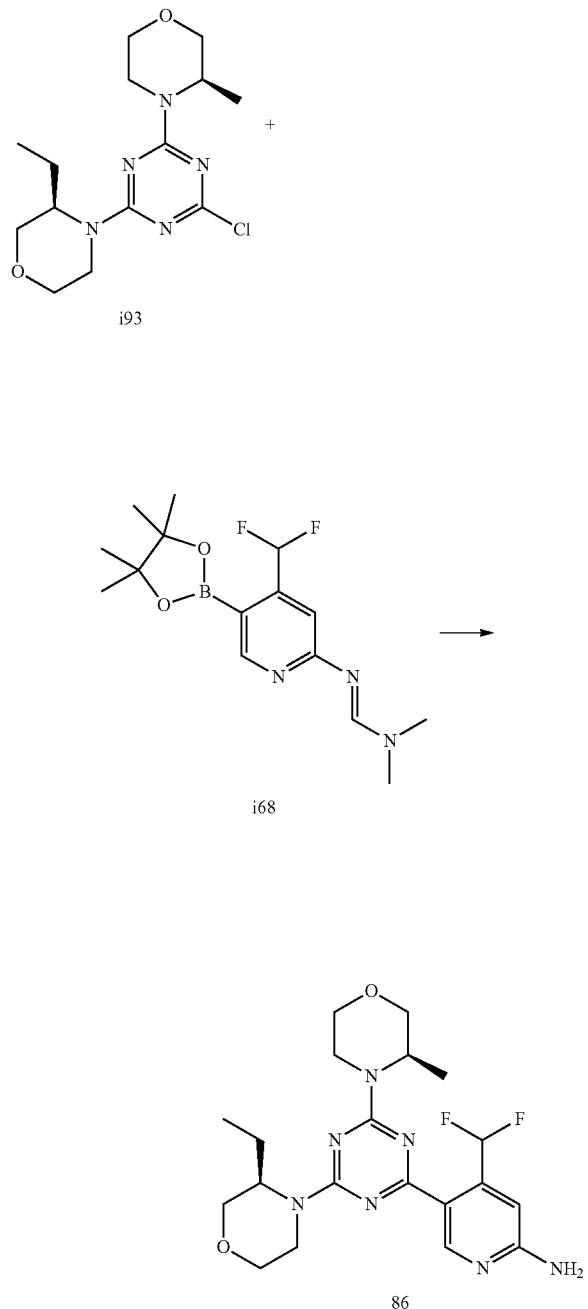

According to general procedure 1, compound 86 is obtained from starting materials i93 and i68 in 47% yield as a colorless solid. $^1$H NMR (400 MHz, (CD$_3$)$_2$SO): δ 8.88 (s, 1H), 7.77 (t, $^2J_{H,F}$=55 Hz, 1H), 6.85 (br s, 2H), 6.76 (s, 1H), 4.65 (m, 1H), 4.49-4.30 (m, 3H), 3.93-3.82 (m, 3H), 3.72 (m, 1H), 3.57 (m, 1H), 3.50 (m, 1H), 3.43-3.37 (m, 2H), 3.19-3.14 (m, 2H), 1.73 (m, 2H), 1.22 (d, $^3J_{H,H}$=6.9 Hz, 3H), 0.86 (m, 3H); $^{19}$F NMR (376 MHz, (CD$_3$)$_2$SO): δ −115.3 (br s, 2 F); MS (MALDI): m/z=436.9 ([M+H]$^+$).

172

Compound 88: 4-(difluoromethyl)-5-[4-[(3R)-3-methylmorpholin-4-yl]-6-(8-oxa-5-azaspiro[3.5]nonan-5-yl)-1,3,5-triazin-2-yl]pyridin-2-amine (88)

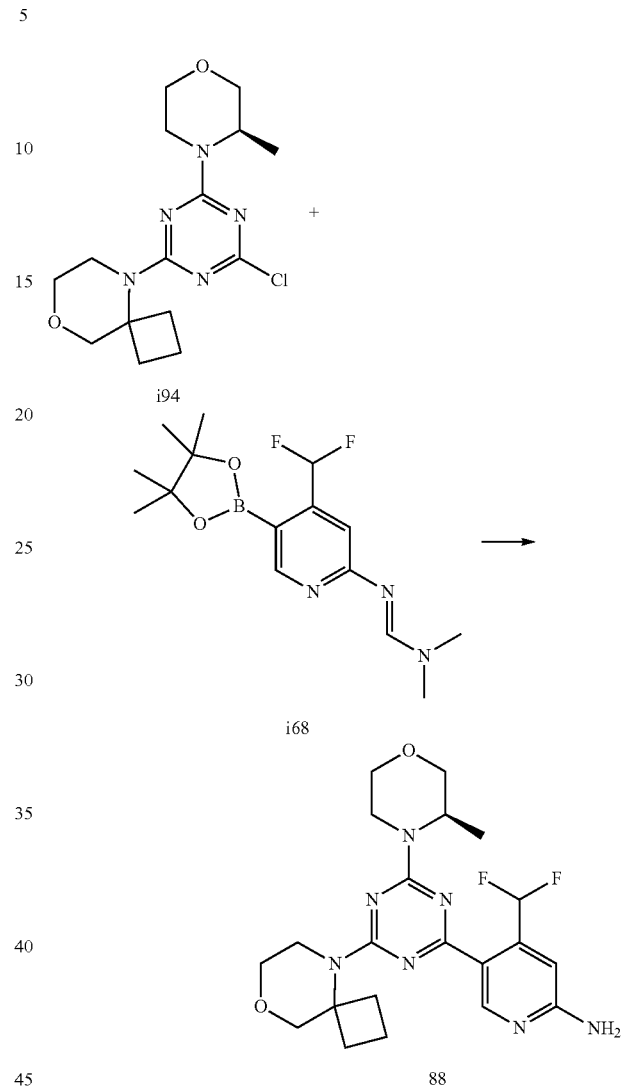

According to general procedure 1, compound 88 is obtained from starting materials i94 and i68 in 50% yield as a colorless solid. $^1$H NMR (400 MHz, (CD$_3$)$_2$SO): δ 8.82 (s, 1H), 7.71 (t, $^2J_{H,F}$=55 Hz, 1H), 6.84 (br s, 2H), 6.75 (s, 1H), 4.55 (m, 1H), 4.23 (m, 1H), 3.91 (m, 1H), 3.78 (m, 2H), 3.69 (m, 3H), 3.56 (m, 1H), 3.50 (m, 2H), 3.41 (m, 1H), 3.16 (m, 1H), 2.50 (m, 2H), 2.26 (m, 2H), 1.73 (m, 2H), 1.21 (d, $^3J_{H,H}$=6.9 Hz, 3H); $^{19}$F NMR (376 MHz, (CD$_3$)$_2$SO): δ −114.9 (br s, 2 F); MS (MALDI): m/z=446.8 ([M+H]$^+$).

Example 2

In Vitro mTOR Binding Assay and In-Cell Western Blot

In Vitro mTOR Binding Assay
N-terminally GST-tagged mTOR (Cat. No. PR8683B; 0.45 mg/ml; truncated version: amino acids 1360-2549), Alexa Fluor® 647 labeled kinase Tracer 314 (Cat. No. PV6087), LanthaScreen Eu-anti-GST Tag antibody (Cat.

No. PV5594) were purchased from Life Technologies. The 1×mTOR Kinase Buffer consists of 50 mM HEPES pH 7.5, 5 mM MgCl$_2$, 1 mM EGTA, and 0.01% Pluronic F-127 (Sigma Cat. No. P2443-250G).

A 10-point 4-fold serial dilution (highest concentration at 10 μmol/L and lowest concentration at 40 μmol/L) of each compound was tested for mTOR binding in duplicate in a 384-well plate. To perform the LanthaScreen kinase binding assay 5 μl of the test compounds concentrated 3× the final concentration, 5 μl of 9 nM GST-mTOR/6 nM Eu-anti-GST antibody mixture and 5 μl of 30 nM Tracer 314 solution were mixed together resulting to a final concentration of 3 nM GST-mTOR, 2 nM Eu-anti-GST antibody and 10 nM Tracer 314 per well. After 30 min incubation at RT, time-resolved FRET was measured with a Synergy 4 multi-mode microplate reader (Biotek Instruments) using the following settings: 100 microsecs delay before data collection, 200 microsecs time for data collection, 10 measurements per data point. Emission filter: 665 nm/8 nm with sensitivity set to 190 and 620 nm/10 nm with sensitivity set to 130; Excitation filter: 340 nm/30 nm; Dichroic mirror 400 nm.

For data analysis, the mean background (wells with only mTOR kinase buffer) was subtracted and the emission ratio calculated by dividing the signal emitted at 665 nm from the acceptor (Alexa Fluor® 647 labeled Tracer 314) by the signal emitted at 620 nm from the donor (Eu-labeled antibody). IC$_{50}$ values of each compound were determined by plotting the emission ratio versus the compound concentrations (in logarithmic scale) and then by fitting a sigmoidal dose-response curve with variable slope to the data using GraphPad™ Prism.

In-Cell Western Blot

A2058 cells are plated at 20,000 cells/well in a 96-well plate (Perkin Elmer, Cat. No. 6005558) and 24 hours later treated with different compounds for 1 hour. For each compound 7 different concentrations are applied on cells (5 μM, 1.25 μM, 0.625 μM, 0.3125 μM, 0.155 M, 0.08 μM and 0.04 μM). Cells are fixed with 4% paraformaldehyde for 30 minutes at room temperature, washed 2 times with 1% BSA in PBS, permeabilized with 0.1% Triton X-100 in PBS/1% BSA for 30 minutes at room temperature and blocked with 5% goat serum in PBS/1% BSA/0.1% Triton X-100 for 30 minutes at room temperature. Cells are stained with primary antibody either with rabbit anti-pPKB S473 (1:500; Cell Signaling Technology, Cat. No. 4058) combined with mouse anti-α-tubulin (1:2000; used for normalization; Sigma, Cat. No. T9026) or with rabbit anti-pS6 S235/S236 (1:500; Cell Signaling Technology, Cat. No. 4856) combined with mouse anti-α-tubulin (1:2000; used for normalization) over night at 4° C. After 3 times 5 minutes wash with PBS/1% BSA/0.1% triton cells are treated with the secondary antibodies goat-anti-mouse IRDye680 (LICOR, Cat. No. 926-68070) and goat-anti-rabbit IRDye800 (LICOR, 926-32211) (each diluted 1:500 in PBS/1% BSA/0.1% triton) for 1 hour while shaking in the dark. Cells are washed 3 times 5 minutes with PBS/1% BSA/0.1% triton and plate scanned with the Odyssey Infrared Scanning system using both 700 and 800 nm channels. As control for 0% inhibition vehicle (0.2% DMSO) is added to cells. To correct for background staining in the data analysis wells are treated only with secondary antibodies.

For data analysis the mean background signal from channel 700 nm and 800 nm are subtracted from each signal in channel 700 nm and 800 nm, respectively. The signals in each channel are normalized to the 0% inhibition and then signal ratio 800 nm over 700 nm is performed to obtain the values for either pPKB S473 or pS6 S235/S236 normalized to α-Tubulin.

IC$_{50}$ values of each compound are determined by plotting the normalized pPBK S473 and pS6 S235/S236 signals, respectively, versus the compound concentrations (in logarithmic scale) and then by fitting a sigmoidal dose-response curve with variable slope to the data using GraphPad™ Prism.

TABLE 1

Comparative biological activities

| | Compound 1 | Compound 1* |
|---|---|---|
| | 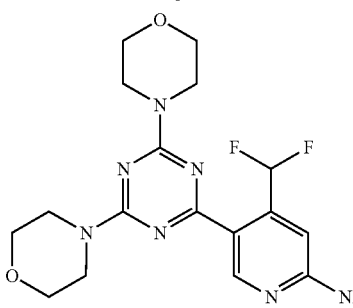 | 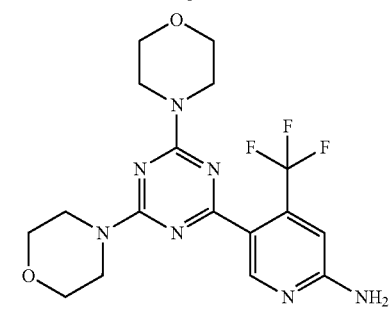 [SMILES: Nc1cc(C(F)(F)F)c(-c2nc(N3CCNCC3)nc(N3CCOCC3)n2)cn1] |
| pPKB S473 IC$_{50}$ [nM] | 108 | 149 |
| pS6 S235/236 IC$_{50}$ [nM] | 196 | 340 |
| mTOR IC$_{50}$ [nM] | 8 | 190 |

TABLE 1-continued

Comparative biological activities

| | Compound 2 | Compound 2* |
|---|---|---|
| pPKB S473 IC$_{50}$ [nM] | 34 | 64 |
| pS6 S235/236 IC$_{50}$ [nM] | 80 | 650 |
| mTOR IC$_{50}$ [nM] | 59 | 199 |

TABLE 2

Comparative biological activities

| | Compound 6 | Compound 6* |
|---|---|---|
| pPKB S473 IC$_{50}$ [nM] | 155 | 255 |
| pS6 S235/236 IC$_{50}$ [nM] | 215 | 433 |
| mTOR IC$_{50}$ [nM] | 23 | nd |

| | Compound 7 | Compound 7* |
|---|---|---|
| pPKB S473 IC$_{50}$ [nM] | 59 | 118 |

TABLE 2-continued

| Comparative biological activities | | |
|---|---|---|
| pS6 S235/236 IC$_{50}$ [nM] | 97 | 224 |
| mTOR IC$_{50}$ [nM] | 71 | nd |

TABLE 3

| Comparative biological activities | | |
|---|---|---|
| | Compound 8 | Compound 8* |
| pPKB S473 IC$_{50}$ [nM] | 74 | 196 |
| pS6 S235/236 IC$_{50}$ [nM] | 68 | 90 |
| mTOR IC$_{50}$ [nM] | 10 | nd |
| | Compound 9 | Compound 9* |
| pPKB S473 IC$_{50}$ [nM] | 35 | 91 |
| pS6 S235/236 IC$_{50}$ [nM] | 72 | 164 |
| mTOR IC$_{50}$ [nM] | 24 | nd |

TABLE 4
Comparative biological activities
| | Compound 12 | Compound 12* |
|---|---|---|
| | 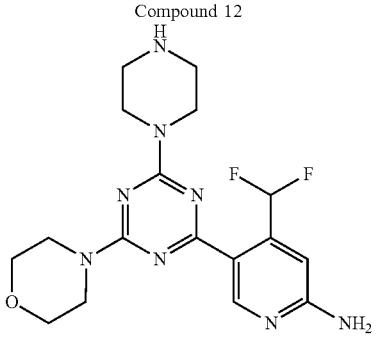 | 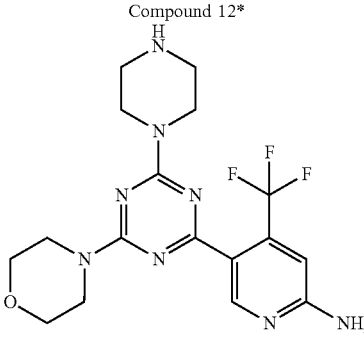 |
| pPKB S473 IC$_{50}$ [nM] | 208 | 302 |
| pS6 S235/236 IC$_{50}$ [nM] | 515 | 743 |
| mTOR IC$_{50}$ [nM] | 543 | 796 |
| | Compound 13 | Compound 13* |
| | 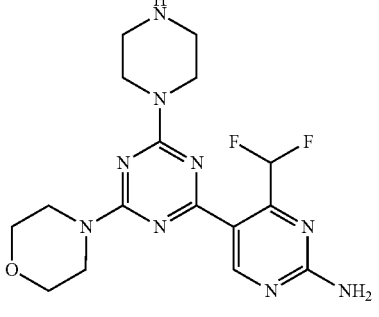 | 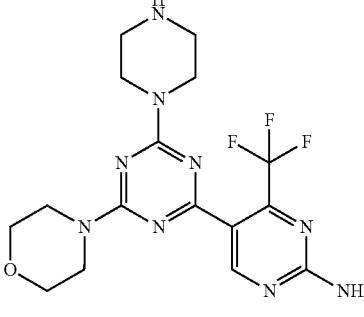 |
| pPKB S473 IC$_{50}$ [nM] | 43 | 116 |
| pS6 S235/236 IC$_{50}$ [nM] | 150 | 416 |
| mTOR IC$_{50}$ [nM] | 1015 | 2834 |
TABLE 5
Comparative biological activities
| | Compound 16 | WO2007/084786 |
|---|---|---|
| | 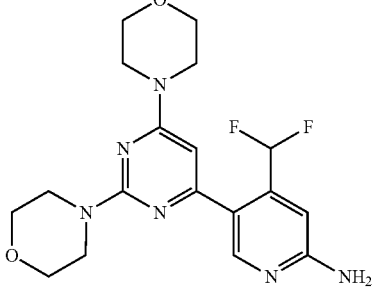 | 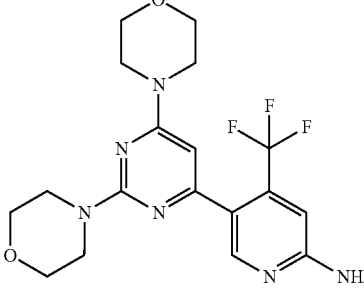 |
| pPKB S473 IC$_{50}$ [nM] | 207 | 263 |

TABLE 5-continued
Comparative biological activities
| | | |
|---|---|---|
| pS6 S235/236 IC$_{50}$ [nM] | 184 | 277 |
| mTOR IC$_{50}$ [nM] | 30 | 179 |
| Compound 17 | WO2007/084786 |
|---|---|
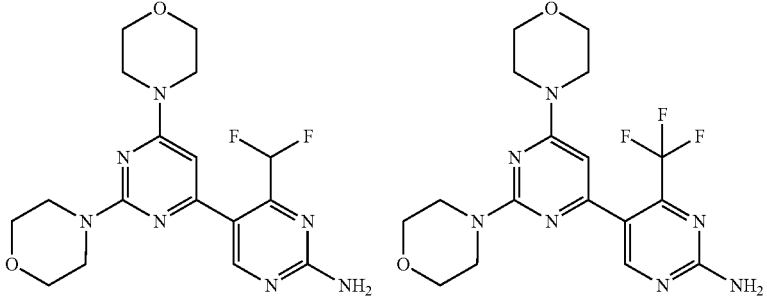
| | | |
|---|---|---|
| pPKB S473 IC$_{50}$ [nM] | 90 | 194 |
| pS6 S235/236 IC$_{50}$ [nM] | 149 | 384 |
| mTOR IC$_{50}$ [nM] | 155 | 644 |
TABLE 6
Comparative biological activities
| Compound 18 | WO2008/098058 |
|---|---|
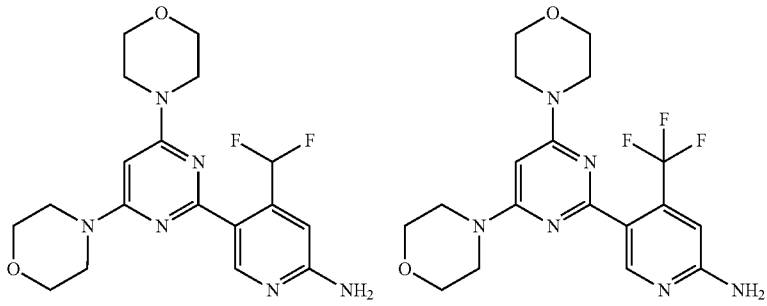
| | | |
|---|---|---|
| pPKB S473 IC$_{50}$ [nM] | 243 | 555 |
| pS6 S235/236 IC$_{50}$ [nM] | 256 | 665 |
| mTOR IC$_{50}$ [nM] | 31 | 366 |

TABLE 6-continued
Comparative biological activities
Compound 19
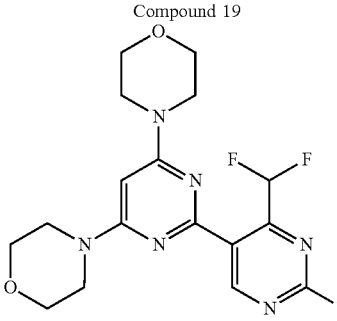
WO2008/098058
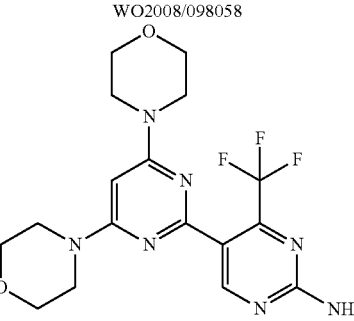
| | Compound 19 | WO2008/098058 |
|---|---|---|
| pPKB S473 IC$_{50}$ [nM] | 78 | 175 |
| pS6 S235/236 IC$_{50}$ [nM] | 147 | 370 |
| mTOR IC$_{50}$ [nM] | 158 | 1925 |
TABLE 7
Comparative biological activities
Compound 20
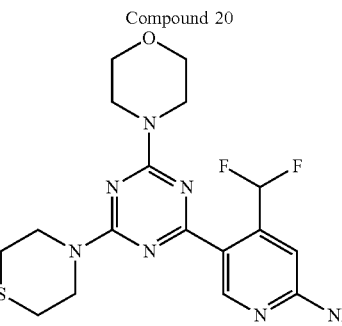
Compound 20*
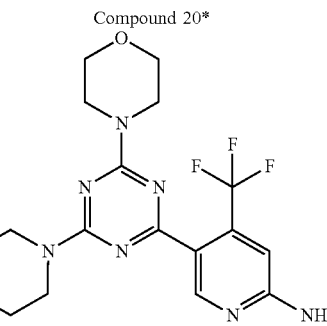
| | Compound 20 | Compound 20* |
|---|---|---|
| pPKB S473 IC$_{50}$ [nM] | 146 | 311 |
| pS6 S235/236 IC$_{50}$ [nM] | 250 | 559 |
| mTOR IC$_{50}$ [nM] | 13 | 118 |
Compound 21
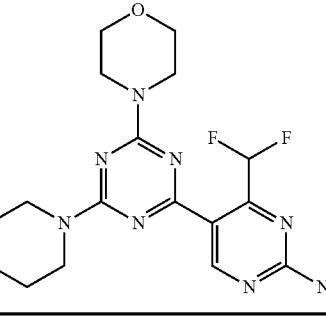
Compound 21*
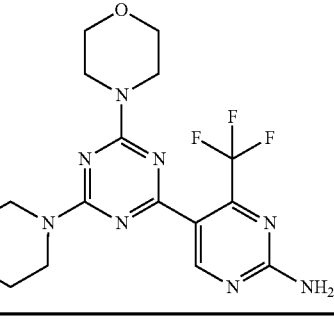
| | Compound 21 | Compound 21* |
|---|---|---|
| pPKB S473 IC$_{50}$ [nM] | 57 | 343 |

TABLE 7-continued

| Comparative biological activities | | |
|---|---|---|
| pS6 S235/236 IC$_{50}$ [nM] | 216 | 996 |
| mTOR IC$_{50}$ [nM] | 54 | 394 |

TABLE 8

Comparative biological activities

| | Compound 25 | WO2007/084786 |
|---|---|---|
| pPKB S473 IC$_{50}$ [nM] | 303 | 452 |
| pS6 S235/236 IC$_{50}$ [nM] | 294 | 553 |
| mTOR IC$_{50}$ [nM] | 32 | 152 |
| | Compound 26 | WO2007/084786 |
| pPKB S473 IC$_{50}$ [nM] | 87 | 193 |
| pS6 S235/236 IC$_{50}$ [nM] | 191 | 617 |
| mTOR IC$_{50}$ [nM] | 47 | 287 |

TABLE 9
| | Comparative biological activities | |
|---|---|---|
| | Compound 27 | WO2007/084786 |
| | 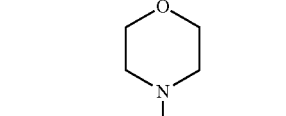 | |
| pPKB S473 IC$_{50}$ [nM] | 614 | 883 |
| pS6 S235/236 IC$_{50}$ [nM] | 766 | 1100 |
| mTOR IC$_{50}$ [nM] | 65 | 376 |
| | Compound 28 | WO2007/084786 |
| pPKB S473 IC$_{50}$ [nM] | 77 | 290 |
| pS6 S235/236 IC$_{50}$ [nM] | 146 | 1027 |
| mTOR IC$_{50}$ [nM] | 23 | 1253 |
TABLE 10
| | Comparative biological activities | |
|---|---|---|
| | Compound 23 | WO2007/084786 |
| | 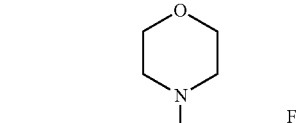 | |
| pPKB S473 IC$_{50}$ [nM] | 285 | 564 |

TABLE 10-continued
Comparative biological activities
| | | |
|---|---|---|
| pS6 S235/236 IC$_{50}$ [nM] | 230 | 562 |
| mTOR IC$_{50}$ [nM] | 40 | 88 |
| Compound 24 | WO2007/084786 |
|---|---|
| 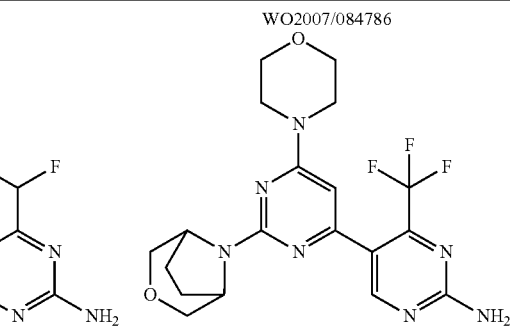 | |
| | | |
|---|---|---|
| pPKB S473 IC$_{50}$ [nM] | 84 | 340 |
| pS6 S235/236 IC$_{50}$ [nM] | 167 | 740 |
| mTOR IC$_{50}$ [nM] | 35 | 121 |
TABLE 11
Comparative biological activities
| Compound 31 | WO2007/084786 |
|---|---|
| | | |
|---|---|---|
| pPKB S473 IC$_{50}$ [nM] | 146 | 248 |
| pS6 S235/236 IC$_{50}$ [nM] | 124 | 228 |
| mTOR IC$_{50}$ [nM] | 15 | 28 |

TABLE 11-continued

Comparative biological activities

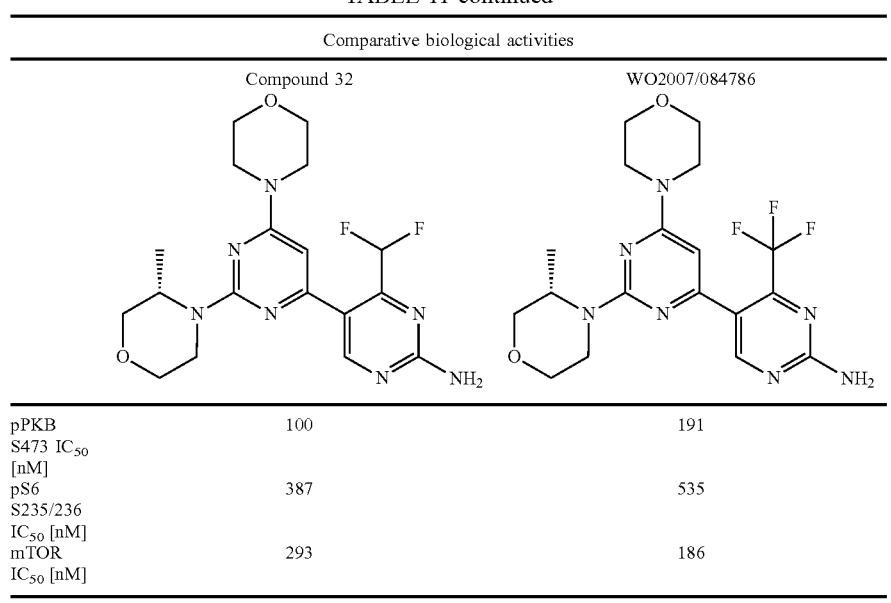

| | Compound 32 | WO2007/084786 |
|---|---|---|
| pPKB S473 IC$_{50}$ [nM] | 100 | 191 |
| pS6 S235/236 IC$_{50}$ [nM] | 387 | 535 |
| mTOR IC$_{50}$ [nM] | 293 | 186 |

TABLE 12

Results of in-cell Western Blot and mTOR binding

| | In-cell Western blot | | binding |
|---|---|---|---|
| Compound | pPKB S473 IC$_{50}$ [nM] | pS6 S235/S236 IC$_{50}$ [nM] | mTOR IC$_{50}$ [nM] |
| 1 | 108 | 196 | 8 |
| 2 | 34 | 80 | 59 |
| 3 | 231 | 105 | 8 |
| 4 | 178 | 135 | nd |
| 5 | 85 | 135 | nd |
| 6 | 155 | 215 | 23 |
| 7 | 59 | 97 | 71 |
| 8 | 74 | 68 | 10 |
| 9 | 35 | 72 | 24 |
| 10 | 138 | 93 | nd |
| 11 | 61 | 96 | nd |
| 12 | 219 | 407 | 543 |
| 13 | 37 | 120 | 1015 |
| 14 | 349.5 | 883 | nd |
| 15 | 49 | 286 | nd |
| 16 | 207 | 184 | 30 |
| 17 | 90 | 149 | 155 |
| 18 | 243 | 256 | 31 |
| 19 | 78 | 147 | 158 |
| 20 | 146 | 250 | 13 |
| 21 | 57 | 216 | 54 |
| 22 | 57 | 216 | 18 |
| 23 | 285 | 230 | 40 |
| 24 | 84 | 167 | 35 |
| 25 | 303 | 294 | 32 |
| 26 | 87 | 191 | 47 |
| 27 | 614 | 766 | 65 |
| 28 | 77 | 146 | 23 |
| 31 | 146 | 124 | 15 |
| 32 | 100 | 387 | 293 |
| 37 | 533 | 268 | 49 |
| 38 | 219 | 79 | nd |
| 39 | 106 | 47 | 1 |
| 40 | 252 | 160 | 5 |
| 41 | 436 | 261 | 22 |
| 42 | 54 | 45 | 3 |
| 44 | 197 | 87 | 5 |
| 45 | 234 | 93 | 7 |
| 46 | 956 | 426 | 36 |
| 47 | 469 | 176 | 29 |
| 50 | 1561 | 407 | nd |
| 51 | 875 | 352 | nd |
| 52 | 1050 | 332 | nd |
| 53 | 1318 | 612 | nd |
| 54 | 354 | 209 | nd |
| 55 | 942 | 526 | nd |
| 56 | >10000 | >10000 | nd |
| 66 | 244 | 139 | 4 |
| 67 | 787 | 395 | nd |
| 68 | 682 | 415 | nd |
| 69 | 244 | 140 | 21 |
| 70 | 914 | 906 | nd |
| 71 | 2337 | 3141 | nd |
| 77 | 476 | | nd |
| 78 | 506 | 392 | 38 |
| 79 | 200 | 136 | 10 |
| 80 | 94 | 117 | nd |
| 82 | 329 | 169 | 40 |
| 83 | 379 | 294 | 32 |
| 84 | 116 | 146 | nd |
| 85 | 249 | 241 | nd |
| 86 | 231 | 236 | nd |
| 88 | 271 | 192 | 18 |

Example 3

A: Kinase Binding

In order to test binding of Cpd. 1 to PI3K isoforms and related kinases, a biochemical assay was performed at DiscoveRx (Fremont, USA) (Table 13, Rows 1-7).

B: Kinase Inhibition

Furthermore, compound 1* and reference compounds were analyzed for their ability to inhibit kinase function of PIK3CA and related kinases (Proqinase, Germany) (Column3 of Table 13). Lipid kinases PIK3CA, PIK3CB, PIK3CG, PIK3CD, (PI3K α, β, γ and δδ), PIK3C2A, PIK3C2B, PIK3C2G, PIK3C3, PIK4B were tested in an ADP-Glo assay (Promega, USA). Protein kinases mTOR and DNAPK were tested in a radiometric $^{33}$P-γATP assay ($^{33}$PanQinase® Activity Assay, Proqinase, Germany). IC$_{50}$ values were measured by testing 10 semi-log concentrations of each compound in the range from 1×10-04 M to 3×10-09 M, in singlicate. Prior to testing, the compounds dissolved to 1×10-02M stock solutions in volumes of 100% DMSO as stated in the compound submission form (CSF). 100 µl of each stock solution were transferred into column 2 of a microtiter plate. Subsequently, the 1×10-02 M stock solutions in column 2 of the master plate were subjected to a serial, semi-logarithmic dilution using 100% DMSO as a solvent. This resulted in 10 distinct concentrations, with a dilution endpoint of 3×10-07 M/100% DMSO. Pure DMSO was used as control. Compounds were diluted with water and then transferred into the assay resulting in a 1% DMSO solution in a concentration range of 1×10-04 M to 3×10-09 M.

For measuring lipid kinase inhibition, assays were performed in 96-well half-area microtiter plates. The following solutions were mixed and incubated for 30° C. for 40 minutes: 10 µl of ATP solution (50 mM HEPES-NaOH, pH 7.5, 1 mM EGTA, 100 mM NaCl, 0.03% CHAPS, 2 mM DTT, ATP (PIK3C3, 20 µM; PIK3CA, 150 µM, PIK3CB 300 µM, PIK3CG 500 µM, PIK3CG 100 µM), kinase (PK3C3, 25 ng/25 µl; PIK3CA, 2 25 ng/25 µl, PIK3CB 10 25 ng/25 µl, PIK3CG 5 25 ng/25 µl, PIK3CG 40 25 ng/25 µl) and substrate (50 or 100 µM, respectively), 5 µl of test sample in 5% DMSO and 10 µl of enzyme/substrate mixture. The assay for PIK3C3 additionally contained 3 mM MnCl2, the assay for PIK3CA/PIK3R1, PIK3CB/PIK3R1, PIK3CD/PIK3R1 and PIK3CG additionally contained 3 mM MgCl2. 50 µl kinase detection reagent per well was added followed by an incubation for further 60 minutes at room temperature. Signal was measured with a microplate reader (Victor2, Perkin Elmer, Boston, Ma, USA), in luminescence mode.

For measuring protein kinase activity, the reaction mixture was pipetted into a 96 well plate in four steps in the following order: 20 µl of assay buffer, 5 µl of ATP solution (in H2O), 5 µl of test compound (in 10% DMSO), 20 µl enzyme/substrate mix. The assay for all protein kinases contained 70 mM HEPES-NaOH pH 7.5, 3 mM MgCl2, 3 mM MnCl2, 3 µM Na-orthovanadate, 1.2 mM DTT, 50 µg/ml PEG20000, 1 µM ATP, [γ-33P]-ATP (approx. 1.8× 1006 cpm per well), protein kinase (0.1 nM DNA-PK; 2.4 nM mTOR), and substrate (2 µg/well for DNA-PK and 1 µg/well for mTOR). The DNA-PK assay additionally contained 2.5 µg/ml DNA. The reaction cocktails were incubated at 30° C. for 60 minutes. The reaction was stopped with 50 µl of 2% (v/v) H3PO4, plates were aspirated and washed two times with 200 µl 0.9% (w/v) NaCl. Incorporation of 33Pi was determined with a microplate scintillation counter (Microbeta, Wallac). All assays were performed with a BeckmanCoulter/SAGIAN™ Core System.

The compound IC$_{50}$ values for all kinases tested were calculated using Quattro Workflow V3.1.0 (Quattro Research GmbH, Germany).

In order to specify the affinities of Compound 1* towards kinases that showed >50% inhibition in the Kinome Scan, dissociation constants (Kd) for Compound 1* were determined from dose-response curves with the KINOMEscan technology for the class I PI3Ks (α, β, γ and δ), for the class II PI3K PIK3C2B, for the class III PI3K PIK3C3 (Vps34), for the PIKKs (Class IV) mTOR and DNAPK and for the PI4 kinase PIK4B. The smaller the dissociation constant, the higher is the affinity between test compound and kinase. Determination of Kd revealed that Compound 1* was binding with high affinities to the ATP-site of PI3K Class-I family PI3Kα, PI3Kβ, PI3Kγ and PI3Kδ with 0.002 µM, 0.011 µM, 0.025 µM and 0.025 µM, respectively (Table 13, Column 2). Weak binding was observed to Class II PIK3CB (Kd: 0.82 µM), and to the Class III family kinase PIK3C3 (Kd: 0.23 µM). Compound 1* showed high affinity to the Class-IV PIKK mTOR (Kd: 0.012 µM) while binding to the other PIKK-member, DNAPK, was about 130-fold weaker (Kd: 1.6 µM) and no binding was observed to the P14 kinase PIK4B (Kd>40 µM).

In order to investigate its selectivity and interactions across the human kinome, Compound 1* was tested in the KINOMEscan™. Developed by DiscoveRx, KINOMEscan™ employs proprietary active-site dependent competition binding assays allowing the determination of affinities of compounds to the ATP site of protein and lipid kinases. KINOMEscan assays do not require ATP and thereby report true thermodynamic interaction affinities, as opposed to IC50 values, which can depend on the ATP concentration (See more at: http://www.discoverx.com/technologies-platforms/competitive-binding-technology/kinomescan-technology-platform#sthash.TRziYTmK.dpuf.

In a primary screen, Compound 1* was tested at a single concentration of 10.0 µM against 456 human protein and lipid kinases. In these assays, binding of the test compound to a kinase results in reduction of the signal and the results for the primary screen are reported as % Ctrl (percentage of control), where lower numbers indicate stronger hits (FIG. 2).

TABLE 13

|  | Binding assay | | Kinase assay |
| --- | --- | --- | --- |
|  | % inh@10 µM | Kd (µM) |  |
| PIK3CA | 100 | 0.002 | 0.03 |
| PIK3CA(C420R) | 100 | nd | nd |
| PIK3CA(E542K) | 100 | nd | nd |
| PIK3CA(E545A) | 100 | nd | nd |
| PIK3CA(E545K) | 100 | nd | nd |
| PIK3CA(H1047L) | 86 | nd | nd |
| PIK3CA(H1047Y) | 99 | nd | nd |
| PIK3CA(I800L) | 100 | nd | nd |
| PIK3CA(M1043I) | 87 | nd | nd |
| PIK3CA(Q546K) | 100 | nd | nd |
| PIK3CB | 97 | 0.011 | 0.66 |
| PIK3CG | 99 | 0.025 | 0.71 |
| PIK3CD | 97 | 0.025 | 0.45 |
| PIK3C2B | 59 | 0.82 | nd |
| PIK3C2G | 93 | n.d. | nd |
| PIK3C3 | nd | 0.23 | 8.5 |
| mTOR | 100 | 0.012 | 0.09 |
| DNAPK | nd | 1.6 | 8.6 |
| PIK4B | 5 | >40 | nd |

Binding assays: A 11-point 3-fold serial dilution of each test compound was prepared in 100% DMSO at 100× final test concentration and subsequently diluted to 1× in the assay (final DMSO concentration=2.5%) as described by DiscoveRx (Fremont, USA) (Table 13). As shown in Table 13 (Column1), a potent inhibition of binding at 10.0 µM of Compound 1* was observed for the PI3K Class-I family (PI3Kα, β, γ and δ), the relevant PI3Kα (PIK3CA) mutants as well as mTOR and to certain degree also Class-II (PIK3CB with a Kd=0.82 µM). Determination of Kd revealed that Compound 1* was binding to the ATP-site of PI3K Class-I family PI3Kα, PI3Kβ, PI3Kγ and PI3Kδ with 2 nM, 11 nM, 25 nMM and 25 nM, respectively. Also potent binding to the ATP site of mTOR (Kd: 12 nM) was observed. Compound 1* inhibits potently the lipid kinase activity of all recombinantly produced PI3K Class-I subtpyes including the mutant version of PI3Kα and mTOR with $IC_{50}$ in the nanomolar range [2 to 25 nM] and o certain degree also Class-II (PIK3CB with a Kd=0.82 μM) without affecting significantly other lipid and protein kinase tested in biochemical assays (456 kinases of Kinomescan, DiscoverX).

Kinase assay: We also analyzed Compound 1* for its ability to inhibit kinase function of PIK3CA and related kinases (Proqinase, Germany). Lipid kinases PIK3CA, PIK3CB, PIK3CG, PIK3CD, PIK3C2A, PIK3C2B, PIK3C2G, PIK3C3, PIK4B were tested in an ADP-Glo assay (Promega, USA). Protein kinases mTOR and DNAPK were tested in a radiometric $^{33}$P-γATP assay ($^{33}$PanQinase® Activity Assay, Proqinase, Germany). $IC_{50}$ values were measured by testing 10 semi-log concentrations of each compound in the range from 1×10-04 M to 3×10-09 M, in singlicate.

Example 4

The anti-proliferative activity of Compound 1* was tested in a panel of cells with epidermoid origin. The data demonstrate that Compound 1* with the exception of the MC7 cells inhibited all cell lines between 1598 nM and 1485 nM.

TABLE 14

| Cell line name | Disease | $GI_{50}$ (nM) |
| --- | --- | --- |
| RPMI-7951 | Malignant melanoma | 775 |
| MeWo | Malignant melanoma | 1043 |
| A375 | Malignant melanoma | 1153 |
| CAL 27 | Squamous cell carcinoma, tongue | 1523 |
| LOX IMVI | melanotic melanoma, non epithelia (metastatic site: lymph node) | 572 |
| M14 | Melanotic melanoma; non epithelial | 482 |
| MALME-3M | Melanotic melanoma; metastatic site: lung; mix | 140 |
| MDA-MB-435 | Melanoma | 413 |
| SK-MEL-2 | Melanoma; metastatic site: skin of thigh; polygonal | 411 |
| SK-MEL-28 | Melanoma; polygonal | 343 |
| SK-MEL-5 | Melanoma; metastatic site: axillary node; stellate | 171 |
| UACC-62 | Melanotic melanoma; non epithelial | 212 |
| A-431 | Skin; epidermoid carcinoma | 1170 |
| MDA-MB-231 | Breast cancer; adenocarcinoma | 1430 |
| MDA-MB-361 | Breast cancer; adenocarcinoma | 1485 |
| CAL-33 | HeadNeck - Squamous cell carcinoma, tongue | 163 |
| HSC-4 | HeadNeck - Squamous cell carcinoma, tongue | 680 |
| BICR 31 | HeadNeck - Tongue squamous carcinoma | 158 |
| BHY | HeadNeck (tongue) - Oral squamous cell carcinoma | 348 |
| BICR 16 | Headneck (tongue) - squamous cell carcinoma, hypopharynx | 362 |
| YD-10B | HeadNeck - Squamous cell carcinoma, tongue | 393 |
| SNU-1041 | HeadNeck squamous cell carcinoma, hypopharyngeal | 658 |
| HSC-4 | HeadNeck - Squamous cell carcinoma, tongue | 680 |
| SCC-9 | HeadNeck - Squamous cell carcinoma, tongue | 682 |
| YD-8 | HeadNeck - Squamous cell carcinoma, tongue | 1004 |

All cell lines have been licensed from the American Type Culture Collection (ATCC) Manassas, Virginia (US). Master and working cell banks (MCB and WCB) were prepared by subculturing in ATCC-recommended media and freezing according to ATCC recommended protocols (www.atc-c.org). Cell line stocks for the assays were prepared from the WCB. The MCB, WCBs and assay stocks were prepared within respectively 3, 6 and 9 passages of the ATCC vial. Solid powders of reference compounds were stored as indicated by the supplier. Compounds were weighed on a calibrated balance and dissolved in 100% DMSO. DMSO samples were stored at room temperature. At the day of the experiment, the compound stock was diluted in 3.16 fold steps in 100% DMSO to obtain a 9-point dilution series. This was further diluted 31.6 times in 20 mM sterile Hepes buffer pH 7.4. A volume of 5 μl was transferred to the cells to generate a test concentration range from 3.16×10-5 M to 3.16×10-9 M (31.6 μM to 3.16 nM) in duplicate. The final DMSO concentration during incubation was 0.4% in all wells. If a compound showed extremely potent activity, it was further diluted 100 times and a new dose-response curve in duplicate measured. An assay stock was thawed and diluted in its ATCC recommended medium and dispensed in a 384-well plate, depending on the cell line used, at a concentration of 400-1600 cells per well in 45 μl medium. For each used cell line the optimal cell density was used. The margins of the plate were filled with phosphate-buffered saline. Plated cells were incubated in a humidified atmosphere of 5% $CO_2$ at 37° C. After 24 hours, 5 μl of compound dilution was added and plates were further incubated for another 72 hours. After 72 hours, 25 μl of ATPlite 1Step™ (PerkinElmer) solution was added to each well, and subsequently shaken for 2 minutes. After 10 minutes of incubation in the dark, the luminescence was recorded on an Envision multimode reader (PerkinElmer).

Dose response curves were generated and GI50, TGI and LC50 values were calculated from the dose response curves. Growth inhibition of 50% ($GI_{50}$) is the drug concentration resulting in a 50% reduction in the net increase in cell number during the drug incubation as compared to the (untreated) control. TGI (total growth inhibition) stands for the compound concentration causing 0% growth (keeping the cell number constant during the whole experiment=cytostatic effect). The lethal concentration of 50% ($LC_{50}$) is the concentration of drug resulting in a 50% reduction in cell number at the end of the drug treatment as compared to that at the beginning indicating a net loss of cells following treatment due to toxic effects of the drug.

Example 5

K14-Fyn Y528F transgenic mouse is a model of cSCC that develops pre-cancerous lesions and cSCCs resembling human lesions (Skin tumors in K14-Fyn (Y528F) transgenic mice resemble AK and cSCC and demonstrate strong activation of the PDK-1/mTOR/S6 pathway Zhao L, Li W, Marshall C, Griffin T, Hanson M, Hick R, Dentchev T, Williams E, Werth A, Miller C, Bashir H, Pear W, Seykora J T (2009), Cancer Res; 69:9439-9447. Src family tyrosine kinases (SFK) regulate cell proliferation, and increased SFK activity is common in human carcinomas, including cutaneous squamous cell carcinomas (cSCC) and its precursors. The elevated SFK activity in cutaneous cSCC was modeled using K14-Fyn Y528F transgenic mice, which spontaneously form punctate keratotic lesions, scaly plaques, and large tumors resembling actinic keratoses, cSCC in situ, and cSCC, respectively. Lesional tissue showed increased levels of activated SFKs, PDK1, STAT3, and ERK1/2, whereas Notch1/

NICD protein and transcript levels were decreased. p53 levels also were decreased in cSCC in situ and cSCC.

We asked whether topically applied PI3K/mTOR inhibitors specifically targeting the PI3K/mTOR pathway should induce regression of cSCCs in K14 Fyn Y528F mice by either topical or systemic (PO) application (50 mg/kg PO QD). The oral application of 50 mg/kg PO QD is known to produce pharmacological significant levels of Compound 1* (Cmax: 2-4 uM).

6-week-old cohorts of K14-Fyn Y528F mice were treated with a topical application of a gel containing Compound 1* (10 mg of Compound 1*) or nothing (control) were dissolved in 75 ul of DMSO and then propyleneglycol was added to 1000 mg (final concentration is 1% (w/w) (FIG. 1B).

The Compound 1* treated cohort contained 6 mice with 20 cSCC lesions (FIG. 1B) while the control cohort contained 6 mice with 15 cSCC lesions (FIG. 1A). The size of each SCC was measured using calipers before treatment and weekly thereafter. The cSCCs varied from 4-68 mm² in size (size range of cSCCs in each cohort was similar. Gels were applied to lesions daily once Mo-Fr.

As shown in FIGS. 1B and 1C, the once daily topical application of Compound 1* gel induced almost complete regression of all cSCC lesions in the K14-Fyn Y528F model without prominent inflammation or ulceration within 4 weeks. These data strongly suggest that topical application of potent dual PI3K/mTOR inhibitors may be useful for treating cSCC. The efficacy of the oral application is determined as is the histology and IHC.

For histology and immune-histochemical (IHC) analysis of the PI3K/mTOR biomarker (pAKT and pS6), minimally invasive (2-3 mm thick) skin biopsies are taken and analyzed at several time points, such as 1) at start of oral treatment, 2) after 1 week, 3) after 3 weeks, in addition to taking and analyzing blood levels of Compound 1*. Biopsies are taken at areas of low sensitivity, e.g. on shoulders and must be taken in close neighbourhood in order to ensure comparability (skin has different thickness at different body areas). The skin is frozen and analysis is done by IHC and extraction, followed by LC/MS analysis of Compound 1*. Rough estimation of drug concentration needed for therapeutic effect, which depends on potency and physicochemical properties, are around 0.1-3 microgram/gram tissue. This procedure will be replicated also during the peroral treatment.

Example 6

Daily oral application of Compound 1* gel induced almost complete regression of all cSCC lesions in the K14-Fyn Y528F model without prominent side effects. The histology and IHC for the biomarker in tumor lesions and blood is performed and the assessment of skin and plasma level of Compound 1* are addressed in clinical neoadjuvant study in man.

Example 7

Pig Skin Penetration of the Inventive Compounds

The assessment of percutaneous permeation is key to the successful development of new products and formulations intended for human use. Moreover, it is further important for bioequivalence assessments of locally acting products in the pharmaceutical industry. More commonly used models to conduct skin-permeation studies are ex vivo human or animal skin. Through the standardization of protocols and techniques, the available skin models can be useful as surrogate models for in vivo human skin to evaluate the bioequivalence of topical products. A wide range of animal models has been used as alternatives to human skin to evaluate percutaneous permeation of substances. Since porcine (pig) skin is histologically similar to human skin with a comparable SC thickness of 21-26 μm. In addition, the average hair-follicle density in porcine ear skin is 20/cm² compared to 14-32/cm² in human forehead skin. As well as being similar to human skin, porcine ear skin is also convenient to obtain and has been widely used in skin-permeation studies. Therefore to mimic human skin penetration the use of pig skin either ex vivo or in vivo is sufficient and predictable.

Ex vivo and in vivo models to assess the penetration of various drug substances including the inventive compounds in the skin of pigs have been established. This model allows to assess the PK profile of several drug candidates including the inventive compounds in one subject, thereby enhancing comparability and avoiding inter-subject variability.

In the first study (FIG. 3, Table 15) the PK profiles of nine test formulations have been assessed using 80% SBECD either at pH3 or pH 7. Cpd1* and Cpd3 as 1% experimental formulations penetrated into pig skin (lower epidermis and dermis) to a significant extent ex vivo, despite drying up on the skin after a few hours post application. In comparison with Aldara, a cream containing 5% of the TLR7 agonist imiquimod, the intrinsic penetration properties of Cpd1* were estimated to be similar to imiquimod, while those of Cpd3 were slightly lower.

TABLE 15

Nine formulations comprising inventive compounds and one control formulation.

| Compound | Formulation | Nominal conc. [mg/mL] | Applied amount of formulation[1] | Applied amount of compound |
|---|---|---|---|---|
| Cpd 1* pH 3 | 1% (base, w/v) | 10.01 | 46 μL | 460.5 μg |
| Cpd 1* pH 7 | 1% (base, w/v) | 10.01 | 46 μL | 460.5 μg |
| Cpd 8 pH 3 | 0.5% (base, w/v) | 5.03 | 46 μL | 231.4 μg |
| Cpd 3 pH 3 | 1% (base, w/v) | 10.03 | 46 μL | 461.4 μg |
| Cpd 13 pH 3 | 0.5% (base, w/v) | 5.00 | 46 μL | 230.0 μg |
| Cpd 2* pH 3 | 0.2% (base, w/v) | 1.82 | 46 μL | 83.7 μg |
| Cpd 21 pH 3 | 0.1% (base, w/v) | 0.74 | 46 μL | 34.0 μg |
| Cpd 20 pH 3 | 0.5% (base, w/v) | 4.35 | 46 μL | 200.1 μg |
| Cpd 42 pH 3 | 0.5% (base, w/v) | 5.05 | 46 μL | 232.3 μg |
| Imiquimod (Aldara - MEDA AB, Sweden) | 5% cream | — | 56 mg | 2.8 mg |

[1]Application area 4 cm × 2 cm = 8 cm²; applied formulation of 5.75 μL/cm² or 7 mg/cm² corresponding to 46 μL or 56 mg A further study was performed to investigate the skin PK profile of 4 test formulations in ex vivo pig skin: 1% Cpd1* in a 90% propylene glycol (PG)/10% oleyl alcohol (OA), 1% Cpd1* in a 100% PG formulation, 1% Cpd3 in a 90% PG/10% OA formulation and the control formulation Aldara (containing 5% imiquimod). The PK profiles are presented in Table 16 and in FIG. 4. Cpd1* in a 90% PG and 10% OA formulation showed the highest skin penetration followed by the Cpd3 in 90% PG and 10% OA. The skin concentration of Cpd1* in 100% PG alone was lower compared with the preparation containing 10% OA, but was still much higher than the skin concentration of the control formulation Aldara. The skin PK profile of Cpd3 in 100% PG was comparable to Cpd1*. Thus, both Cpd1* and Cpd3 do not need the penetration enhancer oleyl alcohol for significant skin penetration.

In conclusion, topical treatment of pig skin ex vivo with Cpd1* and Cpd3 in 1% experimental preparations containing the standard solvent propylene glycol resulted in high drug concentrations in the lower epidermis and dermis, which were higher compared to skin concentrations achieved after topical treatment with the standard product Aldara (containing 5% imiquimod).

TABLE 16

Three formulations comprising inventive compounds and one control formulation.

| Compound | Formulation | Nominal conc. [mg/mL] | Applied amount of formulation[1] | Applied amount of compound |
|---|---|---|---|---|
| Cpd 1* | 1% Cpd 1* in 90% PG and 10% OA | 10.0 | 46 μL | 460 μg |
| Cpd 1* (100% PG) | 1% Cpd 1* in 100% PG | 10.0 | 46 μL | 460 μg |
| Cpd 3 | 1% Cpd 3 in 90% PG and 10% OA | 10.0 | 46 μL | 460 μg |
| Imiquimod (Aldara - MEDA AB, Sweden) | 5% cream | — | 56 mg | 2.8 mg |

[1]Application area 4 cm × 2 cm = 8 cm²; applied formulation of 5.75 μL/cm² or 7 mg/cm² corresponding to 46 μL or 56 mg In conclusion, topical treatment of pig skin ex vivo with Cpd1* and Cpd3 in 1% experimental preparations containing the standard solvent propylene glycol resulted in high drug concentrations in the lower epidermis and dermis, which were higher compared to skin concentrations achieved after topical treatment with the standard product Aldara (containing 5% imiquimod).

Thus, the formulations of Cpd1* and Cpd3 (each 1% in propylene glycol) has been tested in a pig skin ex-vivo study and high penetration into epidermis and dermis found, superior to Aldara (5% imiquimod). The aim of a further study is to measure the skin penetration of the same formulations of Cpd1* and Cpd3 in pigs in vivo. The following formulations were tested:

1% Cpd1* in propylene glycol (PG)
1% Cpd1* propylene glycol with thickener (PG+TH)
1% Cpd1* in PEG
Imiquimod as control formulation (Aldara 5% cream)

Except for the PEG formulation significant levels of Cpd1* were found after the stratum corneum removed by tape stripping in epidermis and dermis of the living pig (FIG. 5).

Example 8

Pig Skin Penetration of the Inventive Compounds

The hairless (Hr) gene encodes a transcriptional co-repressor highly expressed in the mammalian skin. In the mouse, several null and hypomorphic Hr alleles have been identified resulting in hairlessness in homozygous animals, characterized by alopecia developing after a single cycle of relatively normal hair growth. Mutations in the human ortholog have also been associated with congenital alopecia. Although a variety of hairless strains have been developed, outbred SKH1 mice are the most widely used in dermatologic research. These unpigmented and immunocompetent mice allow for ready manipulation of the skin, application of topical agents, and exposure to UVR, as well as easy visualization of the cutaneous response. Wound healing, acute photobiologic responses, and skin carcinogenesis have been extensively studied in SKH1 mice and are well characterized. In addition, tumors induced in these mice resemble, both at the morphologic and molecular levels, UVR induced skin malignancies in man (Benavidesa F, Oberyszynb T M, VanBuskirkc A M, Reeved V E, Kusewitta, D F (2009). The hairless mouse in skin research. *J Dermatol Sci*. 2009 January; 53(1): 10-18). In fact, irradiation of SKH-1 for 20 minutes with UV-B per day results in an actinic keratosis (AK) that resembles the AK in human.

As shown in FIG. 6 there was a significant effect of the topical daily treatment of Cpd1* compared to non treated (NT) or vehicle treated (V) mice.

The effect of Cpd1* was lost when the treatment was discontinued (FIG. 7).

In summary treatment of AK induced by UV in the SKH-1 mouse model is effectively reduced and prevented by the topical daily treatment with Cpd1*.

The invention claimed is:
1. A method of preventing or treating a skin lesion in a subject in need thereof, wherein said skin lesion is a non-melanoma skin cancer, and wherein said non-melanoma skin cancer is selected from basal cell carcinoma and actinic keratosis; said method comprising administering an effective amount of a compound of formula (I) to said subject,

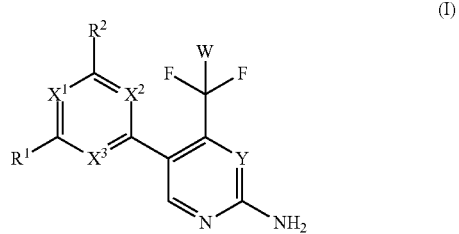

wherein
$X^1$, $X^2$ and $X^3$ are N;
Y is N or CH;
W is F;
$R^1$ and $R^2$ are independently of each other
(i) a morpholinyl of formula (II)

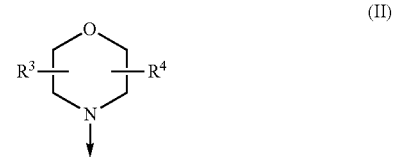

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —$CH_2$—O—$CH_2$—, —$CH_2$—NH—$CH_2$—, or any of the structures

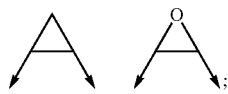

wherein the arrows denote the bonds in formula (II); or (ii) a saturated 6-membered heterocyclic ring Z selected from thiomorpholinyl and piperazinyl, optionally substituted by 1 to 3 R⁷; wherein R⁷ is independently at each occurrence $C_1$-$C_3$alkyl optionally substituted with one or two OH, $C_1$-$C_2$fluoroalkyl, $C_1$-$C_2$alkoxy$C_1$-$C_3$alkyl, $C_3$-$C_6$cycloalkyl; or two R⁷ substituents form together a bivalent residue —R⁸R⁹— selected from $C_1$-$C_3$alkylene optionally substituted with 1 to 4 F, —CH₂—O—CH₂— or —O—CH₂CH₂—O—;

with the proviso that at least one of R¹ and R² is a morpholinyl of formula (II);

and prodrugs, metabolites, tautomers, solvates and pharmaceutically acceptable salts thereof.

2. The method according to claim 1, wherein said R¹ and said R² are independently of each other selected from

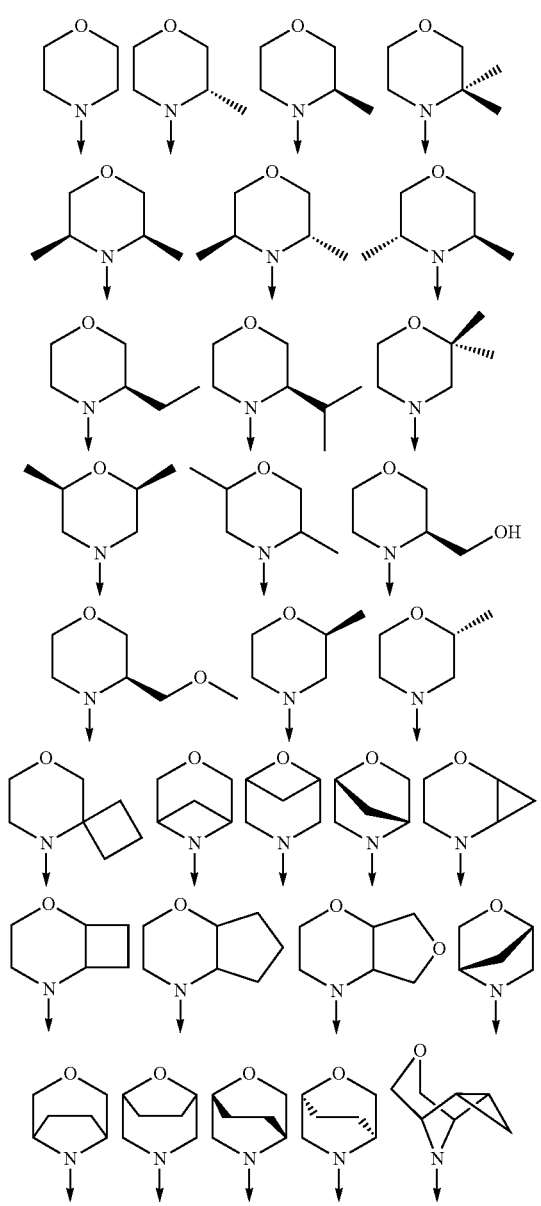

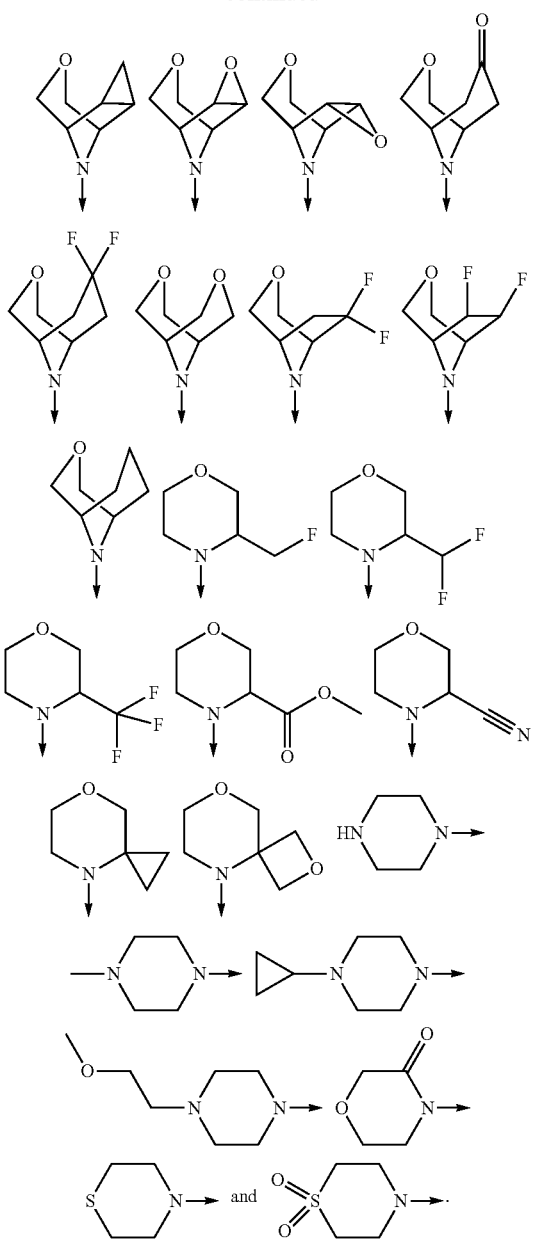

3. The method according to claim 1, wherein R¹ and R² are independently of each other selected from

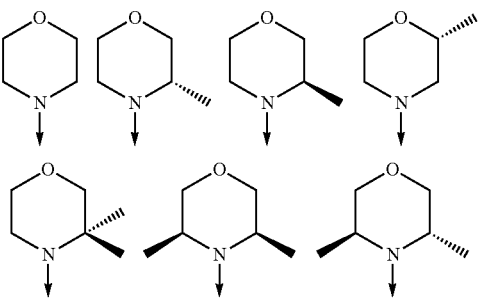

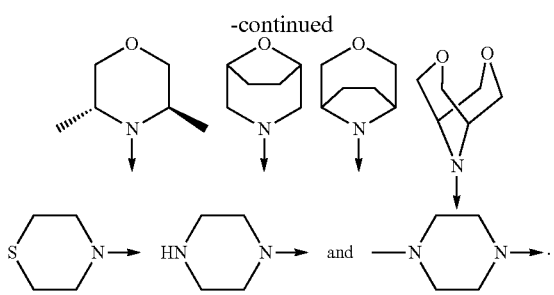

4. The method according to claim 1, wherein said compound is selected from
- 5-(4,6-dimorpholino-1,3,5-triazin-2-yl)-4-(trifluoromethyl)pyridin-2-amine;
- 5-(4,6-dimorpholino-1,3,5-triazin-2-yl)-4-(trifluoromethyl)pyrimidin-2-amine;
- 5-[4,6-bis[(3S)-3-methylmorpholin-4-yl]-1,3,5-triazin-2-yl]-4-(trifluoromethyl)pyridin-2-amine;
- 5-[4,6-bis[(3 S)-3-methylmorpholin-4-yl]-1,3,5-triazin-2-yl]-4-(trifluoromethyl)pyrimidin-2-amine;
- 5-[4-[(3S)-3-methylmorpholin-4-yl]-6-morpholino-1,3,5-triazin-2-yl]-4-(trifluoromethyl)pyridin-2-amine;
- 5-[4-[(3S)-3-methylmorpholin-4-yl]-6-morpholino-1,3,5-triazin-2-yl]-4-(trifluoromethyl)pyrimidin-2-amine;
- 5-(4-morpholino-6-piperazin-1-yl-1,3,5-triazin-2-yl)-4-(trifluoromethyl)pyridin-2-amine;
- 5-(4-morpholino-6-piperazin-1-yl-1,3,5-triazin-2-yl)-4-(trifluoromethyl)pyrimidin-2-amine;
- 5-(4-morpholino-6-thiomorpholino-1,3,5-triazin-2-yl)-4-(trifluoromethyl)pyridin-2-amine;
- 5-(4-morpholino-6-thiomorpholino-1,3,5-triazin-2-yl)-4-(trifluoromethyl)pyrimidin-2-amine;

and tautomers, solvates and pharmaceutically acceptable salts thereof.

5. The method according to claim 1, wherein said compound is selected from the group consisting of
- 5-(4,6-dimorpholino-1,3,5-triazin-2-yl)-4-(trifluoromethyl)pyridin-2-amine;
- 5-(4,6-dimorpholino-1,3,5-triazin-2-yl)-4-(trifluoromethyl)pyrimidin-2-amine; and
- 5-[4-[(3 S)-3-methylmorpholin-4-yl]-6-morpholino-1,3,5-triazin-2-yl]-4-(trifluoromethyl)pyridin-2-amine;

and tautomers, solvates and pharmaceutically acceptable salts thereof.

6. The method according to claim 1, wherein said compound is selected from
- 5-(4,6-dimorpholino-1,3,5-triazin-2-yl)-4-(trifluoromethyl)pyridin-2-amine;

and tautomers, solvates and pharmaceutically acceptable salts thereof.

7. The method according to claim 1, wherein $R^1$ and $R^2$ are independently of each other a morpholinyl of formula (II).

8. The method according to claim 7, wherein R1 is equal to R2.

9. The method according to claim 7, wherein $R^1$ is not equal to $R^2$.

10. The method according to claim 1, wherein said skin lesion is a non-melanoma skin cancer, and wherein said non-melanoma skin cancer is a basal cell carcinoma.

11. The method according to claim 1, wherein said form of non-melanoma skin cancer is actinic keratosis.

12. The method according to claim 1, wherein said compound of formula (I) is administered topically to said subject.

13. The method according to claim 1, wherein said non-melanoma skin cancer is actinic keratosis; and wherein said compound is 5-(4,6-dimorpholino-1,3,5-triazin-2-yl)-4-(trifluoromethyl)pyridin-2-amine;
or a tautomer, solvates, or pharmaceutically acceptable salt thereof.

14. The method according to claim 1, wherein said non-melanoma skin cancer is basal cell carcinoma; and wherein said compound is 5-(4,6-dimorpholino-1,3,5-triazin-2-yl)-4-(trifluoromethyl)pyridin-2-amine;
or a tautomer, solvates, or pharmaceutically acceptable salt thereof.

* * * * *